US011793392B2

(12) United States Patent
Tilson et al.

(10) Patent No.: US 11,793,392 B2
(45) Date of Patent: Oct. 24, 2023

(54) EXTERNAL WORKING CHANNELS

(71) Applicant: Neptune Medical Inc., Burlingame, CA (US)

(72) Inventors: Alexander Q. Tilson, Burlingame, CA (US); Mark C. Scheeff, Oakland, CA (US); Garrett J. Gomes, Pleasant Hill, CA (US); Francisco G. Lopez, San Mateo, CA (US); Justin Kirschbrown, San Mateo, CA (US); Wei Li Fan, San Francisco, CA (US); William Evans, San Francisco, CA (US); Viet Anh Nguyen, San Jose, CA (US); Stephan T. Hoffmann, Danville, CA (US); Kassidy MacPhail, San Francisco, CA (US); Thomas Hsiu, Palo Alto, CA (US)

(73) Assignee: NEPTUNE MEDICAL INC., Burlingame, CA (US)

(*) Notice: Subject to any disclaimer, the term of this patent is extended or adjusted under 35 U.S.C. 154(b) by 0 days.

(21) Appl. No.: 17/940,906

(22) Filed: Sep. 8, 2022

(65) Prior Publication Data

US 2023/0014281 A1 Jan. 19, 2023

Related U.S. Application Data

(63) Continuation-in-part of application No. 17/604,203, filed as application No. PCT/US2020/013937 on Jan.
(Continued)

(51) Int. Cl.
*A61B 1/00* (2006.01)

(52) U.S. Cl.
CPC ...... *A61B 1/00078* (2013.01); *A61B 1/00135* (2013.01)

(58) Field of Classification Search
CPC .................. A61B 1/00078; A61B 1/00135
See application file for complete search history.

(56) References Cited

U.S. PATENT DOCUMENTS

| 2,268,321 A | 12/1941 | Flynn |
| 2,767,705 A | 10/1956 | Moore |

(Continued)

FOREIGN PATENT DOCUMENTS

| AU | 2013207571 B1 | 8/2013 |
| CN | ON2613655 Y | 4/2004 |

(Continued)

OTHER PUBLICATIONS

Entrada® colonic overtube product brochure downloaded from internet http://www.usendoscopy.com/~/media/Files/Documents/Spec-Sheet-International/760358c_entrada_intl_ss_web.pdf Accessed Date: Jun. 5, 2017 (the year of publication is sufficiently earlier than the effective U.S. filing date and any foreign priority date so that the particular month of publication is not in issue) 2009.

(Continued)

*Primary Examiner* — Carl H Layno
*Assistant Examiner* — Michael J Lau
(74) *Attorney, Agent, or Firm* — Shay Glenn LLP

(57) ABSTRACT

Apparatuses (e.g., devices, systems, etc.) and methods that may provide access to one or more tools to a remote site in the body including expandable and external working channels that may be part of a tube that is coupled to an outer surface of an elongate medical device, such as an endoscope.

25 Claims, 93 Drawing Sheets

Related U.S. Application Data 16, 2020, and a continuation-in-part of application No. PCT/US2021/034292, filed on May 26, 2021.

(60) Provisional application No. 63/342,618, filed on May 16, 2022, provisional application No. 63/165,721, filed on Mar. 24, 2021, provisional application No. 63/128,769, filed on Dec. 21, 2020, provisional application No. 63/030,252, filed on May 26, 2020, provisional application No. 62/854,199, filed on May 29, 2019, provisional application No. 62/835,101, filed on Apr. 17, 2019.

(56) References Cited

U.S. PATENT DOCUMENTS

| | | |
|---|---|---|
| 3,859,986 A | 1/1975 | Okada et al. |
| 3,998,216 A | 12/1976 | Hosono |
| 4,066,071 A | 1/1978 | Nagel |
| 4,141,364 A | 2/1979 | Schultze |
| 4,151,800 A | 5/1979 | Dotts et al. |
| 4,176,662 A | 12/1979 | Frazer |
| 4,425,919 A | 1/1984 | Alston, Jr. |
| 4,551,140 A | 11/1985 | Shinohara |
| 4,690,131 A | 9/1987 | Lyddy, Jr. et al. |
| 4,696,544 A | 9/1987 | Costella |
| 4,717,379 A | 1/1988 | Ekholmer |
| 4,794,412 A | 12/1988 | Casey et al. |
| 4,794,912 A | 1/1989 | Lia |
| 4,815,450 A | 3/1989 | Patel |
| 4,817,613 A | 4/1989 | Jaraczewski et al. |
| 4,893,613 A | 1/1990 | Hake |
| 4,959,058 A | 9/1990 | Michelson |
| 4,961,738 A | 10/1990 | Mackin |
| 5,018,436 A | 5/1991 | Evangelista et al. |
| 5,019,121 A | 5/1991 | Krauter |
| 5,025,778 A | 6/1991 | Silverstein et al. |
| 5,037,386 A | 8/1991 | Marcus et al. |
| 5,105,819 A | 4/1992 | Wollschlager et al. |
| 5,123,421 A | 6/1992 | Sinofsky |
| 5,174,276 A | 12/1992 | Crockard |
| 5,188,595 A | 2/1993 | Jacobi |
| 5,251,611 A | 10/1993 | Zehel et al. |
| 5,337,733 A | 8/1994 | Bauerfeind et al. |
| 5,496,292 A | 3/1996 | Burnham |
| 5,531,685 A | 7/1996 | Hemmer et al. |
| 5,531,719 A | 7/1996 | Takahashi |
| 5,577,992 A | 11/1996 | Chiba et al. |
| 5,601,588 A | 2/1997 | Tonomura et al. |
| 5,607,435 A | 3/1997 | Sachdeva et al. |
| 5,624,381 A | 4/1997 | Kieturakis |
| 5,632,734 A | 5/1997 | Galel et al. |
| 5,662,587 A | 9/1997 | Grundfest et al. |
| 5,662,621 A | 9/1997 | Lafontaine |
| 5,746,692 A | 5/1998 | Bacich et al. |
| 5,749,828 A | 5/1998 | Solomon et al. |
| 5,759,151 A | 6/1998 | Sturges |
| 5,779,624 A | 7/1998 | Chang |
| 5,782,811 A | 7/1998 | Samson et al. |
| 5,823,961 A | 10/1998 | Fields et al. |
| 5,882,347 A | 3/1999 | Laan et al. |
| 5,891,112 A * | 4/1999 | Samson ............ A61M 25/005 604/524 |
| 5,906,591 A | 5/1999 | Dario et al. |
| 5,916,145 A | 6/1999 | Chu et al. |
| 5,916,147 A | 6/1999 | Boury |
| 5,951,539 A | 9/1999 | Nita et al. |
| 5,976,074 A | 11/1999 | Moriyama |
| 6,090,099 A | 7/2000 | Samson et al. |
| 6,159,187 A | 12/2000 | Park et al. |
| 6,162,171 A | 12/2000 | Ng et al. |
| 6,179,776 B1 | 1/2001 | Adams et al. |
| 6,190,357 B1 | 2/2001 | Ferrari et al. |
| 6,217,565 B1 | 4/2001 | Cohen |
| 6,296,644 B1 | 10/2001 | Surat et al. |
| 6,309,346 B1 | 10/2001 | Farhadi |
| 6,364,878 B1 | 4/2002 | Hall |
| 6,368,315 B1 | 4/2002 | Gillis et al. |
| 6,468,203 B2 | 10/2002 | Belson |
| 6,485,409 B1 | 11/2002 | Voloshin et al. |
| 6,503,225 B1 | 1/2003 | Kirsch et al. |
| 6,517,477 B1 | 2/2003 | Wendlandt |
| 6,547,724 B1 | 4/2003 | Soble et al. |
| 6,572,538 B2 | 6/2003 | Takase |
| 6,572,590 B1 | 6/2003 | Stevens et al. |
| 6,579,277 B1 | 6/2003 | Rabiner et al. |
| 6,610,007 B2 | 8/2003 | Belson et al. |
| 6,612,982 B1 | 9/2003 | Ouchi |
| 6,616,628 B2 | 9/2003 | Hayzelden |
| 6,620,126 B2 | 9/2003 | Unsworth et al. |
| 6,623,424 B2 | 9/2003 | Hayakawa et al. |
| 6,712,832 B2 | 3/2004 | Shah |
| 6,726,677 B1 | 4/2004 | Flaherty et al. |
| 6,730,020 B2 | 5/2004 | Peng et al. |
| 6,780,151 B2 | 8/2004 | Grabover et al. |
| 6,783,491 B2 | 8/2004 | Saadat et al. |
| 6,790,173 B2 | 9/2004 | Saadat et al. |
| 6,793,621 B2 | 9/2004 | Butler et al. |
| 6,793,661 B2 | 9/2004 | Hamilton et al. |
| 6,800,056 B2 | 10/2004 | Tartaglia et al. |
| 6,869,393 B2 | 3/2005 | Butler |
| 6,899,673 B2 | 5/2005 | Ogura et al. |
| 6,911,004 B2 | 6/2005 | Kim et al. |
| 6,923,754 B2 | 8/2005 | Lubock |
| 6,960,162 B2 | 11/2005 | Saadat et al. |
| 6,974,411 B2 | 12/2005 | Belson |
| 6,984,203 B2 | 1/2006 | Tartaglia et al. |
| 7,060,199 B2 | 6/2006 | Woydt et al. |
| 7,172,552 B2 | 2/2007 | Wendlandt |
| 7,214,230 B2 | 5/2007 | Brock et al. |
| 7,288,101 B2 | 10/2007 | Deem et al. |
| 7,291,127 B2 | 11/2007 | Eidenschink |
| 7,365,509 B2 | 4/2008 | Park et al. |
| 7,438,712 B2 * | 10/2008 | Chouinard ........ A61M 25/0012 604/527 |
| 7,511,733 B2 | 3/2009 | Takizawa et al. |
| 7,537,562 B2 | 5/2009 | Takano |
| 7,559,916 B2 | 7/2009 | Smith et al. |
| 7,591,782 B2 | 9/2009 | Fujikura |
| 7,598,652 B2 | 10/2009 | Kornbluh et al. |
| 7,695,428 B2 | 4/2010 | Machida |
| 7,736,323 B2 | 6/2010 | Von Weymarn-Scharli |
| 7,749,196 B2 | 7/2010 | Osborne et al. |
| 7,837,615 B2 | 11/2010 | Le et al. |
| 7,850,725 B2 | 12/2010 | Vardi et al. |
| 7,901,347 B2 | 3/2011 | Sekiguchi et al. |
| 7,909,755 B2 | 3/2011 | Itoi |
| 7,918,819 B2 | 4/2011 | Karmarkar et al. |
| 7,918,845 B2 | 4/2011 | Saadat et al. |
| 7,931,661 B2 | 4/2011 | Saadat et al. |
| 7,935,047 B2 | 5/2011 | Yoshida et al. |
| 7,947,000 B2 | 5/2011 | Vargas et al. |
| 7,957,790 B2 | 6/2011 | Kleen |
| 7,970,455 B2 | 6/2011 | Zilberstein et al. |
| 7,988,621 B2 | 8/2011 | Smith et al. |
| 8,047,236 B2 | 11/2011 | Perry |
| 8,075,476 B2 | 12/2011 | Vargas |
| 8,092,374 B2 | 1/2012 | Smith et al. |
| 8,109,953 B1 | 2/2012 | King, III et al. |
| 8,123,739 B2 | 2/2012 | McQueen et al. |
| 8,125,755 B2 | 2/2012 | Garcia et al. |
| 8,192,422 B2 | 6/2012 | Zubiate et al. |
| 8,206,287 B2 | 6/2012 | Matsuo |
| 8,226,548 B2 | 7/2012 | Kucklick |
| 8,241,299 B2 | 8/2012 | Hibner |
| 8,246,575 B2 | 8/2012 | Viola |
| 8,257,257 B2 | 9/2012 | Takizawa et al. |
| 8,298,161 B2 | 10/2012 | Vargas |
| 8,313,014 B2 | 11/2012 | Bettuchi |
| 8,361,090 B2 | 1/2013 | Belson |
| 8,366,606 B2 | 2/2013 | Watanabe et al. |
| 8,388,519 B2 | 3/2013 | Garcia et al. |
| 8,439,825 B2 | 5/2013 | Sekiguchi |
| 8,460,179 B2 | 6/2013 | Ikeda et al. |

(56) References Cited

U.S. PATENT DOCUMENTS

| | | |
|---|---|---|
| 8,485,968 B2 | 7/2013 | Weimer et al. |
| 8,496,648 B2 | 7/2013 | Rogers |
| 8,506,479 B2 | 8/2013 | Piskun et al. |
| 8,517,923 B2 | 8/2013 | Belson et al. |
| 8,545,491 B2 | 10/2013 | Abboud et al. |
| 8,550,989 B2 | 10/2013 | Dohi et al. |
| 8,556,804 B2 | 10/2013 | Smith et al. |
| 8,663,096 B2 | 3/2014 | Viola |
| 8,663,196 B2 | 3/2014 | Kassab et al. |
| 8,708,894 B2 | 4/2014 | Smith et al. |
| 8,721,530 B2 | 5/2014 | Ohline et al. |
| 8,753,312 B2 | 6/2014 | Bowe et al. |
| 8,777,844 B1 | 7/2014 | Sadanand |
| 8,920,369 B2 | 12/2014 | Salahieh et al. |
| 8,969,639 B2 | 3/2015 | Xu et al. |
| 9,011,318 B2 | 4/2015 | Choset et al. |
| 9,066,655 B2 | 6/2015 | Stefanchik et al. |
| 9,114,228 B2 | 8/2015 | Zook et al. |
| 9,125,653 B2 | 9/2015 | Kovach |
| 9,155,451 B2 | 10/2015 | Smith et al. |
| 9,192,284 B2 | 11/2015 | Hirsch et al. |
| 9,192,288 B2 | 11/2015 | Okaniwa |
| 9,211,140 B2 | 12/2015 | Lauryssen et al. |
| 9,220,398 B2 | 12/2015 | Woodley et al. |
| 9,226,825 B2 | 1/2016 | Starksen et al. |
| 9,241,611 B2 | 1/2016 | Konno |
| 9,254,123 B2 | 2/2016 | Alvarez et al. |
| 9,295,511 B2 | 3/2016 | Smith et al. |
| 9,358,073 B2 | 6/2016 | Piligian et al. |
| 9,364,955 B2 | 6/2016 | Oyola et al. |
| 9,386,910 B2 | 7/2016 | West |
| 9,498,108 B1 | 11/2016 | Lombardi |
| 9,498,198 B2 | 11/2016 | Hu et al. |
| 9,505,125 B2 | 11/2016 | Zubiate et al. |
| 9,585,546 B2 | 3/2017 | Surti et al. |
| 9,610,068 B2 | 4/2017 | Kappel et al. |
| 9,649,473 B2 | 5/2017 | Gregorich et al. |
| 9,763,562 B2 | 9/2017 | Avitsian et al. |
| 9,814,372 B2 | 11/2017 | Smith et al. |
| 9,913,570 B2 | 3/2018 | Kucharski et al. |
| 9,937,324 B2 | 4/2018 | Kim et al. |
| 10,092,291 B2 | 10/2018 | Voegele et al. |
| 10,307,042 B2 | 6/2019 | Lombardi |
| 10,463,495 B2 | 11/2019 | Rogers et al. |
| 11,122,971 B2 | 9/2021 | Tilson et al. |
| 11,135,398 B2 | 10/2021 | Tilson et al. |
| 11,219,351 B2 | 1/2022 | Tilson et al. |
| 11,478,608 B2 | 10/2022 | Tilson et al. |
| 2002/0107478 A1 | 8/2002 | Wendlandt |
| 2002/0161355 A1 | 10/2002 | Wollschlager |
| 2003/0023259 A1 | 1/2003 | Dubrul et al. |
| 2003/0083546 A1 | 5/2003 | Butler et al. |
| 2003/0153866 A1 | 8/2003 | Long et al. |
| 2003/0208220 A1 | 11/2003 | Worley et al. |
| 2003/0216691 A1 | 11/2003 | Jacobson |
| 2003/0225379 A1 | 12/2003 | Schaffer et al. |
| 2004/0019252 A1 | 1/2004 | Hirata |
| 2004/0044350 A1 | 3/2004 | Martin et al. |
| 2004/0092960 A1 | 5/2004 | Abrams et al. |
| 2004/0186349 A1 | 9/2004 | Ewers et al. |
| 2004/0186350 A1 | 9/2004 | Brenneman et al. |
| 2004/0243227 A1 | 12/2004 | Starksen et al. |
| 2004/0260236 A1 | 12/2004 | Manning et al. |
| 2005/0005363 A1 | 1/2005 | Giori et al. |
| 2005/0010237 A1 | 1/2005 | Niazi |
| 2005/0085829 A1 | 4/2005 | Kraemer et al. |
| 2005/0165275 A1 | 7/2005 | Von Felten et al. |
| 2005/0203340 A1 | 9/2005 | Butler et al. |
| 2005/0272974 A1 | 12/2005 | Iddan |
| 2005/0277966 A1 | 12/2005 | Ewers et al. |
| 2006/0041188 A1 | 2/2006 | Dirusso et al. |
| 2006/0047183 A1 | 3/2006 | Park |
| 2006/0058582 A1 | 3/2006 | Maahs et al. |
| 2006/0129130 A1 | 6/2006 | Tal et al. |
| 2006/0192465 A1 | 8/2006 | Kombluh et al. |
| 2006/0235458 A1* | 10/2006 | Belson ............... A61B 1/00135 606/191 |
| 2006/0258906 A1 | 11/2006 | Binmoeller |
| 2006/0264707 A1 | 11/2006 | Kinney |
| 2006/0287666 A1 | 12/2006 | Saadat et al. |
| 2007/0015965 A1 | 1/2007 | Cox et al. |
| 2007/0038025 A1 | 2/2007 | Yoshida |
| 2007/0045504 A1 | 3/2007 | Wollschlager |
| 2007/0088367 A1 | 4/2007 | Von Weymarn-Scharli |
| 2007/0100414 A1 | 5/2007 | Licata et al. |
| 2007/0106302 A1 | 5/2007 | Ortiz |
| 2007/0118015 A1 | 5/2007 | Wendlandt |
| 2007/0219411 A1 | 9/2007 | Dejima et al. |
| 2007/0239252 A1 | 10/2007 | Hopkins et al. |
| 2007/0250149 A1 | 10/2007 | Oepen et al. |
| 2007/0260121 A1 | 11/2007 | Bakos et al. |
| 2008/0051635 A1 | 2/2008 | Tanaka et al. |
| 2008/0058722 A1 | 3/2008 | Oepen et al. |
| 2008/0091073 A1 | 4/2008 | Park |
| 2008/0103440 A1 | 5/2008 | Ferren et al. |
| 2008/0139887 A1 | 6/2008 | Fitzpatrick |
| 2008/0172037 A1 | 7/2008 | Huang et al. |
| 2008/0188928 A1 | 8/2008 | Salahich et al. |
| 2008/0200762 A1 | 8/2008 | Stokes et al. |
| 2008/0214893 A1 | 9/2008 | Tartaglia et al. |
| 2008/0234546 A1 | 9/2008 | Kawano et al. |
| 2008/0242928 A1 | 10/2008 | Kawano et al. |
| 2008/0262300 A1 | 10/2008 | Ewers et al. |
| 2008/0275299 A1 | 11/2008 | Park |
| 2009/0048483 A1 | 2/2009 | Yamamoto |
| 2009/0062611 A1 | 3/2009 | Toyama |
| 2009/0062837 A1 | 3/2009 | Gasche et al. |
| 2009/0112063 A1 | 4/2009 | Bakos et al. |
| 2009/0131752 A1 | 5/2009 | Park |
| 2009/0157068 A1 | 6/2009 | Kallel et al. |
| 2009/0187163 A1 | 7/2009 | Uihlein |
| 2009/0240202 A1 | 9/2009 | Drasler et al. |
| 2009/0259200 A1 | 10/2009 | Lampropoulos et al. |
| 2009/0264704 A1 | 10/2009 | Shtul |
| 2010/0010308 A1 | 1/2010 | Braun et al. |
| 2010/0010437 A1 | 1/2010 | Miles et al. |
| 2010/0016663 A1 | 1/2010 | Maisch et al. |
| 2010/0069712 A1 | 3/2010 | Yamaya |
| 2010/0069716 A1* | 3/2010 | Chin ............... A61B 1/0051 600/114 |
| 2010/0076451 A1 | 3/2010 | Zwolinski et al. |
| 2010/0087711 A1 | 4/2010 | Edwards |
| 2010/0137686 A1 | 6/2010 | Meron et al. |
| 2010/0145151 A1 | 6/2010 | Fukunaga et al. |
| 2010/0160735 A1 | 6/2010 | Bakos |
| 2010/0204546 A1 | 8/2010 | Hassidov et al. |
| 2010/0268025 A1 | 10/2010 | Belson |
| 2010/0331625 A1 | 12/2010 | Rosemurgy et al. |
| 2010/0331820 A1 | 12/2010 | Prisco et al. |
| 2011/0015729 A1 | 1/2011 | Jimenez et al. |
| 2011/0023888 A1* | 2/2011 | Vazales ............... A61B 1/00142 128/207.14 |
| 2011/0040282 A1 | 2/2011 | Uihlein |
| 2011/0046442 A1 | 2/2011 | Matsushita |
| 2011/0049282 A1 | 3/2011 | Danielsson |
| 2011/0054253 A1 | 3/2011 | Jordá Albiñana et al. |
| 2011/0237888 A1 | 9/2011 | Matsushita |
| 2011/0245611 A1 | 10/2011 | Yeh et al. |
| 2011/0282149 A1 | 11/2011 | Vargas et al. |
| 2011/0306950 A1 | 12/2011 | Cucin |
| 2011/0319714 A1 | 12/2011 | Roelle et al. |
| 2012/0022325 A1* | 1/2012 | Hastings ............... A61B 1/2676 600/104 |
| 2012/0022329 A1 | 1/2012 | Wagh et al. |
| 2012/0041291 A1 | 2/2012 | Ferren et al. |
| 2012/0108902 A1 | 5/2012 | Frassica et al. |
| 2012/0130173 A1 | 5/2012 | Lutze et al. |
| 2012/0143005 A1 | 6/2012 | Yeh et al. |
| 2012/0165607 A1 | 6/2012 | Ashida et al. |
| 2012/0165792 A1 | 6/2012 | Ortiz et al. |
| 2012/0172651 A1 | 7/2012 | Cutrer |
| 2012/0209062 A1 | 8/2012 | Qiao |
| 2012/0277528 A1 | 11/2012 | Qiao |

(56) References Cited

U.S. PATENT DOCUMENTS

| | | | |
|---|---|---|---|
| 2012/0277729 A1* | 11/2012 | Melsheimer | A61M 25/01 604/525 |
| 2013/0131641 A1 | 5/2013 | Jimenez et al. | |
| 2013/0190565 A1 | 7/2013 | Gora et al. | |
| 2013/0338440 A1 | 12/2013 | Sinai et al. | |
| 2014/0005683 A1 | 1/2014 | Stand et al. | |
| 2014/0081169 A1 | 3/2014 | Gerding et al. | |
| 2014/0088459 A1 | 3/2014 | Roush et al. | |
| 2014/0142393 A1 | 5/2014 | Piskun et al. | |
| 2014/0155702 A1 | 6/2014 | Tilson et al. | |
| 2014/0155783 A1 | 6/2014 | Starksen et al. | |
| 2014/0188054 A1 | 7/2014 | Iijima et al. | |
| 2014/0234600 A1 | 8/2014 | Wang et al. | |
| 2014/0243873 A1 | 8/2014 | Franklin | |
| 2014/0275860 A1 | 9/2014 | Rottenberg et al. | |
| 2014/0276601 A1 | 9/2014 | Edward | |
| 2014/0276642 A1 | 9/2014 | Cully et al. | |
| 2014/0343358 A1 | 11/2014 | Hameed et al. | |
| 2014/0371764 A1 | 12/2014 | Oyola et al. | |
| 2015/0018616 A1 | 1/2015 | Kumoyama | |
| 2015/0038919 A1 | 2/2015 | Bramwell et al. | |
| 2015/0073216 A1 | 3/2015 | Papay | |
| 2015/0073409 A1 | 3/2015 | Watson et al. | |
| 2015/0094656 A1 | 4/2015 | Salahieh et al. | |
| 2015/0119640 A1 | 4/2015 | Reydel | |
| 2015/0133729 A1 | 5/2015 | Reydel | |
| 2015/0148602 A1 | 5/2015 | Hill et al. | |
| 2015/0148606 A1 | 5/2015 | Rottenberg et al. | |
| 2015/0164314 A1 | 6/2015 | Peterson | |
| 2015/0216589 A1 | 8/2015 | Wittenberger et al. | |
| 2015/0342608 A1 | 12/2015 | Hernandez | |
| 2015/0369325 A1 | 12/2015 | Bureau et al. | |
| 2016/0007832 A1 | 1/2016 | Shimada | |
| 2016/0066773 A1 | 3/2016 | Cooper et al. | |
| 2016/0096004 A1 | 4/2016 | Gerrans et al. | |
| 2016/0129547 A1 | 5/2016 | Duescher et al. | |
| 2016/0136393 A1 | 5/2016 | Tsai et al. | |
| 2016/0174829 A1 | 6/2016 | Reydel | |
| 2016/0198935 A1 | 7/2016 | Choi et al. | |
| 2016/0270870 A1 | 9/2016 | Kowshik | |
| 2016/0287059 A1 | 10/2016 | Ha et al. | |
| 2016/0324412 A1 | 11/2016 | Hassidov et al. | |
| 2017/0035277 A1* | 2/2017 | Kucharski | A61B 1/012 |
| 2017/0156567 A1 | 6/2017 | Kaneko | |
| 2017/0157363 A1 | 6/2017 | Barrish et al. | |
| 2017/0360281 A1* | 12/2017 | Ponsky | A61B 1/018 |
| 2018/0015257 A1 | 1/2018 | Krolik et al. | |
| 2018/0064366 A1 | 3/2018 | Sweeney et al. | |
| 2018/0132705 A1* | 5/2018 | Higuchi | A61B 1/00059 |
| 2018/0184885 A1 | 7/2018 | St. George | |
| 2018/0249893 A1 | 9/2018 | Yeung et al. | |
| 2018/0263469 A1 | 9/2018 | Okaniwa et al. | |
| 2018/0264239 A1* | 9/2018 | Piskun | A61B 1/0051 |
| 2018/0289925 A1 | 10/2018 | Palmer et al. | |
| 2018/0326197 A1 | 11/2018 | McArthur et al. | |
| 2018/0361116 A1 | 12/2018 | Quick et al. | |
| 2019/0226447 A1 | 7/2019 | Stecher et al. | |
| 2020/0030575 A1 | 1/2020 | Bogusky et al. | |
| 2020/0178763 A1 | 6/2020 | Tilson et al. | |
| 2020/0315433 A1 | 10/2020 | Axon et al. | |
| 2020/0383677 A1 | 12/2020 | Piligian et al. | |
| 2021/0000505 A1 | 1/2021 | Lenker et al. | |
| 2021/0030260 A1 | 2/2021 | Julian et al. | |
| 2021/0045626 A1 | 2/2021 | Hsu et al. | |
| 2021/0114507 A1 | 4/2021 | Alexander et al. | |
| 2021/0137366 A1 | 5/2021 | Tilson et al. | |
| 2022/0000355 A1 | 1/2022 | Tilson et al. | |
| 2022/0104690 A1 | 4/2022 | Tilson et al. | |
| 2022/0323166 A1 | 10/2022 | Tilson et al. | |

FOREIGN PATENT DOCUMENTS

| | | |
|---|---|---|
| CN | 1706349 A | 12/2005 |
| CN | 1732855 A | 2/2006 |
| CN | 1806770 A | 7/2006 |
| CN | 1861011 A | 11/2006 |
| CN | 101119765 A | 2/2008 |
| CN | 101129255 A | 2/2008 |
| CN | 102137628 A | 7/2011 |
| CN | 201899767 U | 7/2011 |
| CN | 102711585 A | 10/2012 |
| CN | 102872519 A | 1/2013 |
| CN | 103384500 A | 11/2013 |
| CN | 104168860 A | 11/2014 |
| CN | 104287684 B | 3/2016 |
| CN | 105759418 A | 7/2016 |
| CN | 105832279 A | 8/2016 |
| CN | 106137397 A | 11/2016 |
| CN | 106455929 A | 2/2017 |
| CN | 106488744 A | 3/2017 |
| CN | 106659367 A | 5/2017 |
| CN | 107296584 A | 10/2017 |
| DE | 102005039601 A1 | 2/2007 |
| EP | 401129 A1 | 12/1990 |
| EP | 0941743 A2 | 9/1999 |
| EP | 1662972 A2 | 6/2006 |
| EP | 1695657 A1 | 8/2006 |
| EP | 1487318 B1 | 3/2008 |
| EP | 2016914 A2 | 1/2009 |
| EP | 1499227 B1 | 10/2010 |
| EP | 2258322 A2 | 12/2010 |
| EP | 2364637 A1 | 9/2011 |
| EP | 2368481 A1 | 9/2011 |
| EP | 2368483 A1 | 9/2011 |
| EP | 3256052 A1 | 12/2017 |
| GB | 2482355 A | 10/2010 |
| GB | 2497544 A | 6/2013 |
| JP | H05293077 A | 11/1993 |
| JP | 2002125921 A | 5/2002 |
| JP | 2005152300 A | 6/2005 |
| JP | 03965108 B2 | 8/2007 |
| JP | 2009507617 A | 2/2009 |
| JP | 2009061173 A | 3/2009 |
| JP | 2011194126 A | 10/2011 |
| JP | 2013176465 A | 9/2013 |
| JP | 2014124475 A | 7/2014 |
| KR | 10-2015-0131502 A | 11/2015 |
| WO | WO97/43941 A1 | 11/1997 |
| WO | WO99/053827 A1 | 10/1999 |
| WO | WO03/013348 A1 | 2/2003 |
| WO | WO2007/035931 A2 | 3/2007 |
| WO | WO2008/041809 A1 | 4/2008 |
| WO | WO2008/122997 A1 | 10/2008 |
| WO | WO2011/018147 A1 | 2/2011 |
| WO | WO2011/018157 A1 | 2/2011 |
| WO | WO2011/148172 A2 | 12/2011 |
| WO | WO2012/054480 A2 | 4/2012 |
| WO | WO2012/080947 A1 | 6/2012 |
| WO | WO2012/122288 A2 | 9/2012 |
| WO | WO2017/041052 A1 | 3/2017 |
| WO | WO2018/035452 A1 | 8/2017 |
| WO | WO2019/054867 A1 | 3/2019 |
| WO | WO2020/018934 A1 | 1/2020 |
| WO | WO-2020018934 A1 * | 1/2020 ........ A61M 25/005 |
| WO | WO2020/214221 A1 | 10/2020 |
| WO | WO2020/237426 A1 | 12/2020 |
| WO | WO2021/202336 A1 | 10/2021 |
| WO | WO2021/242884 A1 | 12/2021 |
| WO | WO2022/051682 A1 | 3/2022 |
| WO | WO2022/159861 A1 | 7/2022 |
| WO | WO2022/165302 A8 | 8/2022 |
| WO | WO2022/192515 A1 | 9/2022 |

OTHER PUBLICATIONS

Filip et al.; Design, Implementation, and Testing of a miniature self-stabilizing capsule endoscope with wireless image transmission capabilities; Intl. Journal "Information Technologies & Knowledge", 5(1); downloaded from http://www.foibg.com/ijitk/ijitk-vol05/ijitk05-1-p01.pdf on Jul. 28, 2016; (the year of publication is sufficiently earlier than the effective U.S. filing date and any foreign

(56) References Cited

OTHER PUBLICATIONS priority date so that the particular month of publication is not in issue) 2011.

Loeve et al.; Endoscope Shaft-Rigidity Control Mechanism: "Forguide" IEEE Trans. On Biomed. Eng.; 59(2); pp. 542-551; Feb. 2012.

Loeve et al.; Vacuum packed particles as flexible endoscope guides with controllable rigidity; Granular Matter; 12(6); pp. 543-554; Jun. 24, 2010.

Shah et al.; Magnetic Imaging of Colonoscopy: An Audit of Looping, Accuracy and Ancillary maneuvers; Gastrointest. Endosc.; 52(1); pp. 1-8; Jul. 1, 2000.

Simi et al.; Design, Fabrication, and Testing of a Capsule With Hybrid Locomotion for Gastrointestinal Tract Exploration; IEEE/ASME Trans on Mechatronics; 15(2); pp. 170-x; Apr. 2010.

Valdastri et al.; Advanced Technologies for Gastrointestinal Endoscopy; Annu. Rev. Biomed. Eng.; 14; pp. 397-429; May 2012.

Zhao et al.; Development of a variable stiffness over tube based on low-melting-point-alloy for endoscopic surgery; J. Med. Devices; 10(2); 8 pages; May 12, 2016.

Tilson et al.; U.S. Appl. No. 17/903,879 entitled "Rigidizing devices," filed Sep. 6, 2022.

Tilson et al.; U.S. Appl. No. 17/902,770 entitled "Nested rigidizing devices," filed Sep. 2, 2022.

Lopez et al.; U.S. Appl. No. 17/995,294 entitled "Layered walls for rigidizing devices," filed Sep. 30, 2022.

Dow, Dow white paper: Can you estimate modulus from durometer hardness for silicones: Yes, but you only roughly and you must choose your modulus carefully!; 5 pages; retrieved from the internet (https://www.dow.com/content/dam/doc/documents/en-us/tech-art/11/11-37/11-3716-01-durometer-hardness-for-silicones.pdf) on Jan. 18, 2023.

Scheeff et al.; U.S. Appl. No. 18/000,062 entitled "Rigidizing devices," filed Nov. 28, 2022.

* cited by examiner

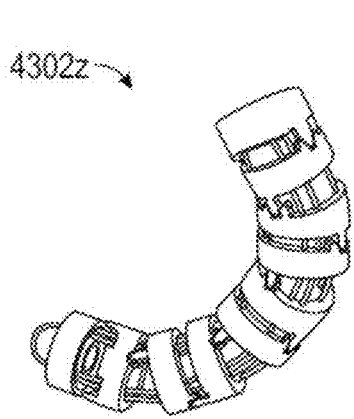
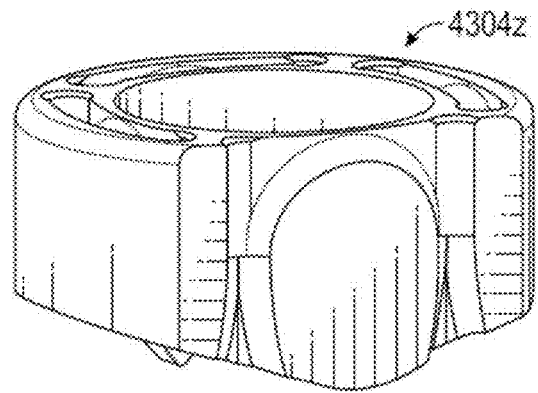
FIG. 9A  FIG. 9B
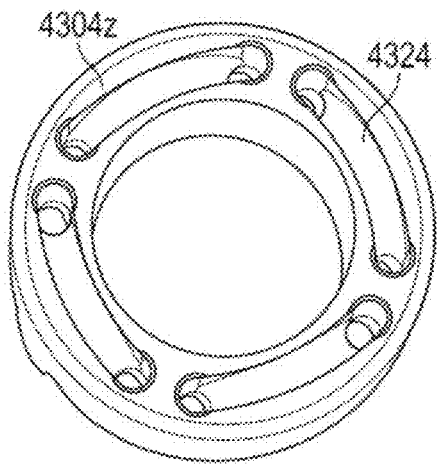
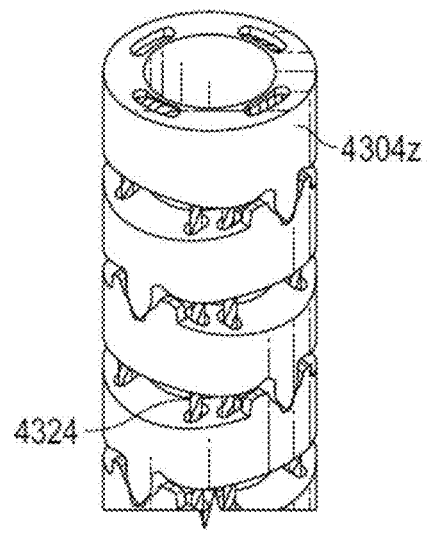
FIG. 9C
FIG. 9D
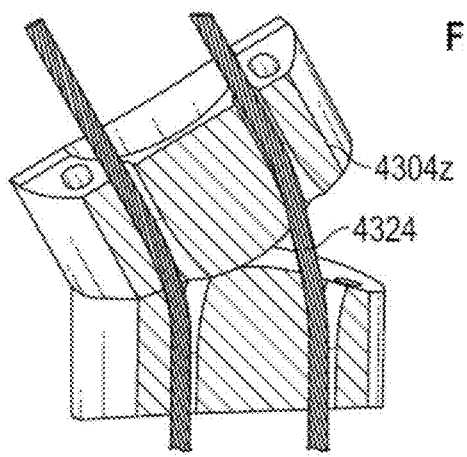
FIG. 9E

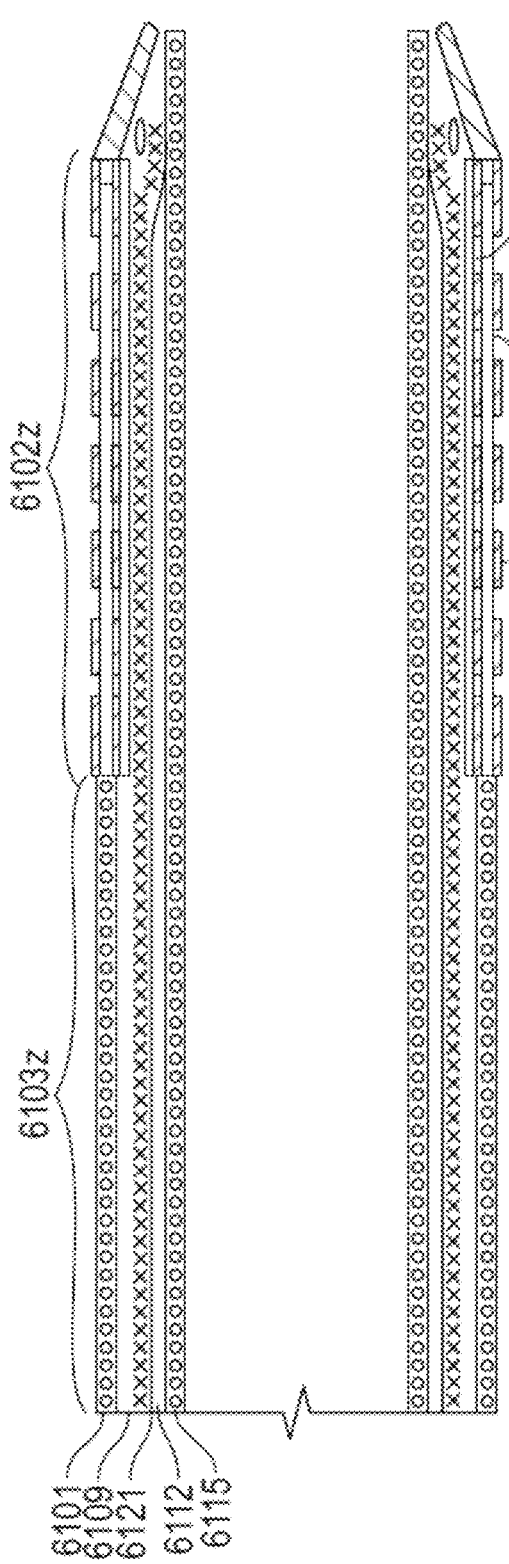
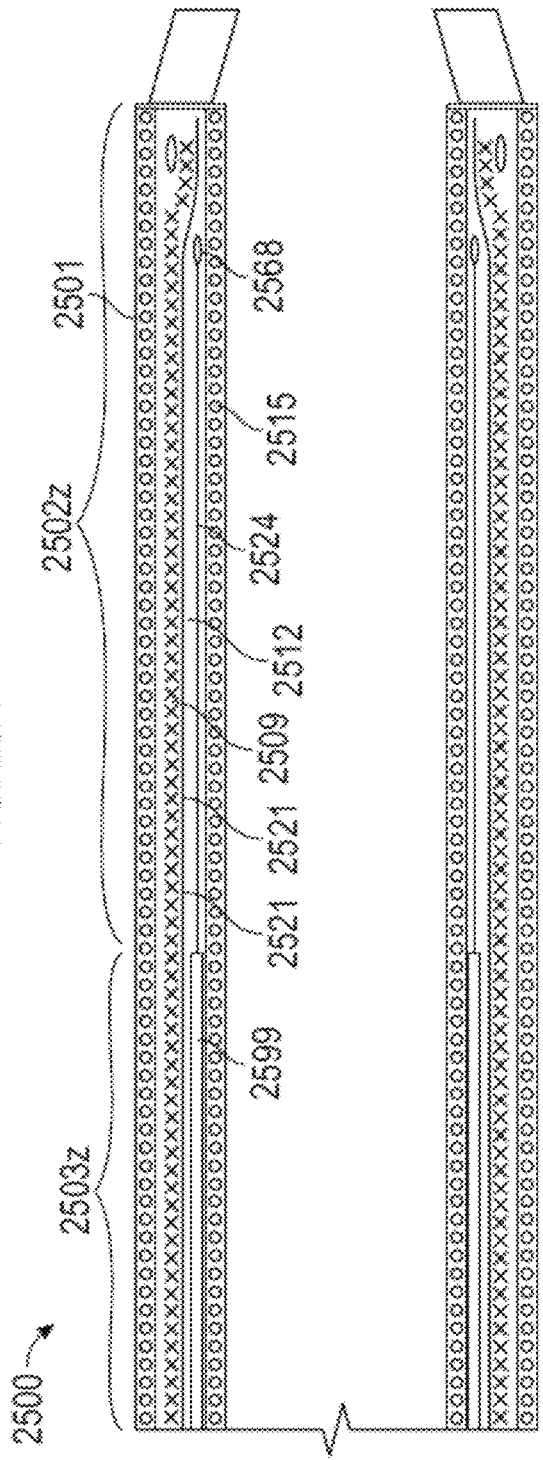

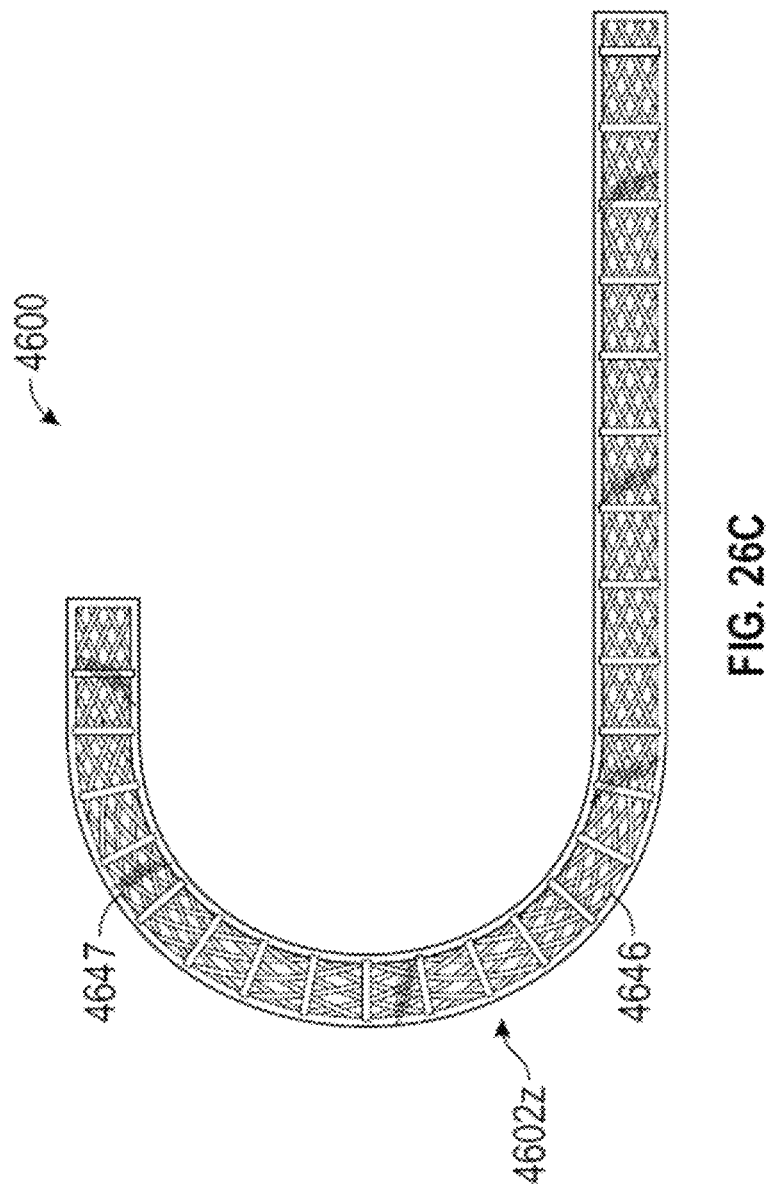

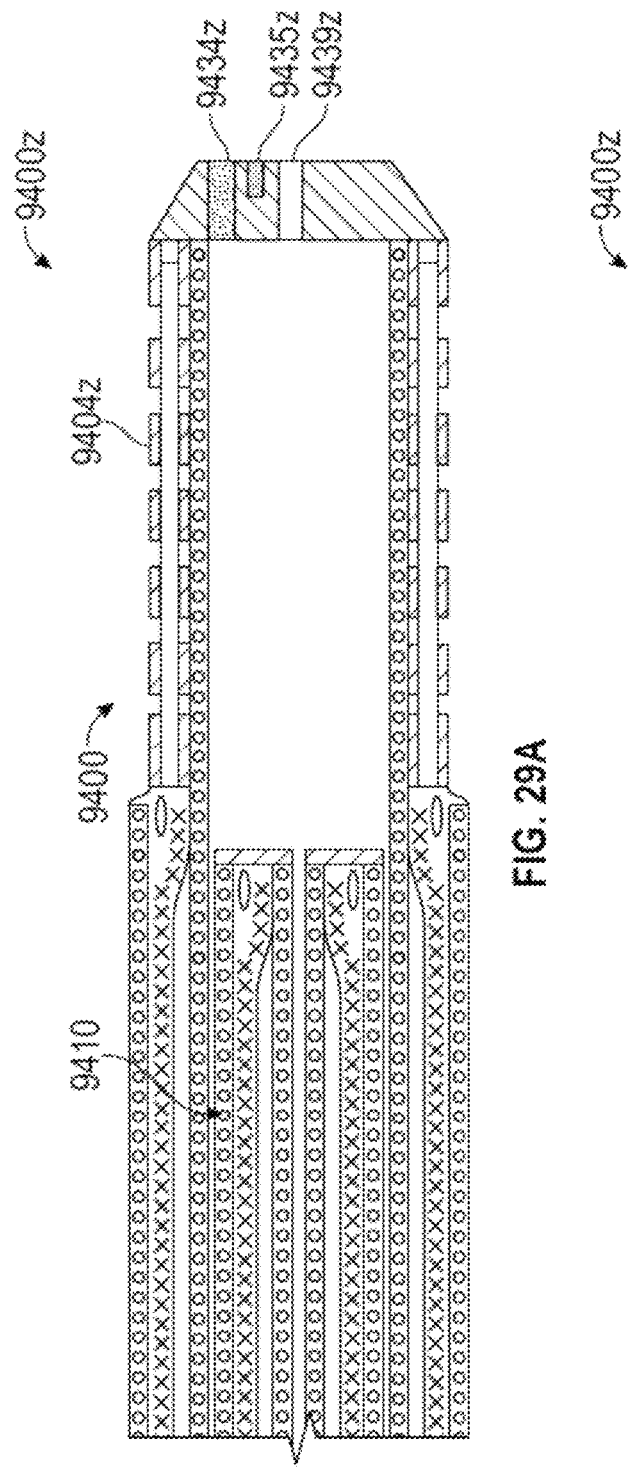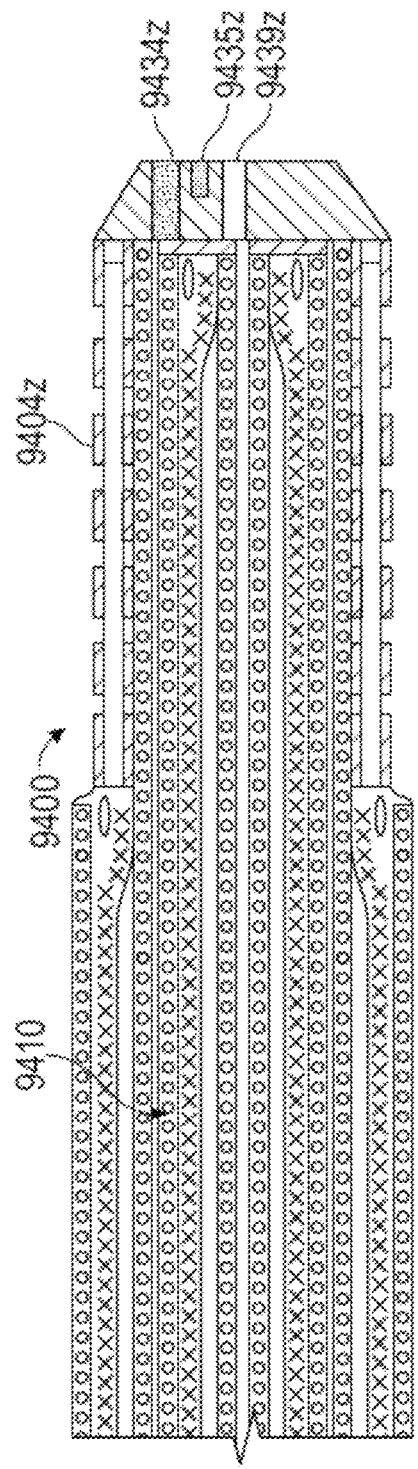
FIG. 29A
FIG. 29B

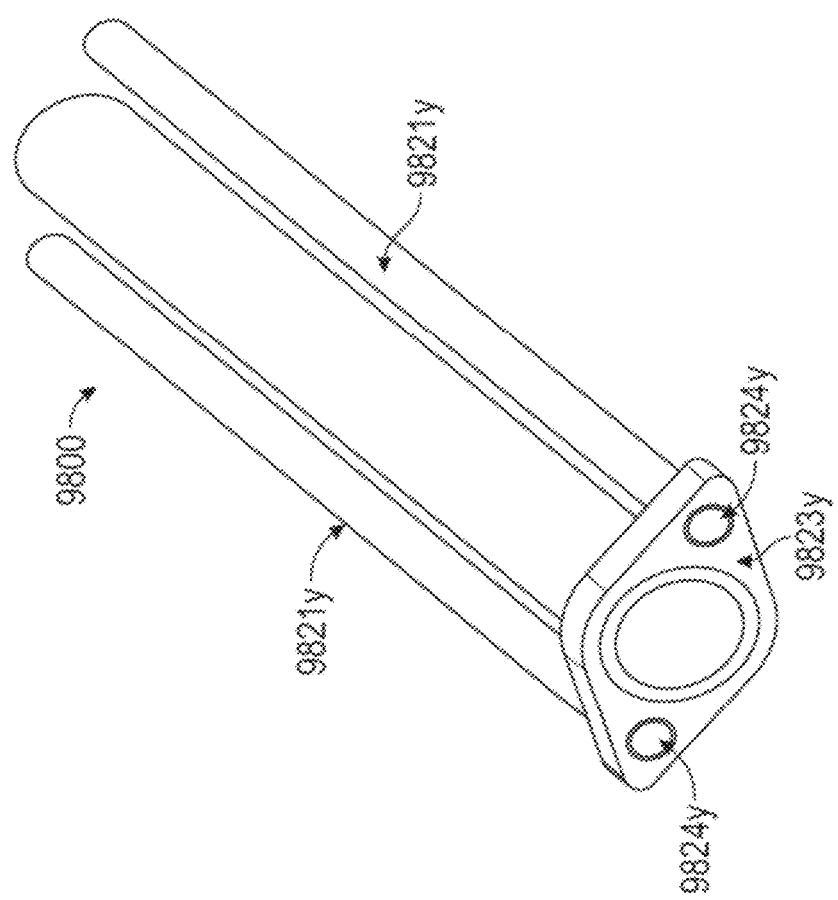
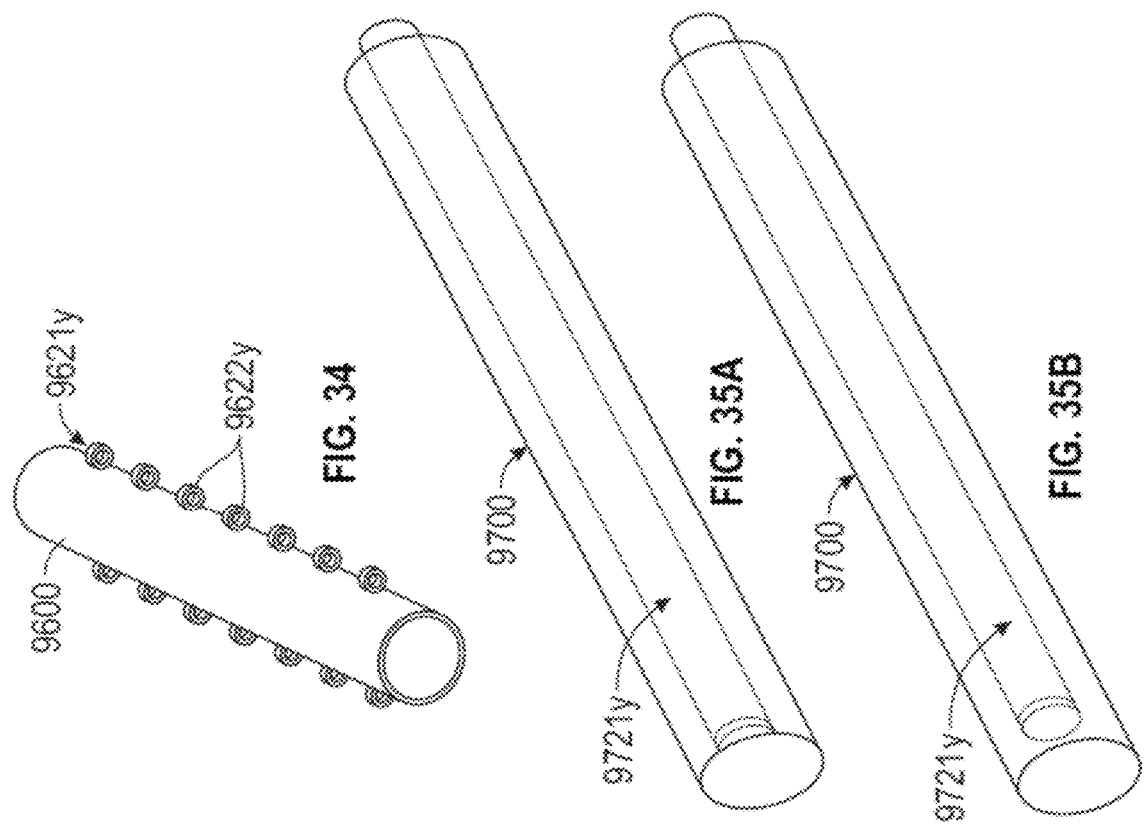

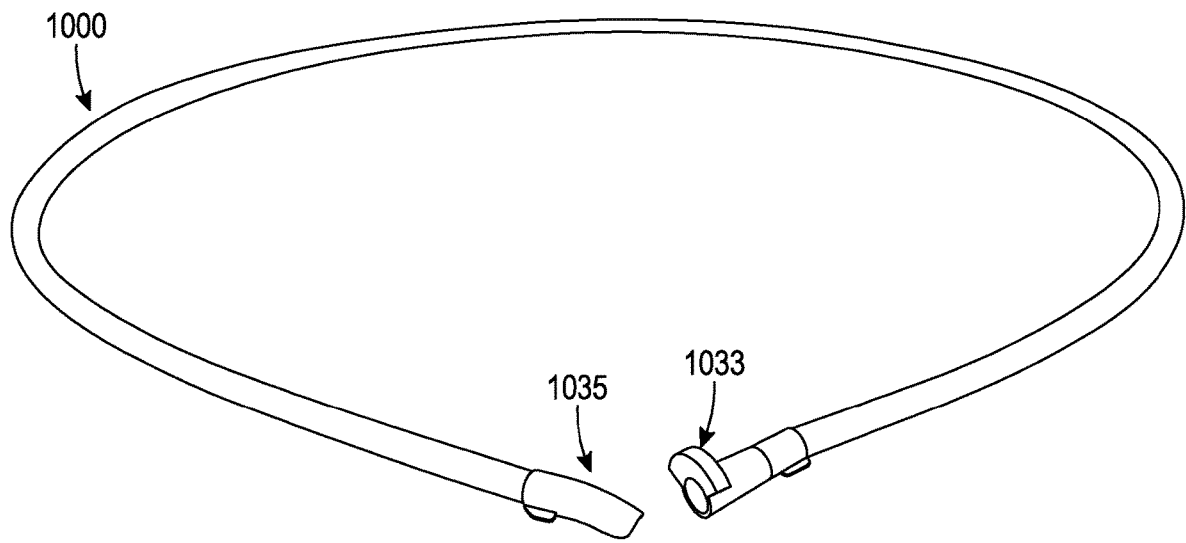
FIG. 85A
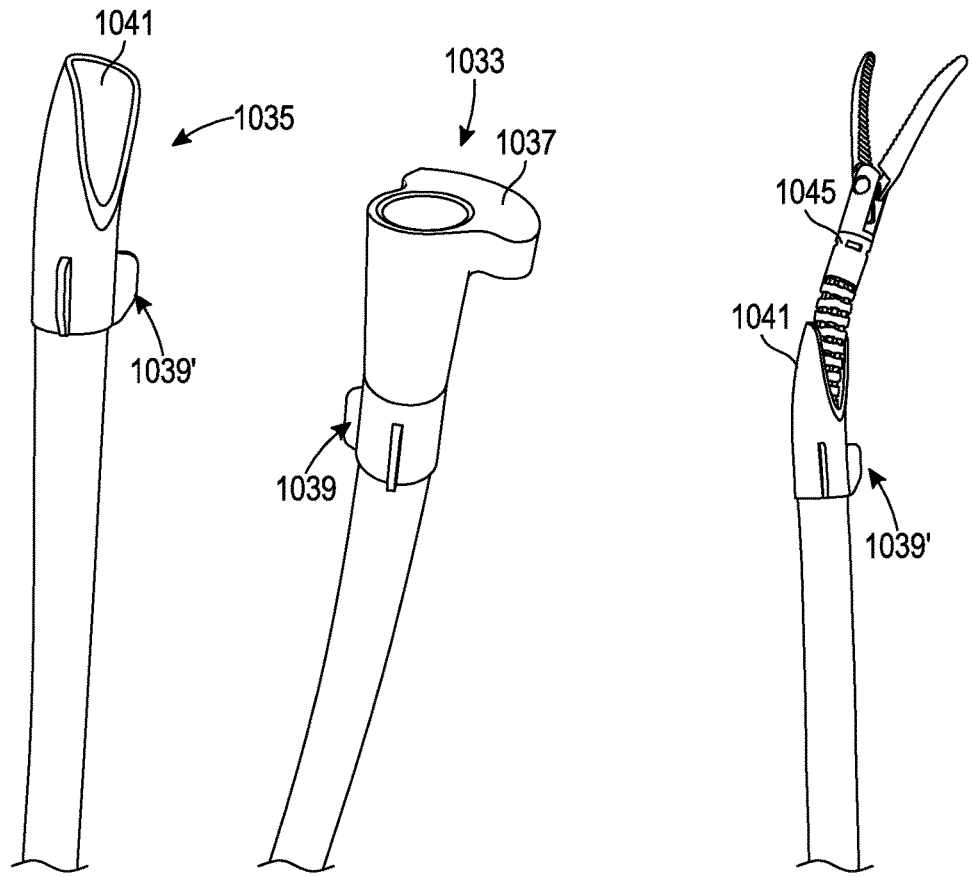
FIG. 85B  FIG. 85C

EXTERNAL WORKING CHANNELS

CROSS REFERENCE TO RELATED APPLICATIONS

This application claims priority as a continuation-in-part to U.S. patent application Ser. No. 17/604,203, titled "DYNAMICALLY RIGIDIZING COMPOSITE MEDICAL STRUCTURES," filed on Oct. 15, 2021, which is a U.S. National Stage Entry of International Patent Application No. PCT/US2020/013937, titled "DYNAMICALLY RIGIDIZING COMPOSITE MEDICAL STRUCTURES," filed Jan. 16, 2020, which claims priority to U.S. Patent Provisional Application No. 62/835,101, filed on Apr. 17, 2019, titled "DYNAMICALLY RIGIDIZING COMPOSITE MEDICAL STRUCTURES," and U.S. Patent Provisional Application No. 62/854,199, filed on May 29, 2019, titled "DYNAMICALLY RIGIDIZING COMPOSITE MEDICAL STRUCTURES," which is herein incorporated by reference in its entirety.

This application also claims priority as a continuation-in-part to International Patent Application No. PCT/US2021/034292, titled "RIGIDIZING DEVICES," filed on May 26, 2021, which claims priority to U.S. Provisional Patent Application No. 63/030,252, filed on May 26, 2020, titled "RIGIDIZING DEVICES," to U.S. Provisional Patent Application No. 63/128,769, filed on Dec. 21, 2020, titled "RIGIDIZING DEVICES," and to U.S. Provisional Patent Application No. 63/165,721, filed on Mar. 24, 2021, titled "RIGIDIZING DEVICES", which is herein incorporated by reference in its entirety.

This application also claims priority to U.S. Provisional Patent Application No. 63/342,618, titled "EXTERNAL WORKING CHANNELS FOR ENDOSCOPIC DEVICES," filed on May 16, 2022, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

During medical procedures, a medical device can provide access to the anatomy through one or more lumen formed within the medical device. When these lumens are found in endoscopic devices (typically rigid or flexible, 'endoscopes' or 'scopes'), they are typically referred to as 'working channels'. Working channels are an important part of an endoscope: a working channel can be used to insert a tool through the endoscope's proximal end, have it travel through the lumen through the body of the endoscope (and through the patient's anatomy), and emerge at the distal end of the endoscope, at the patient's target location. As a tool emerges from the endoscope, it can be used for a many different clinically relevant actions, including, for example: biopsy, grasping, manipulating, cutting, snaring, suturing, spraying, suctioning, clipping, or applying a treatment to tissue, that can include heat, cold, energy, RF, or radiation.

However, a lumen formed within the device will increase the dimensions (e.g., diameter, as most endoscopes have a circular cross-section) of the device. An increase in diameter may result in an increase in bending stiffness and a decrease in the flexibility of the device. Because the bending stiffness of a device scales exponentially with its diameter, even a small increase in the diameter of a device can lead to highly significant (and typically undesirable) decrease in device stiffness, which can have a highly deleterious effect as the flexible device attempts to navigate through highly tortuous anatomy. Therefore, most endoscopes have small diameter working channels, and a small number of working channels (typically only one).

In general, there is a need for increased working channel diameters and/or an increase in the number of working channels. Increased working channel diameters enable larger tools, which can be more complex, stronger, easier to build, and can have increased clinical utility. Larger tools for suctioning and spraying can simply accomplish more, faster. As endoscopic procedures become more advanced, the use of multiple working channels may be particularly beneficial. Whereas most endoscopes have a single working channel, and some have two, there could be high clinical utility to have three, four, five, or even more working channels.

As endoscopes are used for increasingly complex procedures, there is also a need for a working channel that can be moved or actuated relative to the endoscope. A working channel that could be moved independently from the endoscope, including by being incorporated into a separate device (for example, an overtube) would allow additional levels of kinematic control: for example, independent axial control, the ability to be positioned in different radial positions, and the ability to remain stable while the bending section of the endoscope is angulated.

It may also be advantageous to be able to deploy multiple tools (including large diameter tools) through working channels, without disturbing the shape of the endoscope and how it is positioned in the anatomy. This may be particularly helpful in devices (e.g., endoscopes) that may be selectively rigidized during use. These apparatuses may be referred to has dynamically rigidizing devices.

Thus, there is a need for apparatuses and methods that can effectively address these needs.

SUMMARY OF THE DISCLOSURE

In general, in one embodiment, a rigidizing system includes an elongate rigidizing device configured to be rigidized by vacuum or pressure from a flexible configuration to a rigid configuration and an outer tube configured to be positioned around the rigidizing device. The outer tube includes a plurality of expandable channels therein configured to enable passage of a working tool therethrough.

This and other embodiments can include one or more of the following features. The rigidizing system can further include at least one guide configured to be removably inserted into a channel of the plurality of expandable channels. The at least one guide can include a lumen configured to enable passage of the working tool therethrough. The channel can be configured to expand as the at least one guide is inserted therethrough. The channel can be configured to collapse as the at least one guide is removed. The at least one guide can include an atraumatic distal end. The lumen can be configured to point radially inwards towards the elongate rigidizing device when the at least one guide is positioned within the channel. The lumen can include a bend of 30°-60° at a distal end thereof to point the lumen radially inwards. The at least one guide can include an asymmetric cross-section configured to enable rotational alignment of the at least one guide relative to the elongate rigidizing device. The at least one guide can include an angled or curved surface configured to substantially conform to the outer circumference of the elongate rigidizing device. The at least one guide can have a higher stiffness than the rigidizing device in the flexible configuration and a lower stiffness than the rigidizing device in the rigid configuration. A ratio of an outer diameter of the elongate rigidizing device and the inner diameter of each of the expandable channels of the plurality of channels can be 1:1 to 6:1. The outer tube can be a sleeve having a wall thickness of less than 0.03 inches. The outer tube can include an elastomeric, plastic, or cloth structure. The outer tube can be permanently attached to the elongate rigidizing device. Each channel can include a proximal marker thereon configured to indicate a distal circumferential position of the working tool relative to the rigidizing device when the working tool is inserted into the channel. The elongate rigidizing device can be configured to rigidized by supplying vacuum or pressure within a wall of the elongate rigidizing device. The wall can include a braid layer. The working tool can have a higher stiffness than the rigidizing device in the flexible configuration and a lower stiffness than the rigidizing device in the rigid configuration. The elongate rigidizing device can be part of an overtube, and the overtube can be configured to pass a scope therethrough.

In general, in one embodiment, a method of positioning a working tool within a body lumen includes inserting a rigidizing device and an outer tube having a plurality of expandable channels therein into a body lumen while the rigidizing device in in a flexible configuration, supplying vacuum or pressure to the rigidizing device to transition the rigidizing device from the flexible configuration to a rigid configuration, inserting a working tool through a channel of the expandable channels while the rigidizing device is in the rigid configuration, and performing a medical procedure in the body lumen with the working tool.

This and other embodiments can include one or more of the following features. The method can further include inserting a guide through the channel of the plurality of expandable channels while the rigidizing device is in the rigid configuration and prior to inserting the working tool. The method can further include removing the working tool from the guide and removing the guide from the channel. Removing the guide from the channel can cause the channel to collapse radially inwards. A shape of the rigidizing device in the rigid configuration can remain fixed during the step of inserting the guide. The guide can be asymmetric. The step of inserting the guide can include inserting the guide such that an angled or curved surface substantially conforms to an outer circumference of the rigidizing device. The step of inserting the working tool can include inserting the working tool such that the working tool extends through a preset bend in a lumen of the guide and points towards a central axis of the rigidizing device. Inserting the guide through the channel can cause the channel to expand radially outwards from a collapsed configuration to an expanded configuration. The at least one guide can have a higher stiffness than the rigidizing device in the flexible configuration and a lower stiffness than the rigidizing device in the rigid configuration. The step of supplying vacuum or pressure to the rigidizing device can include supplying vacuum or pressure to a wall of the rigidizing device. The step of performing a medical procedure can be performed while the rigidizing device is in the rigid configuration. The working tool can have a higher stiffness than the rigidizing device in the flexible configuration and a lower stiffness than the rigidizing device in the rigid configuration. The method can further include passing a scope through the rigidizing device while the rigidizing device is in a rigidized configuration. A shape of the rigidizing device in the rigid configuration can remain fixed during the step of inserting the working tool. The method can further include selecting the channel of the plurality of channels prior to inserting the guide. Selecting the channel can include selecting based upon a proximal marker indicating a distal circumferential position of the channel.

In general, in one embodiment, a rigidizing system includes an elongate rigidizing device configured to be rigidized by vacuum or pressure and a plurality of rails extending longitudinally along a length of the rigidizing device. Each of the rails is configured to slideably engage with an elongate tubular guide.

This and other embodiments can include one or more of the following features. When an elongate tubular guide is engaged with a rail of the plurality of rails, the elongate tubular guide can be parallel to the elongate rigidizing device. Each of the plurality of rails can be a T-shaped rail. The rigidizing device can further include a tubular guide. The tubular guide can include a T-shaped slot therein configured to engage with a rail of the plurality of rails. The plurality of rails can include a male extension. The rigidizing device can further include a tubular guide, where the tubular guide includes a female slot therein configured to engage with a rail of the plurality of rails. The plurality of rails can include a female slot therein. The rigidizing device can further include a tubular guide, where the tubular guide includes a male extension thereon configured to engage with a rail of the plurality of rails. One or more of the plurality of rails can be serrated. The plurality of rails can be positioned equidistant around a circumference of the rigidizing device.

In general, in one embodiment, a rigidizing system includes a first rigidizing device, a second rigidizing device positioned radially within the first rigidizing device, and a plurality of tool channels extending longitudinally along an exterior of the first rigidizing device. The second rigidizing device is axially slideable relative to the first rigidizing device. The first and second rigidizing devices are configured to be alternately rigidized by vacuum or pressure.

This and other embodiments can include one or more of the following features. The plurality of tool channels can be positioned substantially adjacent to one another. The plurality of tool channels can be positioned only along less than 120 degrees of a circumference of the first rigidizing device. The plurality of tool channels can be configured to move around a circumference of the rigidizing device after insertion of the rigidizing system into a body lumen. At least one tool channel can be configured to hold an articulating camera therein. The plurality of tool channels can have notches therein for increased flexibility. The rigidizing system can further include an outer sheath around the outside of the first rigidizing device and the plurality of tool channels and a vacuum inlet between the outer sheath and the first rigidizing device. The inlet can be configured to provide vacuum to suction the outer sheath against the tool channels. The plurality of tool channels can include spiral-cut tubing or a coil. The rigidizing system can further include a fitting configured to slideably move along the first rigidizing device. The plurality of tool channels can be attached to the fitting. The rigidizing system can further include a plurality of cables configured, when pulled proximally, to move the fitting distally. The plurality of tool channels can be an integral part of an outer tube configured to slide over the first rigidizing device. The outer tube can include flexures therealong. The outer tube can include a longitudinal slit to enable snapping of the outer tube over the first rigidizing device. An inner wall or an outer wall of the outer tube can be configured to rigidize via the application of pressure or vacuum.

In general, in one embodiment, a rigidizing device includes an elongate flexible tube having a tubular wall having a proximal section and a distal section, a braid layer extending within the proximal section, a plurality of linkages extending within the distal section, a plurality of cables extending through or parallel to the proximal section and the distal section attached to the linkages for steering of the distal section, and a clamping mechanism at a junction between the proximal section and the distal section. The clamping mechanism includes a plurality of clamp engagers positioned around the plurality of cables. Supplying vacuum or pressure to the tubular wall rigidizes the braid layer to transition the proximal section from a flexible configuration to a rigid configuration and activates the clamping mechanism to lock a shape of the distal section.

This and other embodiments can include one or more of the following features. A distal portion of each of the cables of the plurality of cables can include a plurality of cable engagers configured to engage with the clamp engagers. The clamp engagers can be female engagers, and the plurality of cable engagers can be male engagers. The rigidizing device can further include an outer layer extending over the braid layer and the plurality of linkages. The clamping mechanism can further include a clamp bladder configured to press against the clamp engagers when vacuum or pressure can be supplied to the tubular wall.

In general, in one embodiment, a rigidizing device includes an elongate flexible tube having a tubular wall having a proximal section and a distal section, a braid layer extending within the proximal section, a plurality of linkages extending within the distal section, a plurality of steering cables extending through proximal section and the distal section attached to the linkages for steering of the distal section, a plurality of locking cables extending through the distal section, and a clamping mechanism at a junction between the proximal section and the distal section including a plurality of clamp engagers positioned around the plurality of locking cables. Supplying vacuum or pressure to the tubular wall rigidizes the braid layer to transition the proximal section from a flexible configuration to a rigid configuration and activates the clamping mechanism to lock a shape of the distal section.

This and other embodiments can include one or more of the following features. A distal portion of each of the cables of the plurality of locking cables can include a plurality of cable engagers configured to engage with the clamp engagers.

In general, in one embodiment, a rigidizing device includes an elongate flexible tube having a tubular wall including a proximal section and a distal section, a plurality of linkages extending within the distal section, a plurality of channels extending through or parallel to the linkages, and a plurality of pressure lines extending through a channel of the plurality of channels. Each of the plurality of pressure lines is configured to inflate against the plurality of linkages to transition the distal section from a flexible configuration to a rigid configuration.

This and any other embodiments can include one or more of the following features. The rigidizing device can further include a plurality of support members extending through a channel of the plurality of channels. Inflation of a pressure line within a channel can urge the support member against the plurality of linkages. Each of the channels can include engaging elements on an interior circumference thereof. Each of the support elements can include mating engaging elements around an exterior thereof configured to engage upon application of pressure from the pressure line. Each of the support members can include a wire. The rigidizing device can further include a plurality of cables extending through or parallel to the proximal section and the distal section and attached to the plurality of linkages for steering of the distal section. Each pressure line of the plurality of pressure lines can have a diameter of less than 0.060". The distal section can be configured to form a bend with a radius of curvature of less than 1". The plurality of pressure lines can be configured to support a pressure of greater than 5 atm. Each of the pressure lines can have a circumference in the flexible configuration that is smaller than a circumference in the rigid configuration. Each of the pressure lines can include a compliant material. Each of the pressure lines can have a circumference in the flexible configuration that is greater than a circumference in the rigid configuration. Each of the pressure lines can include a non-compliant material. The proximal section can include a braid layer extending within the proximal section. Supplying vacuum or pressure to the tubular wall can rigidize the braid layer to transition the proximal section from a flexible configuration to a rigid configuration. The pressure line can include a braid layer therearound.

In general, described herein are apparatuses (e.g., instruments, tools, devices, systems, etc.) and methods that may provide access to one or more tools to a remote site in the body. In particular, described herein are working channel sleeve apparatuses (device, system, etc.) that may include an inner tube (tubular region) configured to fit over an elongate medical device, and one or more (e.g., a plurality of) external working channels along the length of the internal tube. Any of these working channel sleeve apparatuses may also be referred to equivalently as working channel sleeves or the like. Any of these working channel sleeves may include expandable working channels. These working channels may be constructed of a material that is may be one or more of the following: extensible, deflectable, elastic and/or lubricous. In some examples the material is a fabric material, including knitted, braided, and/or woven materials. In some examples, the material may be sewn or bonded. In some examples, the material comprises one or more laminated sheets of material. The material forming the working channels and elongate tubular body of the working channel sleeve(s) may be formed of one or more filaments, fibers, or wires.

These materials may be knitted, braided, woven or laminated. In some examples the material is formed of elements that do not cross. The materials may be precisely oriented, or they may be of a comparatively random orientation. In some examples, the working channels may be expandable working channels and may be formed as part a tubular device and may be coupled to an outer surface of an elongate medical device, such as an overtube or an endoscope.

In particular, described herein are braided, knitted or woven (and in particular knitted) working channel sleeves. The knitted working channel sleeves described herein may be similar to and may improve on the layflat working channels described in international (e.g., PCT) patent application number WO2021242884A1, herein incorporated by reference in its entirety.

For example, the working channel sleeves described herein include a central tube (e.g., a sleeve, sock, or cover portion) that may be formed of an elastic and/or lubricious material. One or more external working channels may be formed on (e.g., woven into) the central tube so that the entire working channel sleeve may be worn over and/or affixed to an elongate medical device, including a highly flexible medical device. In some examples the medical device may be part of the same system as the working channel sleeve. In some cases the working channel sleeve may be permanently or semi-permanently, or removably attached to the elongate medical device.

As mentioned, either or both the elongate tubular body and the external working channels may be formed of a filament or filaments (or bundle of filament) that are knitted, woven or braided. Thus, the external and expandable working channels described herein may be knitted, braided, woven, or laminated, and may be manufactured from multiple parts that are assembled together, or they may come off a piece of automated and computer-controlled equipment in substantially complete form.

The working channel sleeves described herein may be attached, mounted, or otherwise combined with an elongate medical device (e.g., catheter, endoscope, overtube, etc.). The tubular body may be attached to the outer surface of the elongate medical device, either at discrete locations along the length of the elongate medical device, e.g., the distal end region and the proximal end region, every 1 mm (or every 2 mm, or every 3 mm, or every 4 mm, every 5 mm, ever 10 mm, every 15 mm, every 20 mm, etc.), or continuously along the entire length of the inner tube (tubular body).

In some examples the external working channels described herein may be configured to easily allow the relative sliding of adjacent devices, materials, and anatomy. In some examples, the working channel sleeve apparatuses herein may be configured to allow the precise termination of exits from the working channel(s). For example, the working channels described herein may be configured to direct one or more apparatuses leaving the working channel in a predefined direction (e.g., radially inward, radially outward, etc.). Any of the apparatuses described herein may be configured so that a device may be easily inserted into the working channel proximally.

In any of the working channel sleeve apparatuses described herein the one or more external working channels may be internally configured to allow a tool to enter the working channel from a small aperture, including through a small incision or orifice. In some examples, the external working channel may be configured to have a small initial profile, and only expand as-needed. In any of the working channel sleeve apparatuses descried herein the external working channels may be pre-installed as part of the device. Alternatively, the working channel sleeve may be attached or installed by the user onto the endoscope or other elongate member. The working channels may be configured to be lubricious and elastic and may therefore be configured to allow easier sliding of tools within the working channel(s). As tortuosity increases, capstan drag equations typically dictate exponential decay in device performance, the elastic and lubricous working channels described herein may allow tools inserted into the working channel(s) to slide with the lowest possible drag. Similarly, the capstan drag equation may dictate the ease of endoscope sliding relative to anatomy, and the elastic and lubricous working channels described herein may be configured to provide the lowest possible drag relative to a patient's anatomy.

The working channel sleeves, including either or both the tubular body and/or the external working channels described herein formed of an elastic and lubricous material may be used with an endoscope. In general, the methods and apparatuses described herein may be used with endoscopes adapted for use across a wide range of endoscopic procedures, including colonoscopy, enteroscopy, esophagogastroduodenoscopy (EGD), enteroscopy, endoscopic retrograde cholangiopancreatography (ERCP), interventional endoscopy procedures (including ESD (Endoscopic Submucosal Dissection) and EMR (Endoscopic Mucosal Resection)), robotic flexible endoscopy, trans-oral robotic surgery (TORS), altered anatomy cases (including Roux-en-Y), and during NOTES (Natural Orifice Transluminal Endoscopic Surgery) procedures. Any of the methods and apparatuses described herein may be configured for use with endoscopes for both manual and/or robotically operated configurations.

As the device moves through the anatomy, it may be configured in a highly tortuous pathway, and it may be torqued or manipulated. It could be advantageous to configure the working channel sleeve apparatus such that the working channels descried herein are expandable and configured to prevent kinking, wrinkling, buckling, on either the inner diameter (i.d.) and/or outer diameter (o.d.). In some instances, the prevention of kinking, wrinkling and buckling could be advantageous to the passage of devices within the channels. In some examples these external working channels may be formed of a material that is both lubricous (e.g., slippery) and elastic (e.g., stretchy). This configuration may be advantageous for the easiest insertion, passage, sliding, and manipulation of a medical tool.

In some examples, a tool may be inserted directly through an external working channel (e.g., an expandable working channel) of a working channel sleeve.

In some examples, a liner insert tube ('liner') may be utilized in a working channel of a working channel sleeve. In some examples, the working channel(s) is/are expandable working channels that are configured to be used with a liner insert tube that maintains the patency of a channel or lumen through the external working channel. The liner insert tube may be coupled at a proximal end region of the device and to a distal end region of the device. The liner insert tube may be an enclosed tube or an open channel. The liner insert tube may be inserted into an external working channel of a working channel sleeve after an elongate medical device onto which the working channel sleeve is applied (e.g., worn, attached, etc.) has been positioned at or near a target region within the body.

The liner insert tube may be configured to be inserted into an external working channel to form a continuous and open inner channel through the elastic external working channel. The liner insert tube may be registered with the external working channel, e.g., using one or more wings, and/or engaging (e.g., locking) to the distal end region and/or proximal end region of the elongate medical device and/or tube. Precise attachment at the distal end enables precise movement of the tools that are used within the liner. The precise diameter of the liner tool assists in more precise movement of a tool through its lumen. The utilization of high-performance coatings on the liner enables precise movement of a tool through its lumen.

In general, the inner lumen or channel of the liner insert tube may include a lubricous surface (e.g., a surface having a low friction) to allow easy passage of a medical tool within, as well as easy of sliding of the liner within the expandable channel. In one example, the inner surface is hydrophilic. The liner insert tube may also include engagement members (clips, locks, etc.) distally and/or proximally for securing to the elongate medical device and/or the tube. Thus, in some examples the liner insert tube may be configured to engage the distal end region of the elongate medical device so that it may secure (e.g., lock on to) the distal end region of the elongate medical device. In some examples the liner insert tube includes one or more projections (e.g., wings) at one or more positions along the length of the liner insert tube, or along the entire length of the liner insert tube. These projections may help keep the liner insert tube oriented relative to the elongate medical device.

The liner insert tube may generally form a channel or lumen that is held open along the length of the elongate medical device once positioned. A variety of different liner insert tubes may be used having different sizes/dimensions. For example, different liner insert tubes may have different diameters for passing different medical devices. Tools or 'instruments' may insert through the liner, including custom endoscopic tools and 'standard' endoscopic tools. Standard endoscopic tools are typically designed to fit through working channels of the following inner diameters: 4.2 mm, 3.8 mm, 3.2 mm, 2.8 mm, 2.0 mm. Multiple liner insert tubes may be inserted into different external working channels of the working channel sleeve apparatuses described herein. Since the working channels of the tube are normally maintained in a collapsed configuration but may be allowed to slide slightly with respect to the outer surface of the elongate medical device, the resulting structures may remain highly flexible while still having a relatively small outer profile when positioning within the body. Once positioned, the profile may be expanded by inserting one or more liner insert tubes and/or tools (e.g., directly, without requiring a liner insert tool).

The liner insert tube may be constructed using a variety of different techniques. For example, the liner insert tube may be an extrusion, typically of plastic or an elastomer. The liner insert tube may be a composite catheter shaft, including with a braid or with a fluoropolymer or ePTFE layer. In some examples the liner insert tube comprises a coil wound tube, or it may utilize a laser cut tube. The liner insert tube may be configured to have a key combination of parameters that are best achieved through the utilization of a composite structure: fantastic lubricity, good 'pushability' (e.g., high column strength and high axial stiffness,) low bend stiffness, good hoop stiffness, and a very reliably circular cross-section (even when it is bent through a tight radius of curvature).

In some examples the distal end of the liner insert tube may include a deflector. The deflector may be a blunt or rounded extension of the liner insert tube that may be configured to enable enhanced passage through the external working channel. The deflector may also be configured to prevent snagging as the liner insert tube is inserted into the external working channel. In some examples the deflector at the distal end of the liner insert tube is configured to have an atraumatic geometry so that it does cause anatomical damage as it emerges from the working channel. A deflectable tip portion may be useful for directing a tool as it exits the distal end region, thereby manipulation it in a particular direction (e.g., radially inward relative to the elongate medical tool). In some examples the deflector may include an eccentrically affixed pull wire.

For example, described herein are systems including tubes having one or more working channels configured to receive a medical tool inserted therethrough, each working channel may be positioned longitudinally along an exterior surface of the tube. The tube may be elastically expandable. Both the tube and the one or more working channels may be comprised of a fabric material. The same material may be used for the body of the tube and the expandable (e.g., elastically expandable) working channels or different materials may be used.

In general, as used herein the term "expandable" may refer to elastically expandable so that the expandable structure (e.g., tube, external working channel, etc.) may be returned from an expanded configuration back to a collapsed configuration. In some examples the expandable tube may provide for ease of sliding by the use of a coating applied to the outside of the elastic component. For example, the coating could be a hydrophilic coating.

The working channel sleeve apparatuses described herein may achieve the dual goals of high elasticity and low friction through the external working channels by using a composite material: e.g., a low friction material covering, encasing and/or coating an elastomeric core. In some examples the low-friction material is a material (e.g., yarn) that may cover or wrap around the elastomeric core. Typically, elastomers have high sliding friction. A low friction yarn could be, for example, a polyethylene, a polypropylene, or a fluoropolymer (for example, a PTFE). The composite material may be in a single layer or in multiple layers. For example, the composite material may include a knit structure of filament(s) (e.g., between 10-80 filaments, between 12-40 filaments, between 10-36 filaments, etc.) having a lubricious outer region over an elastic core.

The elasticity of the elastic material used may vary, in some cases within the same apparatus. For example, different elastic element materials may be used, and/or the filament count, filament thickness, etc. may be different among different elastic materials within the same or different apparatuses. Elasticity percentages can be, for example, 5%, 10%, 20% or 30%. In some examples, a material such as spandex may be used. Spandex is a type of urethane that is a synthetic fiber known for its exceptional elasticity. Silicone may also be used, as it is highly biocompatible.

The requisite elasticity could be achieved by a material that is both sufficiently elastic and sufficiently slippery.

The requisite elasticity could be achieved by a structure that utilizes a material that is not elastic, but does have great ability to handle repeat deflections of large magnitude (for example, by embedded deflectable nitinol elements).

Alternatively or additionally, the working channel sleeve apparatuses described herein may achieve the dual goals of high elasticity and low friction through the working channel(s) by positioning or arranging the elastomeric core of the filaments forming the working channel, so that it is spaced apart from (e.g. facing away from) materials with low sliding friction. For example, the elastomer "core" may not be encased, but it may be positioned in the cross section of the structure (the working channel) to ensure that devices moving within the working channel do not directly slide against the elastomeric material.

In examples in which the apparatus is knitted (e.g., the tube and/or elastic external working channels), the apparatus may be knitted on a computer-controlled knitting machine. Any appropriate needle gauge and/or stitch pattern may be used. For example, needle gages of knitting machine can be, for example, 10-14 or a 16-18 (with the 10 and 16 meaning needle gage and the 14 and 18 meaning the machine gage). A 16-18 machine enables much finer knitting.

The working channel sleeve apparatuses described herein may generally include a tube (e.g., a tubular body) that is configured to extend over an outer surface of an elongate medical device (e.g., catheter) and one or more external working channels formed along a length of the tube that are configured to receive a medical tool inserted therethrough. The one or more external working channels may also be referred to herein as a type of layflat tube. The elongate tubular body may also be referred to herein as an inner tube.

The external working channels may be referred to equivalently herein as outer pockets. In some cases the working channels (e.g., outer pockets) are configured as external working channels that include an elastic element, e.g., may be formed of a knitted material that includes an elastic core, while in some examples the external working channels (e.g., outer pockets) do not include an elastic elements. Thus, the working channels described herein may be elastic or inelastic.

In working channel sleeve apparatuses including an inner tube and one or more outer working channels, the outer working channels may be formed of one or more filaments (or bundles of filaments) forming the outer working channels. The inner tube may also be formed of the same or a different filaments (or filaments or bundles of filaments) forming the inner tube, e.g., tubular body.

In particular, described herein are working channel sleeve apparatuses that are knitted. In some examples the working channel sleeve apparatus is formed by weft knitting. The working channel sleeve apparatus may be formed by warp knitting, including but not limited to tricot, Milanese knit, Raschel knit, and stitch-bonding. Any appropriately sized filament(s) may be used. For example in some examples the filament(s) forming the outer working channel(s) may be about 100 denier to 6000 denier for the outer wrap. Fiber(s) for the inner elastic core could be 400 to 6000 denier for the inner wrap. As used herein a filament or filaments (or bundles of filaments) forming all or part of a working channel sleeve apparatus may be referred to equivalently as a fiber or fibers (or bundle of fibers). These filaments may be natural or artificial and/or may be hybrid filaments as described herein.

The expandable tube of the working channel sleeve apparatus may be configured to slide over an elongate medical device. It may be unsecured between its distal and proximal ends. It may be secured at one or more points on the outer surface of the elongate medical device, such as the distal end region and/or the proximal end region. In some examples the tube may be secured at discrete points or intervals, between every 1-300 mm (e.g., between every 1-2 mm, 1-3 mm, 1-4 mm, 1-5 mm, 1-7 mm, 1-10 mm, 1-15 mm, 1-20 mm, 1-25 mm, 5-10 mm, 5-15 mm, 5-20 mm, 5-25 mm, 5-30 mm, 5-35 mm, 5-40 mm, 10-20 mm, 20-30 mm, 10-100 mm, 10-200 mm, 100 mm-200 mm, 100 mm-300 mm, etc.). The expandable tube may be attached circumferentially or at one or more points or lines. The expandable tube may be configured to slide relative to the outer surface of the elongate medical device in regions where it is not attached, which may help prevent wrinkling and/or blocking of the external working channel(s).

In some examples, the working channels can be created as a sewn structure from flat cloth. The cloth can be an expandable cloth, such as a stretchy mesh. A lubricious coating can be used with the cloth (e.g., mesh) so that tools can readily slide within the working channel. The cloth (e.g., mesh) may have openings or pores. The pores may change shape as the cloth is stretched or compressed, including expanding and contracting and distorting from their original shape. The material could be polyester or polypropylene or Teflon with an elastic stretch core that could be, for example, urethane (including spandex), or silicone. In general, the pore size of the working channels (and/or inner tubular body) can vary from about 0.05 mm to about 4 mm, in knitted, woven and/or cloth embodiments.

As mentioned, any of these working channel sleeve apparatuses may include or be used with a liner, including but not limited to a liner insert tube. In any of the apparatuses described herein a liner may be used within the external working channels. The material forming the working channel may be stretchy enough to hold and control the liner. If a cloth material forming the working channel is too stretchy, the liner may distort the material, and may poke out from the working channel, and/or may buckle or wrinkle as the apparatus is put through curvature. If the cloth material forming the working channel is not stretchy enough, the liner insertion force may become too high, making it difficult, if not impossible, to insert. The performance of the material, e.g., knit material and/or fabric material, may be modulated by changing the orientation of the weft and the warp. For example, a woven cloth can be sewn in-line, or can be sewn at a 45 degree bias. In some examples the cloth can be comprised of yarns with filament counts. Filament counts can very, for example, from 5 to 100. High filament count yarns can create more lubricious cloths.

In any of these examples of working channel sleeve apparatuses, the working channels can be created as a laminated structure. For example, by inserting a layer of a thermoplastic elastomer between layers of cloth, the working channels can be adhered in a manner that is non-penetrating and elastic. The bonding may occur with the assistance of heat, pressure, and the passage of time. Similarly, structures can be laminated with other material layers. For example, elastomeric layers can be laminated with fiber layers, with layers that are selective cut-out (for example, by lasers, die-cutting, or CNC knife-cutting profiles).

Any of the working channel sleeve apparatuses described herein may be used with an elongate medical device. For example the elongate medical device may include a catheter, endoscope, overtube, etc. In some examples the elongate medical device is a rigidizing device (e.g., a rigidizing system). Although examples including rigidizing (e.g., selectively rigidizing member) are provided herein and incorporated by reference in their entirety, including but not limited to those described in international patent application PCTUS2019042650 ("DYNAMICALLY RIGIDIZING COMPOSITE MEDICAL STRUCTURES", filed Jul. 19, 2019, herein incorporated by reference in its entirety), the systems and methods described herein are not limited to rigidizing apparatuses, or any particular type of rigidizing apparatus.

The working channels described herein may be elastically expandable and may be configured to contour the shape of the medical tool or a liner insert tube inserted therethrough. As mentioned, in some examples it may be advantageous to include a liner insert tube that may be inserted into the working channel, and particularly expandable working channels, in order to maintain patency of the working channel for insertion of one or more medical tools. The liner insert tube described herein may include a closed or open lumen (e.g., open along all or some of the elongate length of the liner insertion tube). The liner insert tube may also be equivalently referred to herein as a liner insert or liner insert channel. In any of these examples the liner insert tube may include a lubricous inner lumen that extends therethrough. The outer surface of the liner insert tube may be lubricious and/or may include a lubricous coating or material. In some examples the inner lumen may be hydrophilic or hydrophobic (e.g., may include a hydrophilic or hydrophobic coating) on the inner and/or outer surface of the liner insert tube. The liner insert tube may be used when inserting a tool into an external working channel, particularly when it would be beneficial to expand or hold the expandable working channel open for inserting a tool, particularly a tool that may otherwise catch or snag on the external working channel (e.g., when the external working channel is formed of a knit, woven or braided material, or any other material having pores/openings).

The liner insert tube may be inserted into one of the one or more working channels from a proximal end to a distal end of the working channel. Once inserted, a medical tool may be passed through the lumen of the liner insert tube for use at or near the distal end of the elongate medical device.

As mentioned above, the external working channels may generally be constructed of one or more filaments (e.g., knit, woven, etc.) having a low friction outer region that at least partially encloses an elastic inner region. In any of these apparatuses the external working channels may also include one more filaments that do not include an elastic core (and/or may be non-elastic). For example, the external working channels may be a mix of elastic and non-elastic (or less elastic) filaments.

The body of the tube and/or the working channels of the working channel sleeve apparatus may be formed as a non-uniform weave, braid or knit pattern. In some examples, the weave pattern of the tube body and the one or more external working channels is the same. In some examples, the weave pattern of the one or more external working channels is different than a weave pattern of the body of the tube. Additionally, the tube can comprise more than one segment defined by a change in a weave pattern of the (e.g., along the length of the tube). Similarly, the one or more working channels can have more than one segment defined by a change in the weave pattern of the fabric, which may allow modulation of the elasticity of the length of the tube and/or may bias a tool or the linear insert tube to be retained at a particular longitudinal position of the tube.

As mentioned, the tube body of the working channel sleeve apparatus may be formed of a woven braid of one or more filaments. The one or more filaments may be formed of a core of an elastic material configured to elastically expand and retract and a lubricious coating, winding, wrapping and/or layer over the elastic core. In some examples the lubricious coating/winding/wrapping/layer may be a wrap substantially or completely encompassing the elastic core, forming a coil-wound filament.

The tube may include any appropriate number of external working channels, such as between 1 and 12 (e.g., between 1-10, between 1-9, between 1-8, between 1-7, between 1-6, between 1-5, between 1-4, between 1-3, between 1-2, or just one). The channels could be the same shape or size, or they may be different shapes or sizes.

The tube body of the working channel sleeve apparatus may generally conform to the shape of the elongate medical device as it is bent or otherwise navigated through the body. Apparatuses including the tube comprising the external working channels may be configured to allow bending without substantially increasing the stiffness of the elongate medical device or without. Each of the external working channels of the working channel sleeve apparatus may be expandable to accommodate a tool and/or a liner insert tube inserted therethrough. The channels may expand independent of one another and independent of the expandable tube. Each of the channels may be positioned around a perimeter of the expandable tube. In some examples, when the working channel sleeve has multiple external working channels, the external working channels can be equidistant from one another on the exterior surface of the tube body of the working channel sleeve apparatus. For example, where there are four channels, each of the channels may be separated by 90 degrees on center about a longitudinal axis of the expandable tube. The tube and the working channels of the working channel sleeve apparatus may include or be composed of materials that are elastomeric, plastic, and/or fabric. The channels may have spaces between them, or they may be immediately adjacent to each other. In some examples the channels may overlap. The channels may be attached over their entire length. The channels may be attached at discrete points or lines. The channels may be attached at an intermediate value between a point or line and over their entire length.

Any of the elongate medical devices described (e.g., catheters, endoscopes, etc.) may include an imaging element positioned at a distal end, such that the imaging element may be used to identify and assist in operation of tools passed through the external working channels of the working channel sleeve apparatus during a medical procedure. The elongate medical device can also have corresponding imaging element positioned at a proximal end.

For example, described herein are working channel sleeve apparatuses including an expandable external working channel, the system comprising: an elongate medical device; a tube extending over an outer surface of the elongate medical device; and one or more external working channels formed along a length of the tube and configured to receive a medical tool inserted therethrough. Thus a working channel sleeve apparatus may also include the elongate medical device onto which the elongate body of the working channel sleeve is worn or applied, forming the elongate external channels extending down the length of the elongate medical device.

In any of these apparatuses, the tube may comprise a woven, knit or braided tube, or a combination thereof. In some examples the tube is formed of one or more elastic and lubricious filaments. The tube may be slidably connected to the elongate medical device. The tube may be coupled to a proximal end region and to a distal end region of the elongate medical device.

Any of the apparatuses (e.g., devices, systems, etc.) described herein may be formed of a material (or materials) that is/are laminated.

In any of these systems, the elongate medical device may comprise a catheter, overtube or an endoscope. In some examples, the elongate medical device comprises a selectively rigidizing device.

Any of these systems may include a liner insert tube configured to be inserted within one of the one or more expandable working channels and removably coupled to a distal end of one or both of the elongate medical device and tube. The liner insert tube may have a hydrophilic interior and or exterior surface. In some examples the liner insert tube comprises one or more wings extending proud of a side of the liner insert tube configured to limit torque of the liner insert tube within the one of the one or more expandable working channels. The wings can provide distal to axial registration, and may prevent torquing and lateral motion. In some examples the liner insert tube may include a deflector at a distal end opening of the liner insert tube configured to deflect a tool exiting the liner insert tube away from a radially outward direction relative to the elongate medical device.

The inner tube of the working channel sleeve apparatus may be formed of one or more filaments, including in particular filaments comprising an inner elastic material and an outer lubricious material. The tube may be formed of a coil-wound filament comprising an elastic core wrapped in a lubricious material. In some examples, the lubricious material comprises a polypropylene, a polyethylene, or a polytetrafluoroethylene. The tube may have a non-uniform weave pattern, or a uniform weave pattern. In some examples, the tube may be sheet of elastomer (e.g., elastomeric material) with cutouts so that it resembles a fine mesh potentially working for this application.

For example, a working channel sleeve system including an expandable external working channel may include: an elongate medical device having a flexible or selectively rigidizable body; a knit or woven tube extending over an outer surface of the elongate medical device wherein the tube is coupled to a distal end region and a proximal end region of the elongate medical device and is slidable relative to the outer surface over at least a portion of the flexible or selectively rigidizable body between the distal end region and the proximal end region; and one or more external working channels formed along a length of the tube and configured to receive a medical tool inserted therethrough.

In some examples the system (e.g., the working channel sleeve system including an expandable external working channel) includes: an elongate medical device; a knit or woven tube extending over an outer surface of the elongate medical device, the tube comprising one or more external working channels extending along a length of the tube and configured to receive a medical tool inserted therethrough; and a liner insert tube configured to be inserted within one of the one or more expandable working channels and removably coupled to a distal end of one or both of the elongate medical device and tube.

Also described herein are methods of using any of these working channel sleeve apparatuses (e.g., systems, devices, etc.). For example, a method of positioning a tool within a body may include: inserting an elongate medical device into the body in a flexible configuration; inserting a liner insert tube into an expandable working channel of a knit or woven tube extending over an outer surface of the elongate medical device, so that the external working channel expands to accommodate the liner insert tube; and inserting a working tool through the liner insert tube and out of a distal end of the liner insert tube.

Any of these methods may in include performing a medical procedure in the body with the working tool.

In some examples, the method may include locking the distal end of the liner insert tube at a distal end region of the elongate medical device. Alternatively or additionally, the liner insert tube may be locked at the proximal end of the elongate medical device. The length of the liner insert tube may be allowed to slide relative to the inner surface of the working channel as the elongate medical device is navigated within the body, while the liner insert tube is fixed at the distal (and/or proximal) end of the elongate medical device.

Any of these methods may include maintaining patency of the liner insert tube while it is inserted into the expandable working channel.

The methods described herein may be used with a rigidizing elongate medical device. For example, any of these methods may include rigidizing the elongate medical device. In some examples the method may include rigidizing the elongate medical device before inserting the liner insert tube. Any of these methods may include deflecting the working tool radially inwards as it is extended out of the distal end of the liner insert tube using a deflector at a distal end region of the liner insert tube. Inserting the liner insert tube into the expandable working channel may include engaging one or more wings on the liner insert tube with the expandable working channel. In some examples inserting the liner insert tube comprises sliding the liner insert tube against a lubricious outer surface of one or more filaments forming the expandable working channel of the knit or woven tube.

As mentioned above, the expandable working channel of the knit or woven tube may be formed of one or more filaments comprising an inner elastic material and an outer lubricious material. Inserting the liner insert tube may expand the expandable working channel from a collapsed configuration in which the expandable working channel is flush against the outer surface of the elongate medical device.

For example, a method of positioning a tool within a body may include: inserting an elongate medical device into a body in a flexible configuration, so that a knit or woven tube extending over an outer surface of the elongate medical device may slide relative to the outer surface; positioning a distal end of the elongate medical device near a target region of the body; inserting a liner insert tube into an expandable working channel of the tube, so that the external working channel expands to accommodate the liner insert tube; and locking a distal end of the liner insert tube to a distal end of the elongate medical device and/or the tube, wherein the liner insert tube maintains patency of a lumen extending through the liner insert tube.

A method of positioning a tool within a body may include: inserting an elongate medical device comprising a rigidizing member into a body while the rigidizing member is in a flexible configuration, so that a knit or woven tube extending over an outer surface of the elongate medical device may slide relative to the outer surface; positioning a distal end of the elongate medical device near a target region of the body; rigidizing the elongate medical device; inserting a liner insert tube into an expandable working channel of the tube, so that the external working channel expands to accommodate the liner insert tube; and inserting a working tool through the liner insert tube and out of a distal end of the liner insert tube. Alternatively, rigidization could occur at different steps in the process.

The methods and apparatuses described may be used with and/or may modify any of the methods and apparatuses described in International Patent Application No. PCT/US2016/050290, filed on Sep. 2, 2016, titled "DEVICE FOR ENDOSCOPIC ADVANCEMENT THROUGH THE SMALL INTESTINE," published as WO 2017/041052, International Patent Application No. PCT/US2018/042946, filed on Jul. 19, 2018, titled "DYNAMICALLY RIGIDIZING OVERTUBE," published as WO 2019/018682, International Patent Application No. PCT/US2019/042650, filed on Jul. 19, 2019, titled "DYNAMICALLY RIGIDIZING COMPOSITE MEDICAL STRUCTURES," published as WO 2020/018934, International Patent Application No. PCT/US2020/013937 filed on Jan. 16, 2020, titled "DYNAMICALLY RIGIDIZING COMPOSITE MEDICAL STRUCTURES," and PCT/US2021/034292, filed on May 26, 2021, entitled "RIGIDIZING DEVICES" the entireties of which are incorporated by reference herein.

All of the methods and apparatuses described herein, in any combination, are herein contemplated and can be used to achieve the benefits as described herein.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIGS. 9A-9E shows a plurality of actively controlled linkages.

FIG. 25A shows a rigidizing device with a distal end section having linkages within a rigidizing section.

FIG. 25B shows a rigidizing device with a steering cable attached to a wall near the distal end thereof.

FIGS. 26A-26C show a rigidizing device having an actively deflected distal end section.

FIGS. 29A-29B show a nested rigidizing system where the outer rigidizing device includes steering and imaging.

FIG. 34 shows a guide for a robotically controlled rigidizing system.

FIGS. 35A-35B show another embodiment of a guide for a robotically controlled rigidizing system.

FIG. 36 shows another embodiment of a fitting for a robotically controlled rigidizing system.

FIG. 84A shows the channels in a collapsed configuration, while FIG. 84B shows the channels in an expanded configuration, driven open by a liner insert tube. FIG. 84C shows an enlarged view of the introducer region or guides for insertion of tubes into the external working channels of an apparatus as described herein. FIG. 84D shows an example of a liner insert tube that is of non-circular outer geometry. FIG. 84E shows a section through a portion of an apparatus including external and expandable working channels.

FIG. 85A shows an example of a liner insert tube. FIG. 85B shows the distal and proximal ends of the liner insert tube of FIG. 85A. FIG. 85C shows the distal end of the liner insert tube of FIG. 85A illustrating a deflectable instrument emerging from the distal end of the liner insert tube.

FIG. 86A shows the proximal end of the elongate medical device and an introducer for introducing a tool and/or a tool liner tube into the expandable external channel, with an instrument entering the liner. FIG. 86B shows a distal end of the tube and expandable external channel at a distal end of the elongate medical device, with the tool liner tube extending distally out of the working channel. FIG. 86C shows a tool extending from the tool liner tube at a distal end of the elongate medical device.

FIG. 89A shows the overall system including the elongate medical device and tube with external working channels that are coded by a colored indicator (e.g. shape, pattern, alphanumeric, etc.). FIG. 89C is a view of a distal end of the apparatus of FIGS. 89A-89B, with two different instruments emerging. In FIG. 89B the tool is an aspiration catheter, and in FIG. 89C a liner insert tube with a deflector and a grasping instrument are shown.

DETAILED DESCRIPTION

Described herein are rigidizing devices (e.g., overtubes) that are configured to aid in transporting a scope (e.g., endoscope) or other medical instrument through a curved or looped portion of the body (e.g., a vessel). The rigidizing devices can be long, thin, and hollow and can transition quickly from a flexible configuration (i.e., one that is relaxed, limp, or floppy) to a rigid configuration (i.e., one that is stiff and/or holds the shape it is in when it is rigidized). A plurality of layers (e.g., coiled or reinforced layers, slip layers, braided layers, bladder layers and/or sealing sheaths) can together form the wall of the rigidizing devices. The rigidizing devices can transition from the flexible configuration to the rigid configuration, for example, by applying a vacuum or pressure to the wall of the rigidizing device or within the wall of the rigidizing device. With the vacuum or pressure removed, the layers can easily shear or move relative to each other. With the vacuum or pressure applied, the layers can transition to a condition in which they exhibit substantially enhanced ability to resist shear, movement, bending, torque and buckling, thereby providing system rigidization.

The rigidizing devices described herein can provide rigidization for a variety of medical applications, including catheters, sheaths, scopes (e.g., endoscopes), wires, overtubes, trocars or laparoscopic instruments. The rigidizing devices can function as a separate add-on device or can be integrated into the body of catheters, sheaths, scopes, wires, or laparoscopic instruments. The devices described herein can also provide rigidization for non-medical structures.

Figure 1:
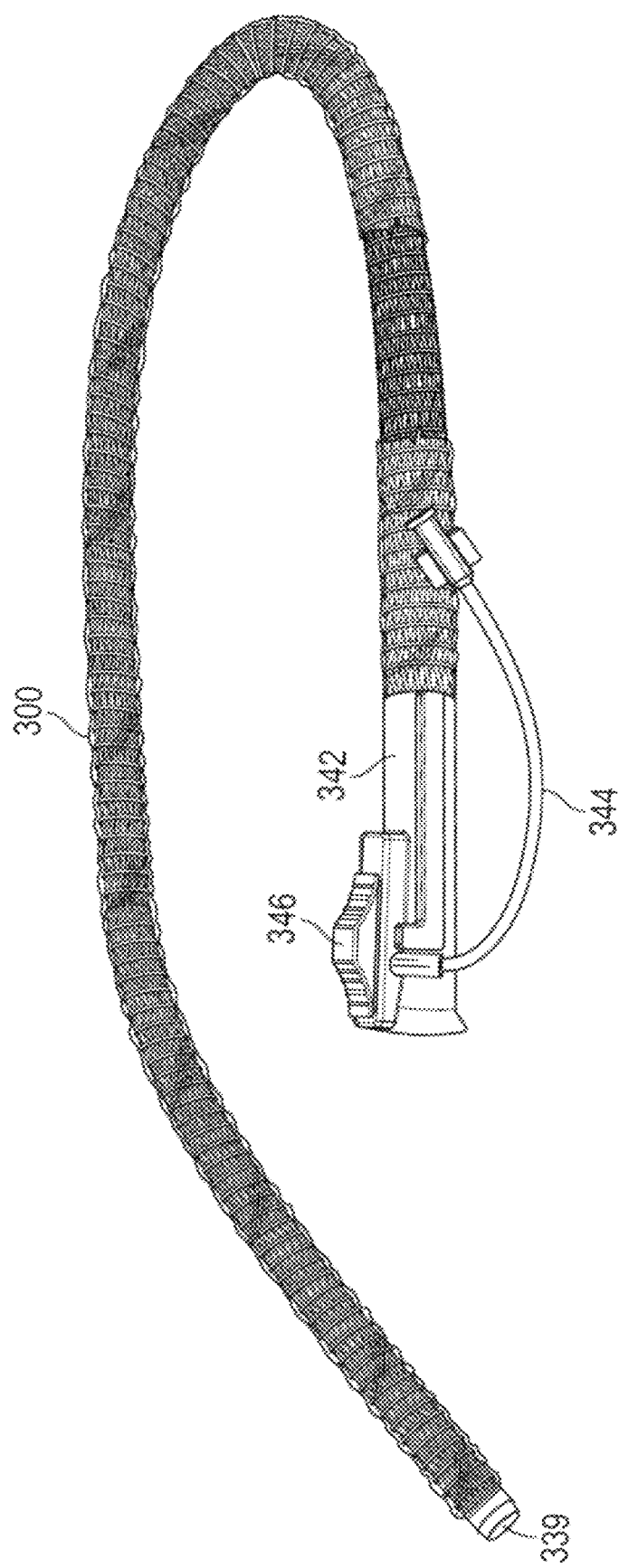
FIG. 1 shows a rigidizing device.

An exemplary rigidizing device system is shown in FIG. 1. The system includes a rigidizing device 300 having a wall with a plurality of layers including a braid layer, an outer layer (part of which is cut away to show the braid thereunder), and an inner layer. The system further includes a handle 342 having a vacuum or pressure inlet 344 to supply vacuum or pressure to the rigidizing device 300. An actuation element 346 can be used to turn the vacuum or pressure on and off to thereby transition the rigidizing device 300 between flexible and rigid configurations. The distal tip 339 of the rigidizing device 300 can be smooth, flexible, and atraumatic to facilitate distal movement of the rigidizing device 300 through the body. Further, the tip 339 can taper from the distal end to the proximal end to further facilitate distal movement of the rigidizing device 300 through the body.

Figure 2A:
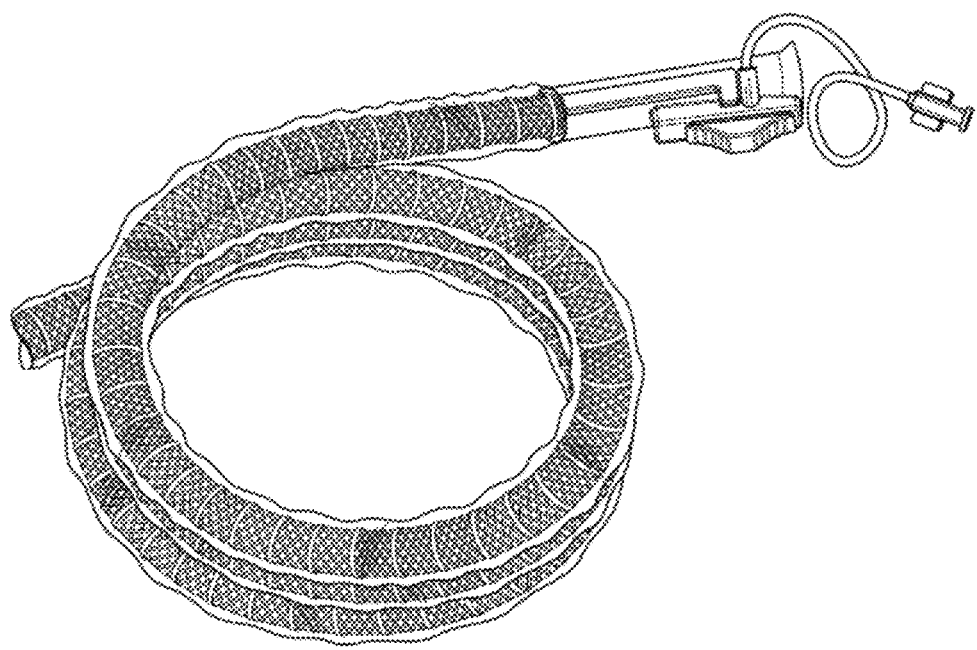
FIGS. 2A-2B show exemplary rigidized shapes of a rigidizing device.
Figure 2B:
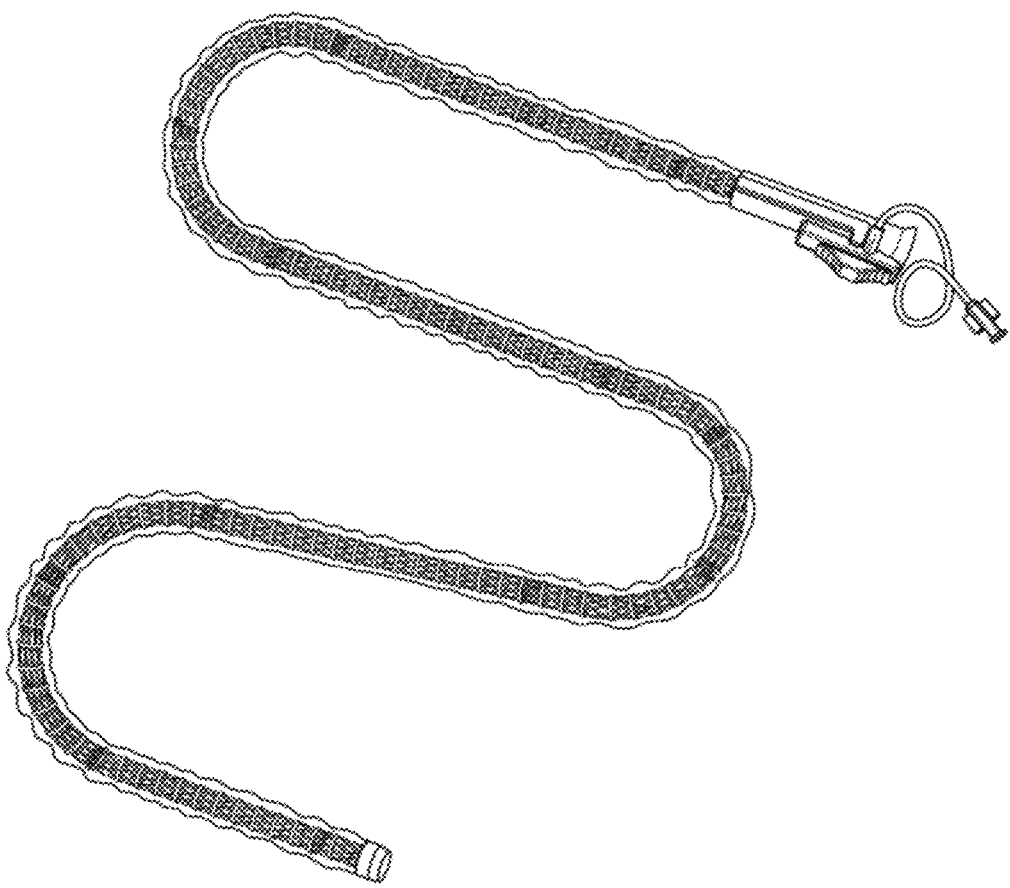

Exemplary rigidizing devices in the rigidized configuration are shown in FIGS. 2A and 2B. As the rigidizing device is rigidized, it does so in the shape it was in before vacuum or pressure was applied, i.e., it does not straighten, bend, or otherwise substantially modify its shape (e.g., it may stiffen in a looped configuration as shown in FIG. 2A or in a serpentine shape as shown in FIG. 2B). This can be because the air stiffening effect on the inner or outer layers (e.g., made of coil-wound tube) can be a small percentage (e.g., 5%) of the maximum load capability of the rigidizing device in bending, thereby allowing the rigidizing device to resist straightening. Upon release of the vacuum or pressure, braids or strands can unlock relative to one another and again move so as to allow bending of the rigidizing device. Again, as the rigidizing device is made more flexible through the release of vacuum or pressure, it does so in the shape it was in before the vacuum or pressure was released, i.e., it does not straighten, bend, or otherwise substantially modify its shape. Thus, the rigidizing devices described herein can transition from a flexible, less-stiff configuration to a rigid configuration of higher stiffness by restricting the motion between the strands of braid (e.g., by applying vacuum or pressure).

The rigidizing devices described herein can toggle between the rigid and flexible configurations quickly, and in some embodiments with an indefinite number of transition cycles. As interventional medical devices are made longer and inserted deeper into the human body, and as they are expected to do more exacting therapeutic procedures, there is an increased need for precision and control. Selectively rigidizing devices (e.g., overtubes) as described herein can advantageously provide both the benefits of flexibility (when needed) and the benefits of stiffness (when needed). Further, the rigidizing devices described herein can be used, for example, with classic endoscopes, colonoscopes, robotic systems, and/or navigation systems, such as those described in International Patent Application No. PCT/US2016/050290, filed Sep. 2, 2016, titled "DEVICE FOR ENDOSCOPIC ADVANCEMENT THROUGH THE SMALL INTESTINE," the entirety of which is incorporated by referenced herein.

The rigidizing devices described herein can additionally or alternatively include any of the features described with respect to International Patent Application No. PCT/US2016/050290, filed on Sep. 2, 2016, titled "DEVICE FOR ENDOSCOPIC ADVANCEMENT THROUGH THE SMALL INTESTINE," published as WO 2017/041052, International Patent Application No. PCT/US2018/042946, filed on Jul. 19, 2018, titled "DYNAMICALLY RIGIDIZING OVERTUBE," published as WO 2019/018682, International Patent Application No. PCT/US2019/042650, filed on Jul. 19, 2019, titled "DYNAMICALLY RIGIDIZING COMPOSITE MEDICAL STRUCTURES," published as WO 2020/018934, and International Patent Application No. PCT/US2020/013937 filed on Jan. 16, 2020, titled "DYNAMICALLY RIGIDIZING COMPOSITE MEDICAL STRUCTURES," the entireties of which are incorporated by reference herein.

The rigidizing devices described herein can be provided in multiple configurations, including different lengths and diameters. In some embodiments, the rigidizing devices can include working channels (for instance, for allowing the passage of typical endoscopic tools within the body of the rigidizing device), balloons, nested elements, and/or side-loading features.

Referring to FIGS. 3A-3D, in one embodiment, a tubular rigidizing device 100 can include a wall having a plurality of layers positioned around the lumen 120 (e.g., for placement of an instrument or endoscope therethrough). A vacuum can be supplied between the layers to rigidize the rigidizing device 100.

The innermost layer 115 can be configured to provide an inner surface against which the remaining layers can be consolidated, for example, when a vacuum is applied within the walls of the rigidizing device 100. The structure can be configured to minimize bend force/maximize flexibility in the non-vacuum condition. In some embodiments, the innermost layer 115 can include a reinforcement element 150z or coil within a matrix, as described above.

The layer 113 over (i.e., radially outwards of) the innermost layer 115 can be a slip layer.

The layer 111 can be a radial gap (i.e., a space). The gap layer 111 can provide space for the braided layer(s) thereover to move within (when no vacuum is applied) as well as space within which the braided or woven layers can move radially inward (upon application of vacuum).

The layer 109 can be a first braid layer including braided strands 133 similar to as described elsewhere herein. The braid layer can be, for example, 0.001" to 0.040" thick. For example, a braid layer can be 0.001", 0.003", 0.005", 0.010", 0.015", 0.020", 0.025" or 0.030" thick.

Figure 3A:
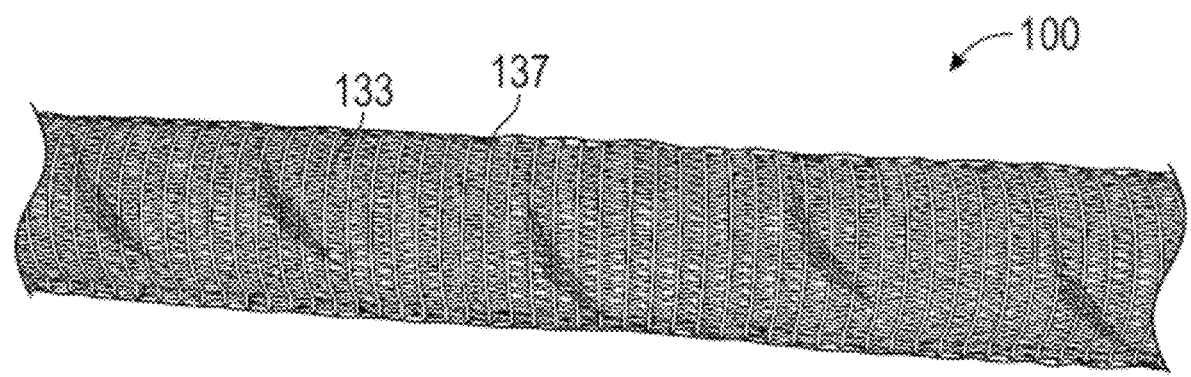
FIGS. 3A-3D show an exemplary vacuum rigidizing device.
Figure 3B:
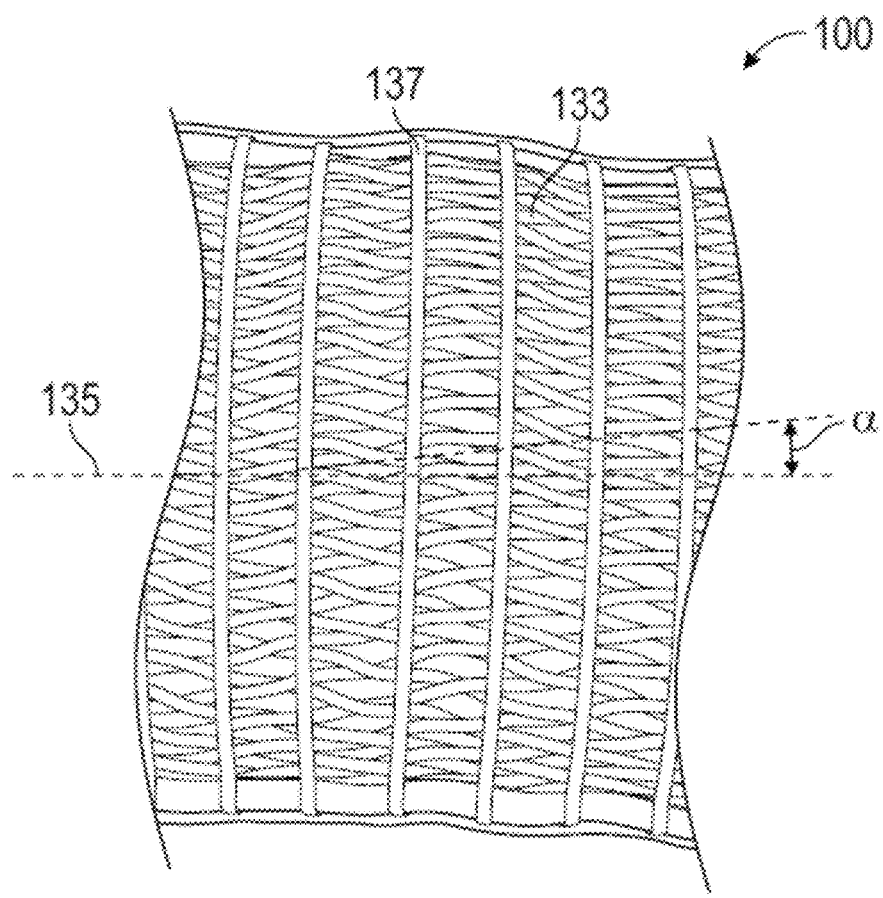

In some embodiments, as shown in FIG. 3B, the braid can have tensile or hoop fibers 137. Hoop fibers 137 can be spiraled and/or woven into a braid layer. Further, the hoop fibers 137 can be positioned at 2-50, e.g., 20-40 hoops per inch. The hoop fibers 137 can advantageously deliver high compression stiffness (to resist buckling or bowing out) in the radial direction, but can remain compliant in the direction of the longitudinal axis 135 of the rigidizing device 100. That is, if compression is applied to the rigidizing device 100, the braid layer 109 will try to expand in diameter as it compresses. The hoop fibers 137 can resist this diametrical expansion and thus resist compression. Accordingly, the hoop fiber 137 can provide a system that is flexible in bending but still resists both tension and compression.

The layer 107 can be another radial gap layer similar to layer 111.

Figure 3C:
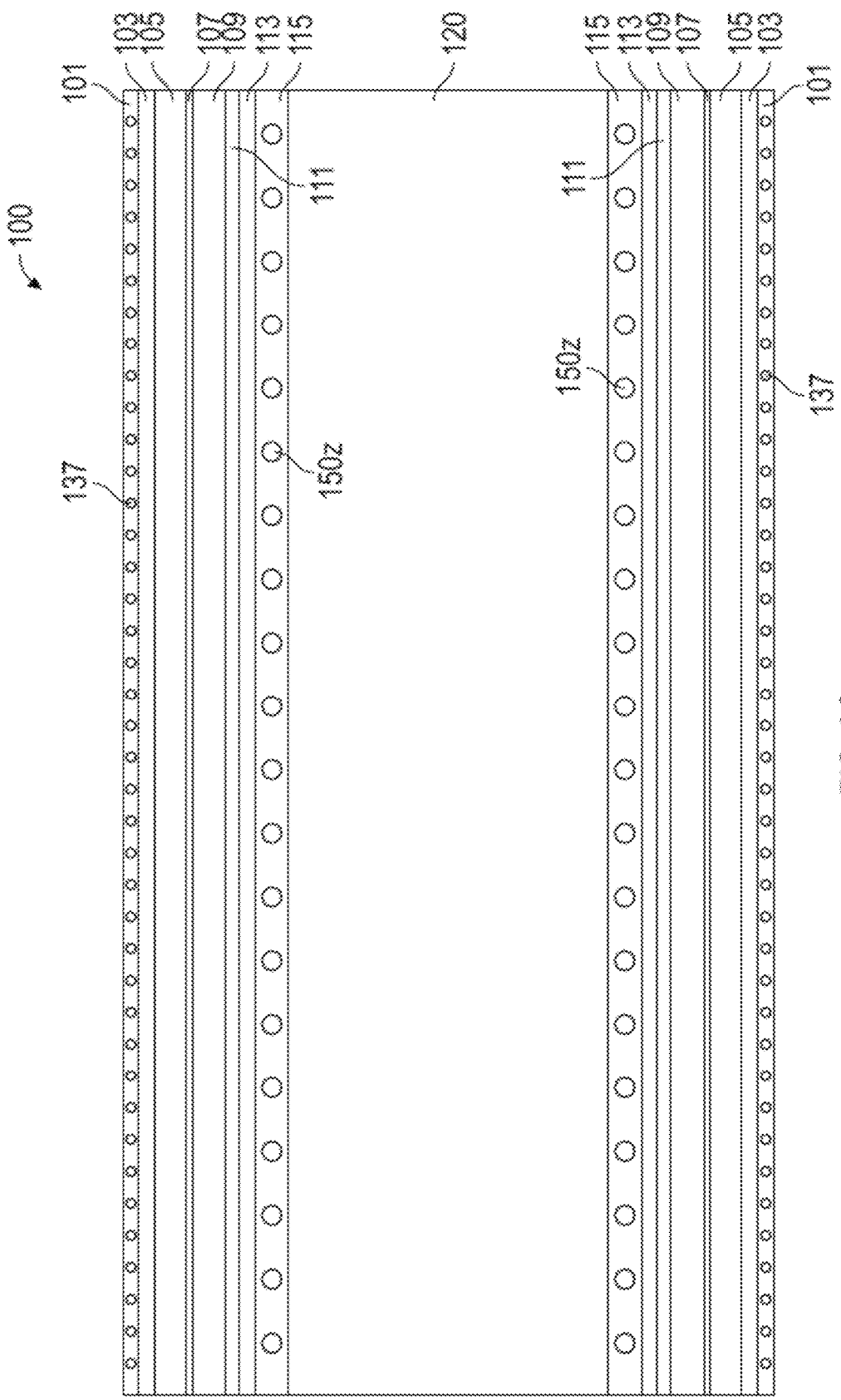
Figure 3D:
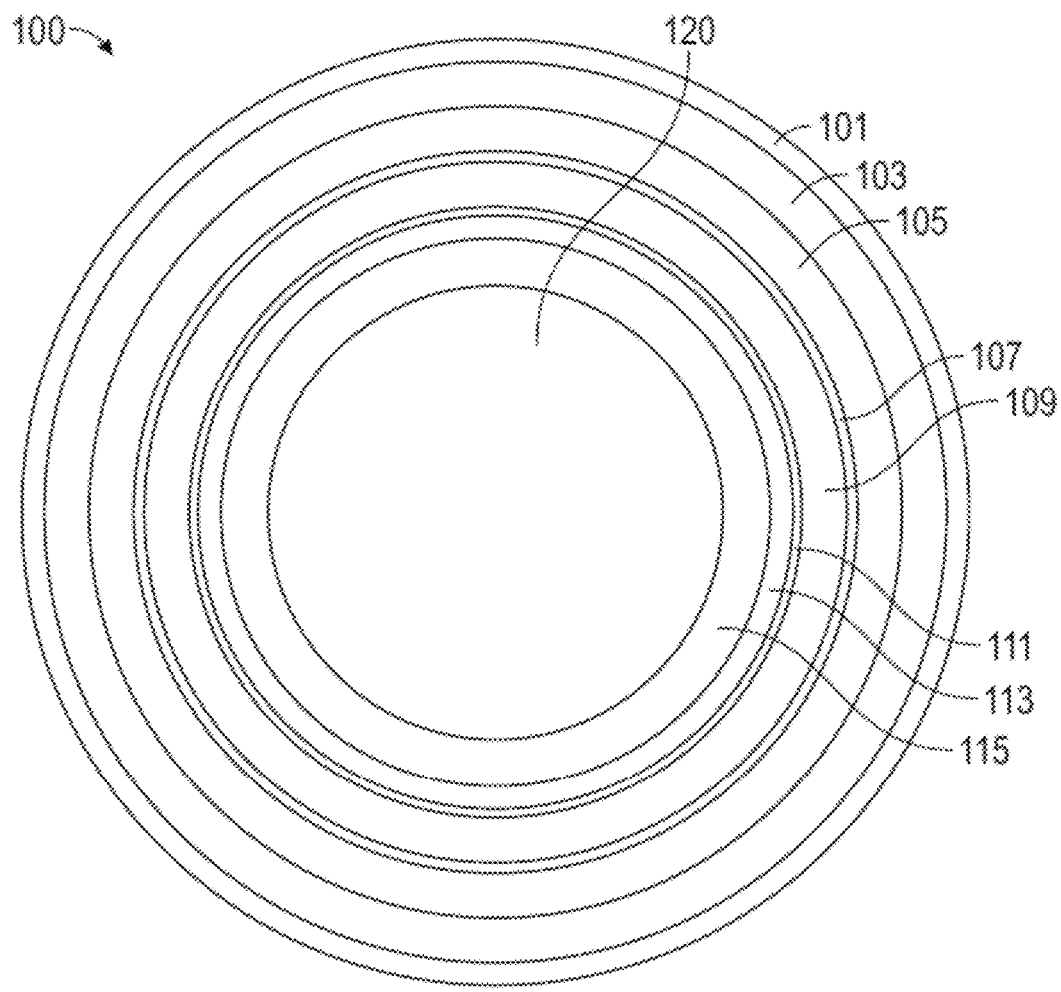

In some embodiments, the rigidizing devices described herein can have more than one braid layer. For example, the rigidizing devices can include two, three, or four braid layers. Referring to FIG. 3C, the layer 105 can be a second braid layer 105. The second braid layer 105 can have any of the characteristics described with respect to the first braid layer 109. In some embodiments, the braid of second braid layer 105 can be identical to the braid of first braid layer 109. In other embodiments, the braid of second braid layer 105 can be different than the braid of the first braid layer 109. For example, the braid of the second braid layer 105 can include fewer strands and have a larger braid angle α than the braid of the first braid layer 109. Having fewer strands can help increase the flexibility of the rigidizing device 100 (relative to having a second strand with equivalent or greater number of strands), and a larger braid angle α can help constrict the diameter of the of the first braid layer 109 (for instance, if the first braid layer is compressed) while increasing/maintaining the flexibility of the rigidizing device 100. As another example, the braid of the second braid layer 105 can include more strands and have a larger braid angle α than the braid of the first braid layer 109. Having more strands can result in a relatively tough and smooth layer while having a larger braid angle α can help constrict the diameter of the first braid layer 109.

The layer 103 can be another radial gap layer similar to layer 111. The gap layer 103 can have a thickness of 0.0002-0.04", such as approximately 0.03". A thickness within this range can ensure that the strands 133 of the braid layer(s) can easily slip and/or bulge relative to one another to ensure flexibility during bending of the rigidizing device 100.

The outermost layer 101 can be configured to move radially inward when a vacuum is applied to pull down against the braid layers 105, 109 and conform onto the surface(s) thereof. The outermost layer 101 can be soft and atraumatic and can be sealed at both ends to create a vacuum-tight chamber with layer 115. The outermost layer 101 can be elastomeric, e.g., made of urethane. The hardness of the outermost layer 101 can be, for example, 30 A to 80 A. Further, the outermost layer 101 can have a thickness of 0.0001-0.01", such as approximately 0.001", 0.002, 0.003" or 0.004". Alternatively, the outermost layer can be plastic, including, for example, LDPE, nylon, or PEEK.

In some embodiments, the outermost layer 101 can, for example, have tensile or hoop fibers 137 extending therethrough. The hoop fibers 137 can be made, for example, of aramids (e.g., Technora, nylon, Kevlar), Vectran, Dyneema, carbon fiber, fiber glass or plastic. Further, the hoop fibers 137 can be positioned at 2-50, e.g., 20-40 hoops per inch. In some embodiments, the hoop fibers 137 can be laminated within an elastomeric sheath. The hoop fibers can advantageously deliver higher stiffness in one direction compared to another (e.g., can be very stiff in the hoop direction, but very compliant in the direction of the longitudinal axis of the rigidizing device). Additionally, the hoop fibers can advantageously provide low hoop stiffness until the fibers are placed under a tensile load, at which point the hoop fibers can suddenly exhibit high hoop stiffness.

In some embodiments, the outermost layer 101 can include a lubrication, coating and/or powder (e.g., talcum powder) on the outer surface thereof to improve sliding of the rigidizing device through the anatomy. The coating can be hydrophilic (e.g., a Hydromer® coating or a Surmodics® coating) or hydrophobic (e.g., a fluoropolymer). The coating can be applied, for example, by dipping, painting, or spraying the coating thereon.

The innermost layer 115 can similarly include a lubrication, coating (e.g., hydrophilic or hydrophobic coating), and/or powder (e.g., talcum powder) on the inner surface thereof configured to allow the bordering layers to more easily shear relative to each other, particularly when no vacuum is applied to the rigidizing device 100, to maximize flexibility.

In some embodiments, the outermost layer 101 can be loose over the radially inward layers. For instance, the inside diameter of layer 101 (assuming it constitutes a tube) may have a diametrical gap of 0"-0.200" with the next layer radially inwards (e.g., with a braid layer). This may give the vacuum rigidized system more flexibility when not under vacuum while still preserving a high rigidization multiple. In other embodiments, the outermost layer 101 may be stretched some over the next layer radially inwards (e.g., the braid layer). For instance, the zero-strain diameter of a tube constituting layer 101 may be from 0-0.200" smaller in diameter than the next layer radially inwards and then stretched thereover. When not under vacuum, this system may have less flexibility than one wherein the outer layer 101 is looser. However, it may also have a smoother outer appearance and be less likely to tear during use.

In some embodiments, the outermost layer 101 can be loose over the radially inward layers. A small positive pressure may be applied underneath the layer 101 in order to gently expand layer 101 and allow the rigidizing device to bend more freely in the flexible configuration. In this embodiment, the outermost layer 101 can be elastomeric and can maintain a compressive force over the braid, thereby imparting stiffness. Once positive pressure is supplied (enough to nominally expand the sheath off of the braid, for example, 2 psi), the outermost layer 101 is no longer is a contributor to stiffness, which can enhance baseline flexibility. Once rigidization is desired, positive pressure can be replaced by negative pressure (vacuum) to deliver stiffness.

A vacuum can be carried within rigidizing device 100 from minimal to full atmospheric vacuum (e.g., approximately 14.7 psi). In some embodiments, there can be a bleed valve, regulator, or pump control such that vacuum is bled down to any intermediate level to provide a variable stiffness capability. The vacuum pressure can advantageously be used to rigidize the rigidizing device structure by compressing the layer(s) of braided sleeve against neighboring layers. Braid is naturally flexible in bending (i.e., when bent normal to its longitudinal axis), and the lattice structure formed by the interlaced strands distort as the sleeve is bent in order for the braid to conform to the bent shape while resting on the inner layers. This results in lattice geometries where the corner angles of each lattice element change as the braided sleeve bends. When compressed between conformal materials, such as the layers described herein, the lattice elements become locked at their current angles and have enhanced capability to resist deformation upon application of vacuum, thereby rigidizing the entire structure in bending when vacuum is applied. Further, in some embodiments, the hoop fibers through or over the braid can carry tensile loads that help to prevent local buckling of the braid at high applied bending load.

The stiffness of the rigidizing device 100 can increase from 2-fold to over 30-fold, for instance 10-fold, 15-fold, or 20-fold, when transitioned from the flexible configuration to the rigid configuration. In one specific example, the stiffness of a rigidizing device similar to rigidizing device 100 was tested. The wall thickness of the test rigidizing device was 1.0 mm, the outer diameter was 17 mm, and a force was applied at the end of a 9.5 cm long cantilevered portion of the rigidizing device until the rigidizing device deflected 10 degrees. The forced required to do so when in flexible mode was only 30 grams while the forced required to do so in rigid (vacuum) mode was 350 grams.

In some embodiments of a vacuum rigidizing device 100, there can be only one braid layer. In other embodiments of a vacuum rigidizing device 100, there can be two, three, or more braid layers. In some embodiments, one or more of the radial gap layers or slip layers of rigidizing device 100 can be removed. In some embodiments, some or all of the slip layers of the rigidizing device 100 can be removed.

The braid layers described herein can act as a variable stiffness layer. The variable stiffness layer can include one or more variable stiffness elements or structures that, when activated (e.g., when vacuum is applied), the bending stiffness and/or shear resistance is increased, resulting in higher rigidity. Other variable stiffness elements can be used in addition to or in place of the braid layer. In some embodiments, engagers can be used as a variable stiffness element, as described in International Patent Application No. PCT/US2018/042946, filed Jul. 19, 2018, titled "DYNAMICALLY RIGIDIZING OVERTUBE," the entirety of which is incorporated by reference herein. Alternatively or additionally, the variable stiffness element can include particles or granules, jamming layers, scales, rigidizing axial members, rigidizers, longitudinal members or substantially longitudinal members.

Figure 4A:
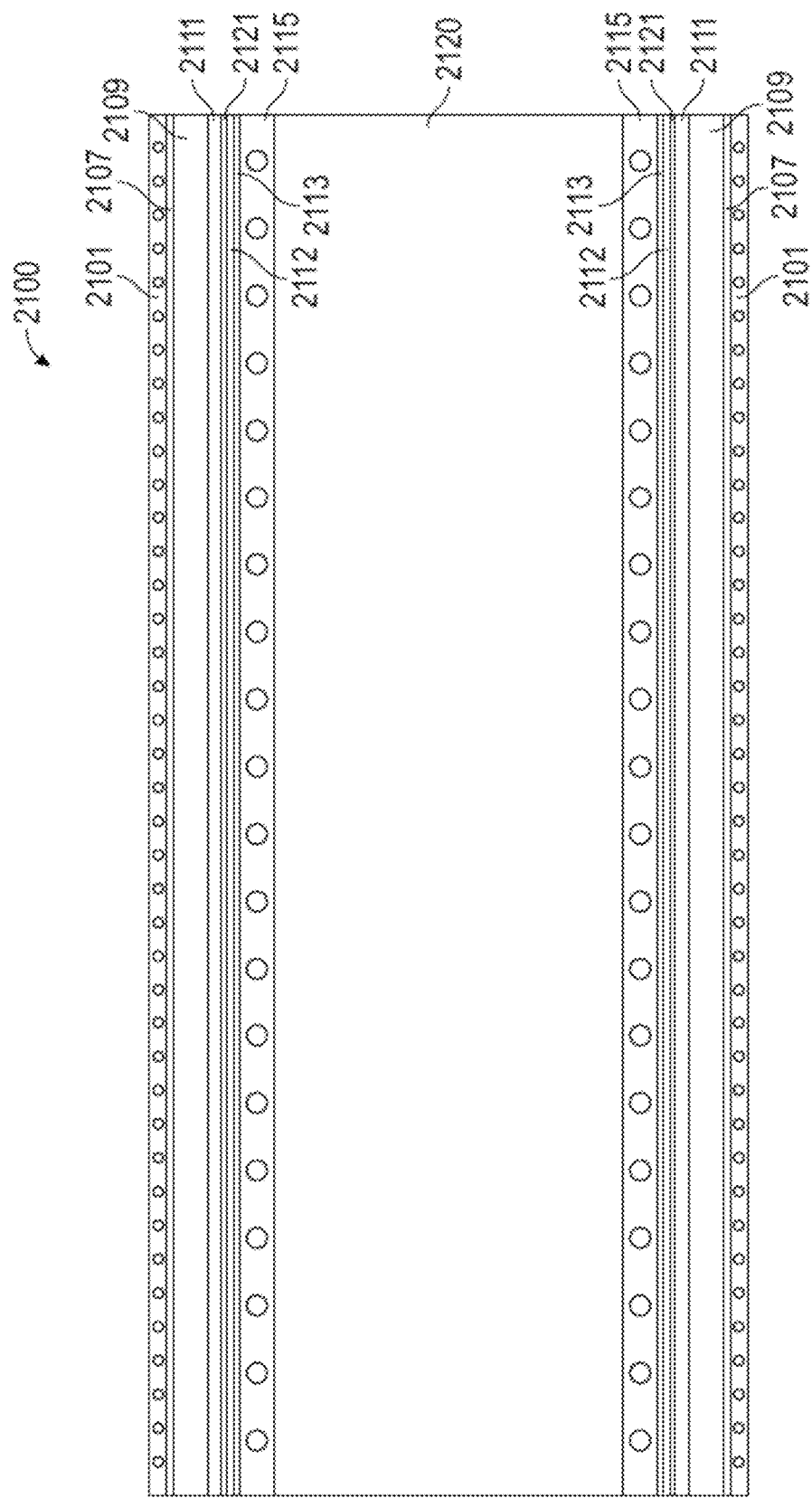
FIGS. 4A-4B show an exemplary pressure rigidizing device.
Figure 4B:
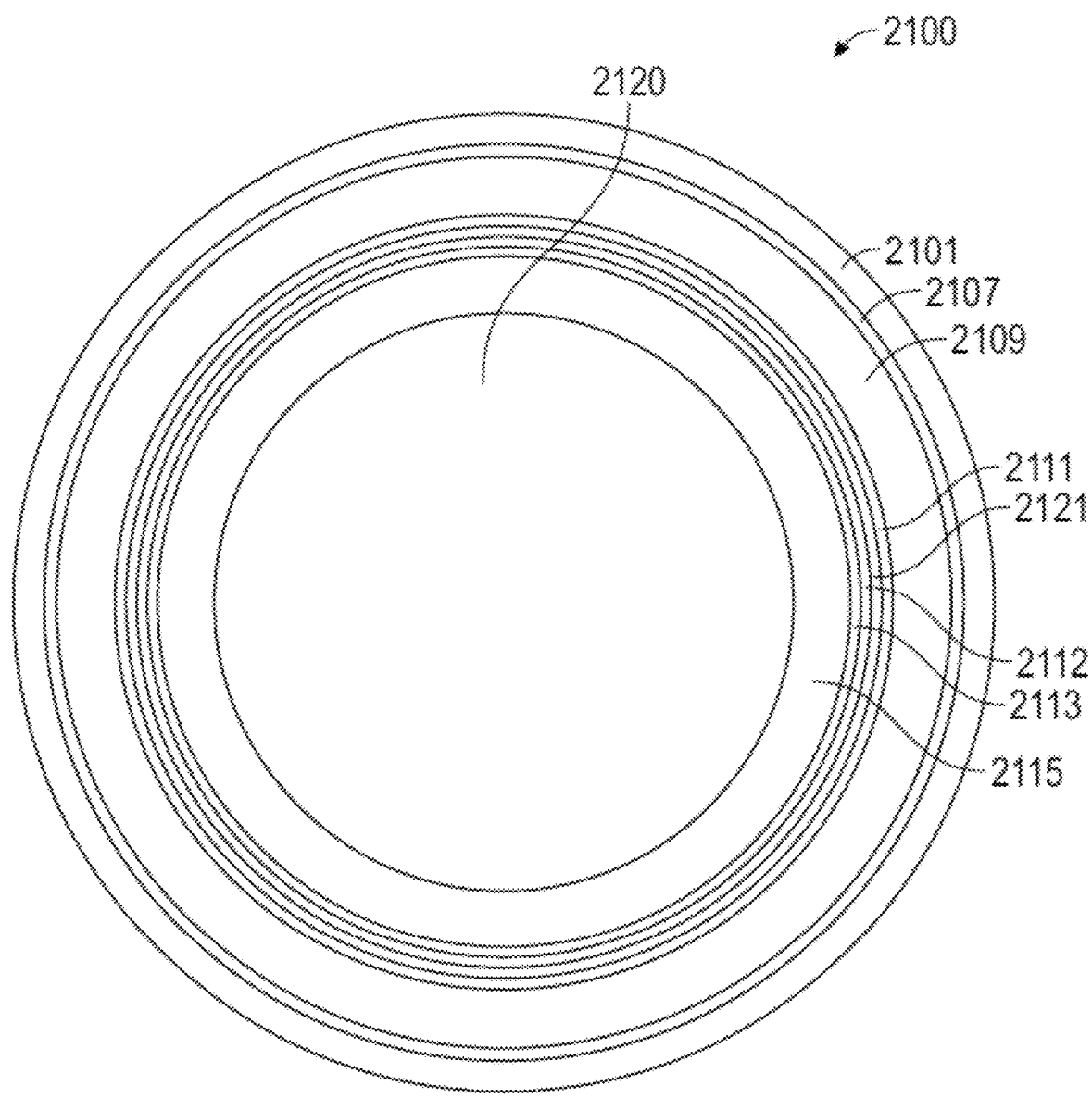

In some embodiments, the rigidizing devices described herein can rigidize through the application of pressure rather than vacuum. For example, referring to FIGS. 4A-4B, the rigidizing device 2100 can be similar to rigidizing device 100 except that it can be configured to hold pressure (e.g., of greater than 1 atm) therein for rigidization rather than vacuum. The rigidizing device 2100 can thus include a plurality of layers positioned around the lumen 2120 (e.g., for placement of an instrument or endoscope therethrough). The rigidizing device 2100 can include an innermost layer 2115 (similar to innermost layer 115), a slip layer 2113 (similar to slip layer 113), a pressure gap 2112, a bladder layer 2121, a gap layer 2111 (similar to gap layer 111), a braid layer 2109 (similar to braid layer 109) or other variable stiffness layer as described herein, a gap layer 2107 (similar to layer 107), and an outermost containment layer 2101.

The pressure gap 2112 can be a sealed chamber that provides a gap for the application of pressure to layers of rigidizing device 2100. The pressure can be supplied to the pressure gap 2112 using a fluid or gas inflation/pressure media. The inflation/pressure media can be water or saline or, for example, a lubricating fluid such as soil or glycerin. The lubricating fluid can, for example, help the layers of the rigidizing device 2100 flow over one another in the flexible configuration. The inflation/pressure media can be supplied to the gap 2112 during rigidization of the rigidizing device 2100 and can be partially or fully evacuated therefrom to transform the rigidizing device 2100 back to the flexible configuration. In some embodiments, the pressure gap 2112 of the rigidizing device 2100 can be connected to a pre-filled pressure source, such as a pre-filled syringe or a pre-filled insufflator, thereby reducing the physician's required set-up time.

The bladder layer 2121 can be made, for example, of a low durometer elastomer (e.g., of shore 20 A to 70 A) or a thin plastic sheet. The bladder layer 2121 can be formed out of a thin sheet of plastic or rubber that has been sealed lengthwise to form a tube. The lengthwise seal can be, for instance, a butt or lap joint. For instance, a lap joint can be formed in a lengthwise fashion in a sheet of rubber by melting the rubber at the lap joint or by using an adhesive. In some embodiments, the bladder layer 2121 can be 0.0002-0.020" thick, such as approximately 0.005" thick. The bladder layer 2121 can be soft, high-friction, stretchy, and/or able to wrinkle easily. In some embodiments, the bladder layer 2121 is a polyolefin or a PET. The bladder 2121 can be formed, for example, by using methods used to form heat shrink tubing, such as extrusion of a base material and then wall thinning with heat, pressure and/or radiation. When pressure is supplied through the pressure gap 2112, the bladder layer 2121 can expand through the gap layer 2111 to push the braid layer 2109 against the outermost containment layer 2101 such that the relative motion of the braid strands is reduced.

The outermost containment layer 2101 can be a tube, such as an extruded tube. Alternatively, the outermost containment layer 2101 can be a tube in which a reinforcing member (for example, metal wire, including round or rectangular cross-sections) is encapsulated within an elastomeric matrix, similar to as described with respect to the innermost layer for other embodiments described herein. In some embodiments, the outermost containment layer 2101 can include a helical spring (e.g., made of circular or flat wire), and/or a tubular braid (such as one made from round or flat metal wire) and a thin elastomeric sheet that is not bonded to the other elements in the layer. The outermost containment layer 2101 can be a tubular structure with a continuous and smooth surface. This can facilitate an outer member that slides against it in close proximity and with locally high contact loads (e.g., a nested configuration as described further herein). Further, the outer layer 2101 can be configured to support compressive loads, such as pinching. Additionally, the outer layer 2101 (e.g., with a reinforcement element therein) can be configured to prevent the rigidizing device 2100 from changing diameter even when pressure is applied.

Because both the outer layer 2101 and the inner layer 2115 include reinforcement elements therein, the braid layer 2109 can be reasonably constrained from both shrinking diameter (under tensile loads) and growing in diameter (under compression loads).

By using pressure rather than vacuum to transition from the flexible state to the rigid state, the rigidity of the rigidizing device 2100 can be increased. For example, in some embodiments, the pressure supplied to the pressure gap 2112 can be between 1 and 40 atmospheres, such as between 2 and 40 atmospheres, such as between 4 and 20 atmospheres, such as between 5 and 10 atmospheres. In some embodiments, the pressure supplied is approximate 2 atm, approximately 4 atmospheres, approximately 5 atmospheres, approximately 10 atmospheres, approximately 20 atmospheres. In some embodiments, the rigidizing device 2100 can exhibit change in relative bending stiffness (as measured in a simple cantilevered configuration) from the flexible configuration to the rigid configuration of 2-100 times, such as 10-80 times, such as 20-50 times. For example, the rigidizing device 2100 can have a change in relative bending stiffness from the flexible configuration to the rigid configuration of approximately 10, 15, 20, or 25, 30, 40, 50, or over 100 times.

Figure 5:
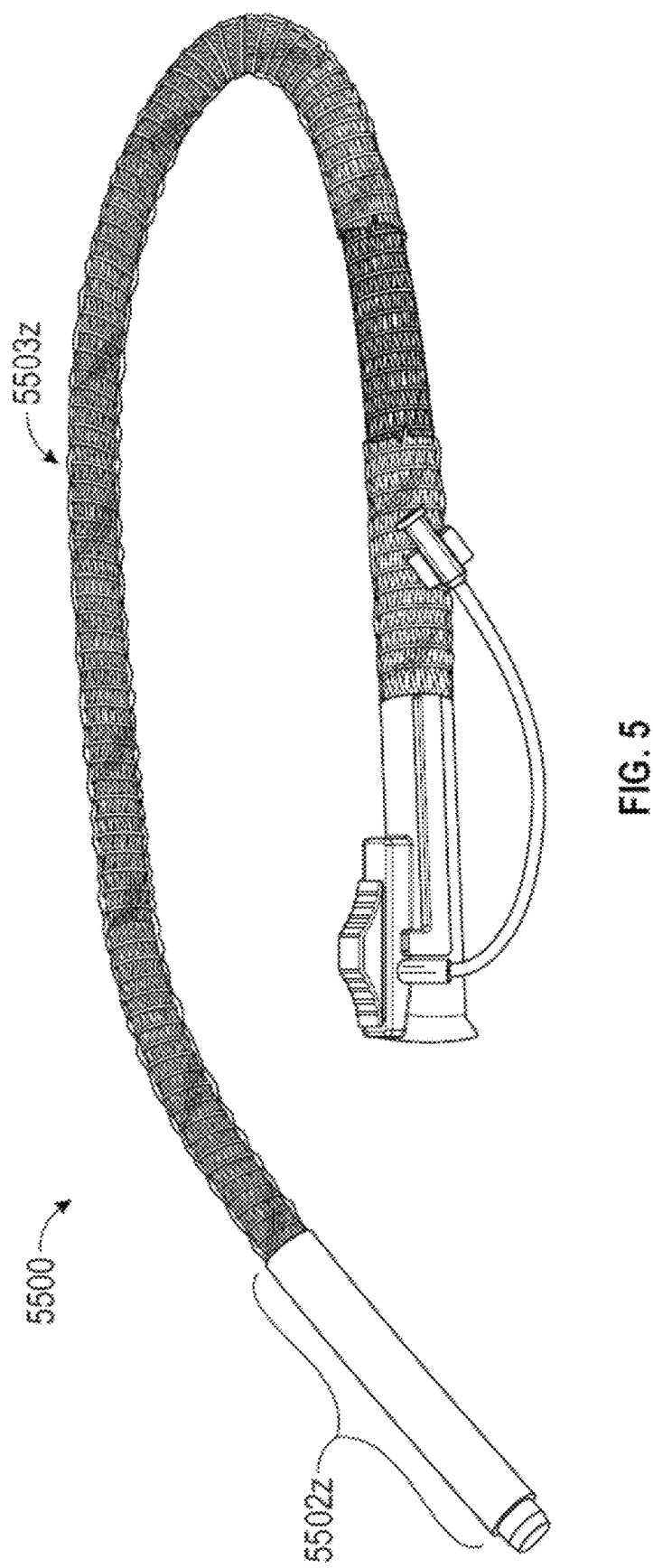
FIG. 5 shows a rigidizing device with a distal end section.

Any of the rigidizing devices described herein can have a distal end section or sections with a different design that the main elongate body of the rigidizing device. As shown in FIG. 5, for example, rigidizing device 5500 can have a main elongate body 5503z and a distal end section 5502z. Only the distal end section 5502z, only the main elongate body 5503z, or both the distal end section 5502z and the main elongate body 5503z can be rigidizing as described herein (e.g., by vacuum and/or pressure). In some embodiments, one section 5502z, 5503z is activated by pressure and the other section 5502z, 5503z is activated by vacuum. In other embodiments, both sections 5502z, 5503z are activated by pressure or vacuum, respectively.

Figure 6:
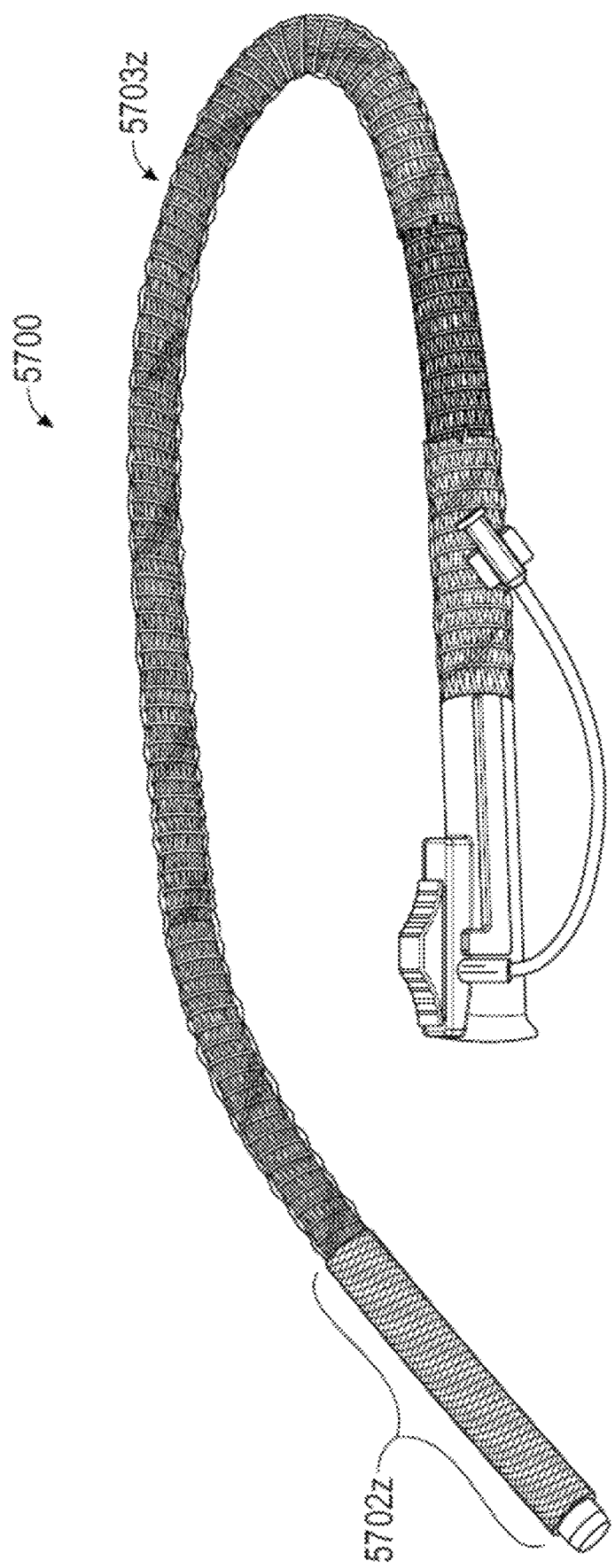
FIG. 6 shows a rigidizing device with a distal end section having a separate braid pattern from the proximal section of the device.

Referring to FIG. 6, in some embodiments, the distal section 5702z can include a rigidizing braid that differs from the braid of the main elongate section 5703z. For example, in one embodiment, the braid angle relative to the longitudinal axis in the distal end section 5702z can be greater than the braid angle of the main elongate body 5703z. For instance, the braid angle in distal section may be 40 degrees while the braid angle in the main elongate body may be 20 degrees. The braids may overlap somewhat and be joined with a flexible adhesive. These designs may give the distal end section 5702z more bending flexibility in a non-rigidized state than the main elongate section 5703z. Having a more flexible distal tip can, for example, advantageously prevent buckling and drag at the tip (caused by fixing the braid ends) and/or can advantageously provide flexibility during navigation through a body lumen to prevent trauma to the anatomy. In another embodiment, the braid angle relative to the longitudinal axis in the distal end section 5702z can be less than the braid angle of the main elongate body 5703z. This may give distal end section 5702z more stiffness in the rigidized state relative to the main elongate body 5703z. Having more stiffness in the distal end section 5702z can, for example, advantageously provide a stable platform for movement or delivery of a medical device through the central lumen and out the distal end of the rigidizing device 5700.

Figure 7:
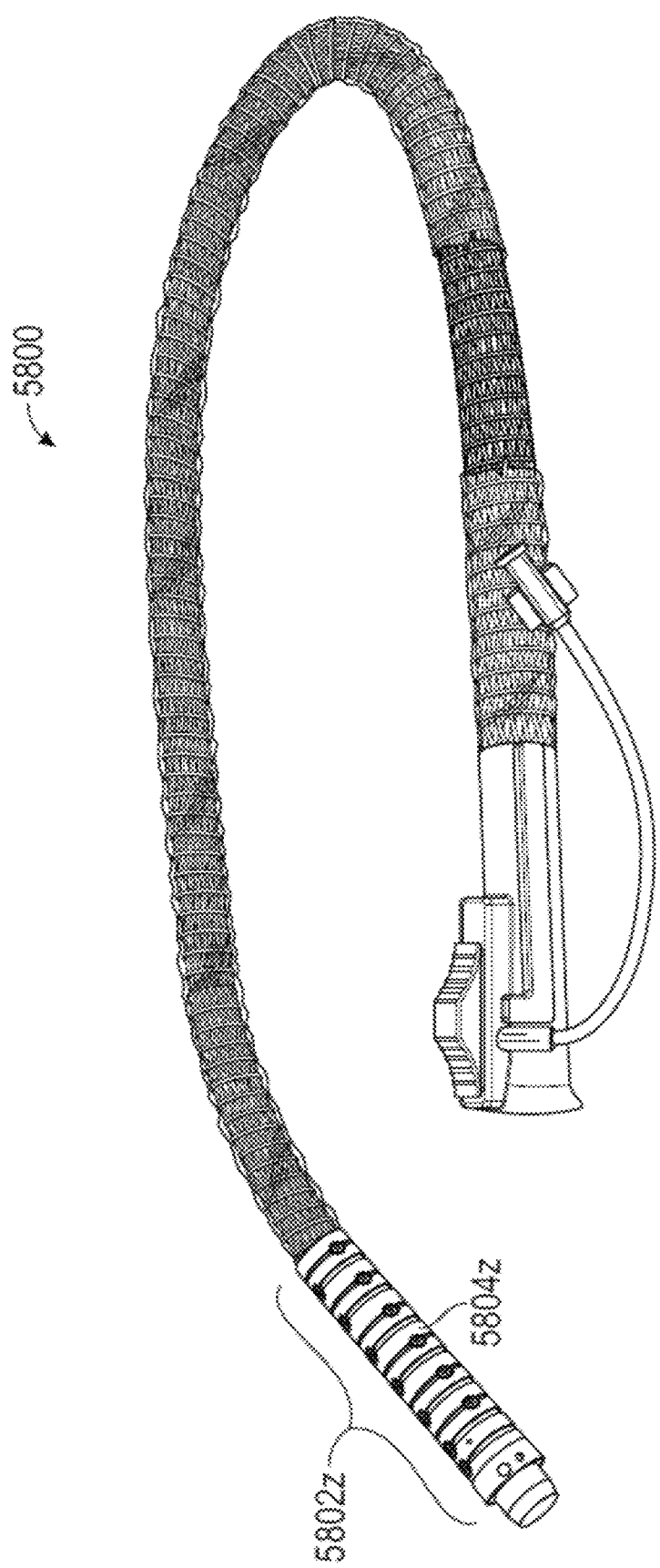
FIG. 7 shows a rigidizing device with a distal end section having a plurality of passive linkages.

Referring to FIG. 7, in some embodiments, the distal end section 5802z can include a plurality of linkages 5804z that are passively activated. The linkages 5804z can be connected together at one or more pivot points and can advantageously provide deterministic bending (i.e., bending in a specific and predetermined direction). Additionally, the linkages 5804z can advantageously provide torsional rigidity to the distal end section 5802z while providing high flexibility for bending. The linkages 5804z can be activated passively, e.g., via flexing as the device 5800 is moved through the anatomy. The distal end section 5802z may, for example, include 1-100 linkages 5804z, such as 1, 2, 4, 6, 8, 10, 16, 20, 30, or 40 links 5504z. In some embodiments, the linkages 5804z can be formed by passively cut flexures, such as laser cut tubes or stents.

Figure 8:
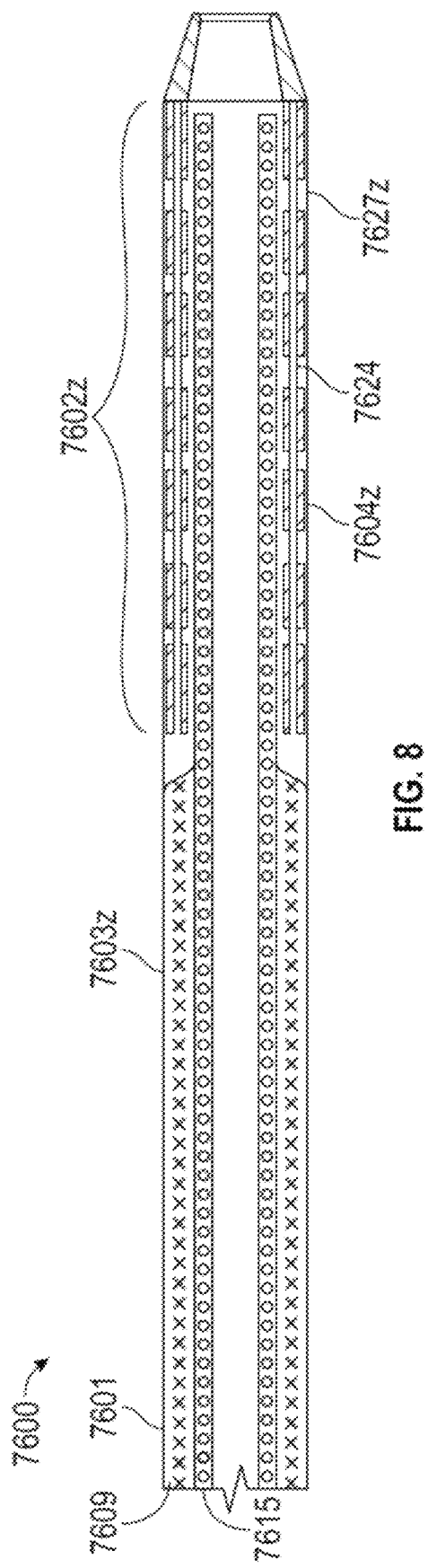
FIG. 8 shows a rigidizing device with a distal end section having a plurality of actively controlled linkages.

Referring to FIG. 8, in other embodiments, the distal end section 7602z can include a plurality of linkages 7604z that are actively controlled, such as via cables 7624, for steering of the rigidizing device 7600. The device 7600 is similar to device 5800 except that it includes cables 7624 configured to control movement of the device. While the passage of the cables 7624 through the rigidizing elongate body 7603z (i.e., with outer wall 7601, braid layer 7609, and inner layer 7615) is not shown in FIG. 26, the cables 7624 can extend therethrough in any manner as described elsewhere herein. In some embodiments, one or more layers of the rigidizing elongate body 7603z can continue into the distal end section 7602z. For example, and as shown in FIG. 26, the inner layer 7615 can continue into the distal end section 7602z, e.g., can be located radially inwards of the linkages 7604z. Similarly, any of the additional layers from the rigidizing proximal section (e.g., the braid layer 7609 or the outer layer 7601 may be continued into the distal section 7602z and/or be positioned radially inwards of the linkages 7604z). In other embodiments, none of the layers of the rigidizing elongate body 7603z continue into the distal section 7602z. The linkages 7604z (and any linkages described herein) can include a covering 7627z thereover. The covering 7627z can advantageously make the distal section 7602z atraumatic and/or smooth. The covering 7627z can be a film, such as expanded PTFE. Expanded PTFE can advantageously provide a smooth, low friction surface with low resistance to bending but high resistance to buckling.

FIGS. 9A-E show another exemplary distal end section 4302z that includes a plurality of linkages 4304z that are actively controlled, such as via cables 4324, for steering of the rigidizing device. In some embodiments, the pivots for the linkages 4304z can be involutes, similar to gear teeth, as shown in FIGS. 9A-E, to reduce the local contact drag. The cables 4324 can be positioned within cable guides (e.g., jackets or coil pipes) that extend the length of the rigidizing device. In some embodiments, the cables 4324 (and cable guides) can extend within the wall of the rigidizing device. The cable guides can advantageously ensure that tensile load is carried through the cable guide, rather than through the wall of the rigidizing device, so that the structure of the wall is not adversely deflected as the load is applied to the linkages 4304z. In some embodiments, the cable guides and cables 4324 can have excess length to account for bending of the rigidizing device. This excess length can, for example, be woven or curled within the wall of the rigidizing device. Further, the cables 4324 can run through apertures and/or grooves in the linkages 4304z (see, e.g., FIG. 9C) while remaining otherwise free to float within the wall (and thereby to account for bending of the rigidizing device. As the cables 4324 are activated, the linkages 4304z pivot relative to one another, thereby providing steering for the distal end section of a rigidizing device. Articulation of the linkages 4304z and cables 4324 for steering can be achieved by actuators (e.g., local motors, current-activated (heat) nitinol wires, proximal actuators (typically stainless steel, tungsten, or composites), hydraulics, and/or EAP (electro-active polymers)). Such steering mechanisms can advantageously provide increased clinical utility. Further, such steering allows the device that is positioned through the central lumen (for example, an endoscope or a guidewire) be steered towards and more easily reach the desired anatomical location.

Figure 10:
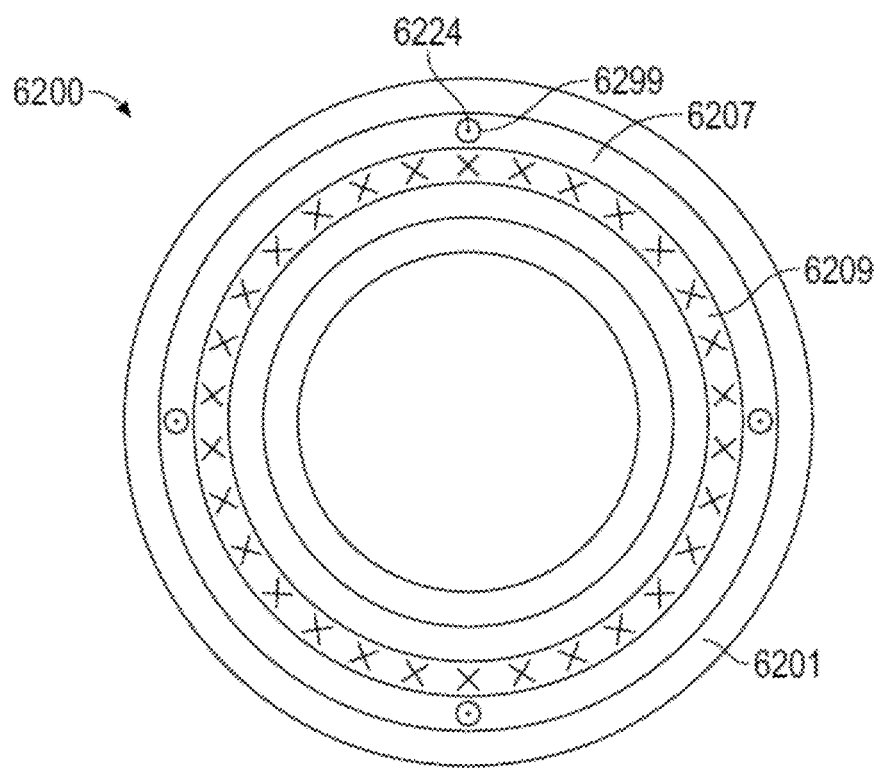
FIG. 10 shows one embodiment of a rigidizing device including cables extending within the layered wall.

When cables are used for steering the distal end section, the cables (which can be in cable guides or not) can be routed through the wall of the rigidizing devices described herein in a number of different ways. FIGS. 10-21B show exemplary configurations of rigidizing devices with cable guides (some wall layers have been omitted in FIGS. 10-21B for clarity). For example, FIG. 10 shows a rigidizing device 6200 having cables 6224 extending in cable guides 6299 within the outer radial gap layer 6207 (and thus between the braid layer 6209 and the outer layer 6201). In some embodiments, each of the cables 6224 and cable guides 6299 can be positioned approximately equidistant around the circumference (i.e., approximately 90 degrees away from neighboring cables when four cables are used). In other embodiments, one or more of the cables 6224 and cable guides 6299 can be grouped closely together (e.g., within the same quadrant) rather than spaced apart. Further, in some embodiments, the cables 6224 and/or guides 6299 can be asymmetrically positioned around the circumference of the rigidizing device 6200.

Figure 11:
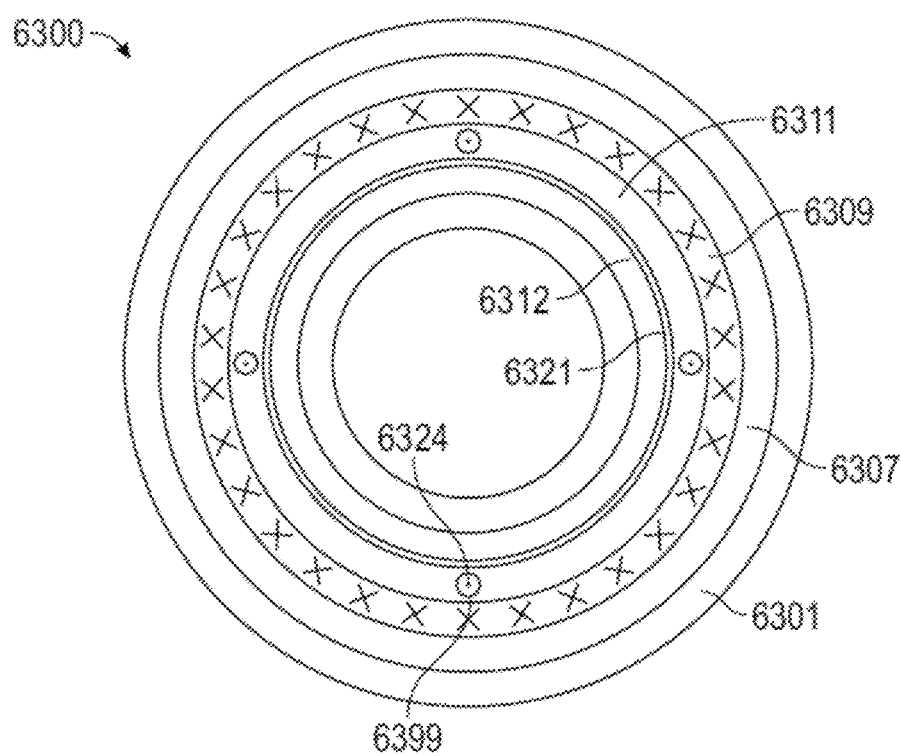
FIG. 11 shows one embodiment of a rigidizing device including cables extending within the layered wall.

FIG. 11 shows a rigidizing device 6300 in which the cables 6324 and cable guides 6399 are positioned within the inner radial gap layer 6311 (and thus between the braid layer 6309 and the inner layers of the rigidizing device, such as the bladder 6321). When, for example, pressure is supplied to pressure gap 6312, the bladder 6321 can push against the braid layer 6309, and the braid layer and correspondingly push against the outer layer 6301 without the braid layer 6309 squeezing or otherwise impacting the cables 6324. Again, the cables 6324 and cable guides can be positioned equidistant or asymmetrically about the circumference of the rigidizing device 6300.

Figure 12:
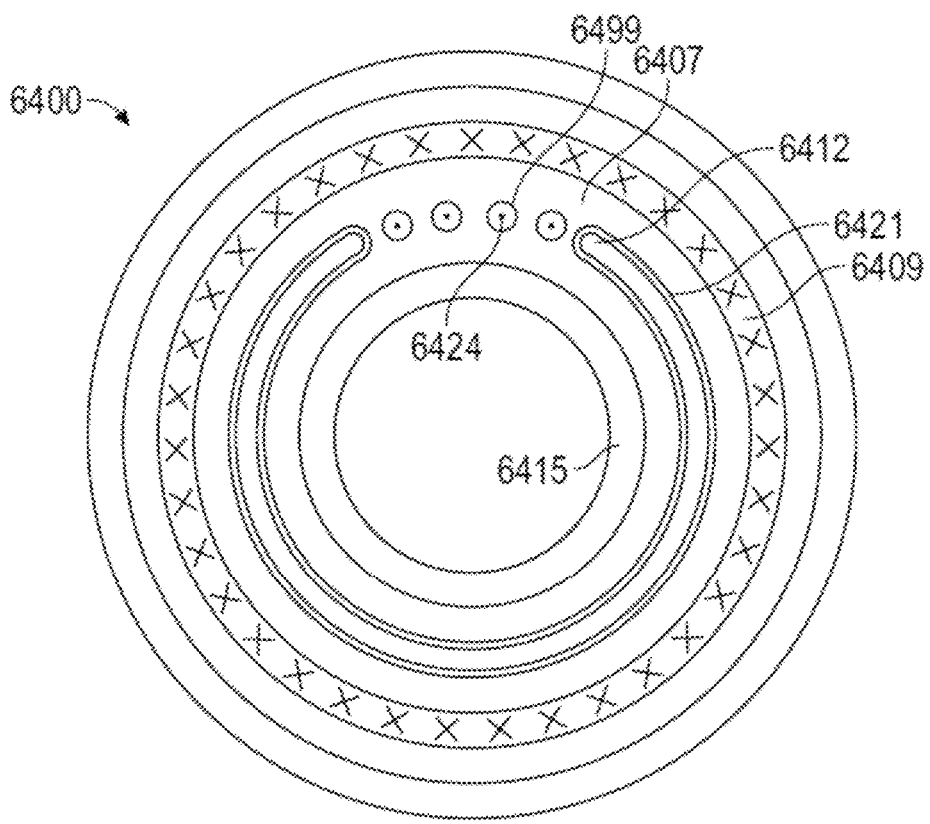
FIG. 12 shows one embodiment of a rigidizing device including cables extending within the layered wall.

Referring to FIG. 12, in some embodiments, the rigidizing device 6400 can have cables 6424 and cable guides 6499 at least partially separated from the pressurized or vacuum zone. For example, as shown in FIG. 12, a tubular bladder layer 6421 can surround the pressure gap 6412. Some or all of the cables 6424 and cable guides 6499 can be positioned in the gap 6407 between the inner layer 6415 and the braid layer 6409 and circumferentially adjacent to the tubular bladder layer 6421. Advantageously, in this configuration, the cables 6424 and cable guides 6499 can both be minimally impacted by pressurization of the bladder layer 6421 and provide substantially no additive stack height or thickness to the wall.

Figure 13:
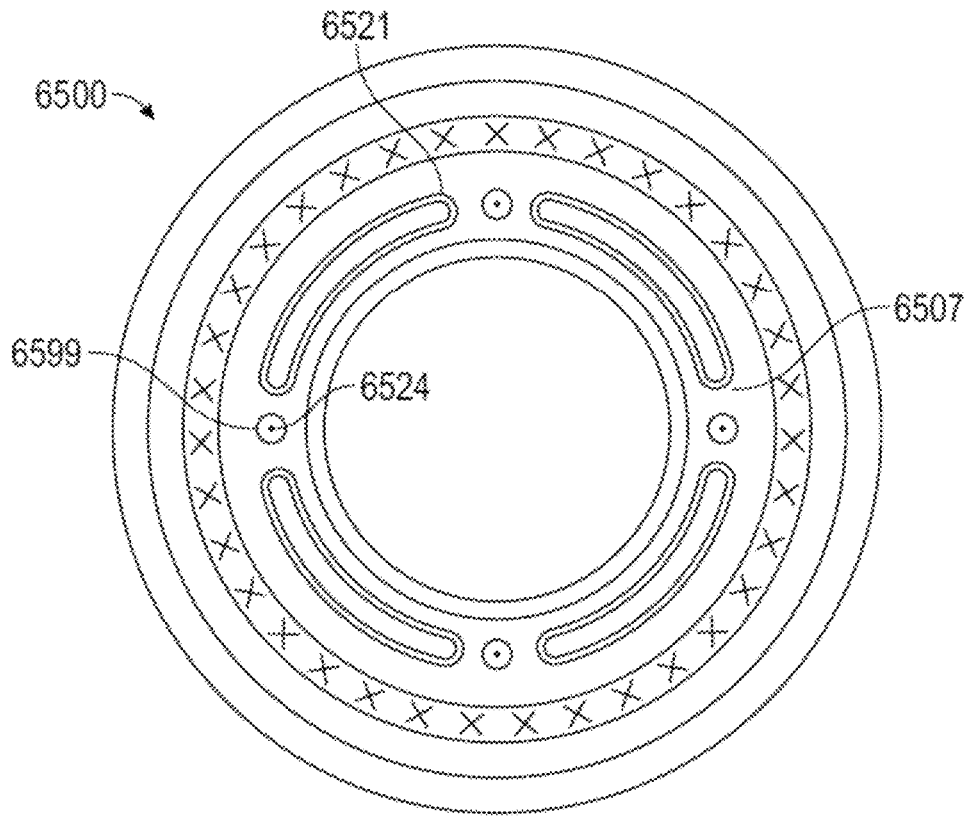
FIG. 13 shows one embodiment of a rigidizing device including cables extending within the layered wall.

Referring to FIG. 13, in some embodiments, the rigidizing device 6500 can include a plurality of tubular bladders 6521 spaced circumferentially apart such that each cable 6524 and cable guide 6599 can fit in the gap 6507 between adjacent tubular bladders 6521.

Figure 14:
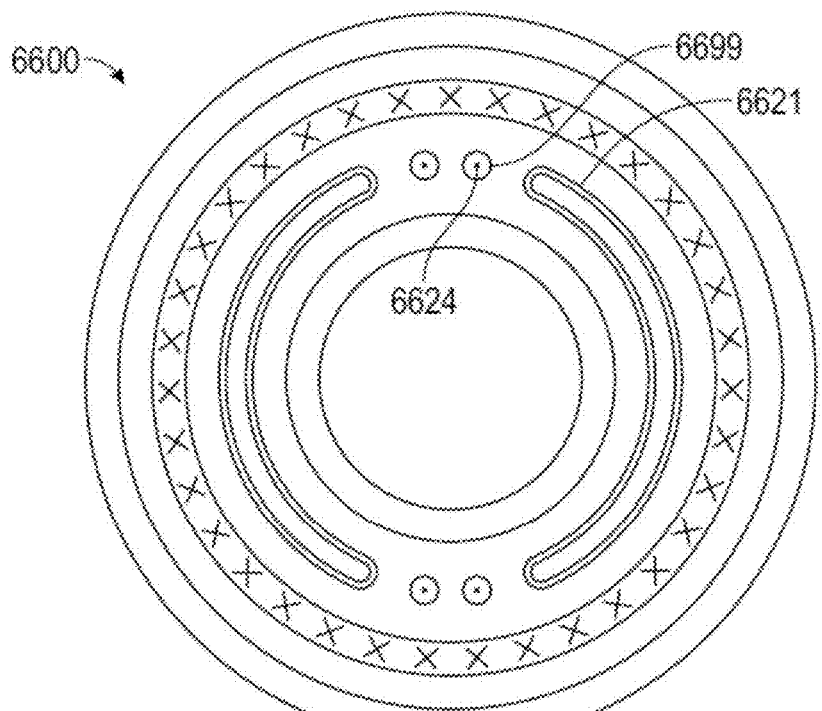
FIG. 14 shows one embodiment of a rigidizing device including cables extending within the layered wall.

Referring to FIG. 14, rigidizing device 6600 is similar to device 6500 except that cables 6624 and guides 6699 are grouped in pairs to reduce the number of tubular bladders 6621 necessary (e.g., there can be two tubular bladders 6621 and a two pair of cables 6624 and guides 6699 positioned therebetween).

Figure 15:
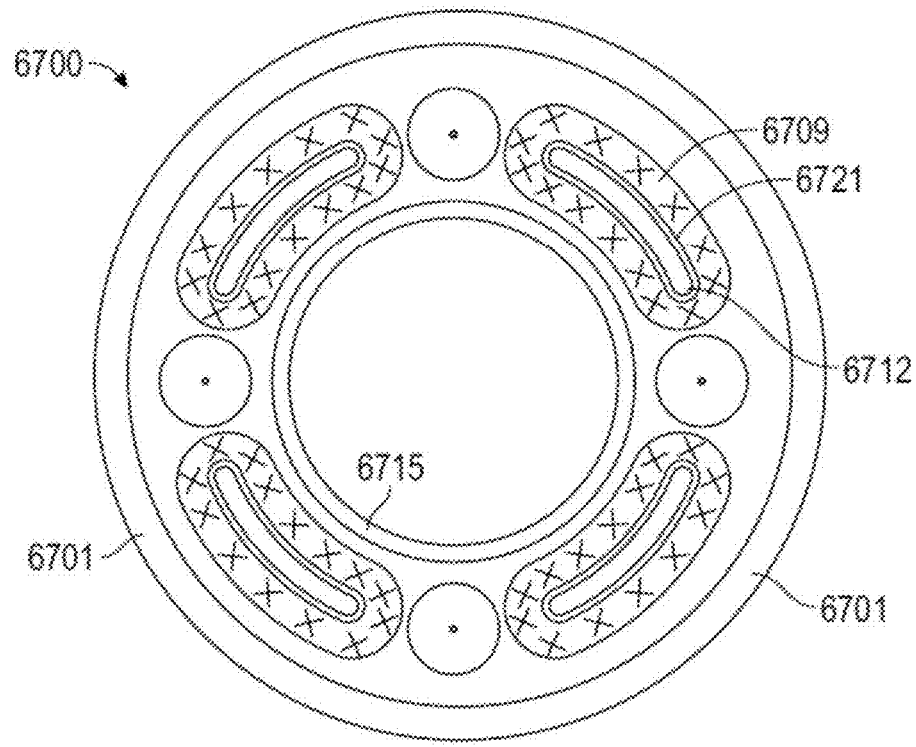
FIG. 15 shows one embodiment of a rigidizing device including cables extending within the layered wall.

Referring to FIG. 15, rigidizing device 6700 is similar to device 6500 except that each tubular bladder 6721 includes a tubular braid layer 6709 therearound (i.e., rather than having a single braid layer 6509 as with device 6500). As pressurizing medium is provided to pressure gaps 6712, the bladder 6721 can expand to press each individual tubular braid 6709, which can expand to press against the inner and outer layers 6715, 6701. Alternately, not all of the bladders can be pressurized at the same time (for instance, just 1 or 2) such that the device is only stiffened partway around the circumference. This may create stiffness along only a portion of the device, while still enabling flexibility amongst the other portion, which may create preferential motion should the device be imparted with a deflection load.

Figure 16:
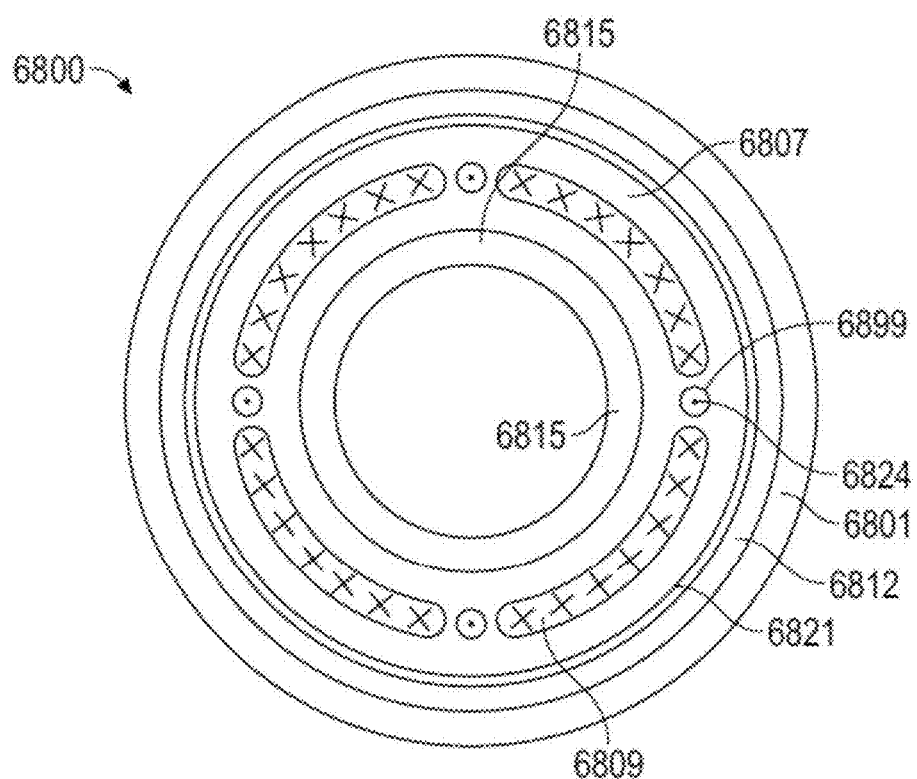
FIG. 16 shows one embodiment of a rigidizing device including cables extending within the layered wall.

Referring to FIG. 16, in some embodiments, a rigidizing device 6800 can include strips of braid layer 6809 (i.e., flat braid rather than tubular braid). Each strip of braid layer 6809 and each cable 6824 and cable guide 6899 can be positioned in the radial gap 6807. Further, the strips of braid layer 6809 can alternate with the cables 6824/6899 so as to minimize the thickness of the wall of the rigidizing device 6800. The bladder 6821 can be positioned radially outwards of the strips of braid layer 6809 and cables 6824/guides 6899. When pressure medium is supplied to the pressure gap 6812, the bladder 6821 can push the strips of braid layer 6809 radially inwards against the innermost layer 6815 to rigidize the device 6800. In other embodiments, the bladder 6821 can be radially inwards of the strips of braid layer 6809 (and cables 6824/guides 6899) and be configured to push the strips of braid layer 6809 against the outer layer 6801.

Figure 17:
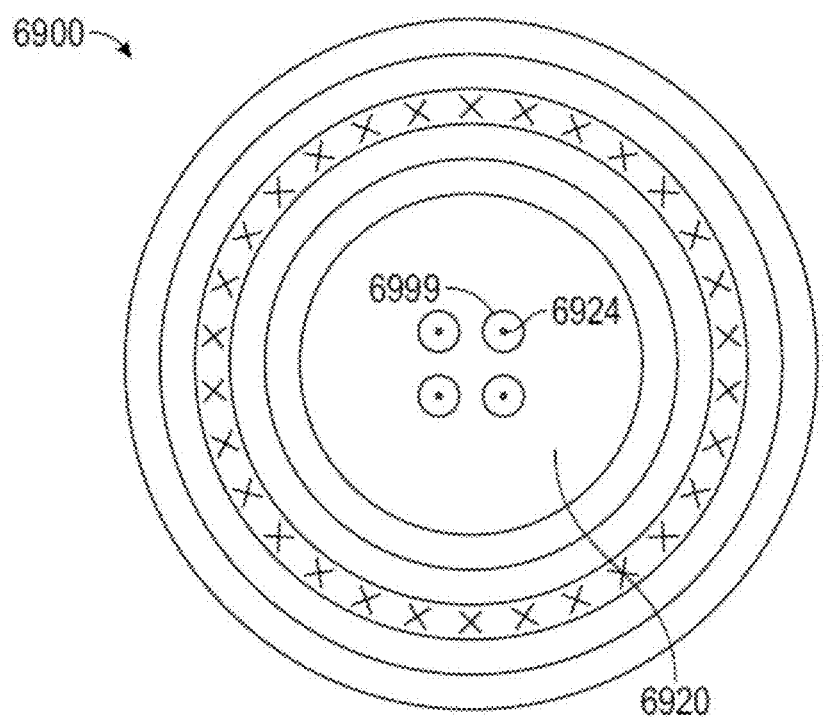
FIG. 17 shows a rigidizing device including cables extending down the central lumen.

In some embodiments, referring to FIG. 17, the cables 6924 and cable guides 6999 can be positioned so as to extend down the central lumen 6920 of the rigidizing device 6900.

Figure 18:
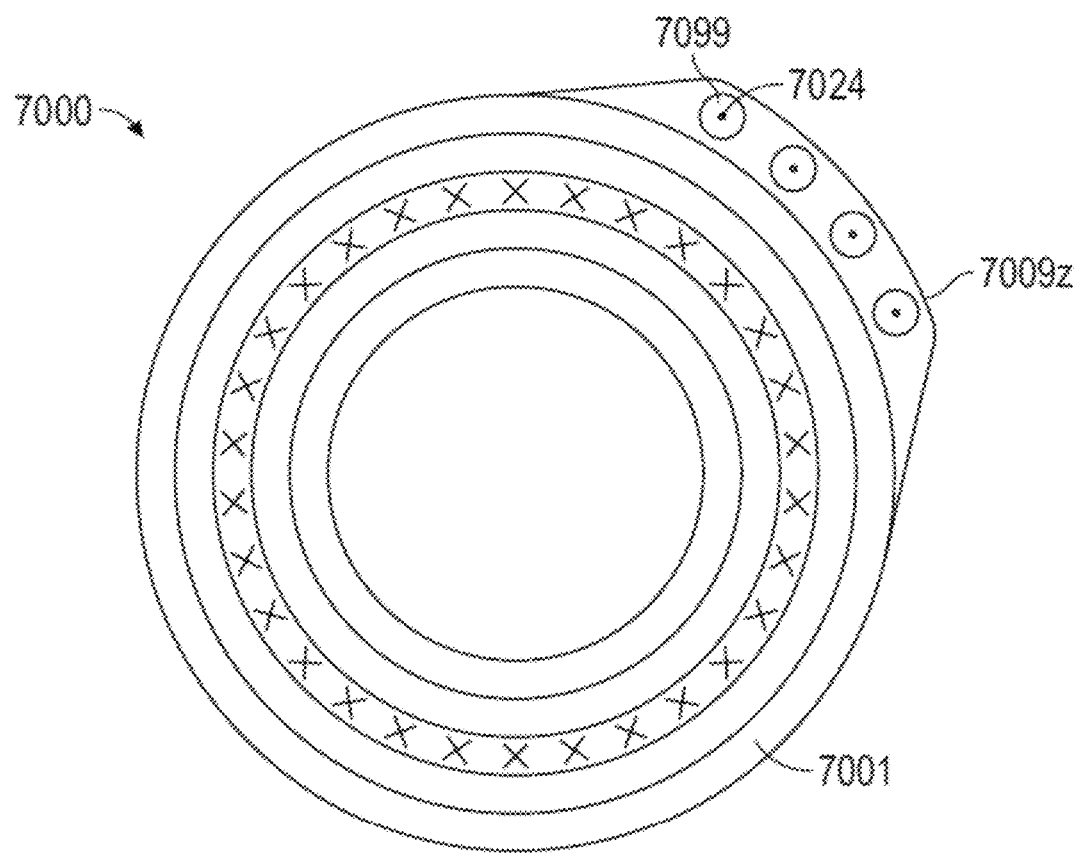
FIG. 18 shows an embodiment of rigidizing device including a cable spiraled therearound.

In some embodiments, referring to FIG. 18, the cables 7024 and cable guides 7099 can be positioned radially outwards of the outer layer 7001. The cables 7024 and guides 7099 can, for example, be positioned in a sheath 7009z that can extend only over the cables 7024 or that can fully encompass the outer layer 7001. The guides 7099 can be only minimally constrained within the sheath 7009z so as to freely bend during movement of the device 7000 (e.g., so as to curl or extend to full length depending on whether the guides 7099 are positioned on the inside or outside of the cure of the rigidizing device 7000 as it bends).

Figure 19:
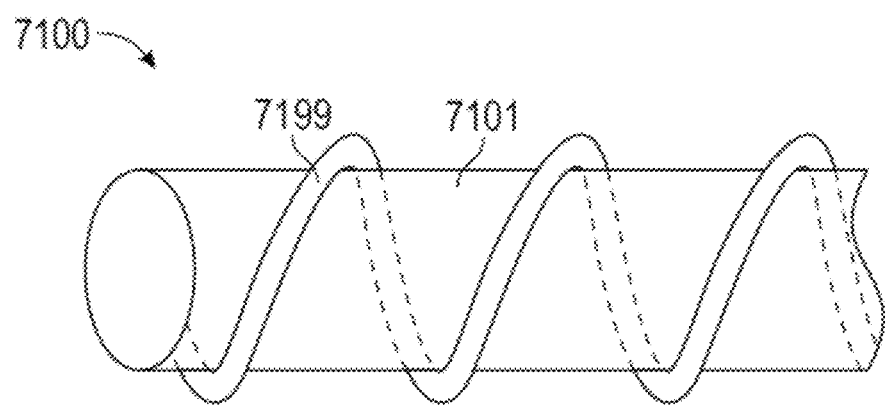
FIG. 19 shows an embodiment of a rigidizing device with a cable spiraled therearound.

Referring to FIG. 19, in some embodiments, a cable guide 7199 (with one or more cables therein) can be spiraled around the outside of the outer layer 7101 of the rigidizing device 7100. Additional cable guides can likewise be spiraled therearound. In some embodiments, the cable guide 7199 can be spiraled around other layers of the rigidizing device 7100, such as around the inner layer.

Figure 20A:
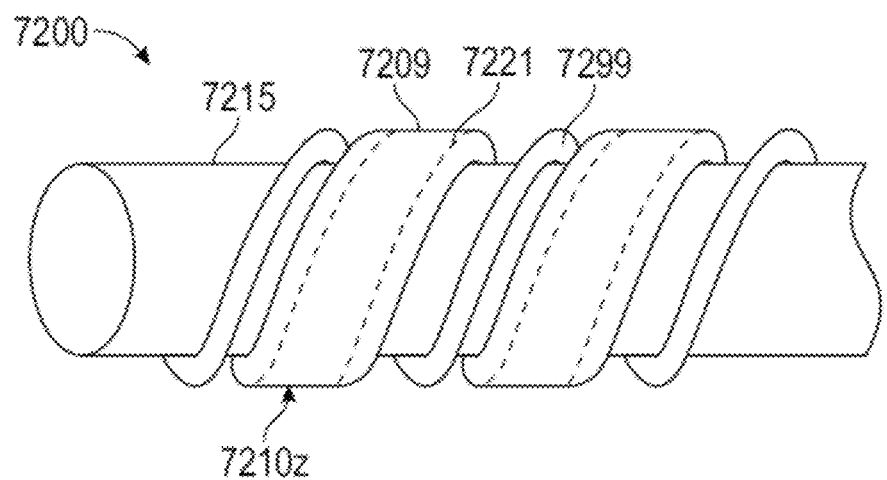
FIGS. 20A-20B show an embodiment of a rigidizing device with a cable spiraled therearound.
Figure 20B:
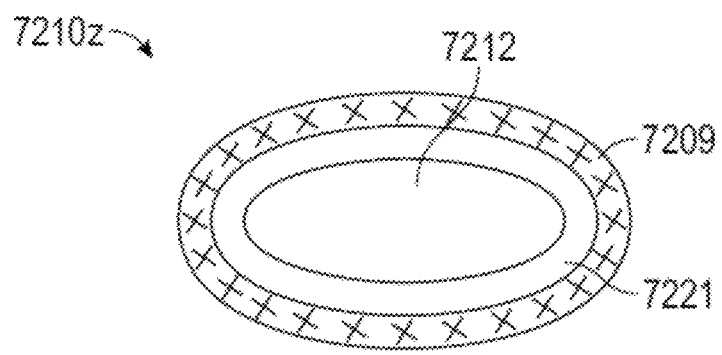

Referring to FIGS. 20A-20B, in some embodiments, a cable guide 7299 (with one or more cables therein) and a tubular element 7210z can be alternately spiraled around the inner layer 7215 (i.e., such that the cable guide 7299 and the tubular element 7210z form approximately a single layer down the length of the rigidizing device 7200. The tubular element 7210z can include an outer tubular braid 7209 with an inner tubular bladder 7221. As pressurizing medium is provided to pressure gap 7212, the bladder 7221 can expand to press outwards on the tubular braid 7209, which can push outwards on the outer layer (not shown for clarity).

Figure 21A:
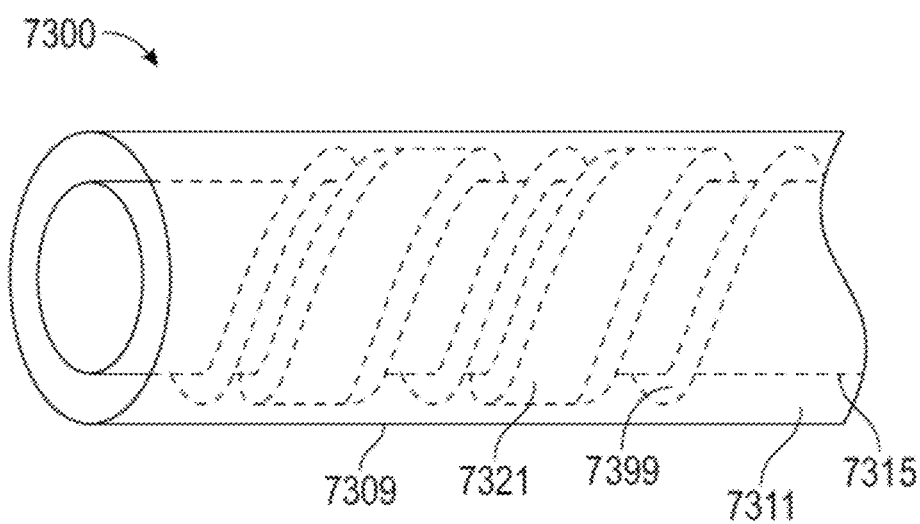
FIGS. 21A-21B show a rigidizing device with a cable spiraled therein.
Figure 21B:
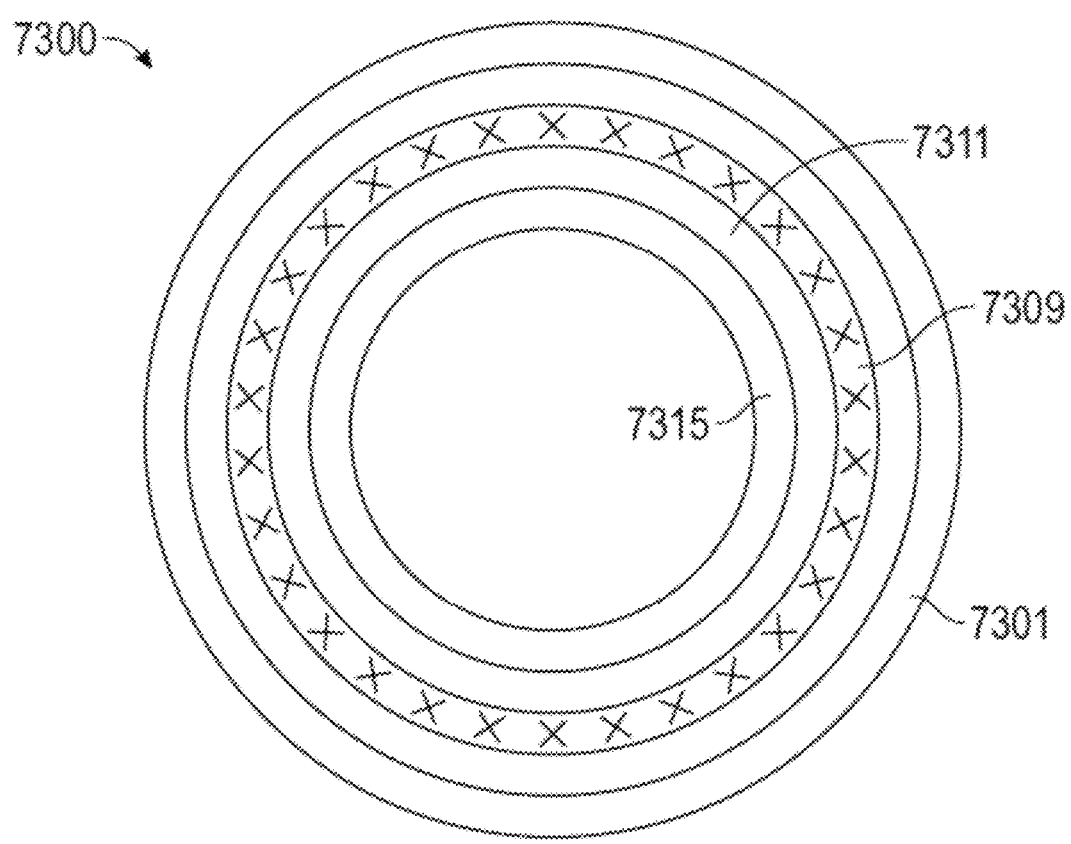
Figure 22A:
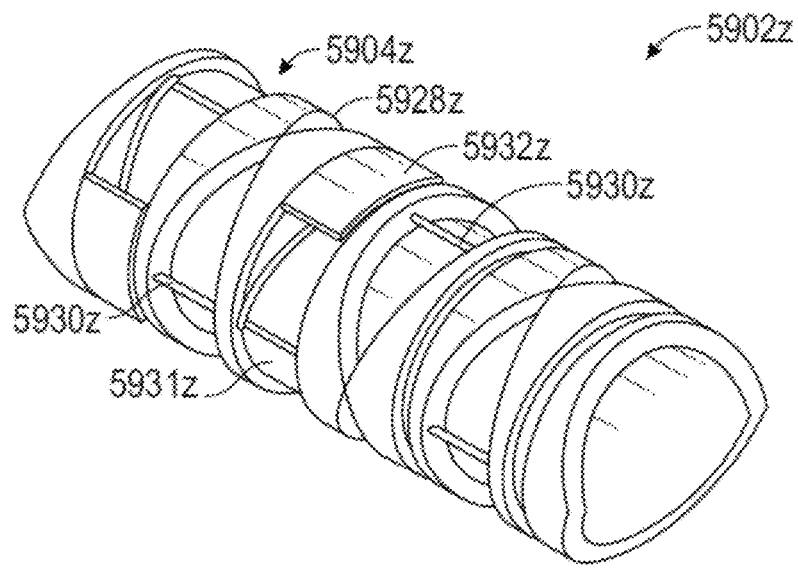
FIGS. 22A-22D show exemplary linkages for a distal end section.
Figure 22B:
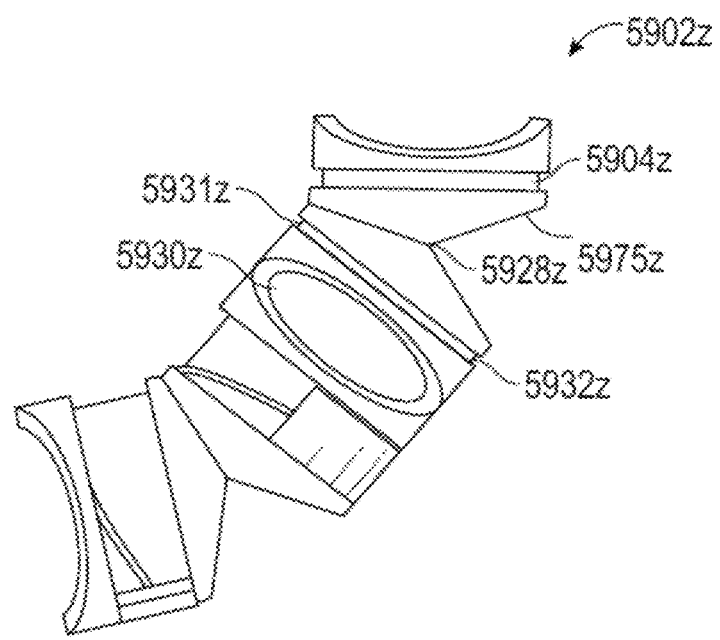
Figure 22C:
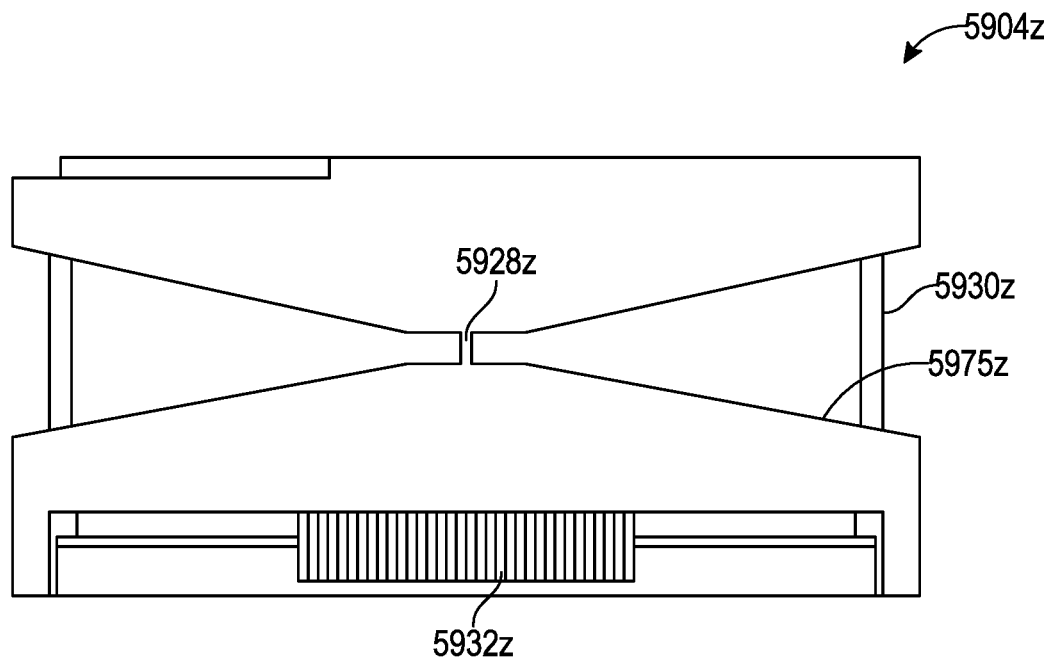
Figure 22D:
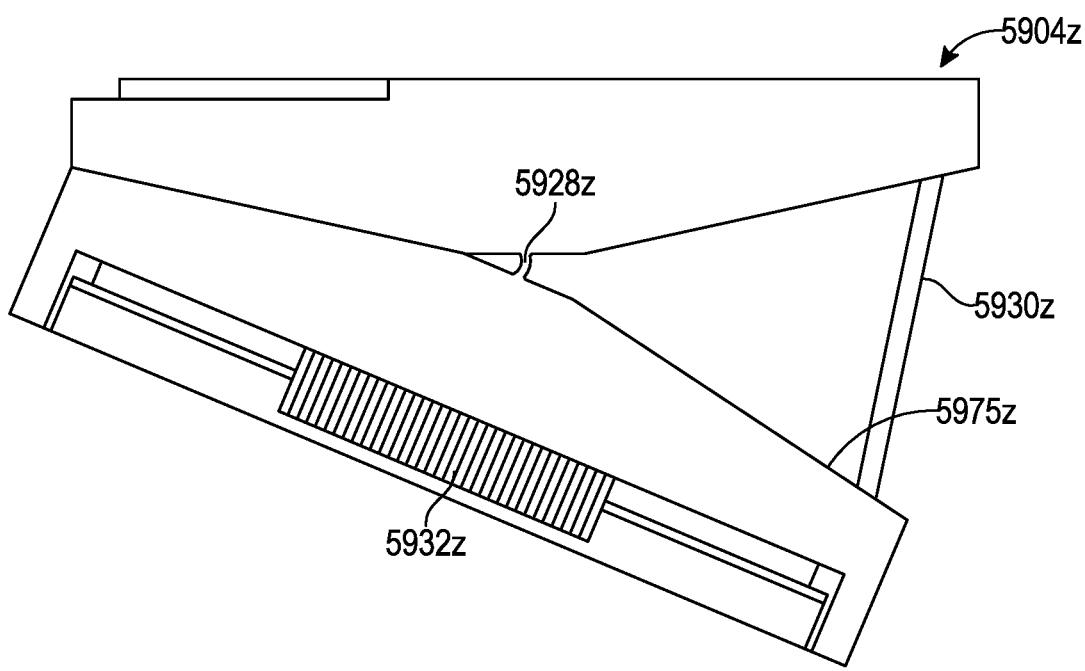

Referring to FIGS. 21A-21B, a rigidizing device 7300 can be similar to device 7200 except that only the cable guide 7399 and a tubular bladder 7321 can be spiraled around the inner layer 7315 within gap 7311 (note that cable guide 7399 and tubular bladder 7321 are not shown in FIG. 21B for clarity). A braid layer 7309 can then be wrapped radially around the gap 7311. When a pressure medium is supplied to the tubular bladder 7321, the bladder 7321 can expand to push the braid layer 7309 against the outer layer 7301 (not shown in FIG. 21A for clarity).

It should be understood that the cable configurations described with respect to FIGS. 10-21B can be used with any number of cables (such as 1, 2, 3, 4, 5, 6, 8, 12, or 16 cables). Further, the cables can be used to steer any tip or a rigidizing device and/or to steer any distal end section (e.g., sections with linkages or different braid angles). Further, the cable guides described herein can be round with round cables, flat, rectangular with flat ribbon tensile elements, or a combination thereof. Further, in some embodiments, other steering elements can be used in addition to or in place of the cables (e.g., pneumatics, hydraulics, shape memory alloys, EAP (electro-active polymers), or motors). Intentionally separating the elements required for steering and the elements required for rigidization can enable the structure to exhibit a continuously high rigidization performance as a function of length, even if the forces available for steering are demonstrably lower than the forces required for nested system rigidization.

Additionally, it should be understood that the cable configurations and placement described with respect to FIGS. 10-21B can similarly be used for the placement of working channels or other lumens (for example, inflation lumens for balloons) within the rigidizing devices.

Referring to FIGS. 22A-22D, in some embodiments, the distal end section 5902z may include a series of linkages 5904z (either active or passive) that are specifically designed to rigidize via the application of pressure or vacuum. For example, the linkages 5904z can be connected to each other through a pivot point 5928z (which can, for example, be wire pivot points). Each pivot point 5928z can allow bending with one degree of freedom between linkages. Further, the linkages 5904z can be arranged in alternating fashion with every other linkage connected with the pivot points 5928z positioned 90 degrees away from the previous linkage. Each linkage 5904z can have cut-outs 5975z at the proximal and distal ends thereof extending from the pivot-points 5928z to as to allow bending of the linkages 5904z relative to one another. Further, each linkage 5904z can be connected to a neighboring linkage 5904z by a respective tensile member 5930z. The tensile member 5930z can be fixed relative to one linkage and at least partially movable within a track 5931z of the neighboring linkage (e.g., within track 5931z of linkage 5904z). Movement of the linkages 5904z allows the tensile member 5930z to lengthen when on the outside of the curve and shorten when on the inside of the curve during bending of the rigidizing device. Further, the proximal end section 5902z can include two sliding clamps 5932z attached to tensile member 5930z along opposite axis (i.e., 90 degrees away from one another). The two tensile members 5930z extend from each of the sliding clamps 5932z to the distal-most end of the distal section 5902z. As the distal end section 5902z is bent, one cable element of each sliding clamp 5932z gets shorter and one cable element of each sliding clamp 5932z gets longer, resulting in circumferential movement of the sliding clamps 5932z. When vacuum or pressure is applied, the outer sleeve can compress the sliding clamps 5932z to the track 5931z surface. The sliding clamps 5932Z and the track 5931z surface may be smooth, rough or have teeth. This compression force may case the sliding clamps 5932Z to lock in place with respect to the links 5904z, thereby fixing the position of tensile members 5930z and making the distal end section stiffer in its current shape. Additional rigidizing linkages and/or engages are described in International Patent Application No. PCT/US2018/042946, filed Jul. 19, 2018, titled "DYNAMICALLY RIGIDIZING OVERTUBE," now PCT Publication No. WO 2019/018682, the entirety of which is incorporated by reference herein.

Figure 23A:
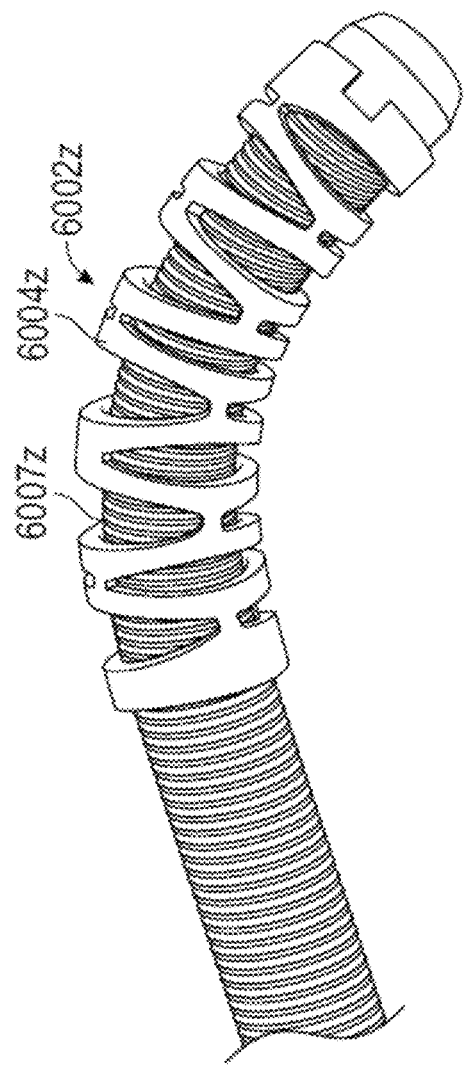
FIGS. 23A-23B show a rigidizing device with a distal end section having linkages over a rigidizing section.
Figure 23B:
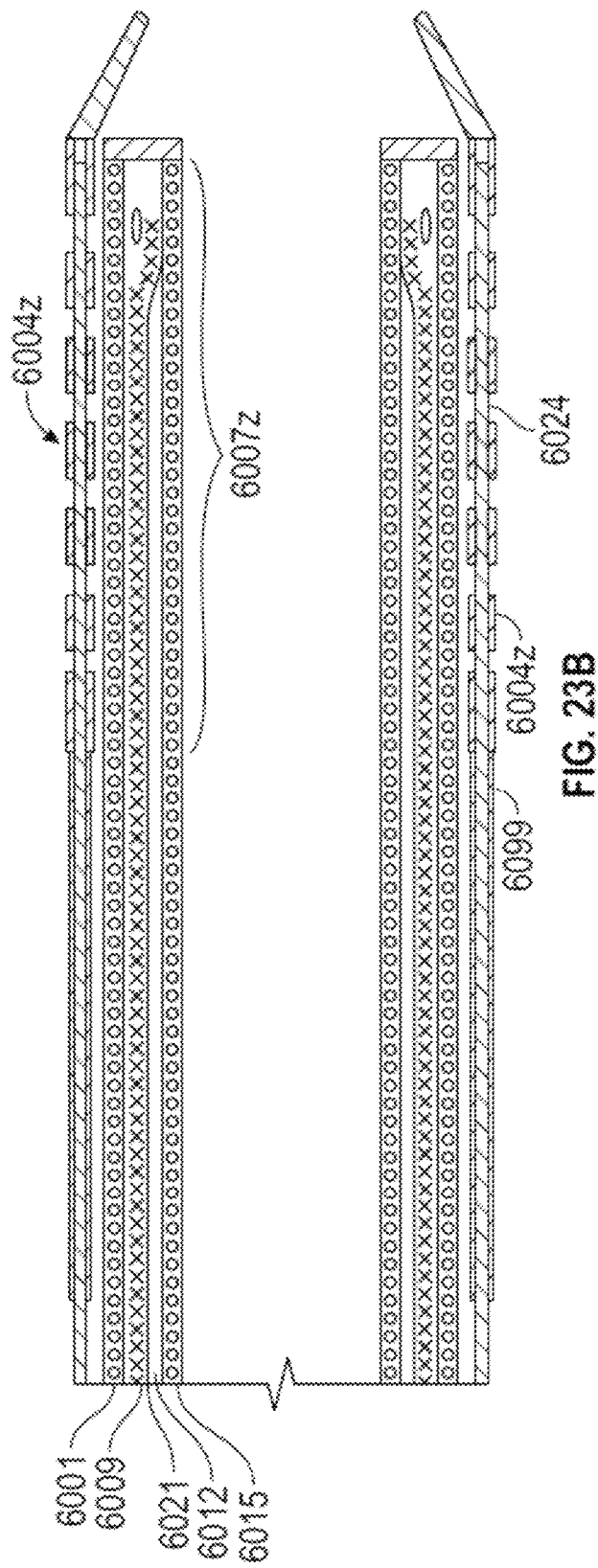
Figure 71A:
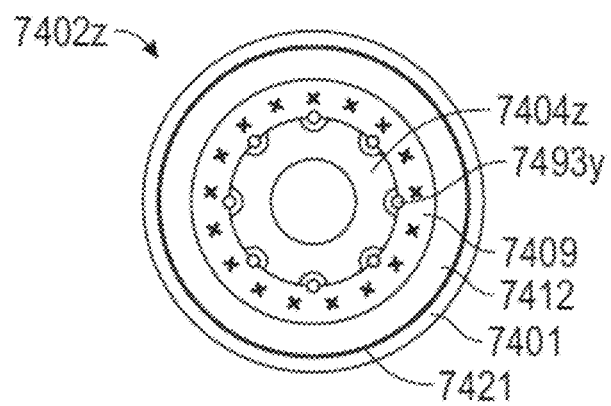
FIGS. 71A-71B show a rigidizing distal end section with support members extending along the linkages.
Figure 71B:
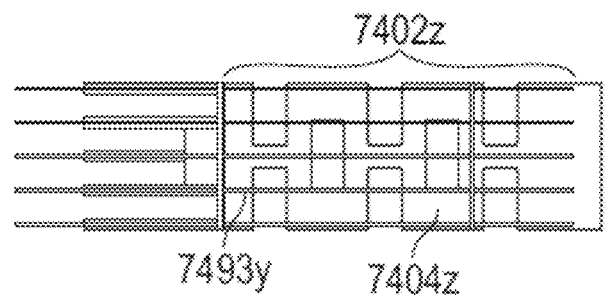

Referring to FIGS. 23A-23B, in some embodiments, the distal end section 6002z can include linkages 6004z (either active or passive) that are placed over a section 6007z that rigidizes via vacuum or pressure as otherwise described herein (i.e., over a rigidizing wall with inner layer 6015, pressure gap 6012, bladder 6021, braid layer 6009, and outer layer 6001). Placing the linkages 6004z over the rigidizing section can provide the advantages of a linked system (e.g., flexibility in bending and torsional stiffness) together with a steering or deterministic bending tip that can be rigidized when the remaining structure is rigidized. Alternatively, linkages can be positioned radially inwards of a rigidizing section, as shown in FIG. 71A. As is also shown in FIG. 71A (and in FIG. 71B), support members 7493y can extend radially outwards of the linkages 7404z (i.e., between the braid layer 7409 and the linkages 7404z). The support members 7493y can be configured to slide relative to the linkages 7404z when the distal end section 7402z is in the flexible configuration. When pressure is supplied to the pressure gap 7412 within the bladder 7421 (positioned between the outer layer 7401 and the braid 7409), the braid 7409 can rigidize against the support members 7493y, pushing the support members 7493y against the linkages 7404z and strengthening the shape of the distal end section 7402z in the rigid configuration. As shown in FIG. 23B, cables 6024 in cable guides 6099 can extend through linkages 6004z to provide optional active steering of the linkages 6004z.

Figure 24:
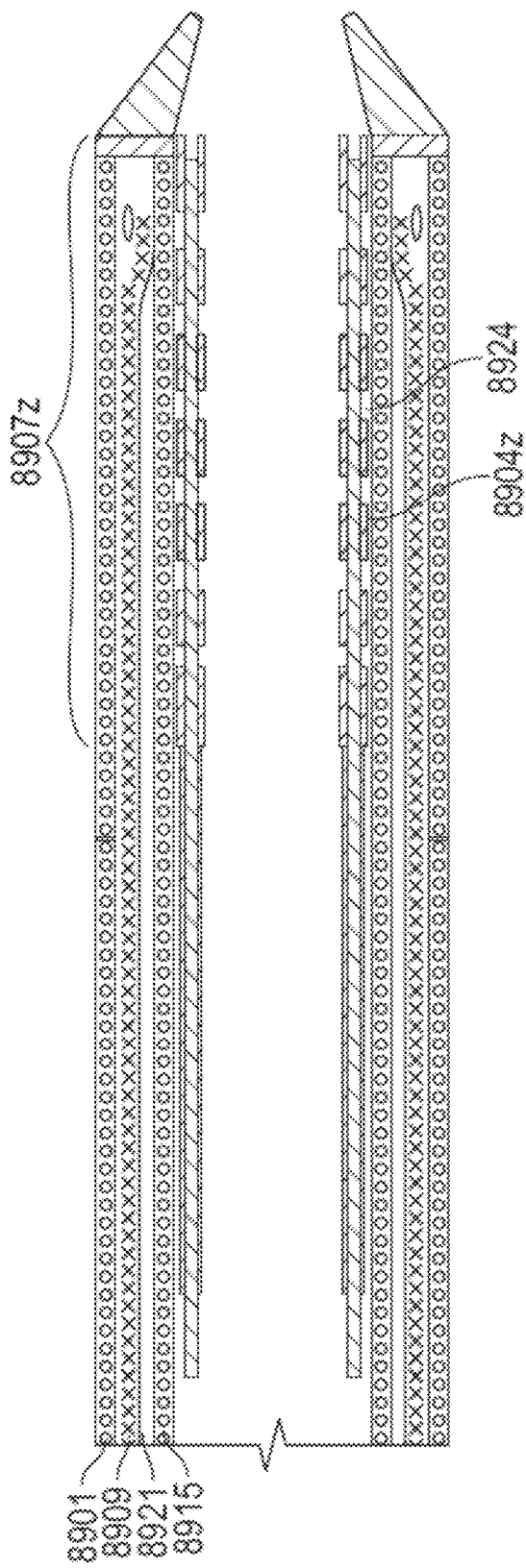
FIG. 24 shows a steerable rigidizing tip.

Referring to FIG. 24, in some embodiments, the distal end section 8907z can include linkages 8904z that are positioned radially inwards of a section 8907z that rigidizes via vacuum or pressure as otherwise described herein. For example, the linkages 8904z (and corresponding cables 8924) can be placed radially inwards of the inner layer 8915 (and thus also bladder 8921, braid layer 8909, and outer layer 8901). When radially inwards of the inner layer 8915, the linkages 8904z can help the inner layer 8915 (e.g., coil wound tube) resist collapse. Further, in such an embodiment, the distal portion of the inner layer 8915 that is coextensive with the linkages 8904z can be thinner and/or more flexible than the proximal portion of the inner layer 8915 that is not coextensive with the linkages 8904z. Having a thinner and/or more flexible distal portion of the inner layer 8915 can provide enhanced maneuverability, flexibility and bendability at the tip.

In one exemplary use of distal end section 8907z (or distal end section 6002z of FIGS. 23A-23B), the linkages 8904z and cables 8924 can be used to steer the rigidizing device when the rigidizing section 8907z is in the flexible configuration. Conversely, when the rigidizing section is in the rigid configuration, the linkages 8904z can be prevented from moving, thereby holding the linkages 8904z in a fixed shape. In some embodiments, section 8907z can be separately rigidizable relative to the proximal portion of the rigidizing device.

Figure 55:
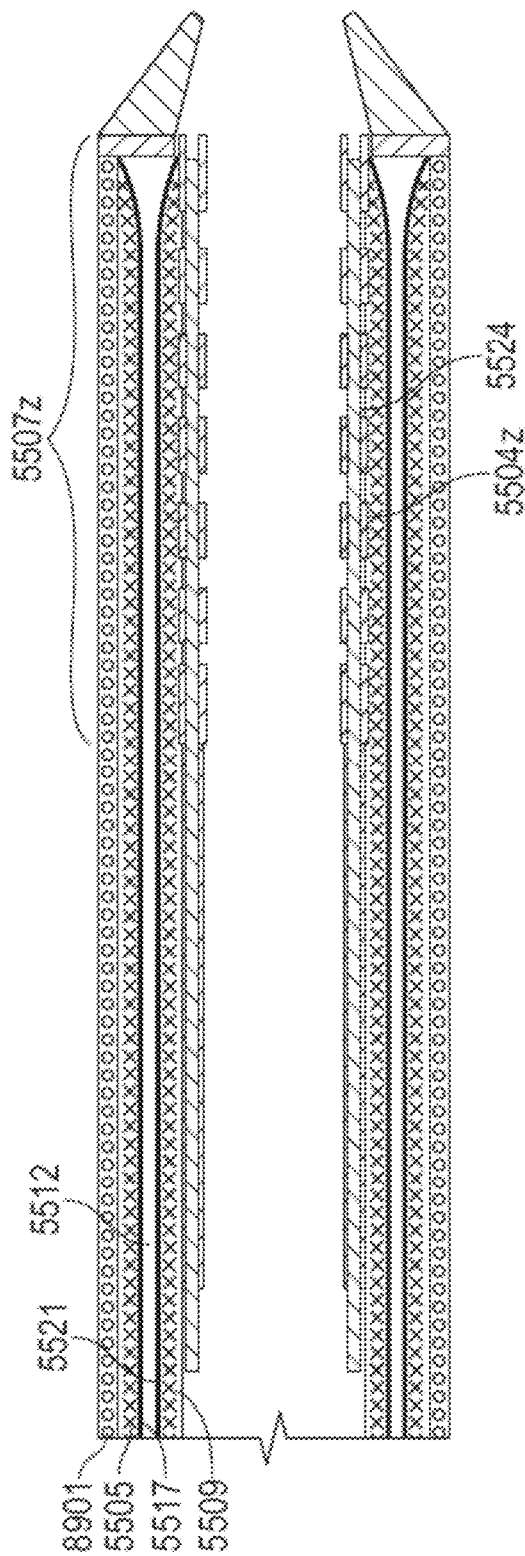
FIG. 55 shows a rigidizing distal tip.

Referring to FIG. 55, in some embodiments, the distal end section 5507z can include a rigidizing wall that includes linkages 5504z and a double braid and double bladder over the linkages 5504z. Thus, the distal end section 5507z can include two braid layers 5509, 5505 sandwiching two bladders 5521, 5517 (and/or a single bladder) therebetween. When pressure is supplied to the pressure gap 5512 between the bladders 5521, 5517, the outer braid layer 5505 can be pushed radially against the outer layer 5501 while the inner braid layer 5509 can be pushed radially inwards against the linkages 5504z to rigidize the device and the distal end section 5507z. Similar to distal end section 8907z, the linkages 5504z and cables 5524 can be used to steer the rigidizing device when the rigidizing section 5507z is in the flexible configuration. Conversely, when the rigidizing section 5507z is in the rigid configuration, the linkages 5504z can be prevented from moving, thereby holding the linkages 5504z in a fixed shape. In some embodiments, one or both of the braid layers 5509, 5505 can include longitudinal fibers running therethrough or adjacent thereto.

Figure 51A:
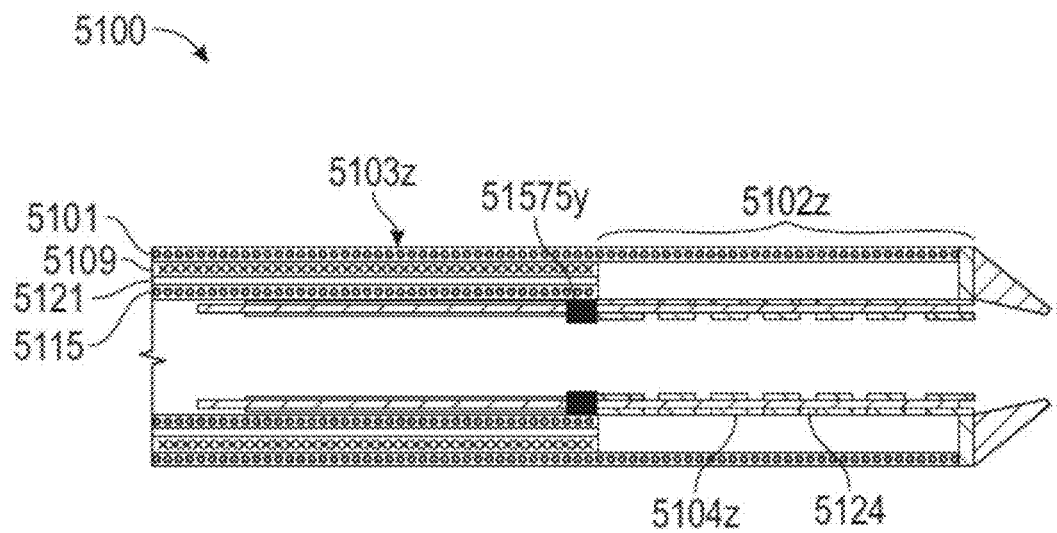
FIGS. 51A-51E show a rigidizing device having an isolated rigidizing distal end section.
Figure 51B:
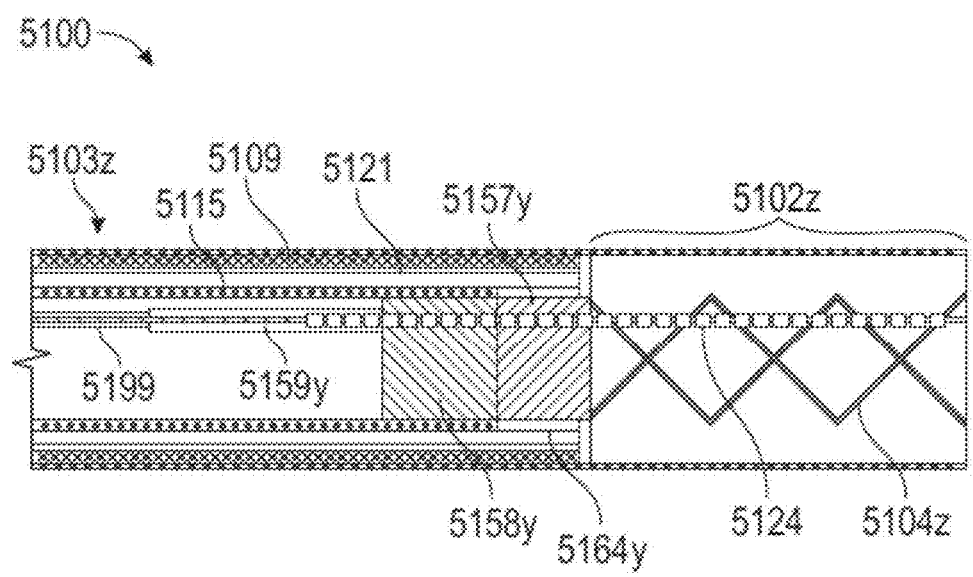
Figure 51C:
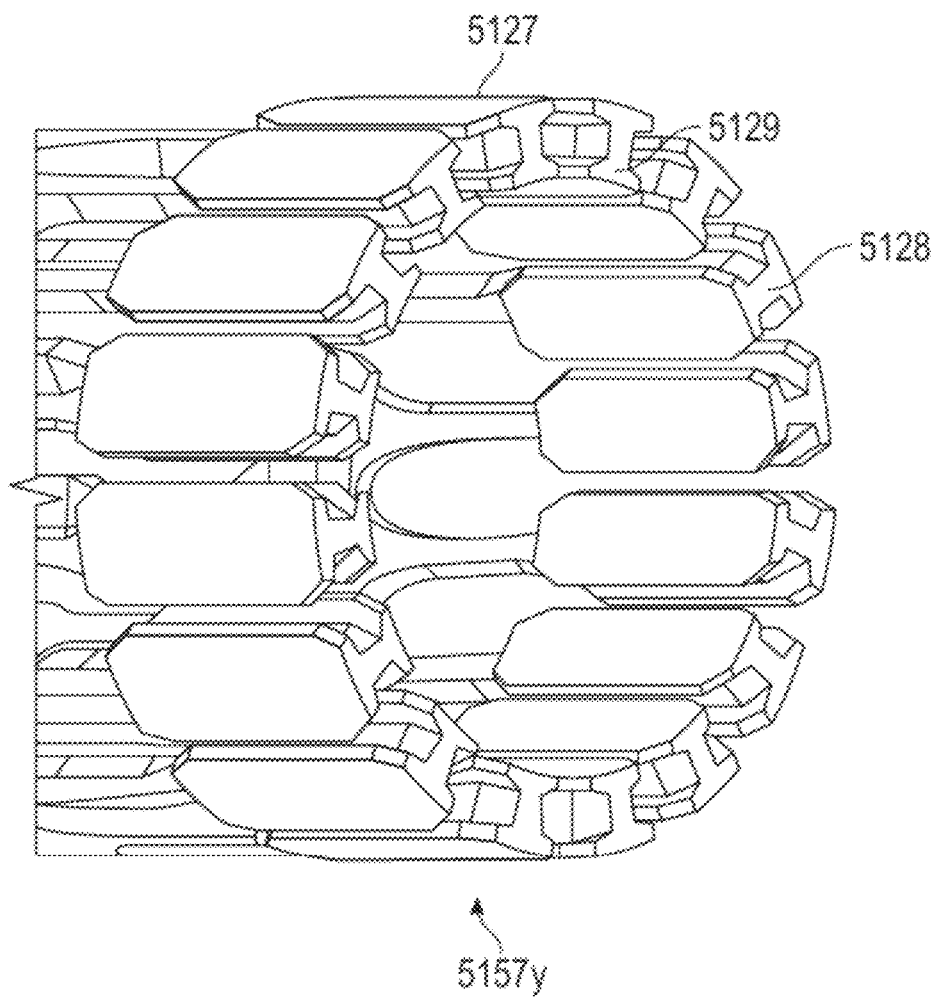
Figure 51D:
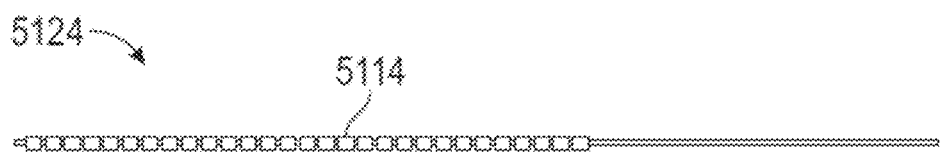
Figure 51E:

Referring to FIGS. 51A-51E, in one embodiment, a rigidizing device 5100 can include a distal end section 5102z having linkages 5104z, one or more cables 5124 to activate the linkages 5104z for steering, and an outermost layer 5101 (which can be continuous with the outermost layer of the main elongate body 5103z). A clamp 5157y can be just proximal to the distal end section 5102z and positioned within the outer most layer 5101, braid layer 5109, and bladder 5121 of the main elongate body 5103z. As shown in FIG. 51C, the clamp 5157y can include, for example a plurality of female engagers 5128 extending therefrom. The clamp 5157y may be surrounded by a clamp bladder 5164y on the outer surface (see FIG. 51B). Further, the distal portion of each of the cables 5124 can include a plurality of male engagers 5114 around the cable 5124 and extending down the distal length thereof. Alternately, the male engagers 5114 may be part of a single continuous piece, rather than plurality of separate pieces shown. The female engagers 5128 can each include an outer flange 5127 and inner flange 5129 configured to fit a male engager 5114 of the cable 5124 therebetween. When the rigidizing device 5100 is in the flexible configuration, the cables 5124 can freely move through the clamp 5157$y$ (e.g., the male engagers 5114 of the cables 5124 can freely move through the female engagers 5128 of the clamp 5157$y$), enabling the cables 5124 to steer the linkages 5104$z$ as desired. Upon the application of pressure (or vacuum) to the wall of the main elongate body 5103$z$, the clamp bladder 5164$y$ can be constricted over the clamp 5157$y$, causing the female engagers 5128 to get circumferentially closer to each other, thus clamping onto the male engagers 5114 of the cables 5124, locking the cables 5124 into place, and thus locking the distal end section 5102$z$ into place simultaneously with the rigidization of the main elongate body 5103$z$.

Advantageously, the clamp 5157$y$ can improve rigidization of the distal section 5102$z$ because the length of the cable 5124 required to hold the shape is small (i.e., due to the effective isolation of the cable 5124 within the distal section 5102$z$ from the cable in the main elongate body 5103$z$). Additionally, locking with the clamp 5157$y$ enables the distal end section 5102$z$ to rigidize with the same actuation mechanism (e.g., pressure or vacuum) as the main elongate body 5103$z$ while keeping the distal end section 5102$z$ thin walled (i.e., the wall can include only a thin outer layer 5101 and the linkages 5104$z$).

As best shown in FIG. 51B, the clamp 5157$y$ can include a sheath termination block 5158$y$ into which cable pipes 5159$y$ terminate. The cable pipes 5159$y$ can be connected at the proximal end to cable guides 5199. The cable pipes 5159$y$ can, like the cable guides, 5199, house the cables 5124. However, because the cable pipes 5159$y$ are at the distal end of the cables 5124 and thus house the portion of the cables 5124 having the male engagers 5114 therearound, the cable pipes 5159$y$ can have a larger diameter to accommodate the male engagers 5114. As shown in FIG. 51B, the cable pipes 5159$y$ can extend further proximally than the male engagers 5114 when the rigidizing device 5100 is straight so as to accommodate proximal motion of the cables 5124 during bending of the rigidizing device 5100.

Exemplary engagers that can be used in addition to or in place of the engagers 5128, 5114 are described in International Patent Application No. PCT/US2018/042946, filed Jul. 19, 2018, titled "DYNAMICALLY RIGIDIZING OVERTUBE," the entirety of which is incorporated by reference herein.

Figure 54:
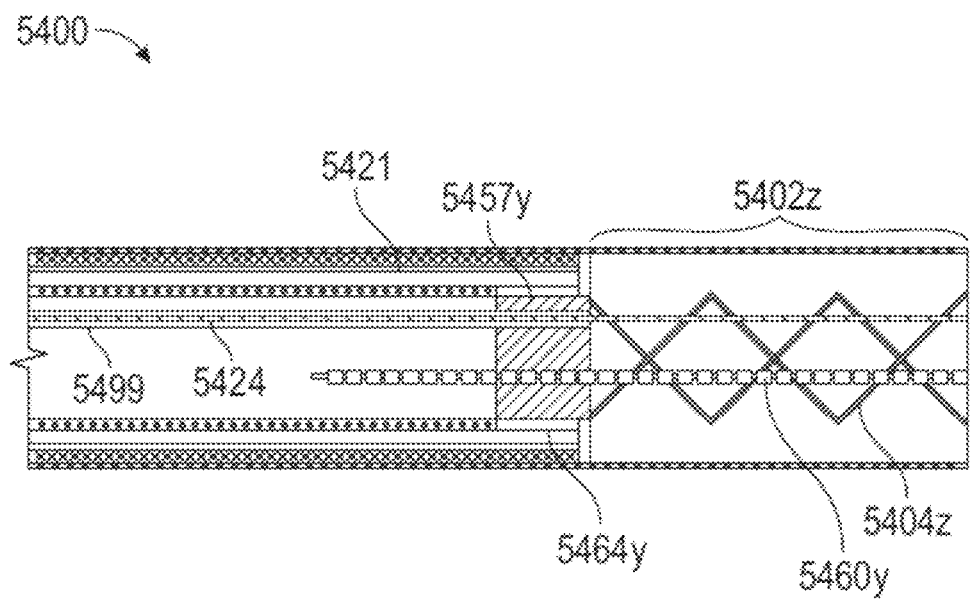
FIG. 54 shows another rigidizing device having an isolated rigidizing distal end section.

In some embodiments, referring to FIG. 54, rather than using the steering cables 5424 connect to linkages 5404$z$ to rigidize the distal end section 5402$z$, separate locking cables 5460$y$ including male rigidizing elements can extend through the distal end section 5402$z$ in conjunction with the standard steering cables 5424. The locking cables 5460$y$ can extend only slightly proximally beyond the clamp 5457$y$ (to accommodate lengthening of the locking cables 5460$y$ during bending of the distal end section 5402$z$). In some embodiments, for example, the locking cables 5460$y$ can alternate with the steering cables 5424 (and surrounding cable guides 5499) around the circumference of the rigidizing device 5400. Upon activation of vacuum or pressure, the locking cables 5460$y$ can be locked into place by the clamp bladder 5464$y$ and the engagers 5428.

Referring to FIGS. 56A-56D, in some embodiments, a rigidizing distal end section 5602$z$ of a rigidizing device 5600 can include linkages 5604$z$ having a plurality of pressure channels 5690$y$ extending therealong, such as along an inner circumference of the linkages 5604$z$. Each of the pressure channels 5690$y$ can further include an expandable pressure line 5691$y$ and a support member 5693$y$ positioned therein. Similar to other rigidizing distal end sections described herein, the linkages 5604$z$ can be connected together via one or more pivot points 5628$z$. Cables 5624 extending within cable guides 5699 can control bending of the linkages 5604$z$ at the pivot points 5628$z$. An outer layer 5698$y$ (not shown in FIG. 56A for clarity) can extend over the linkages 5604$z$. The outer layer 5698$z$ can be continuous with or separate from the outer layer 5601 of the main rigidizing body 5603$z$. In some embodiments, the outer layer 5698$z$ can include ePTFE.

Each inflatable pressure line 5691$y$ can be low in diameter (e.g., can have a diameter of less than 0.060", such as less than 0.050", such as less than 0.040" in diameter) and can also have a low wall thickness (e.g., can have a wall thickness of less than 0.002", such as less than 0.001", such as less than 0.0005", such as less than 0.00025"). The pressure lines 5691$y$ can run from the proximal end of the rigidizing device 5600, through the main rigidizing body 5603$z$, and into the distal end section 5602$z$. Each pressure line 5691$y$ can be the same material the entire length of the rigidizing device 5600 or can be a different material (e.g., can be expandable only in the distal end section 5602$z$ and not within the main rigidizing body 5603$z$). Further, the pressure lines 5691$y$ can be connected to the same pressure line as the main rigidizing body 5603$z$ or can be separately activated and controlled.

Figure 56B:
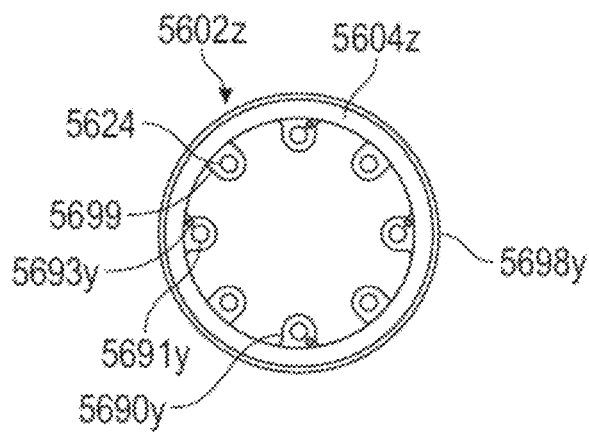
Figure 56C:
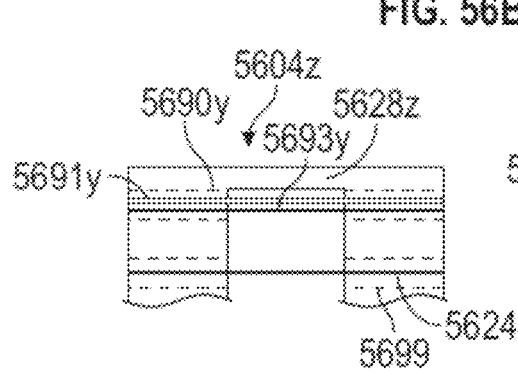
Figure 56D:
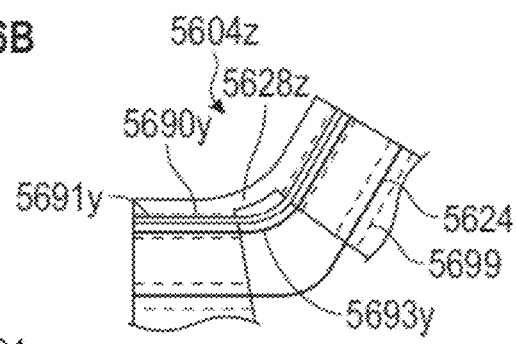
Figure 57:
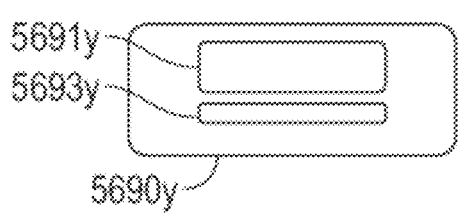
FIG. 57 shows a pressure channel with a rectangular pressure line and support member.
Figure 58:
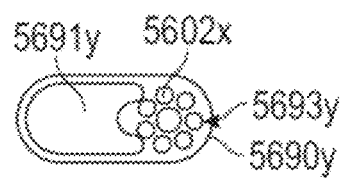
FIG. 58 shows a pressure channel with a pressure line and a cable support line.
Figure 59:
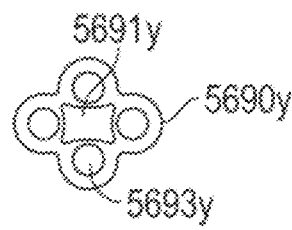
FIG. 59 shows a pressure channel with a pressure line and a plurality of support members.
Figure 60:
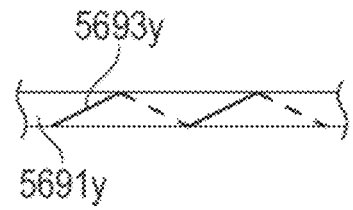
FIG. 60 shows a support member coiled around a pressure line.

Each support member 5693$y$ can extend the length of the rigidizing device 5600 and can run, for example, parallel to the inflatable pressure line 5691$y$ within each channel 5690$y$. The support members 5693$y$ can advantageously bridge the gaps between linkages 5604$z$ to prevent buckling of the distal end section 5602$z$ under compression (e.g., when the distal end section 5602$z$ is in the rigid configuration). The support members 5693$y$ can be a wire. In one embodiment, the wire can be a 0.010" stainless steel spring wire. The channel 5690$y$ and/or support member 5693$y$ can be, for example, circular (as shown in FIG. 56B), rectangular (as shown in FIG. 57), square, or oval. In some embodiments, as shown in FIG. 58, the support member 5693$y$ can include a plurality of filaments 5602$x$ (e.g., can be formed as a cable). In some embodiments, as shown in FIG. 59, each channel 5690$y$ can include a plurality of support members 5693$y$ (and the channel 5690$y$ can include a corresponding conforming shape). In some embodiments, as shown in FIG. 60, the support member 5693$y$ can coil around the inflatable pressure line 5691$y$ rather than extending parallel thereto.

In the flexible configuration, the linkages 5604$z$ can enable the distal end section 5602$z$ to flexibly bend (e.g., form a curve with a radius of curvature of less than 1", such as less than 0.5", such as less than 0.25"). In the flexible configuration, the inflatable pressure line 5691$y$ and/or the support member 5693$y$ can slide within the pressure channel 5690$y$. When pressure is supplied to the inflatable pressure line 5691$y$, the pressure line 5691$y$ can expand within and fill the pressure channel 5690$y$, thereby forcing the support member 5693$y$ against the linkages 5604$z$, preventing the linkages 5604$z$ from moving relative to one another, and transitioning the distal end section 5602$z$ to the rigid configuration. The low diameter pressure line 5691$y$ can advantageously withstand significantly high pressure, such as from 3 atm to 60 atm or greater than 5 atm, thereby enabling increased rigidization.

Figure 61:
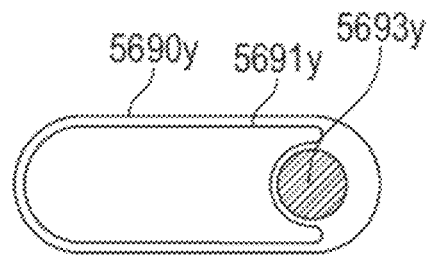
FIG. 61 shows a pressure channel with a pressure line having a circumference smaller than the circumference of the pressure line.

Referring to FIG. 61, in some embodiments, the pressure line 5691y can have, in the flexible configuration, a circumference that is smaller than the circumference of the pressure channel 5690y. In this embodiment, the pressure line 5691y can be made, for example, of a compliant material, such as nylon, pebax, or urethane. Upon the application of pressure, the compliant material of the pressure line 5691y can expand to fill the pressure channel 5690y.

Figure 62:
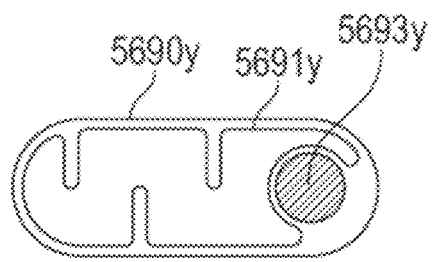
FIG. 62 shows a pressure channel with a pressure line having a circumference larger than the circumference of the pressure line.

Referring to FIG. 62, in some embodiments, the pressure line 5691y can be oversized relative to the diameter of the pressure channel 5690y (e.g., can have a larger circumference than the pressure channel 5690b, but can be folded or pleated therein). In this embodiment, the pressure line 5691y can be made, for example, of a non-compliant material, such as PET. Upon application of pressure, the non-compliant material of the pressure line 5691y can unfurl to fill the pressure channel 5690y.

In some embodiments, the pressure line 5691y and support member 5693y can be free to slide relative to one another. In other embodiments, the pressure line 5691y and support member 5693y can be bonded to one another.

Figure 63A:
FIGS. 63A-63B show an overmolded support member for use with a pressure channel.
Figure 63B:
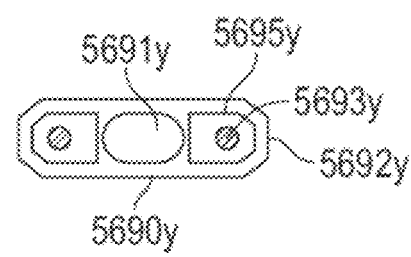
Figure 64A:
FIGS. 64A-64B show another overmolded support member for use with a pressure channel.
Figure 64B:
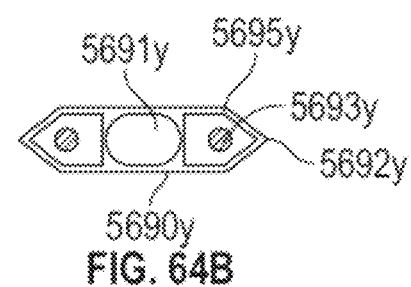
Figure 65:
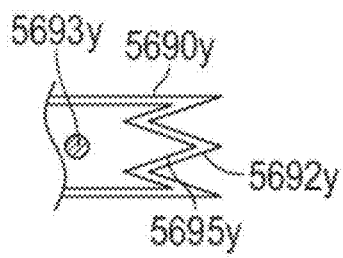
FIG. 65 shows another overmolded support member for use with a pressure channel.

Referring to FIGS. 63A and 63B, in some embodiments, the support member 5693y can be overmolded, for example, with male engagers 5695y (e.g., similar to the male engagers 1554 of FIGS. 51A-51E). The pressure channels 5690y can include corresponding mating female engagers 5692y (e.g., similar to female engagers 5128) on the interior circumference thereof. Alternately, the support members 5693y can include the female engagers and the pressure channels 5690y the male engagers. As pressure is supplied to the pressure line 5691y, the expanding line 5691y can place pressure on the support members 5693y, causing the male 5695y and female 5692y engagers to lock together, providing enhanced rigidization. As shown in FIGS. 64A and 64B, in some embodiments, the engagers 5695y, 5692y can be sharp or pointed. Referring to FIG. 65, in some embodiments, each engager 5695y, 5692y can include a plurality of extensions or elements configured to engage with corresponding elements on the inner circumference of the pressure channel 5690y.

Figure 66A:
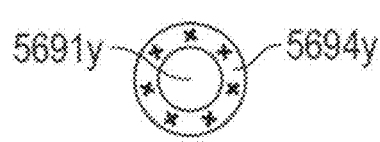
FIGS. 66A-66B show an inflatable pressure line with a braid therearound.
Figure 66B:
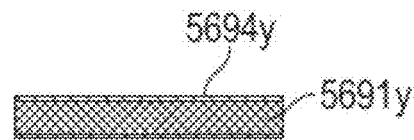

Referring to FIGS. 66A-66B, in some embodiments, rather than including support members 5693y, the inflatable pressure line 5691y can be surrounded by a braid layer 5694y configured to rigidize against the linkages 5604z.

Figure 67:
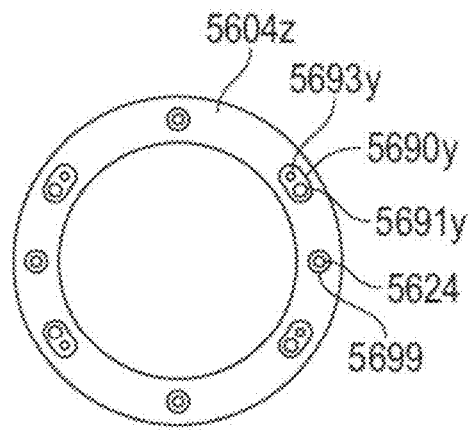
FIG. 67 shows another rigidizing distal end section including a plurality of pressure channels therein.

Referring to FIG. 67, in some embodiments, the channels 5690y can be embedded within and/or through the linkages 5604z (rather than running along the inner circumference). Note that the linkages 5604z in FIG. 67 also have a different shape and configuration from the linkages of FIGS. 56A-56C. It should be understood that any of the linkages 5604z shown in any of the FIGS. can be substituted for or replaced with any of the other linkages described herein.

Figure 56A:
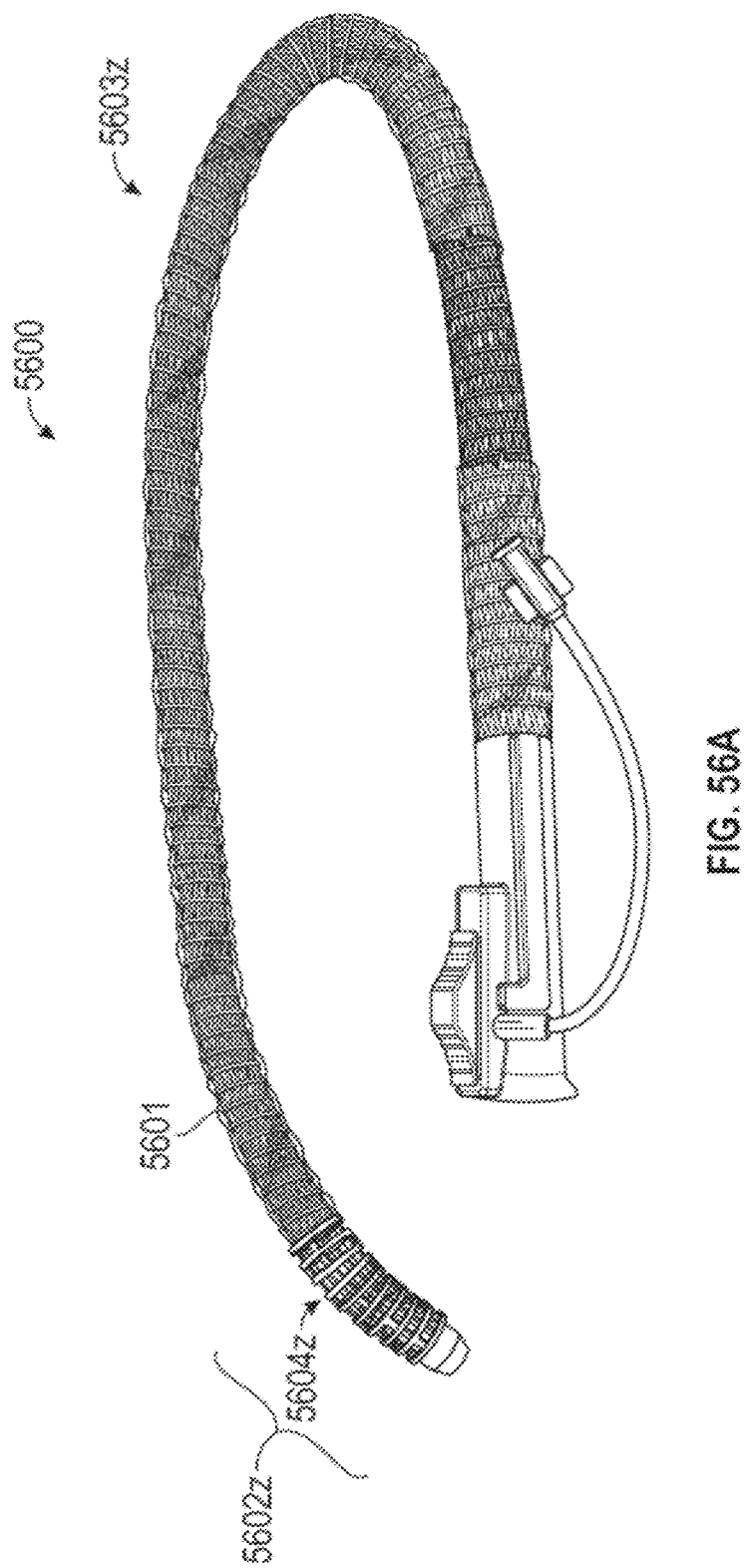
FIGS. 56A-56D show a rigidizing distal end section including a plurality of pressure channels therein.

The channels 5690y in any embodiment described herein may be oblong (as shown in FIG. 67) or circular (as shown in FIG. 56A).

Figure 68A:
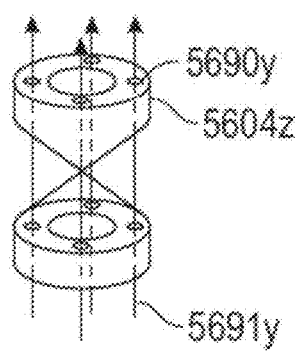
FIGS. 68A-68B show exemplary passage of pressure lines through the pressure channels.
Figure 68B:
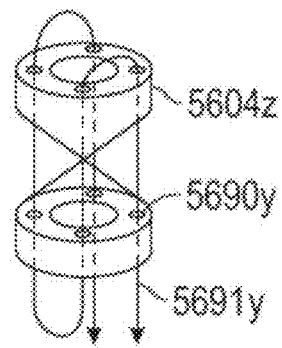

Referring to FIGS. 68A-68B, in some embodiments, the pressure lines 5691y can be separate from one another (as in FIG. 68A) or continuous with one another (as in FIG. 68B).

Figure 69:
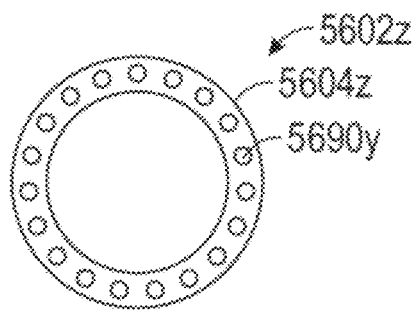
FIG. 69 shows another rigidizing distal end section including a plurality of pressure channels therein.

In some embodiments, the distal end section 5602z can include 2-10 channels 5690y, such as 4 channels (as shown in FIGS. 56A and 67). In other embodiments, the distal end section 5602z can include a greater number of channels 5690y, such as 10-20 channels (as shown in FIG. 69).

Figure 70:
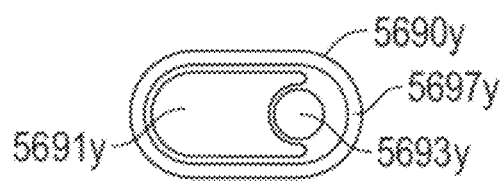
FIG. 70 shows a pressure channel having a nonfriction layer therein.

Referring to FIG. 70, in some embodiments, the inner diameter of the channels 5690y can be coated with a friction layer 5697y configured to enhance rigidization when pressure is applied to the inflatable pressure lines 5691y.

In some embodiments, the linkages 5904z may be passive and not include cables 5624. The linkages 5604z can be made of plastic or metal.

In some embodiments, the entire rigidizing device can include the rigidizing system (e.g., linkages 5604z, channels 5690y, etc.) described with respect to FIGS. 56A-70 (i.e., in place of a separately rigidizing main body 5603z). In some embodiments, the main body may not be rigidizing while the distal end section 5602z is rigidizing.

Figure 72:
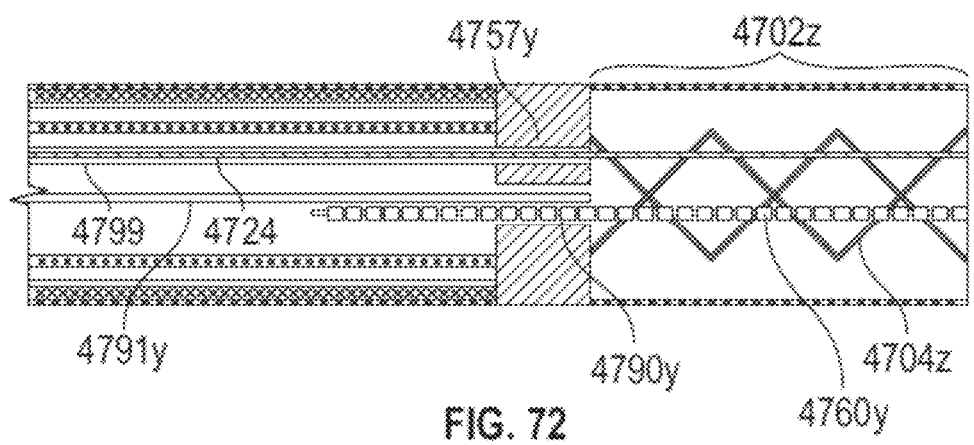
FIG. 72 shows a rigidizing device having a clamp mechanism for the distal end section.

Referring to FIG. 72, in some embodiments, and similar to FIG. 54, a distal end section 4702z can include a plurality of linkages 4704z, a plurality of locking cables 4760y extending alongside the linkages 4704z, and a clamp 4757y. In this embodiment, the clamp 4757y can include a circumferential member having a plurality of channels 4790y extending therethrough (only one channel 4790y is shown for clarity). The locking cables 4760y and inflatable pressure lines 4791y (e.g., similar to the inflatable pressure lines described with respect to FIGS. 56A-70) can extend through the channels 4790y. The clamp 4757y can additionally include a plurality of channels 4799 through which cables 4724 can extend (again, only one channel 4799 is shown for clarity). The pressure channels 4790y can further male or female engagers along the inner circumference thereof (similar to as described with respect to FIGS. 64A-65B) while the locking cables 4760y can include corresponding engagers along at least the portion of the cables 4760y that extends through the channels 4790y (though the engagers 4795y could extend along the entire length thereof). When pressure is applied to the pressure lines 4790y, the pressure lines 4790y can expand within the clamp 4757y, locking the engagers together and rigidizing the distal end section 4702z. Similar to the embodiment of FIGS. 51A-51E, the separate locking cables 4760y could be replaced by cables 4724 with engagers thereon.

Referring to FIG. 25A, in some embodiments, the distal end section 6102z can include a series of linkages 6104z (either active or passive) sealed within a thin layer of material 6108z (e.g., made of an elastomer, PVC, or PEEK). The linkages 6104z and thin layer of material 6108z can, for example, be positioned over (i.e., radially outwards from) the braid layer 6109 and can be continuous with the coil wound tube 6101 of the main elongate body 6103z. In this embodiment, when pressure or vacuum is supplied to the gap 6112, the braid layer 6109 can be compressed by the bladder 6121 against the coil wound tube 6101 in the main elongate body 6103z and against the linkage sheath 6108z in the distal end section 6102z to rigidize. The linkage sheath 6108z is supported by the linkages 6104z such that it can resist the pressure of the braid expanding. This design advantageously provides both rigidization and linkages while maintaining a low wall thickness and/or diameter. The distal end section 6102z can, for example, include cables 6124 extending within cable guides to activate the linkages 6104z.

In some embodiments, the rigidizing structure can be steered from within the wall of the rigidizing structure and optionally without any links. FIG. 25B shows a cross section of a pressure rigidizing structure 2500 where a cable guide 2599 is placed in the pressure gap 2512 and can be attached to the inner layer 2515. The cable 2524 extends from the cable guide 2599 into the distal end section 2502z and is anchored to the inner layer 2515 at anchor point 2568.

Pulling on the cable 2524 will cause the distal end section 2502z (distal to the end of the cable guide 2599) to deflect. In some embodiments, the cable guide 2599 can be omitted, and the rigidizing device 2500 will bend along its entire length when the cable 2524 is pulled. In some embodiments, the device 2500 can be built with a distal end section 2502z that has a lower bending stiffness than the proximal elongate body 2503z (as described herein, for instance by varying the braid angle or using a more flexible reinforcement element in either the inner or outer layer) so that the distal end section 2502z bends more than the body 2503z. The cable guide 2599 and cables 2524 can be located between the bladder 2521 and the braid 2509 or between the braid 2509 and outer layer 2501. The cable guide 2599 and/or the cables 2524 can be attached to the outer wall 2501. Alternately, in a vacuum rigidized structure, the cable guide 2599 and cables 2524 can be located between the inner layer and the braid or between the braid and the outer layer. In some embodiments, the bladder 2521 and the braid of the braid layer 2509 can be omitted in the section where the cable 2524 is not inside the cable guide 2599, leaving only inner and outer layers 2515, 2501, or just an outer layer or just an inner layer.

Figure 26A:
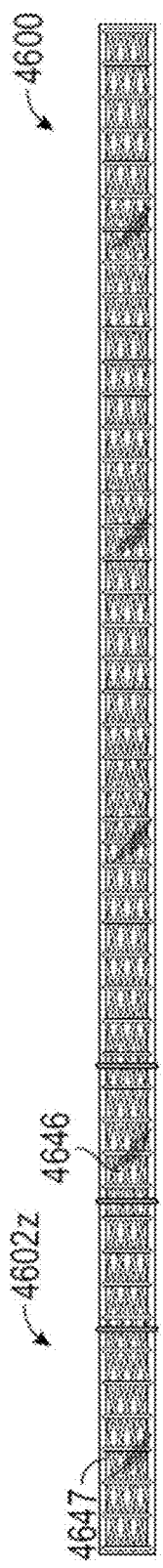
Figure 26B:
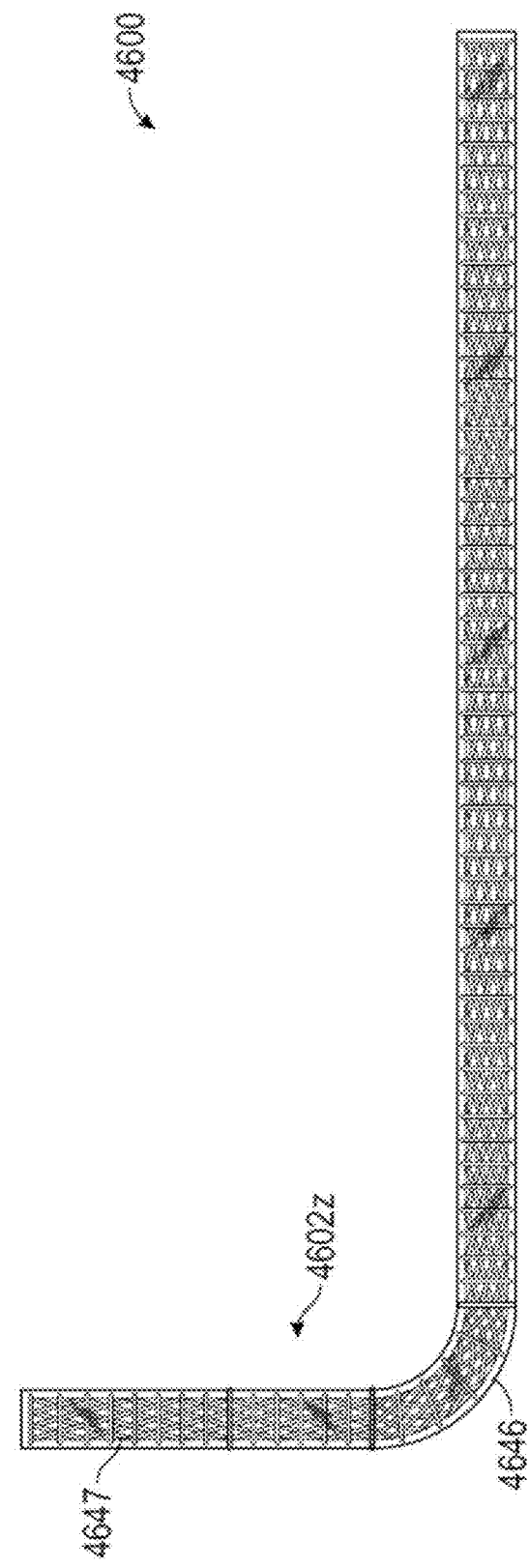

Referring to FIGS. 26A-26C, in some embodiments, the distal end section 4602z can include active deflection segment 4646. The deflection segment 4646 can include a ribbon or spine extending therethrough that provides bending only in one or more predetermined directions upon activation. The active deflection segment 4646 can be deflected, for example, using one or more cables, bladders, pullwires, and/or introduction of a guide wire, to a predetermined shape. The active deflection segment 4646 can thus provide bending of the rigidizing device 4600 at a fixed location and in a fixed direction. In some embodiments, markers (e.g., radiopaque markers) can be positioned within or proximate to the active deflection segment 4646 to indicate where the bend will occur and/or in which direction the active deflection segment 4646 will bend. Bending of the rigidizing device 4600 using the active deflection segment 4646 can be advantageous, for example, where bending is required without assistance from the anatomy (i.e., when the anatomical path for the rigidizing device 4600 is not predefined or constrained by the anatomy). For example, such bending might be useful to create a bend across the open or relatively unconstrained space between the inferior vena cava (IVC) and the atrial septum during transseptal procedures in the mitral valve. The active bending segment 4646 can be configured to be rigidized (i.e., via pressure or vacuum) as described herein to fix or lock the active deflection segment 4646 in the bent configuration. Further, the rigidizing device 4600 can include a steerable distal section 4647 (e.g., with linkages) in addition to the active deflection segment 4646. The steerable distal section 4647 can be used to point or orient the distal end of the rigidizing device 4646 in the desired direction (e.g., via cables and/or along four axes), as described elsewhere herein.

In some embodiments, the rigidizing devices described herein can be used in conjunction with one or more other rigidizing devices described herein. For example, an endoscope can include the rigidizing mechanisms described herein, and a rigidizing device can include the rigidizing mechanisms described herein. Used together, they can create a nested system that can advance, one after the other, allowing one of the elements to always remain stiffened, such that looping is reduced or eliminated (i.e., they can create a sequentially advancing nested system).

Figure 27:
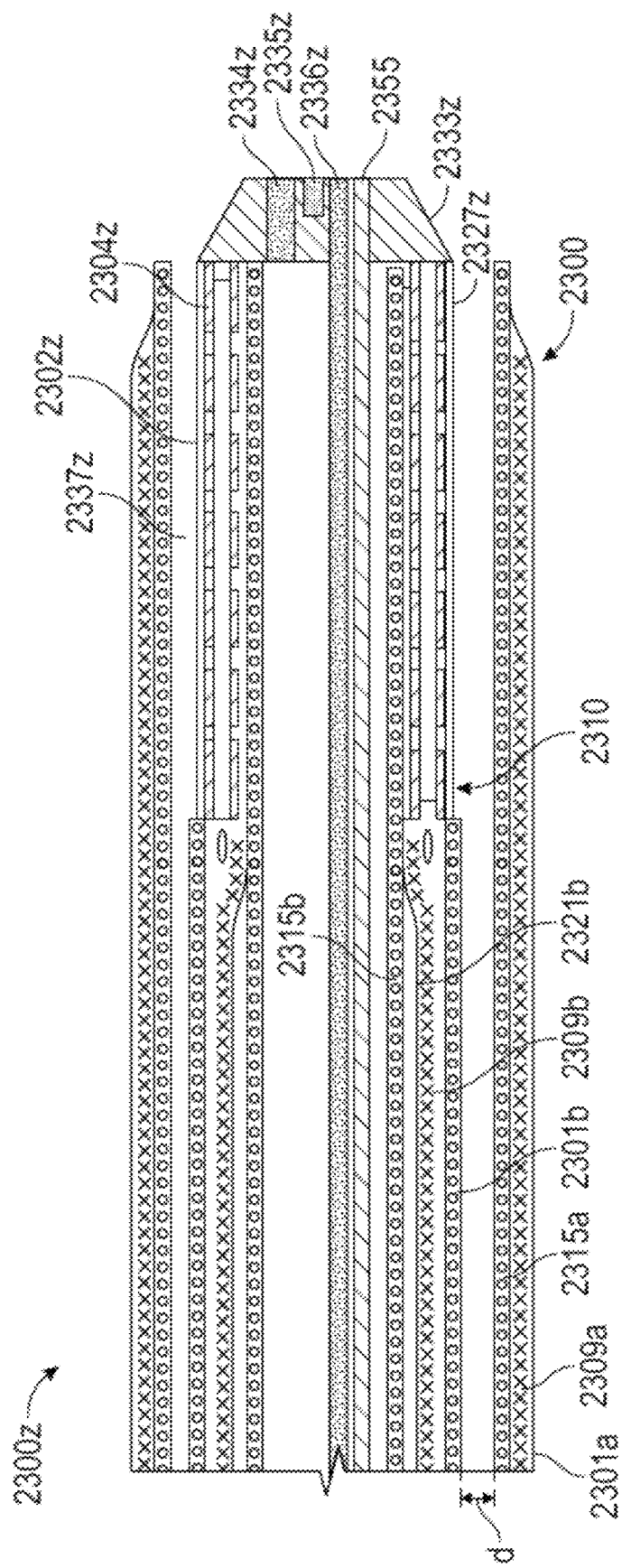
FIG. 27 shows a nested rigidizing system.

An exemplary nested system 2300z is shown in FIG. 27. The system 2300z can include an outer rigidizing device 2300 and an inner rigidizing device 2310 (here, configured as a rigidizing scope) that are axially movable with respect to one another either concentrically or non-concentrically. The outer rigidizing device 2300 and the inner rigidizing device 2310 can include any of the rigidizing features as described herein. For example, the outer rigidizing device 2300 can include an outermost layer 2301a, a braided layer 2309a, and an inner layer 2315a including a coil wound therethrough. The outer rigidizing device 2300 can be, for example, configured to receive vacuum between the outermost layer 2301a and the inner layer 2315a to provide rigidization. Similarly, the inner scope 2310 can include an outer layer 2301b (e.g., with a coil wound therethrough), a braid layer 2309b, a bladder layer 2321b, and an inner layer 2315b (e.g., with a coil wound therethrough). The inner scope 2310 can be, for example, configured to receive pressure between the bladder 2321b and the inner layer 2315b to provide rigidization. Further, an air/water channel 2336z and a working channel 2355 can extend through the inner rigidizing device 2310. Additionally, the inner rigidizing scope 2310 can include a distal section 2302z with a camera 2334z, lights 2335z, and steerable linkages 2304z. A cover 2327z can extend over the distal section 2302z. In another embodiment, the camera and/or lighting can be delivered in a separate assembly (e.g., the camera and lighting can be bundled together in a catheter and delivered down the working channel 2355 and/or an additional working channel to the distalmost end 2333z).

An interface 2337z can be positioned between the inner rigidizing device 2310 and the outer rigidizing device 2300. The interface 2337z can be a gap, for example, having a dimension d (see FIG. 5) of 0.001"-0.050", such as 0.0020", 0.005", or 0.020" thick. In some embodiments, the interface 2337z can be low friction and include, for example, powder, coatings, or laminations to reduce the friction. In some embodiments, there can be seals between the inner rigidizing device 2310 and outer rigidizing device 2300, and the intervening space can be pressurized, for example, with fluid or water, to create a hydrostatic bearing. In other embodiments, there can be seals between the inner rigidizing device 2310 and outer rigidizing device 2300, and the intervening space can be filled with small spheres to reduce friction.

The inner rigidizing device 2310 and outer rigidizing device 2300 can move relative to one another and alternately rigidize so as to transfer a bend or shape down the length of the nested system 2300z. For example, the inner device 2310 can be inserted into a lumen and bent or steered into the desired shape. Pressure can be applied to the inner rigidizing device 2310 to cause the braid elements to engage and lock the inner rigidizing device 2310 in the configuration. The rigidizing device (for instance, in a flexible state) 2300 can then be advanced over the rigid inner device 2310. When the outer rigidizing device 2300 reaches the tip of the inner device 2310, vacuum can be applied to the rigidizing device 2300 to cause the layers to engage and lock to fix the shape of the rigidizing device. The inner device 2310 can be transitioned to a flexible state, advanced, and the process repeated. Although the system 2300z is described as including a rigidizing device and an inner device configured as a scope, it should be understood that other configurations are possible. For example, the system might include two overtubes, two catheters, or a combination of overtube, catheter, and scope.

Figure 28:
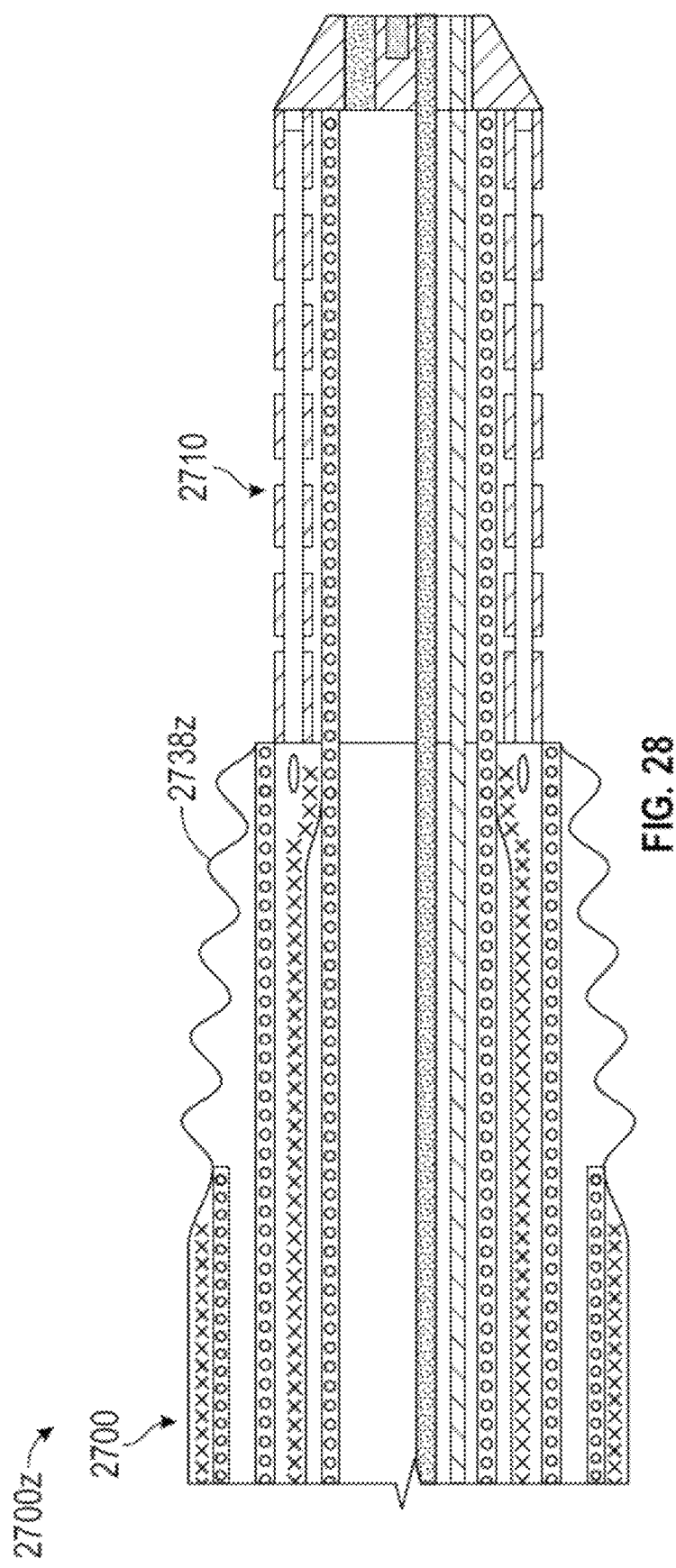
FIG. 28 shows a nested rigidizing system with a cover between the inner and outer rigidizing devices.

FIG. 28 shows another exemplary nested system 2700z. System 2700z is similar to system 2300z except that it includes a cover 2738z attached to both the inner and outer rigidizing device 2710, 2700. The cover 2738z may be, for example, low-durometer and thin-walled to allow elasticity and stretching. The cover 2738z may be a rubber, such as urethane, latex, or silicone. The cover 2738z may protect the interface/radial gap between the inner and outer devices 2710, 2700. The cover 2738z may prevent contamination from entering the space between the inner and outer tubes. The cover 2738z may further prevent tissue and other substances from becoming trapped in the space between the inner and outer tubes. The cover 2738z may stretch to allow the inner device 2710 and outer device 2700 to travel independently of one another within the elastic limits of the material. The cover 2738z may be bonded or attached to the rigidizing devices 2710, 2700 in such a way that the cover 2738z is always at a minimum slightly stretched. This embodiment may be wiped down externally for cleaning. In some embodiments, the cover 2738z can be configured as a "rolling" seal, such as disclosed in U.S. Pat. No. 6,447,491, the entire disclosure of which is incorporated by reference herein.

FIGS. 29A-29B show another exemplary nested system 9400z. In this system 9400z, the outer rigidizing device 9400 includes steering and imaging (e.g., similar to a scope) while the inner device includes only rigidization (though it could include additional steering elements as described elsewhere herein). Thus, outer device 9400 includes linkages or other steering means disclosed herein 9404z, camera 9434z, and lighting 9435z. The outer device 9400 can further include a central passageway 9439z for access to the inner device 9410 (e.g., lumens such as working channels therein). In some embodiments, bellows or a loop of tubing can connect the passageway 9439z to lumens of the inner device 9410. Similar to the other nested systems, at least one of the devices 9410, 9400 can be rigidized at a time while the other can conform to the rigidization and/or move through the anatomy. Here, the outer device 9400 can lead the inner device 9410 (the inner device 9410 is shown retracted relative to the outer device 9400 in FIG. 29A and extended substantially even with the outer device 9400 in FIG. 7B). Advantageously, system 9400z can provide a smooth exterior surface to avoid pinching the anatomy and/or entrance of fluid between the inner and outer devices 9410, 9400. Having the steering on the outer device 9400 can also provide additional leverage for steering the tip. Also, the outer device can facilitate better imaging capabilities due to the larger diameter of the outer device 9400 and its ability to accommodate a larger camera.

Figure 30A:
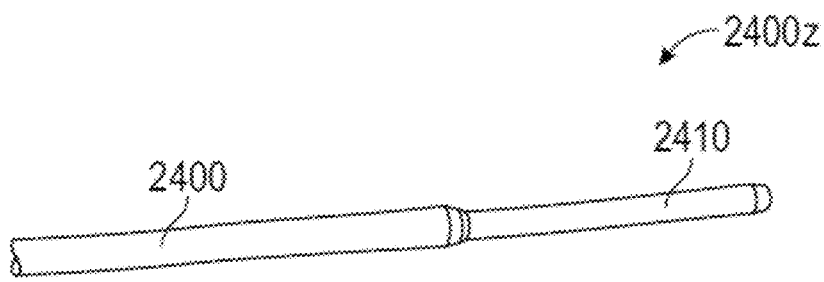
FIGS. 30A-30H show exemplary use of a nested rigidizing system.
Figure 30B:
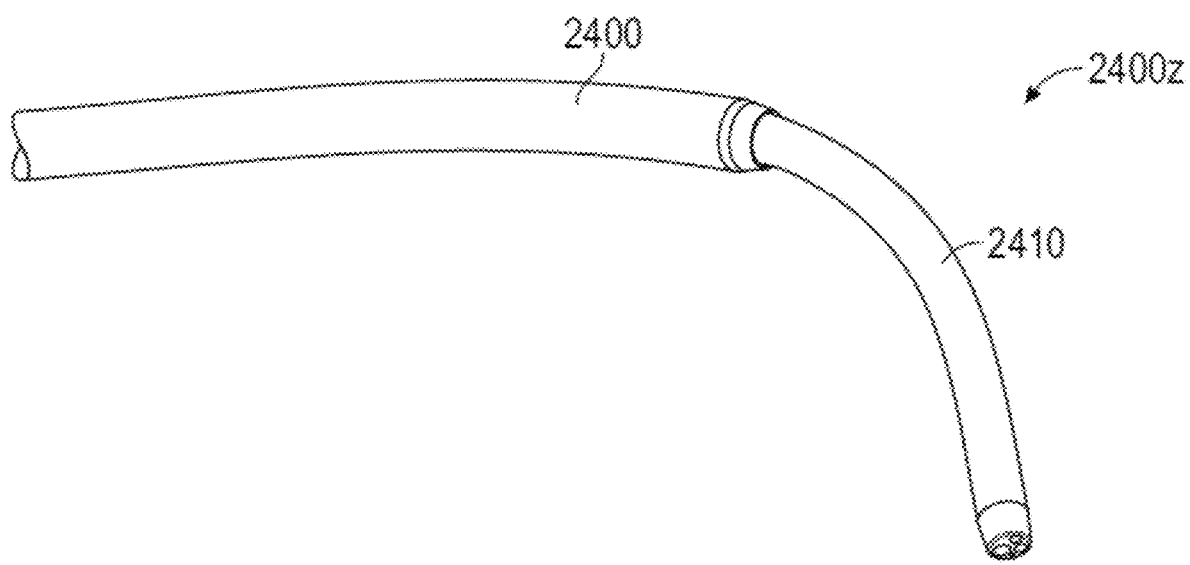
Figure 30C:
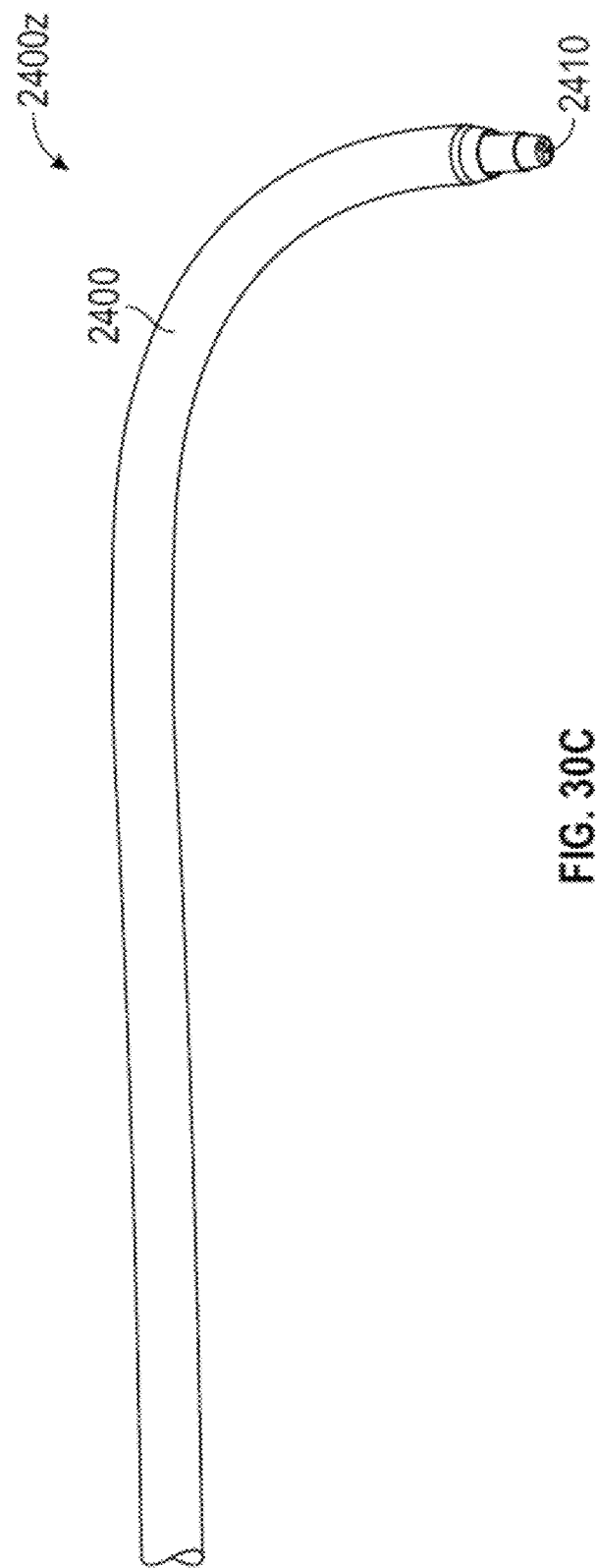
Figure 30D:
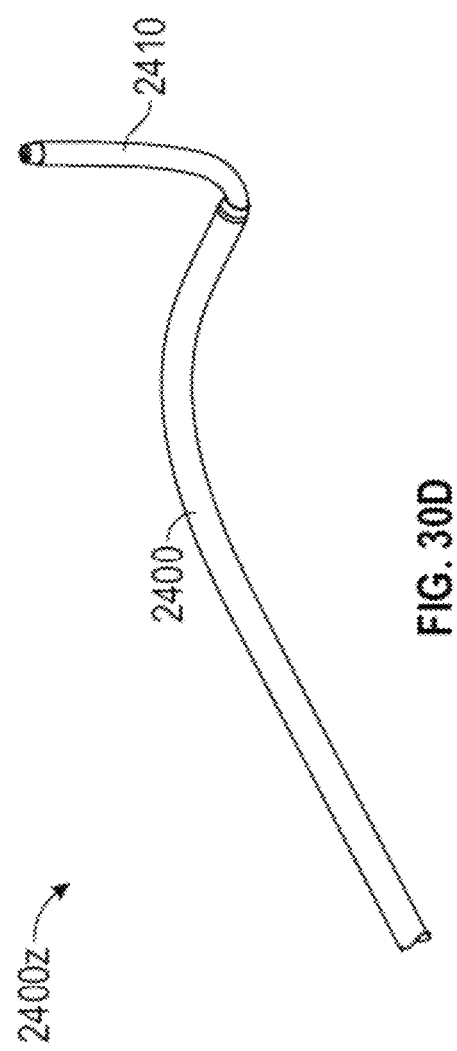
Figure 30E:
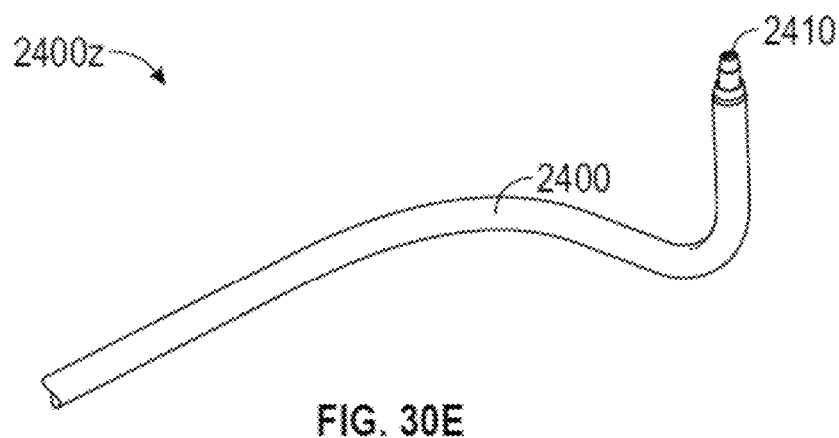
Figure 30F:
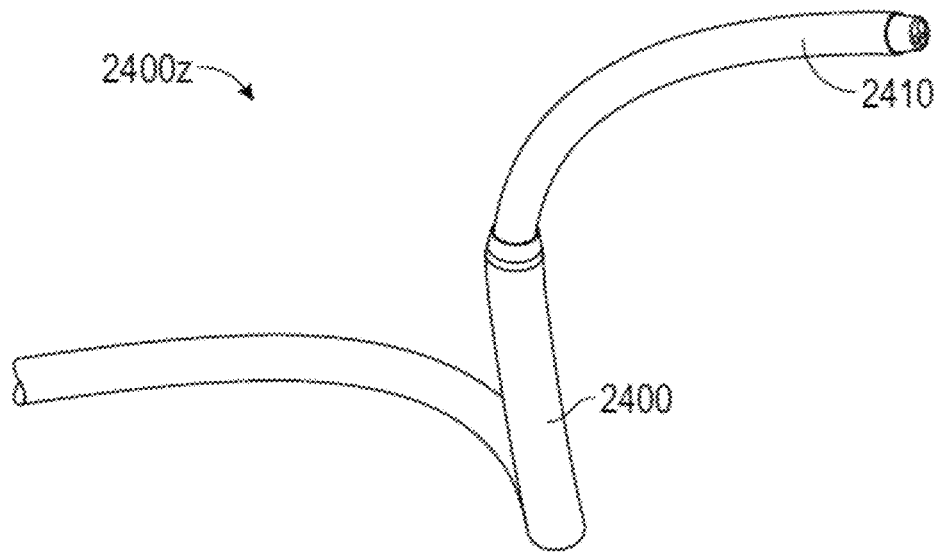
Figure 30G:
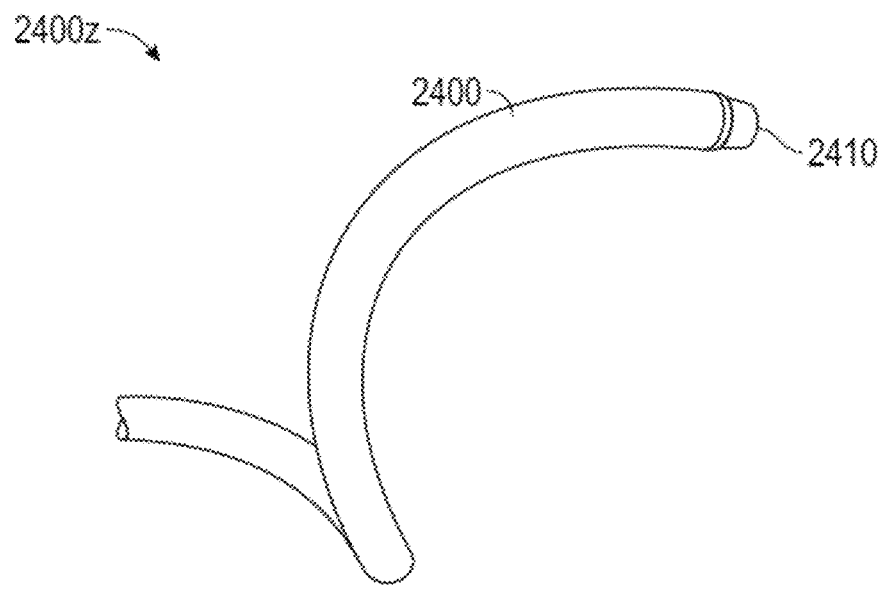
Figure 30H:
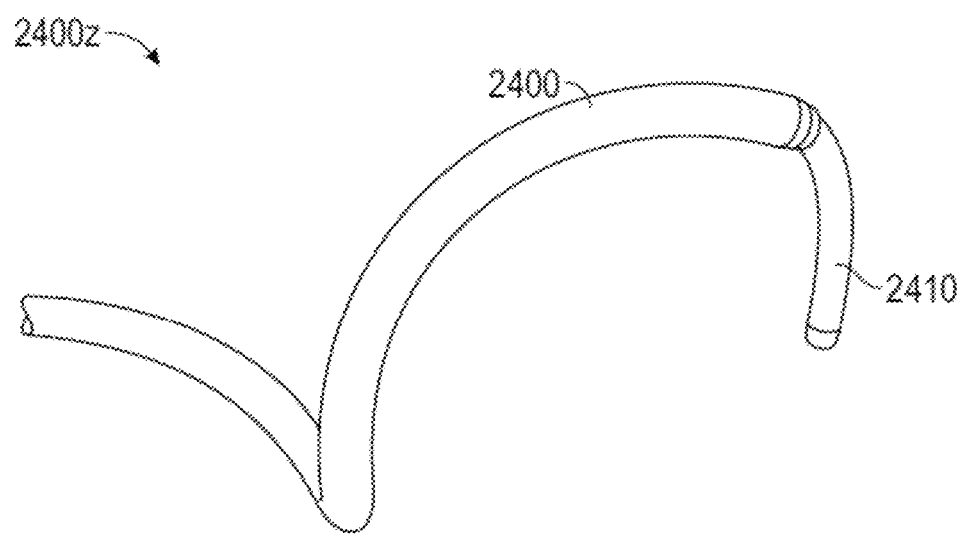

FIGS. 30A-30H show the exemplary use of a nested system 2400z as described herein. At FIG. 30A, the inner rigidizing device 2410 is positioned within the outer rigidizing device 2400 such that the distal end of the inner rigidizing device 2410 extends outside of the outer rigidizing device 2400. At FIG. 30B, the distal end of the inner rigidizing device 2410 is bent in the desired direction/orientation and then rigidized (e.g., using vacuum or pressure as described herein). At FIG. 30C, the outer rigidizing device 2400 (in the flexible configuration) is advanced over the rigidized inner rigidizing device 2410 (including over the bending distal section). Once the distal end of the outer rigidizing device 2400 is sufficiently advanced over the distal end of the inner rigidizing device 2410, then the outer rigidizing device 2400 can be rigidized (e.g., using vacuum or pressure as described herein). At FIG. 30D, the inner rigidizing device 2410 can then be transitioned to the flexible state (e.g., by removing the vacuum or pressure as described herein and by allowing the steering cables to go slack such that tip can move easily) and can be advanced and directed/oriented/steered as desired. Alternately, in FIG. 30D, the inner rigidizing device 2410 can be actively steered (either manually or via computational control) as it emerges such that is minimizes the load on the rigidized outer tube. Minimizing the load on the outer rigidizing device 2400 makes it easier for this tube to hold the rigidized shape. Once the inner rigidizing device 2410 is rigidized, the outer rigidizing device 2400 can be transitioned to the flexible state and advanced thereover (as shown in FIG. 30E). The process can then be repeated as shown in FIGS. 30F-H.

In some embodiments, at the completion of the sequence shown in FIGS. 30A-H, a third rigidizing device can be slid over the first two rigidizing devices (2400, 2410) and rigidized. Rigidizing devices 2400 and 2410 can then be withdrawn. Finally, a fourth rigidizing device can be inserted through the inner lumen of the third tube. This fourth rigidizing device may have a larger diameter and more features than rigidizing device 2410. For instance, it may have a larger working channel, more working channels, a better camera, or combinations thereof. This technique can allow two smaller tubes, which tend to be more flexible and maneuverable, to reach deep into the body while still ultimately deliver a larger tube for therapeutic purposes. Alternately, in the example above, the fourth rigidizing device can be a regular endoscope as is known in the art.

In some embodiments, at the completion of the sequence shown in FIGS. 30A-H, outer rigidizing device 2400 may be rigidized and then the inner rigidizing device 2410 may be removed. For example, the rigidizing device 2410 may be a "navigation" device comprising a camera, lighting and a distal steering section. The "navigation" device 2410 may be well sealed such that it is easy to clean between procedures. A second inner device may then be placed inside the rigidized outer device 2400 and advanced past the distal end of the outer device 2400. The second inner device may be a "therapeutic" tube comprising such elements as a camera, lights, water, suction and various tools. The "therapeutic" device may not have a steering section or the ability to rigidize, thereby giving additional room in the body of the therapeutic tube for the inclusion of other features, for example, tools for performing therapies. Once in place, the tools on the "therapeutic" tube may be used to perform a therapy in the body, such as, for example, a mucosal resection or dissection in the human GI tract.

In another embodiment, after or during the completion of the sequence shown in FIGS. 30A-H, a third device may be inserted inside inner tube 2410. The third device may be rigidizing and/or an endoscope.

Although the outer rigidizing device for the nested systems described herein is often referred to as rigidizing via vacuum and the inner scope rigidizing device as rigidizing via pressure, the opposite can be true (i.e., the outer rigidizing device can rigidize via pressure and the inner rigidizing device via vacuum) and/or both can have the same rigidizing source (pressure and/or vacuum).

Although the inner and outer elements of the nested systems are generally described as including integrated rigidizing elements, the rigidizing elements can be separate (e.g., so as to allow relative sliding between the imaging scope elements and the rigidizing elements).

The rigidizing devices of the nested systems described herein can be designed such that inner rigidizing device can't rotate substantially within outer rigidizing device when they are assembled. For instance, the outer surface of the inner rigidizing device can have longitudinal ridges and grooves that form a spline. The inner surface of the outer rigidizing device can have corresponding ridges and grooves that mate with the same features in the outer rigidizing device.

Either or both of the rigidizing devices of the nested systems described herein can be steerable. If both rigidizing devices are steerable, an algorithm can be implemented that steers whichever rigidizing device is flexible and moving longitudinally. The algorithm can steer the flexible rigidizing device to anticipate the shape of the rigidized device thus minimizing the tendency for the moving, flexible rigidizing device to straighten the rigid device.

If one rigidizing device of the nested systems described herein requires vacuum and the other rigidizing device requires pressure, user controls can be constructed in which moving one vs. the other (outer and inner) involves flipping a switch, with the switch toggling between a first condition in which, for example, one is pressurized for rigidity when the other is vented for flexibility and a second condition in which one is vented for flexibility and the other is vacuumed for stiffness. This, for example, could be a foot pedal or a hand switch.

In some embodiments, the alternate movement of the nested systems described herein can be controlled manually. In other embodiments, the alternate movement can be controlled automatically, via a computer and/or with a motorized motion control system.

The nested systems described herein can advantageously be of similar stiffness. This can ensure that the total stiffnesses of the nested system is relatively continuous. The nested systems described herein can be small so as to fit in a variety of different anatomies. For example, for neurology applications, the outside diameter of the system can be between 0.05"-0.15", such as approximately 0.1". For cardiology applications, the outside diameter of the system can be between 0.1"-0.3", such as approximately 0.2". For gastrointestinal applications, the outside diameter of the system can be between 0.3"-1.0", such as 0.8". Further, the nested systems described herein can maintain high stiffness even at a small profile. For example, the change in relative stiffness from the flexible configuration to the rigid configuration can be multiples of 10×, 20×, 30×, and even larger. Additionally, the nested systems described herein can advantageously move smoothly relative to one another.

The nested systems described herein can advantageously navigate an arbitrary path, or an open, complex, or tortuous space, and create a range of free-standing complex shapes. The nested systems can further advantageously provide shape propagation, allowing for shape memory to be imparted from one element to another. In some embodiments, periodically, both tubes can be placed in a partially or fully flexible state such that, for instance, the radii or curvature of the system increases, and the surrounding anatomy provides support to the system. The pressure or vacuum being used to rigidize the tubes can be reduced or stopped to place the tubes in a partially or fully flexible state. This momentary relaxation (for instance, for 1-10 seconds) may allow the system to find a shape that more closely matches the anatomy it is travelling through. For instance, in the colon, this relaxation may gently open tight turns in the anatomy.

In some embodiments, the stiffness capabilities of the inner or outer rigidizing devices may be designed such that tight turns formed by the inner rigidizing device at its tip, when copied by the outer rigidizing device, are gradually opened up (made to have a larger radius) as the shape propagates proximally down the outer tube. For instance, the outer rigidizing device may be designed to have a higher minimum radius of curvature when rigidized.

The nested systems are continuous (i.e., non-segmented) and therefor provide smooth and continuous movement through the body (e.g., the intestines). The nested systems can be disposable and low-cost.

In some embodiments, the outer rigidizing device can be a dynamically rigidizing overtube (e.g., as described in PCT/US18/42946, the entirety of which is incorporated by reference herein). In some embodiments, the inner rigidizing device can be a rigidizing system or a commercially available scope, for example a 5 mm diameter nasal scope. Utilizing rigidization and a nested system enables the utilization of a smaller scope that delivers, compared to a duodenoscope, more flexibility if desired, more stiffness if desired, enhanced maneuverability, and the ability to articulate at a much smaller radius of curvature.

In some embodiments, upon reaching the target destination, the inner rigidizing device of a nested system can be withdrawn. The outer rigidizing device can remain rigidized and contrast can be injected through the inner element's space to fluoroscopically image.

RF coils can be used in any of the nested systems described herein to provide a 3-D representation of whatever shape the nested system takes. That representation can be used to re-create a shape or return to a given point (e.g., for reexamination by the doctor after an automated colonoscopy).

In some embodiments, the nested systems described herein can be useful as a complete endoscope, with the internal structure carrying the payload of working channels, pressurization lines, vacuum lines, tip wash, and electronics for lighting and imaging (vision systems, ultrasound, x-ray, MRI).

The nested systems described herein can be used, for example, for colonoscopy. Such a colonoscopy nested system can reduce or eliminate looping. It could eliminate the need for endoscopic reduction. Without looping, the procedure can combine the speed and low cost of a sigmoidoscopy with the efficacy of a colonoscopy. Additionally, colonoscopy nested systems can eliminate conscious sedation and its associated costs, time, risks, and facility requirements. Further, procedural skill can be markedly reduced for such colonoscopy procedures by using the nested systems described herein. Further, in some embodiments, the nested systems described herein can provide automated colonoscopy, wherein a vision system automatically drives the nested system down the center of the colon while looking for polyps. Such an automated system would advantageously not require sedation nor a doctor for the basic exam while allowing the doctor to follow up for further examination if required.

In some embodiments, the rigidizing devices (e.g., nested systems) described herein can be robotically controlled. FIGS. 31A-31D show an exemplary use of a nested system 9300z, like that shown in FIGS. 30A-30H, that can be robotically controlled or manipulated (e.g., for rigidization, steering, movement, etc.). As shown in FIGS. 31A-31D, the outer rigidizing device 9300 and the inner rigidizing device 9310 may be terminated together into a common structure, such as a cassette 9357. The outer rigidizing device 9300 can be movable with respect to the inner rigidizing device 9310 by rotation of a disk 9389 that is mounted to the cassette 9357. For example, the disk 9389 can be a pinion, and the outer rigidizing device 9300 may have a rack 9382 including a plurality of small teeth on the outside thereof. Rotating the disk 9389 against teeth 9382 may cause outer rigidizing device 9300 to advance forward or backward relative to the inner rigidizing device 9310. In some embodiments, the possible movement or translation of the rigidizing devices 9300, 9310 is limited by the size or design of the cassette 9357.

The cassette 9357 can further include additional disks 9371*a*, 9371*b* that may connect to cables 9363*a,b* respectively, to steer (e.g., bend or deflect) the tip of the inner rigidizing device 9310 (and/or outer rigidizing device 9300). Other steering mechanisms (e.g., pneumatics, hydraulics, shape memory alloys, EAP (electro-active polymers), or motors) are also possible. Again, in embodiments with different steering mechanisms, one or more disks in the cassette 9357 (e.g., disks 9371*a*, 9371*b*) may be used to actuate the steering.

Figure 31A:
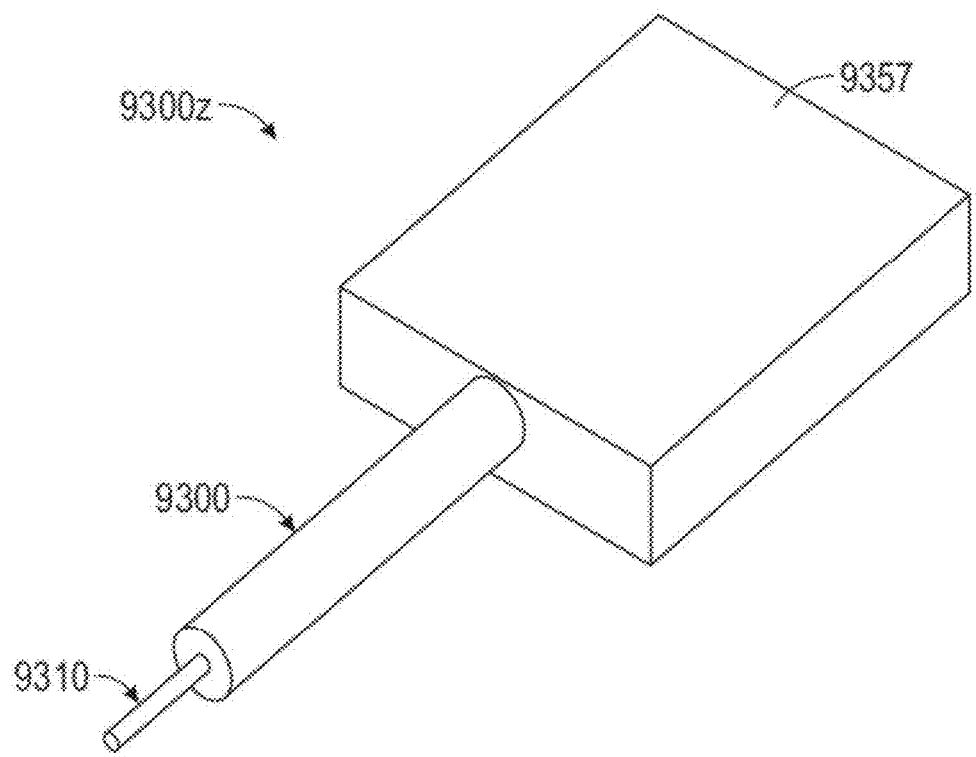
FIGS. 31A-31D show a robotically controlled rigidizing system.
Figure 31B:
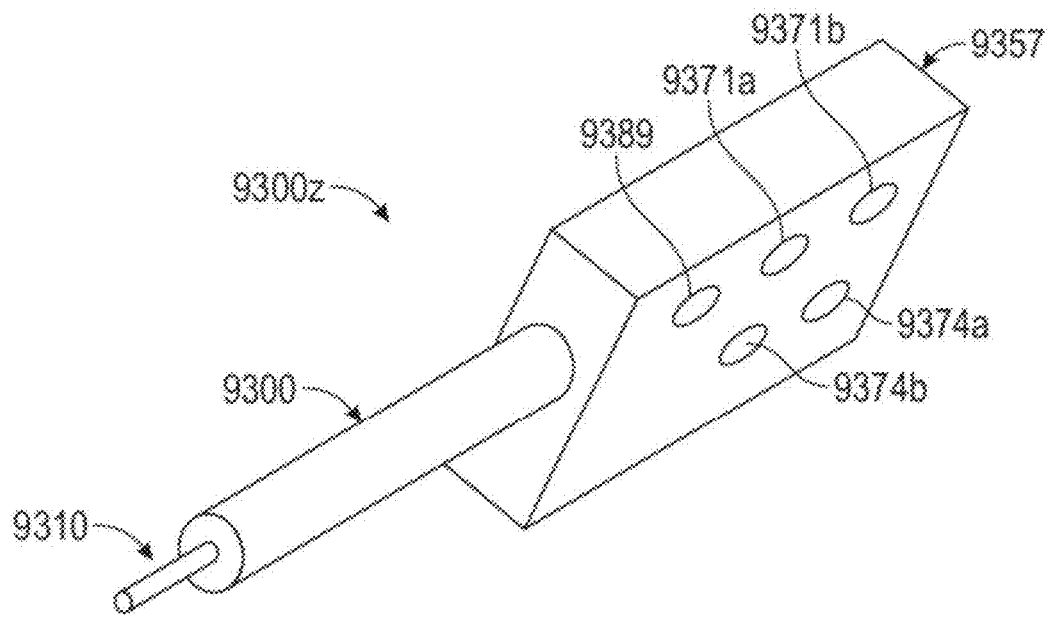
Figure 31C:
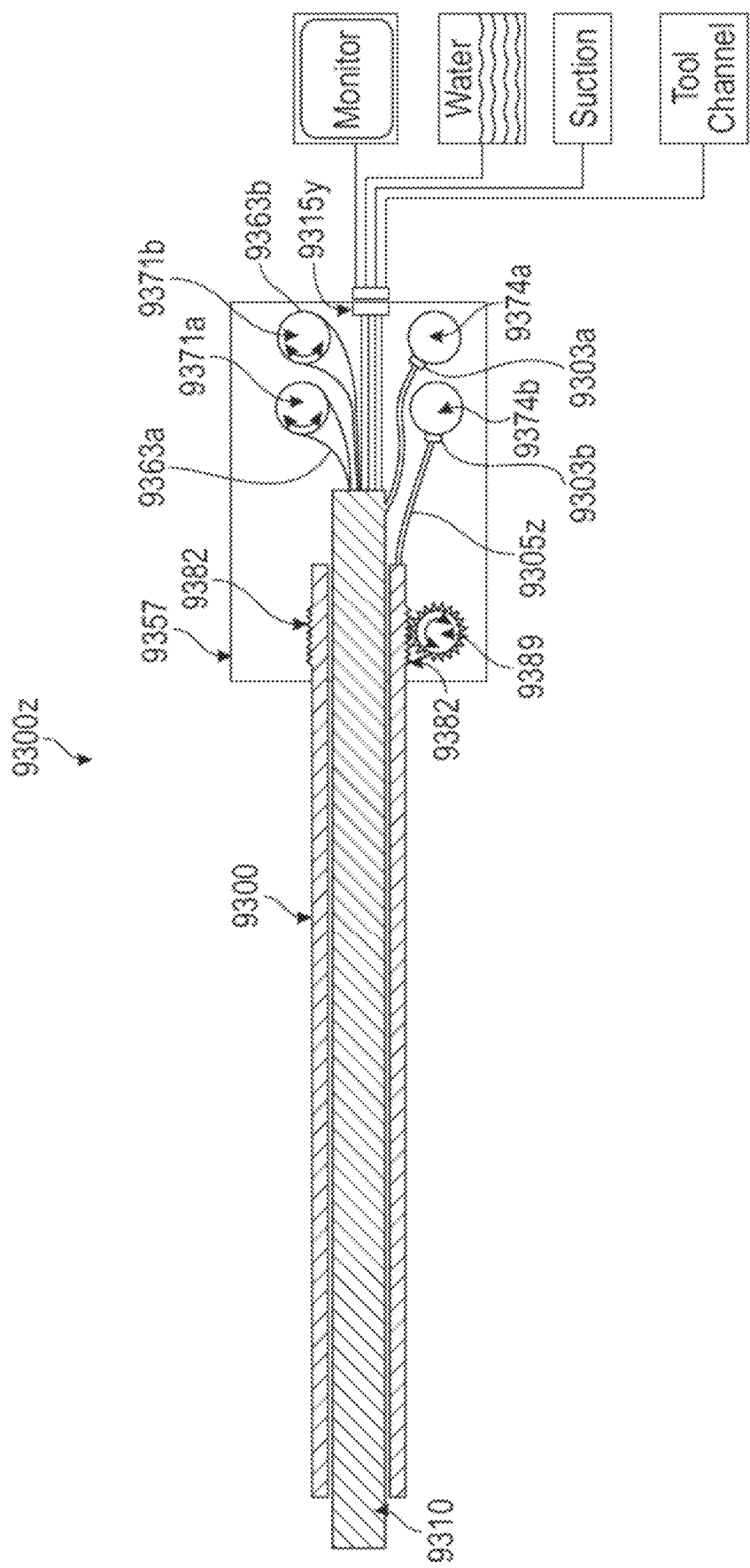
Figures 31D, 32A, 32B:
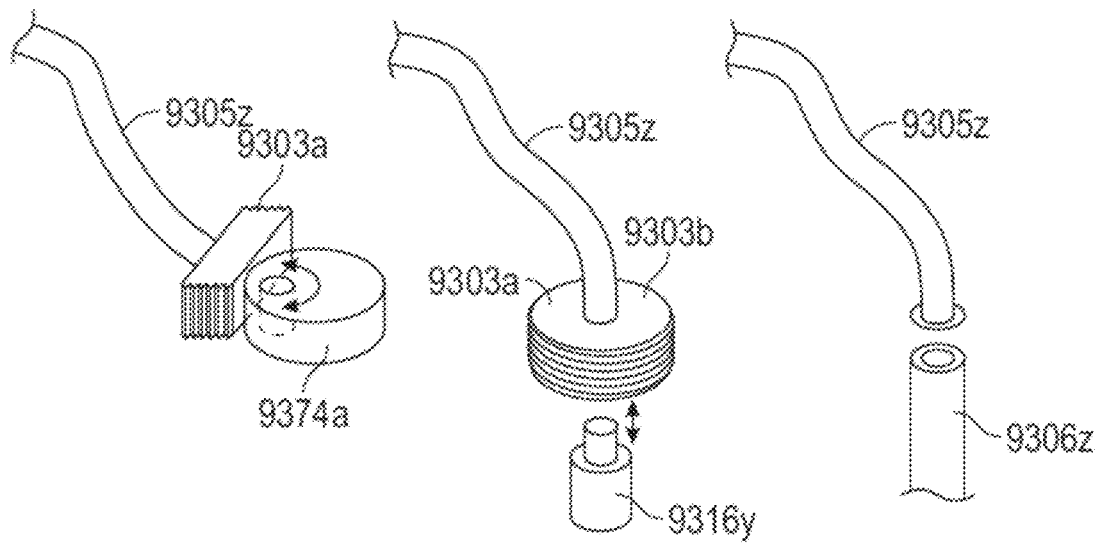
FIGS. 32A-32B show mechanisms of actuating a robotically controlled rigidizing system.

The cassette 9357 can further include bellows 9303*a*, 9303*b* that may connect to the pressure gap of the inner rigidizing device 9310 and the outer rigidizing device 9300, respectively. Compressing bellows 9303*a*, 9303*b* may drive fluid through pressure lines 9305*z*, causing the pressure in the pressure gap of the inner rigidizing devices 9310, 9300 to rise, causing the rigidizing devices 9310, 9300 to become rigid. Activation of the bellows 9303*a*, 9303*b* may be applied sequentially and/or simultaneously. As shown in FIGS. 9A-9D, the cassette 9357 can include eccentric cams 9374*a,b* to control bellows 9303*a,b*. Alternatively, as shown in FIG. 32A, one or more linear actuators 9316*y* (e.g., on cassette 9357 or on drive unit 9517*y*) can be configured to actuate the bellows 9303*a,b*. As another alternative, the devices 9300, 9310 can be rigidized and de-rigidized through one or more sumps (as described herein) or pressure sources 9306*z* (e.g., via pressure line 9305*z*), as shown in FIG. 32B. Other mechanisms causing rigidization of the inner and outer rigidizing devices 9310, 9300 are also possible. For example, in some embodiments, cassette 9357 can include a syringe or other container comprising a fluid that can be delivered to the inner and outer rigidizing devices 9310, 9300 to add pressure for rigidization. In some embodiments, a syringe or other container can be used to draw fluid within the cassette 9357, creating a vacuum that can be applied to the inner and outer rigidizing devices 9310, 9300.

Referring back to FIGS. 31A-31D, the cassette 9357 can include a connector 9315*y* for connecting to additional lumens and/or wiring in the inner rigidizing device 9310. The connector 9315*y* may include a connection for the delivery of both suction and water to the tip of the inner rigidizing device 9310. The connector 9315*y* may include electrical connector to connect to a camera mounted to the tip of inner rigidizing device 9310 to an external monitor and/or video processing unit. The connector 9315*y* may include a mechanical connector that connects to a hollow tube (e.g., working channel) leading all the way to the tip of the inner rigidizing device 9310. By including the connector 9315*y*, the control of all components of the system 9300*z* can be performed with the cassette 9357.

Disks 9389, 9371*a*, 9371*b* and cams 9374*a*, 9374*b* (or the corresponding bellows) may be accessible from the bottom of the cassette 9357, as best shown in the side perspective view of FIG. 93B. Disks 9389, 9371*a*, 9371*b* and/or cams 9374*a*, 9374*b* may have features, such as splines, pins or teeth, to transmit torque. These features can allow the disks 9389, 9371*a*, 9371*b* and/or cams 9374*a*, 9374*b* to be manipulated (e.g., by a drive unit).

Figure 33:
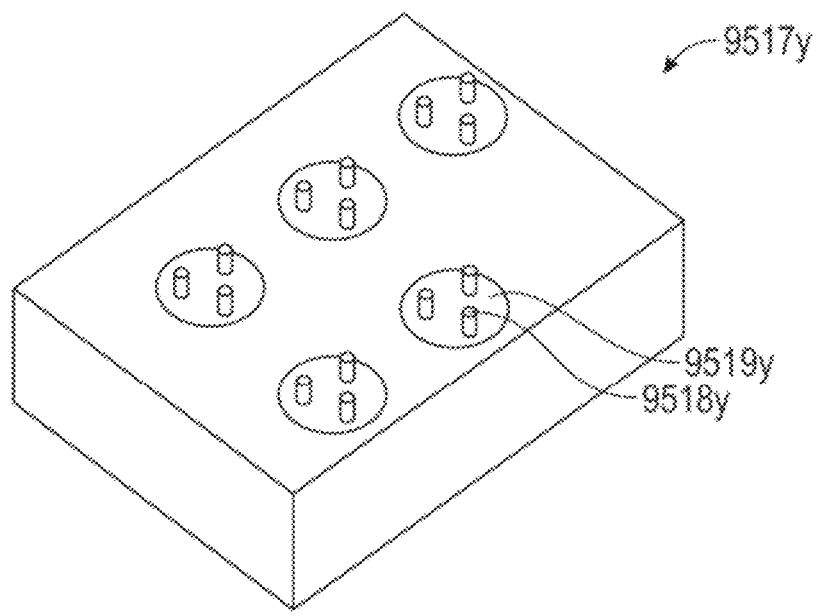
FIG. 33 shows a drive unit for a robotically controlled rigidizing system.

FIG. 33 shows an exemplary drive unit 9517*y* that may be used to drive the disks 9389, 9371*a*, 9371*b* and/or cams 9374*a*, 9374*b*. For example, the drive unit 9517*y* can include drive paddles 9519*y* that may align with disks 9389, 9371*a*, 9371*b* and/or cams 9374*a*, 9374*b* of the cassette 9357. The drive paddles 9519*y* can be driven (i.e., rotated) by one or more motors of the drive unit 9517*y* so as to deliver torque to the disks 9389, 9371*a*, 9371*b* and/or cams 9374*a*, 9374*b* of the cassette 9357. The drive paddles 9519*y* can includes features 9518*y* (e.g., splines, pins, teeth, or the like) to transmit torque to the disks 9389, 9371*a*, 9371*b* and/or cams 9374*a*, 9374*b* of the cassette 9357. The drive unit 9517*y* may attach to the cassette 9357, for example, with clips, screws, or magnets.

In some embodiments, the rigidizing systems described herein can include one or more guides to allow the advancement of tools (i.e., working tools), such as surgical or laparoscopic tools, graspers, articulating graspers, fecal wash devices, and/or fecal-suctioning devices therethrough. In some embodiments, the tool can be a scope (e.g., so as to enable a secondary scope within or alongside a primary scope). The guide can allow a tool to be guided along or through the rigidizing device until the distal end of the tool advances distally past the distal end of the rigidizing device to perform the desired procedure. Further, in some embodiments, the rigidizing systems can include more than one guide so as to provide for differing placement and/or the use of multiple tools. For example, as shown in FIG. 36, a rigidizing device 9800 can include two guides 9821*y* on opposite sides thereof. The guides 9821*y* can comprise the same or a different design. More than two guides and associated tools are also possible. In some embodiments, guides may be located within the volume of inner rigidizing device (e.g., rigidizing device 9310).

The guides described herein can be used with a single rigidizing system (e.g., a rigidizing scope or overtube) or with a nested rigidizing system (e.g., a robotically controlled nested system). If used as part of a nested system, the guides can be included on or within the inner rigidizing device or the outer rigidizing device. Additionally, the tool guides described herein can be used when the rigidizing system is in the flexible, partially flexible, or fully rigidized configuration.

Referring to FIG. 34, in some embodiments, a rigidizing system as described herein (e.g., robotic system 9300*z*) can include one or more guides 9621*y* extending along the outer diameter of the outer rigidizing device 9600. The guide 9621*y* may be, for example, a series of atraumatic rings 9622*y*. The rings 9622*y* may be spaced apart from each other along the longitudinal axis such they do not touch each other even when the outer rigidizing device 9600 is deflected to its maximum bend radius. In some embodiments, the rings 9622*y* can have an inner diameter of about 2-9 mm. In some embodiments, the rings 9622*y* may tilt at their connection to the rigidizing device 9600 such that they can lay flat against device 9600 when being inserted into the body and then tilt up to a position approximately perpendicular to the circumference of the device 9600 for use. In some embodiments, the rings 9622*y* can be pre-biased to self-expand radially outwards. In other embodiments, the rings 9622*y* can be configured to be actively expanded (e.g., by applying tension on a pullwire connected to the rings 9622*y*).

Referring to FIGS. 35A-35B, a guide 9721*y* for a rigidizing system or device can be, for example, a layflat tube that is adhered along one side to the rigidizing device 9700. In a first configuration (shown in FIG. 35A), the layflat tube guide 9721*y* can be flat against the outside of the rigidizing device 9700. In a second configuration, the guide 9721*y* can be expanded to its tubular shape. The layflat tube guide 9721*y* can include a fiber wound in a hoop pattern therearound to reinforce the expanded diameter. The fiber may be, for example, an aramid such as Technora, an ultrahigh molecular weight polyethylene such as Dyneema, or a liquid crystal polymer such as Vectran. The inner diameter of the guide 9721y in the expanded configuration can be, for example, between 2 mm and 9 mm. The layflat tube guide 9721y may assume the second configuration, for example, when a tool is passed through the layflat tube guide 9721y. The layflat tube guide 9721y may have a series of perforations along its length to allow a tool to be inserted into the lumen of the tube guide 9721y at any perforation along the length of the rigidizing device 9700. In one exemplary method of manufacturing, the layflat tube guide 9721y can be stretched in length and then, while still stretched, bonded to the side of the rigidizing device 9700. For example, the layflat tube guide 9721y can be strained 20%, 30%, 40%, 50% or more before being bonded to the rigidizing device 9700. This technique may result in a layflat tube guide 9721y with a residual strain in its wall. When the rigidizing device 9700 (and associated layflat tube guide 9721y) is bent around a curve and the layflat tube guide 9721y undergoes a compressive force (for instance, if the working channel is on the inside of a bend in the rigidizing device 9700), the residual strain in the walls of the layflat tube guide 9721y may advantageously result in less compression in the wall and thus less wrinkling of the layflat tube guide 9721y.

The tool guides used herein can advantageously be designed so as to be flexible and thereby enable bending of the rigidizing devices during insertion of the rigidizing device. For example, the rings 9622y can be spaced apart to enable flexible bending of the rigidizing device. Similarly, the layflat tube 9'721y can be thin and flexible to enable bending of the rigidizing device.

Figure 44:
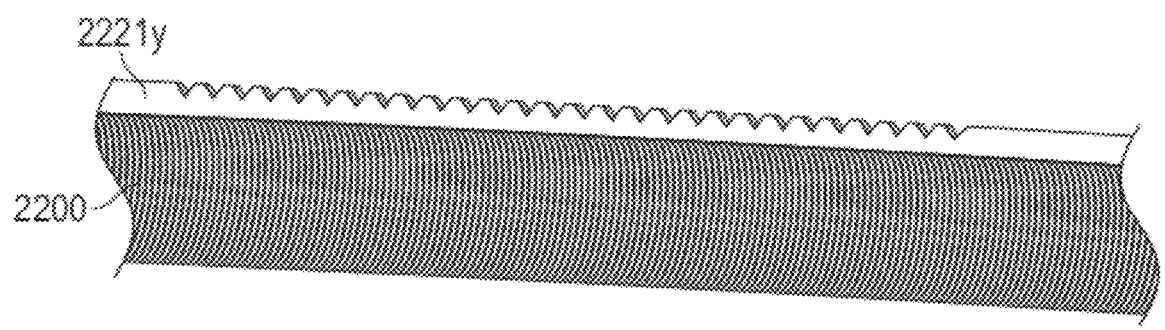
FIG. 44 shows a rigidizing device with a serrated working channel attached thereto.

As another example, as shown in FIG. 44, the guide(s) 2221y can be a notched or serrated tube configured to bend easily when attached along its length to the rigidizing device 2200.

Figure 45:
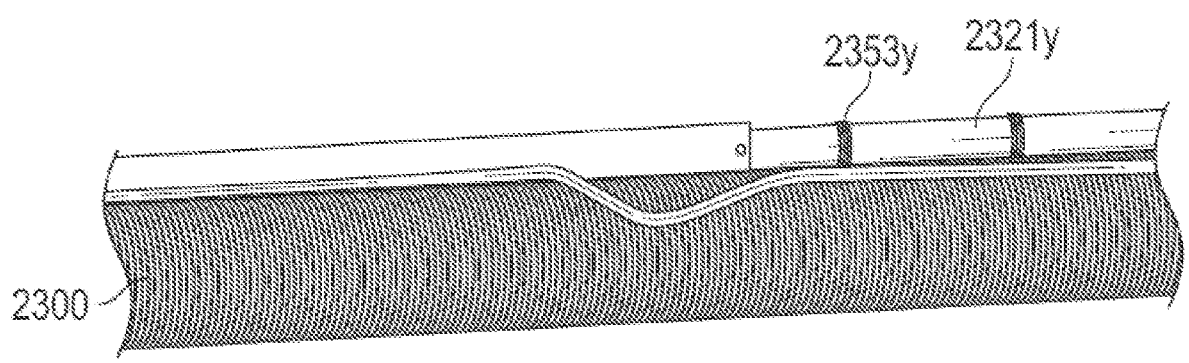
FIG. 45 shows a rigidizing device with a telescoping working channel attached thereto.

As another example, shown in FIG. 45, the guide(s) 2321y can be a series of telescoping rigidizing devices, shaped like bellows, or combinations thereof. The guide(s) 2321y can be periodically attached to the outer rigidizing device 2300 with rings 2353y spaced longitudinally along the length of the outer rigidizing device 2300.

Figure 46:
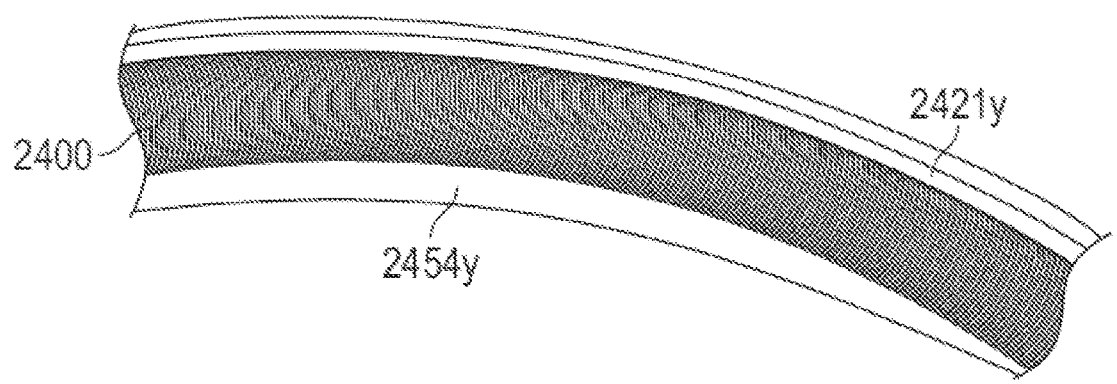
FIG. 46 shows a rigidizing device with one or more working channels free-floating within an outer sheath that is configured to be vacuum activated.

As another example, shown in FIG. 46, the guide(s) 2421y can be flexible tubing that is attached to the outer rigidizing device 2400 only at the proximal and distal ends. A device sheath 2454y can be sealed over the top of the outer rigidizing device 2400 and the guide(s) 2421y. In some embodiments (e.g., after the device has reached its desired location), vacuum can be applied in the space between the device sheath 2454y and the outer rigidizing device 2400, thereby suctioning the guide(s) 2421y to the rigidizing device 2400 for firm attachment thereto. Such firm attachment can enable tools to be easily passed through the guide(s) 2421y.

Figure 47:
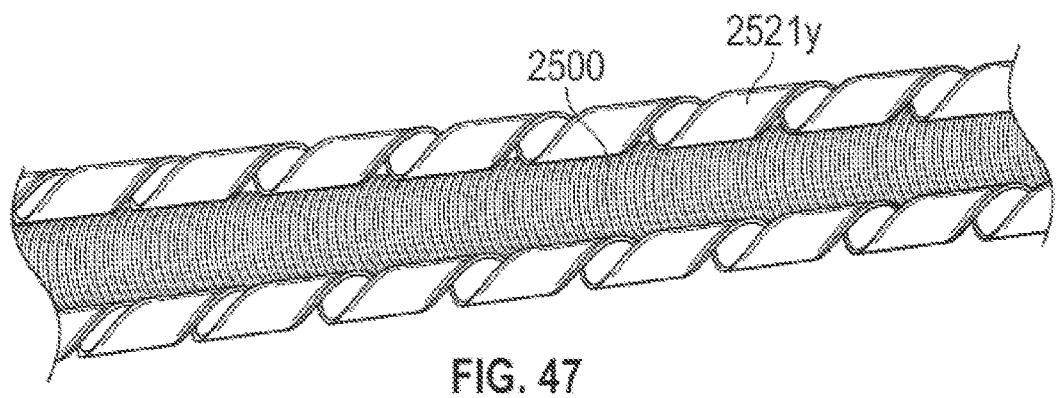
FIG. 47 shows a rigidizing device with a spiral-cut working channel attached thereto.

As another example, shown in FIG. 47, the guide(s) 2521y can be made of spiral cut tubing. The spiral cut guide(s) 2521y can be periodically attached to the outer rigidizing device 2500 along the length of the guide(s) 2521y or attached with a thin sheet of material, such as a thin sheet of highly flexible elastomer.

Figure 48:
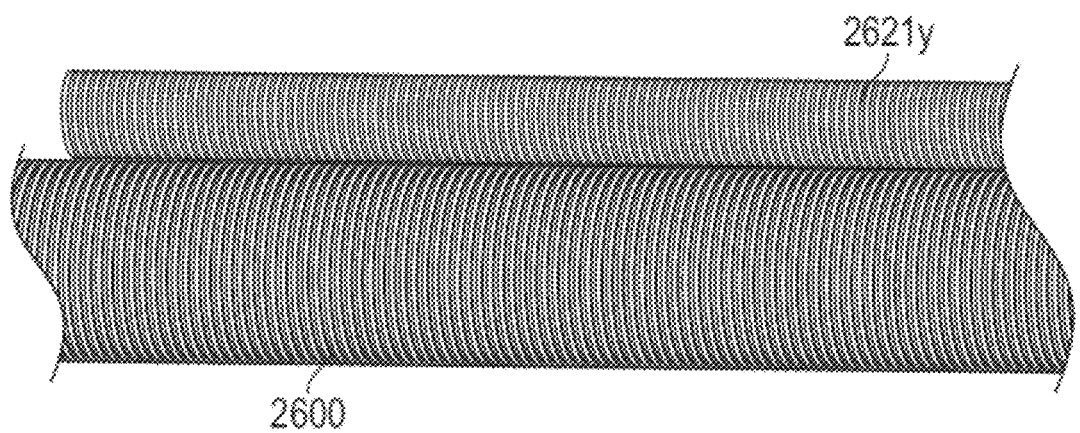
FIG. 48 shows a rigidizing device with a coiled working channel attached thereto.

As another example, shown in FIG. 48, the guide(s) 2621y can be a spring (e.g., a metal spring) with gaps between the coils. The guide(s) 2621y can be periodically attached to the outer rigidizing device 2600.

As another example, the guide(s) can be configured to expand and/or fold outwards after placement in the body and/or as the tool is placed therethrough.

Figure 41A:
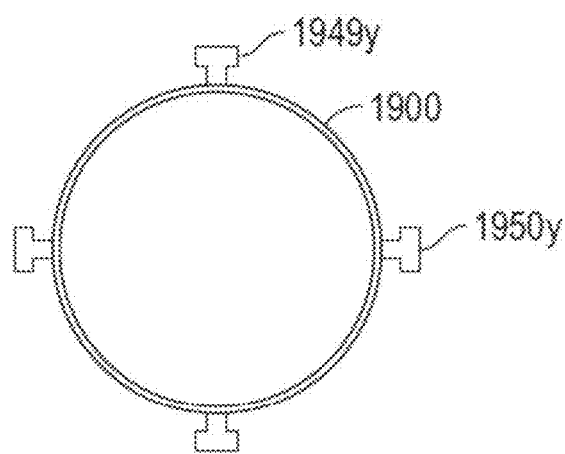
FIGS. 41A-41C show a rigidizing device with a rail system for attachment of a working channel.
Figure 41B:
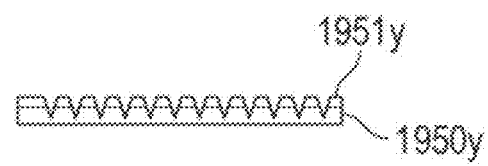
Figure 41C:
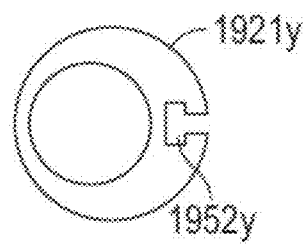

In some embodiments, a rigidizing system (e.g., a robotically controlled nested system) can be designed so as to include guides that can be attached after insertion of the system into the body. For example, referring to FIGS. 41A-41C, the rigidizing device 1900 can include a plurality of rails 1949y extending the length of the outer rigidizing device 1900. The rails 1949y can, for example, include a male extension, such as a T-bar (e.g., such that a ledge is formed between the outermost edge 1950y of the rail 1949y and the outer diameter of the outer rigidizing device 1900). In some embodiments, as shown in FIG. 41B, the outermost surface of the edge 1950y can include serrations 1951y (e.g., blunt serrations) along the longitudinal length thereof to enhance flexibility of the rail 1949y (e.g., to help enable the rail 1949y to bend as the outer rigidizing device 1900 bends). There can, for example, be 1-10 rails 1949y positioned around the circumference of the rigidizing device 1900 (e.g., equidistant or at varying positions). In one specific embodiment, there can be four rails 1949y positioned approximately 90 degrees apart from one another around the circumference. As shown in FIG. 41C, the guide(s) 1921y can be a tubular body having a female slot 1952y (e.g., a T-slot) extending along the longitudinal length of the guide 1921y and configured to mate with, and ride along, the rail 1949y.

In use, the rigidizing device 1900 can be inserted into a body lumen until the location of interest (e.g., lesion) is reached. Once at the location, one or more guides 1921y can be inserted along the rails 1949y. In some embodiments, the proximal end of the guides 1921y can be snapped or broken off after insertion to reduce the unneeded length of the guide 1921y. One or more tools can then be inserted through the guides 1921y as desired (e.g., to treat a lesion).

Advantageously, having rails 1949y with connectable guides 1921y can reduce the diameter and the stiffness of the rigidizing system as the system is inserted into place, thereby making it easier to move and/or steer the system to the area of interest. Further, the connection between the guides 1921y and the rails 1949y can advantageously be secure, and the guide 1921y can be relatively stiff (e.g., without impacting the movement of the system), ensuring that tools can be placed therethrough for use at the location of interested (e.g., lesion). Additionally, having multiple rails 1949y can advantageously allow the user to choose the desired rotational position of the guide 1921y, thereby ensuring that the tool can be positioned at the correct orientation relative to the location of interest (e.g., lesion) without having to substantially rotate the entire system. Finally, having attachable guides 1921y can allow the user to choose a guide 1921y with a diameter or characteristic that is specific to the treatment plan.

In some embodiments, the rail 1949y can have a female slot, and the guide 1921y can have a male extension. In some embodiments, the rail 1949y can have discrete disconnected pieces along the longitudinal length of the outer rigidizing device 1900 rather than serrations.

Figure 52A:
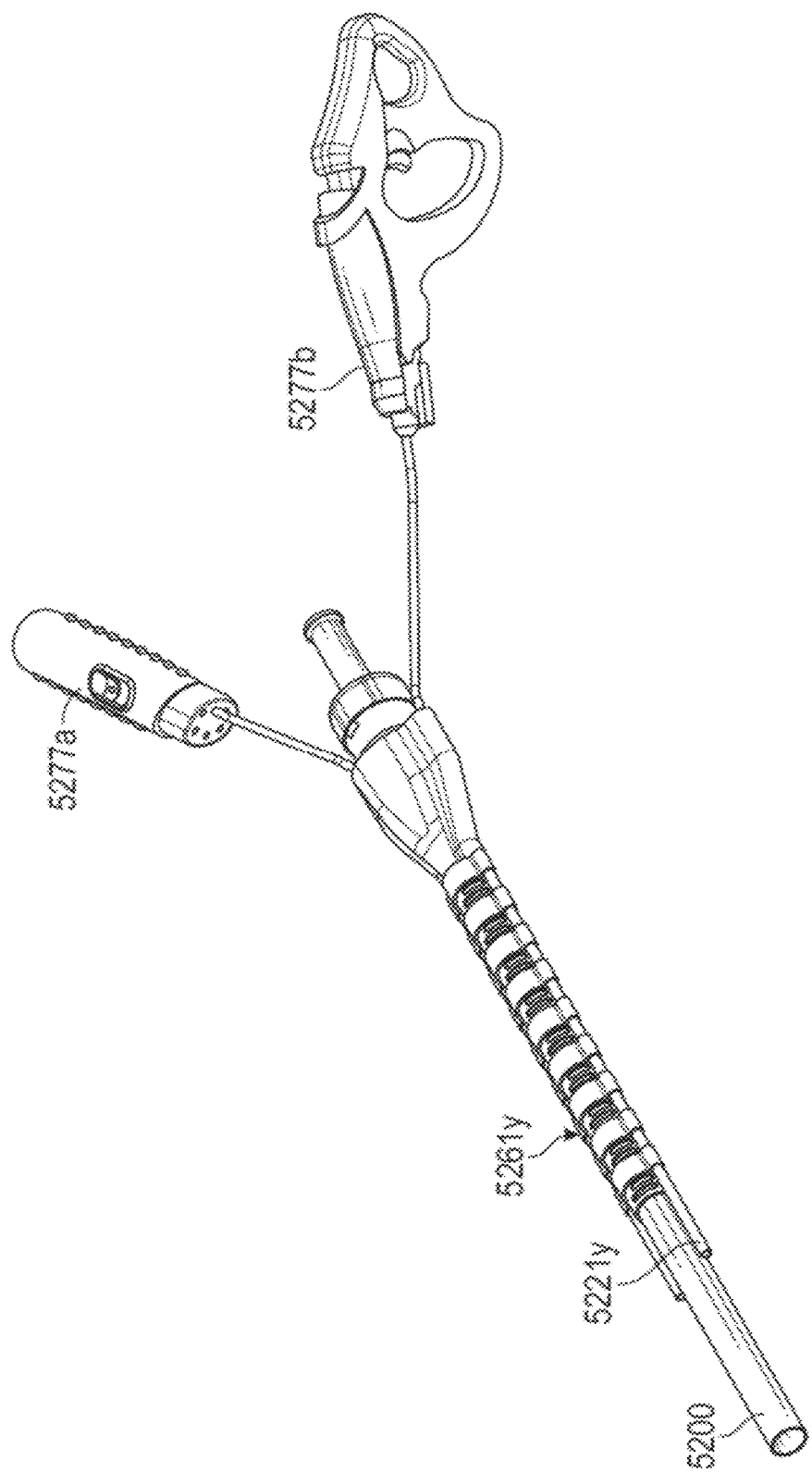
FIGS. 52A-52B show a rigidizing device including a flexible outer tube with working channels.
Figure 52B:
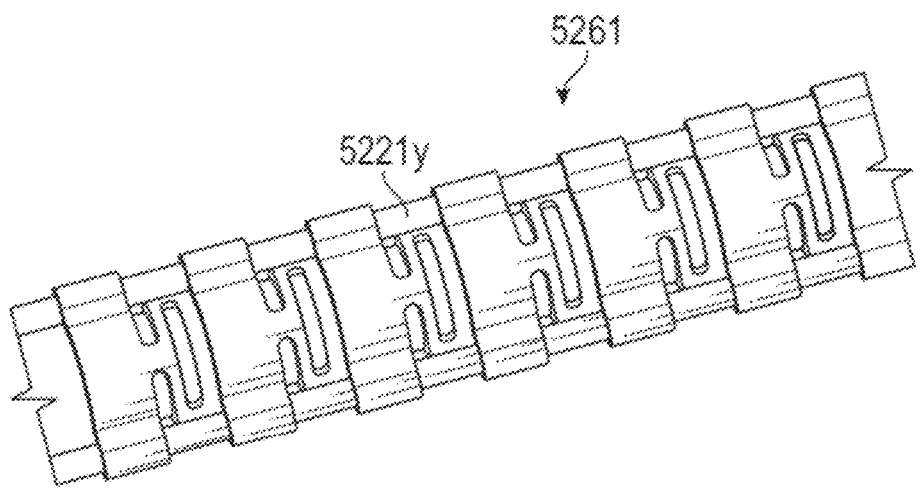

In some embodiments, the plurality of guides can be part of a unitary structure that slides over the rigidizing device after insertion of the rigidizing device into the body. For example, as shown in FIGS. 52A-52B, a plurality of guides 5221y (for passage of exemplary tools 5277a,b) can be built into an outer tube 5261y. The outer tube 5261y can be configured to slide over the outer rigidizing device 5200. In some embodiments, for example, the outer tube 5261y can have a coating on the interior thereof to reduce friction during sliding. Further, as shown in FIGS. 52A-52B, the outer tube 5261y can include a plurality of flexures or linkages to enhance flexibility of the tube 5261y. In other embodiments, the outer tube 5261y can be a solid tube and/or a coil-wound tube. In some embodiments, the outer tube 5261y can have a slit down the longitudinal length thereof and/or can be semi-circular so as to snap onto the outer rigidizing device 5200. In some embodiments, the proximal end of the outer tube 5261y can be configured to be broken or snapped off after insertion to reduce the unneeded length. The outer tube 5261y can advantageously have torsional stiffness to enable rotational adjustment of the location of the guides 5221y after insertion of the outer tube 5261y over the outer rigidizing device 5200. In some embodiments, the outer tube 5261y can include an outer sheath thereover such that vacuum can be supplied between the outer sheath and the outer rigidizing device 5200 to suction the guides 5221y to the outer rigidizing device 5200.

In another embodiment, shown in FIGS. 73A-73M, the plurality of guides 7321y can be configured to be removably positioned within an outer tube 7361y to act as a liner for the channels 7348x. The outer tube 7361y can be a thin-walled sleeve, such as an elastomeric sleeve, a plastic sleeve, or a cloth sleeve. In some embodiments, the outer tube 7361y can be a sleeve that is fiber reinforced or wire reinforced. In one specific example, the outer tube 7631y can be a cloth material that inherently has some stretch and/or a cloth material that is sewn at a 45° angle (e.g., such that being off-bias provides compliance and/or stretch). In some embodiments, the tube 7361y can be permanently attached to (e.g., bonded, heat welded, sewn, or ultrasonically welded) the outer surface of the rigidizing device 7300 (e.g., can be an additional layer of the wall of the rigidizing device 7300). The outer tube 7631y can, for example, have a wall thickness of 0.001"-0.030", such as 0.010". The outer tube 7361y can include a plurality of channels 7348x (e.g., 2-8 channels 7348x, such as 3 channels 7348x) positioned around the outer tube 7361y. The channels 7348x can be, for example, layflat or expandable channels 7348x. In some embodiments, the channels 7348x can be straight (i.e., axially aligned with the outer tube 7361y). In other embodiments, the channels 7348x can be spiraled. In some embodiments, the channels 7348x can be co-joined by sewing, bonding, or heat-sealing. In some embodiments, the channels 7348x can be lined with a hydrophilic, hydrophobic, or low friction (e.g., PTFE) coating.

The guides 7321y can be inserts (e.g., molded or extruded inserts) that are configured to be positioned within the channels 7348x for use. For example, the guides 7321y can be configured to be inserted into one or more channels 7348x after the rigidizing device 7300 has been placed and/or rigidized in the body lumen. Each guide 7321y can include a lumen 7350x therein (configured for passage of a tool 7377). Each guide 7321y can have a stiffness sufficient to open or expand the channel 7348x as it extends therethrough. In some embodiments, the guides can have an inner diameter of 1 mm-7 mm, such as 3 mm-5 mm, and a wall thickness of ½ mm to 1 mm. Further, in some embodiments, the guide 7321y can be made of a polymer, such as Teflon, FEP or a polyethylene (such as HDPE or LDPE). The lumen 7350x can be lubricious to help enable passage of the tool 7377 therethrough. For example, the lumen 7350x can be made of a material (e.g., the same material as the guide itself 7321y) having a low coefficient of friction, such as Teflon, FEP or a polyethylene (such as HDPE or LDPE). As another example, the lumen 7350x can be coated with a separate lubricious coating, such as a hydrophilic coating.

Figure 73A:
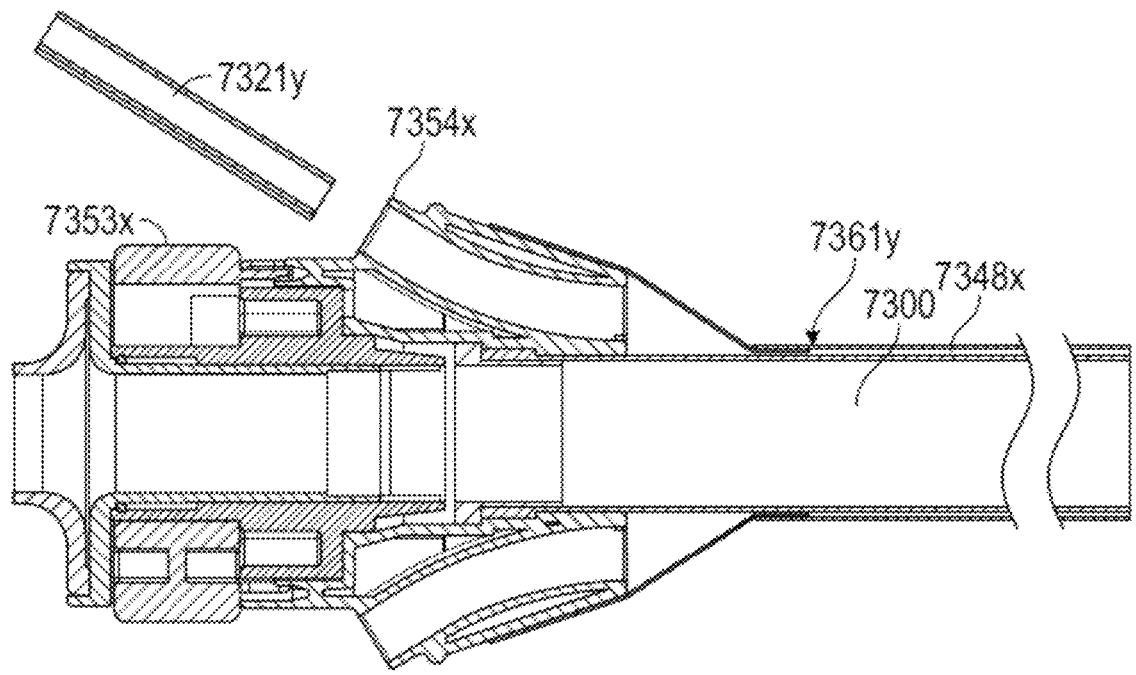
FIGS. 73A-73M show a rigidizing system having an outer tube with removable guides configured to enable insertion of a working tool therethrough.
Figure 73B:
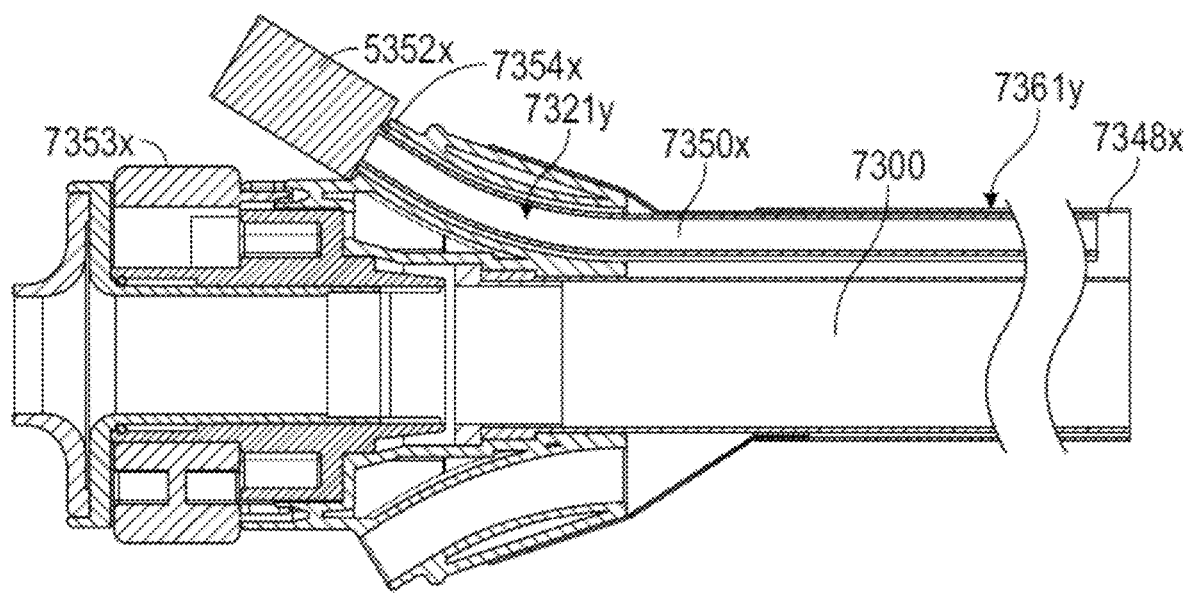
Figure 73C:
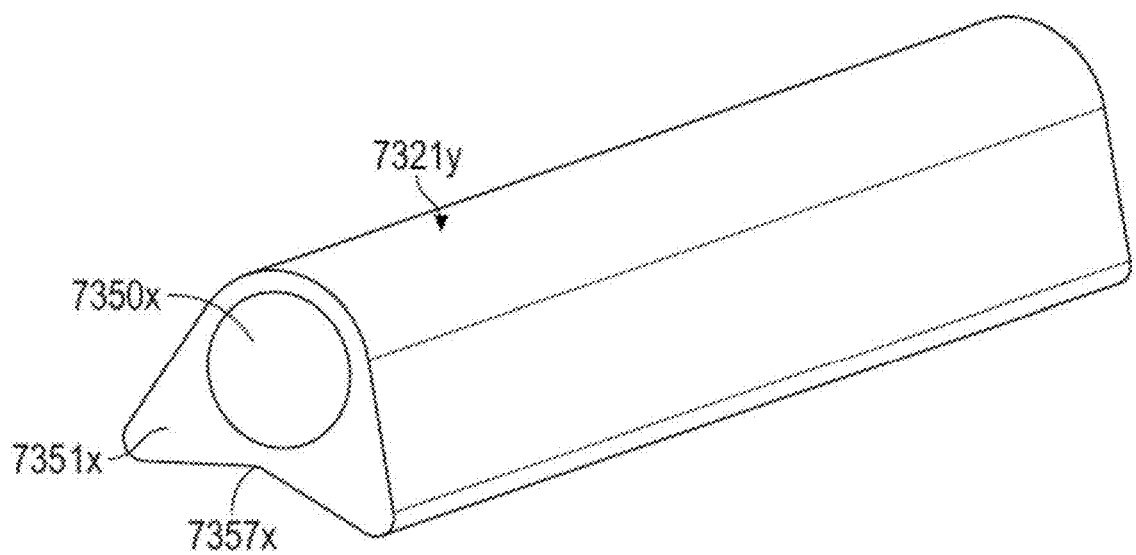
Figure 73D:
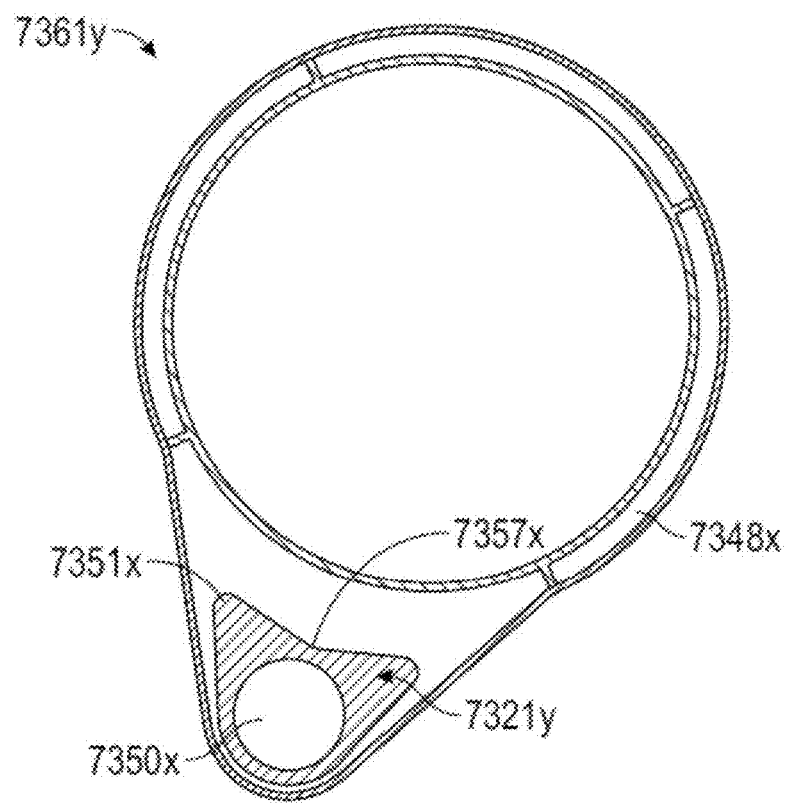
Figure 73E:
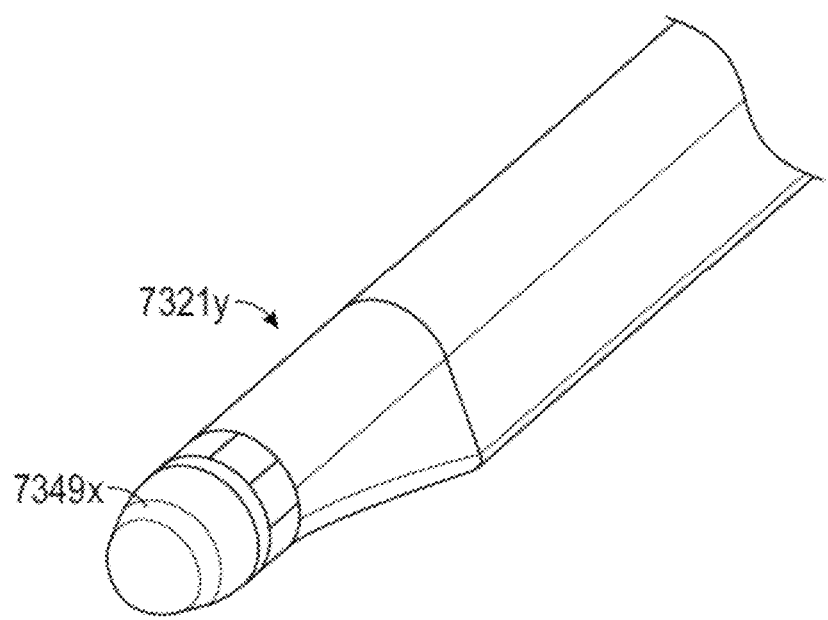
Figure 73F:
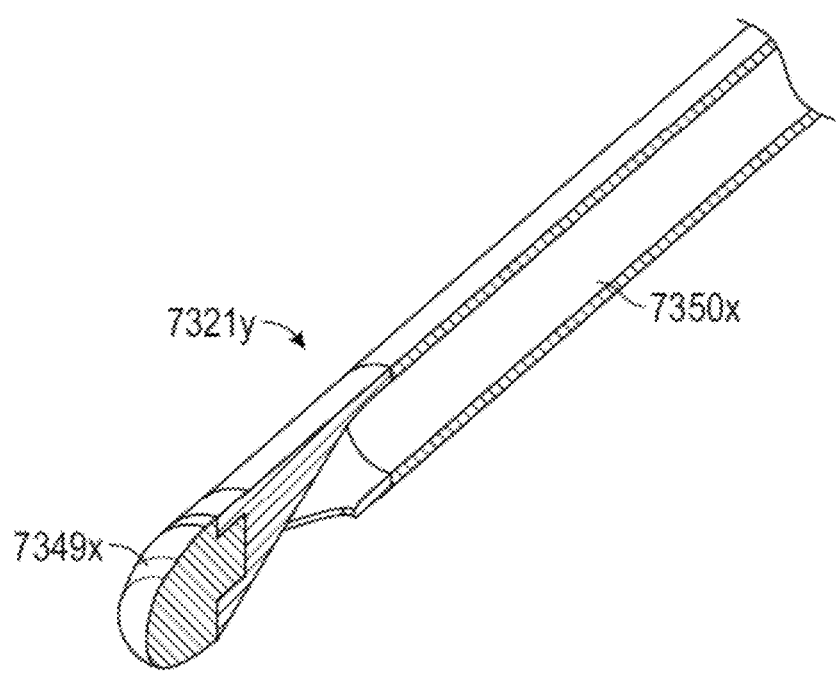
Figure 73G:
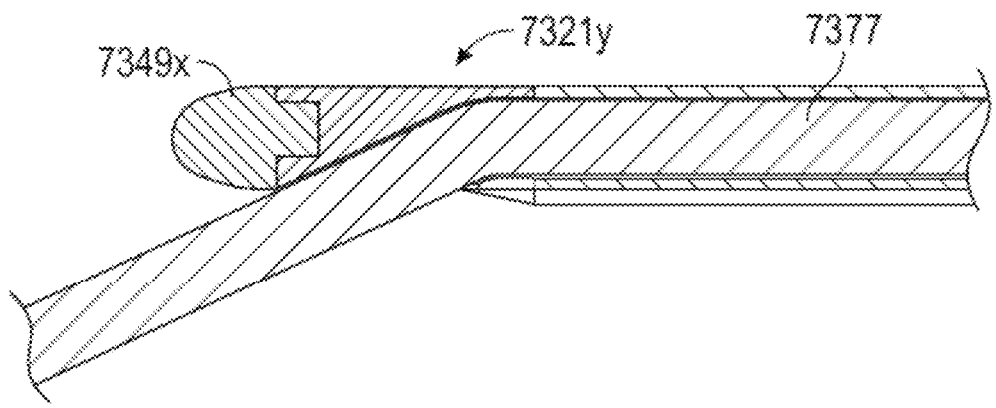
Figure 73H:
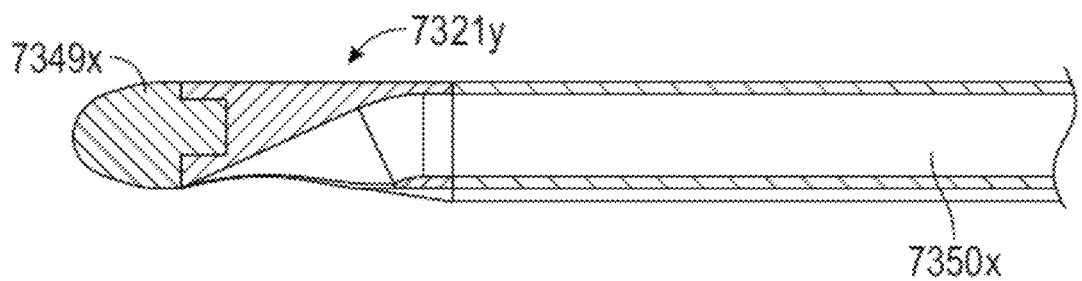
Figure 73I:
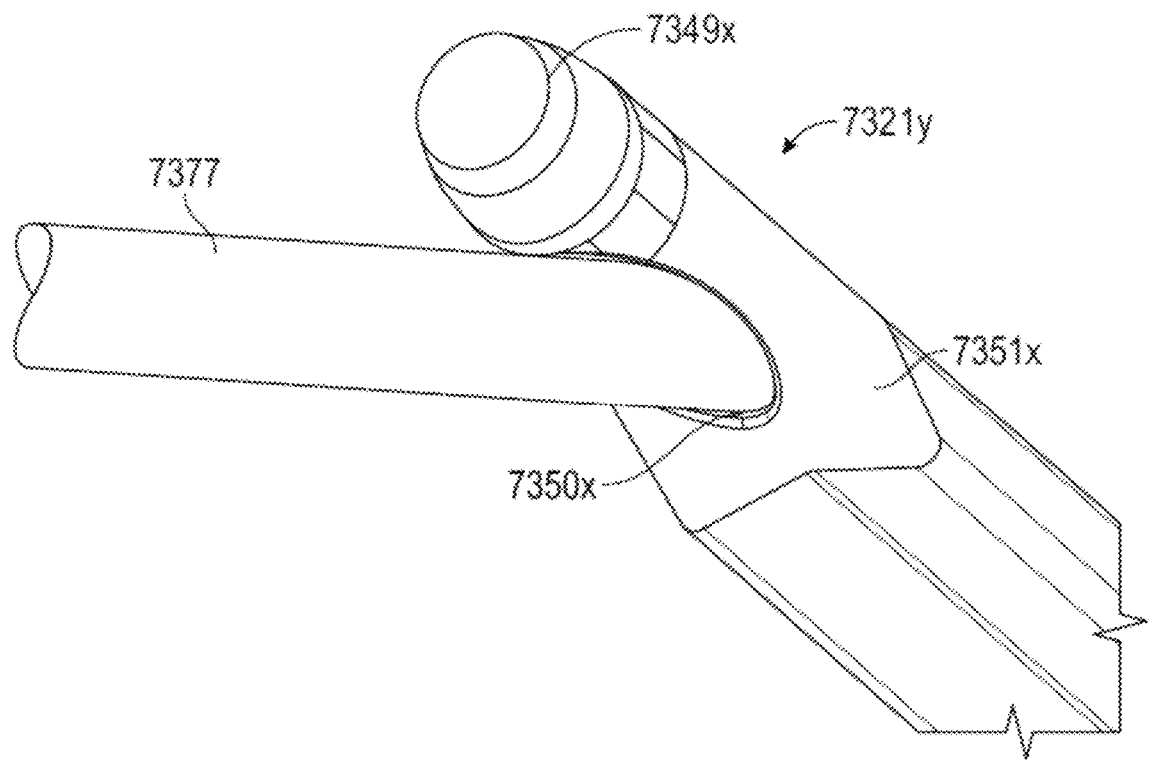
Figure 73J:
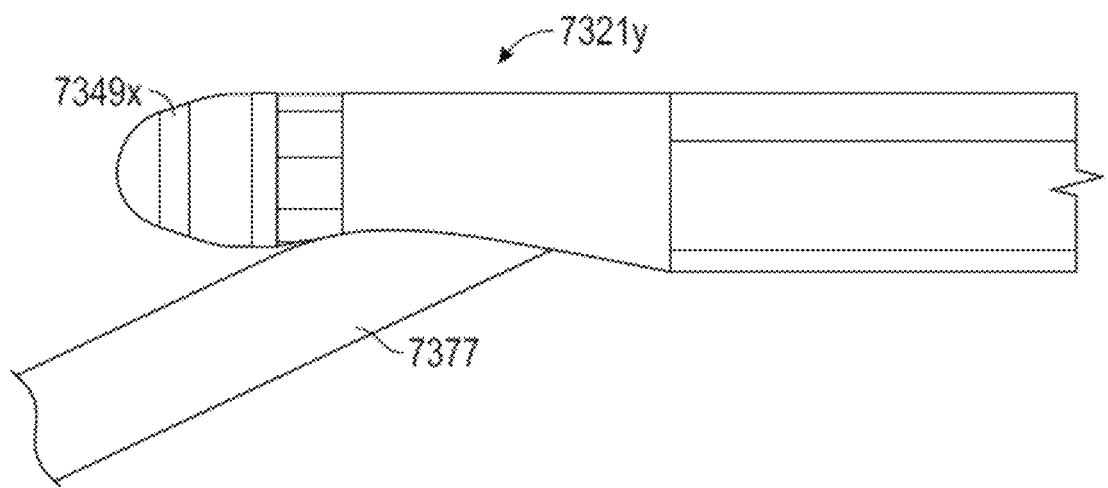
Figure 73K:
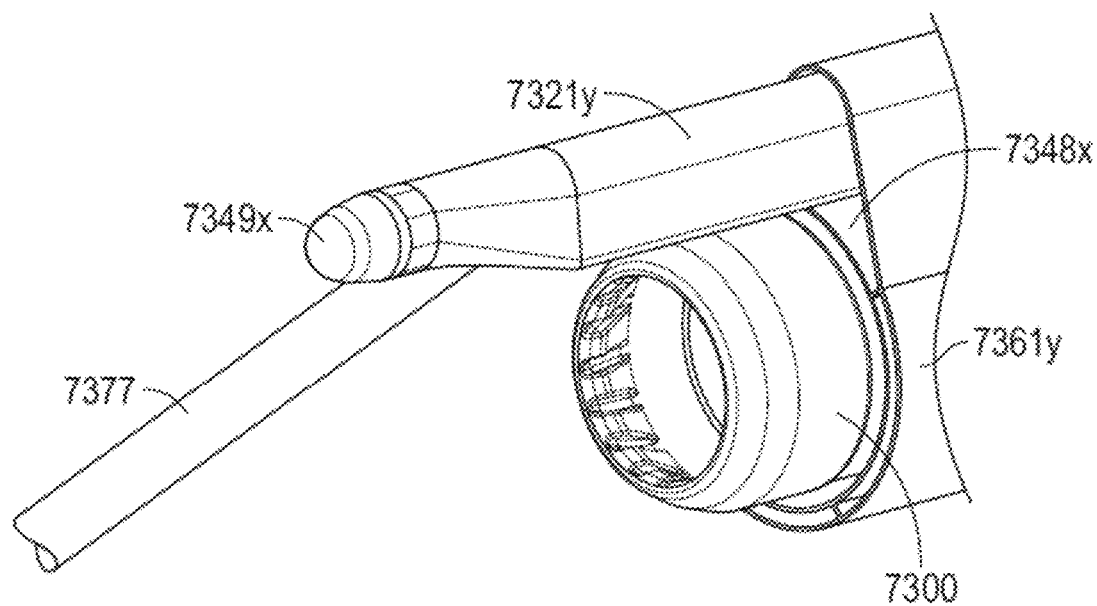
Figure 73L:
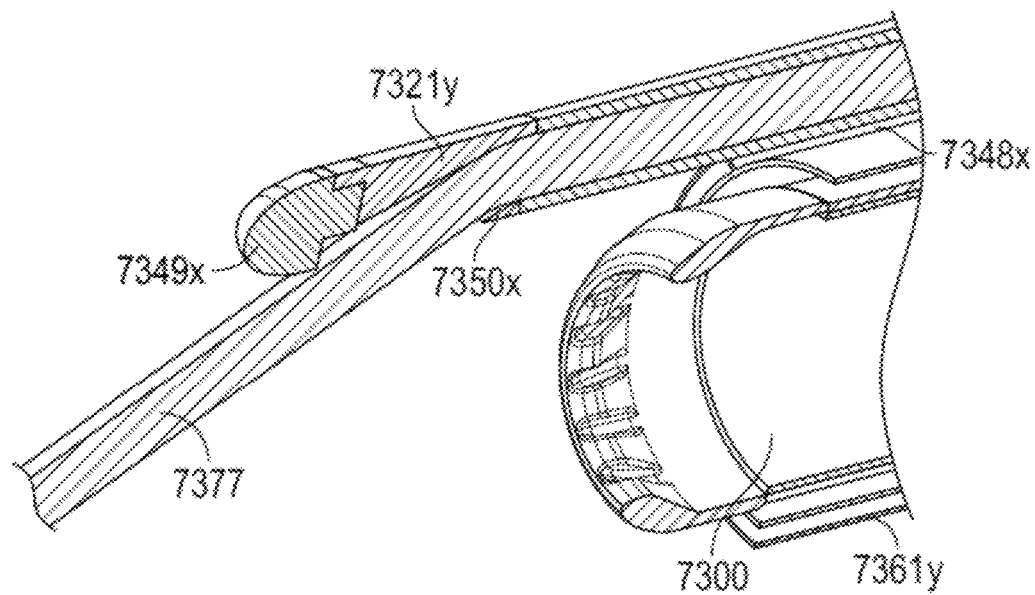

As shown best in FIGS. 73E-73L, each guide 7321y can include an atraumatic and/or soft distal end 7349x configured to extend distally beyond the respective channel 7348x (as shown in FIGS. 73K-L). Further, as shown best in FIGS. 73G-73H, the lumen 7350x can extend substantially axially within the guide 7321y, but can be curved or slanted radially inwards (e.g., at a 30°-60°, such as a 45° angle) just proximal to the soft distal end 7349x so as to direct the tool 7377 towards the center of the rigidizing device 7300. Directing the tool 7377 towards the center of the rigidizing device 7300 can similarly advantageously direct the tool 7377 towards the center of the body lumen (e.g., to avoid puncturing through the wall of the body lumen with the tool 7377).

As shown best in FIGS. 73C-73D, in some embodiments, the guides 7321y can include an asymmetric cross-section. For example, the asymmetric cross-section can include a circular shape with wings 7351x (e.g., rounded triangular-shaped wings) extending from the circle. In some embodiments, the wings 7351x can meet at a central junction so as to form an angled surface 7357x (e.g., having an angle of 110° to 130°, such as approximately 120°) configured to conform closely to the outer circumference of the rigidizing device 7300. The asymmetric cross section can advantageously ensure proper radial alignment of the guides 7321y (e.g., so that the distal end of the lumen 7350x points radially inwards with respect to the rigidizing device 7300). Additionally, the asymmetric cross section can advantageously prevent rotational movement of the guides 7321y within the channels 7348x. This can be particularly advantageous when the rigidizing device is in a rigid configuration, as the asymmetric cross-section can help provide rigid and stable access to the desired working area. In other embodiments, the guides 7321y can be symmetric and/or otherwise configured to be rotatable within the channels 7348x. In some embodiments, the proximal end of the guide 7321y may include an indicator mark configured to indicate the rotational position of the distal end of the guide 7321y relative to the channel 7348x and/or relative to the rigidizing device 7300.

Figure 73M:
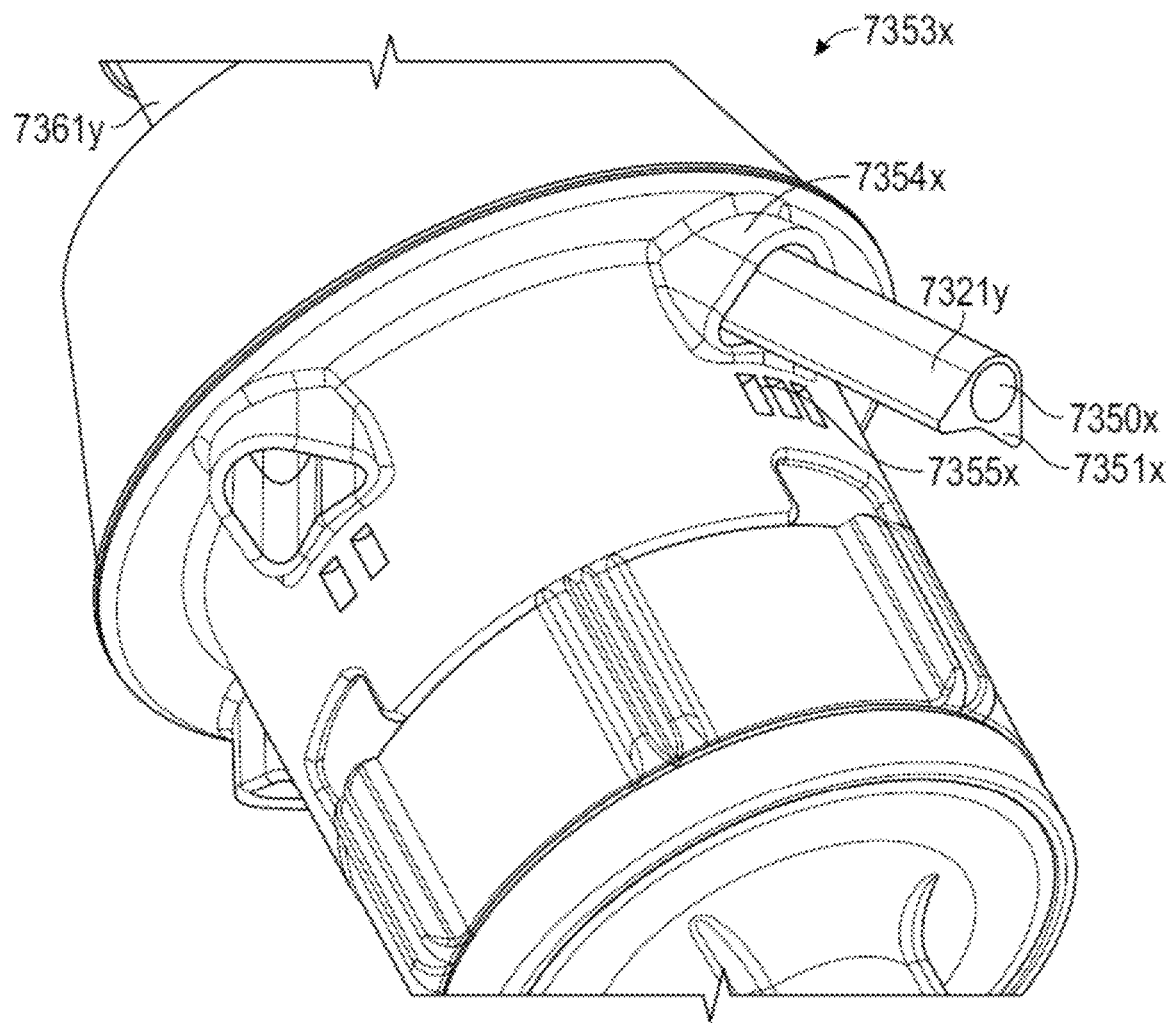

As shown best in FIGS. 73A-73B and 73M, the outer tube 7361y can include a proximal manifold 7353x attached thereto and configured to enable insertion of the guides 7321y therein. For example, the manifold 7353x can include ports 7354x enabling access to each channel 7348x. In some embodiments, each port 7354x can include a corresponding marker 7355x configured to enable identification of the channel 7348x (and thus identification of the distal circumferential position of a tool 7377 inserted therethrough). The markers 7355x can be shapes, numbers, colors, or any one of a wide variety of input/output matching identifiers. In some embodiments, the ports 7354x can include a valve thereon and/or can be vacuum-sealed (e.g., to enable the guides 7321y within the channels 7348x to provide additional rigidization to the device 7300).

In some embodiments, the guides 7321y can include a handle or stop 5352x (see FIG. 73B) at the proximal end thereof to limit axial movement of the guide 7321y too far within the channel 7348x and/or the manifold 7353x.

In use, the rigidizing device 7300 with outer tube 7361y attached therearound can be placed at a desired anatomical location (see FIG. 73A). For example, the rigidizing device 7300 can first be placed at the desired anatomical location and rigidized (e.g., via the application of pressure or vacuum as described herein). If use of a tool 7377 is desired, the user can select the desired channel 7348x (based upon the marker 7355x and desired position of the tool 7377). The user can then insert a guide 7321y through a channel 7348x while the rigidizing device 7300 is in the rigid configuration. Inserting the guide 7321*y* can result in expanding the channel 7348*x* (see FIG. 73B or 73D). The tool 7377 can then be inserted through the guide 7321*y* such that it points towards the center of the device 7300 (see FIGS. 73G-73M) and/or body lumen. After the procedure is complete, the tool 7377 and guide 7321*y* can be removed, and the channel 7348*x* can collapse back down. Advantageously, the outer tube 7361*y* described herein can enable passage of tools therethrough while being thin and flexible (i.e., not significantly adding to the diameter or bending stiffness of the rigidizing device 7300) when not in use.

The guide 7321*y* and/or the working tool 7377 can have a higher stiffness than the rigidizing device 7300 in the flexible configuration, but a lower stiffness than the rigidizing device 7300 in the rigid configuration. Advantageously, these relative stiffnesses can enable a stiff guide 7321*y* and/or working tool 7377 to be used (e.g., increasing access and/or performance at the site of treatment) while still ensuring that the guide 7321*y* and/or working tool 7377 does not affect the shape of (e.g., does not straighten) the rigidized device 7300. Additionally, these relative stiffnesses can enable a large working tool 7377 to be used with the rigidizing device 7300 without affecting the shape of the working device. For example, in some embodiments, a ratio of the outer diameter of the rigidizing device 7300 and the outer diameter of the expanded guide 7321*y* can be between 1:1 and 6:1, such as between 2:1 and 4:1.

The guides 7321*y* can advantageously come in different sizes (e.g., with different sized lumens 7350*x*, such as lumens that range from 1 mm-7 mm, such as 2 mm-6 mm in diameter) and can be interchangeably used in the channel 7348*x*. In some embodiments, the guides 7321*y* can have a lumen with no bend at the distal end. In other embodiments, the bend and/or asymmetric elements of the guides 7321*y* can be configured so as to direct the tool in a direction other than towards the center of the rigidizing device (e.g., so as to direct the tool radially outwards for performing a procedure on a wall of the lumen). In some embodiments, the guides 7321*y* can be steerable (e.g., via pullwires or other steering mechanisms) so as to enable further manipulation or directing of working tools 7377 passed therethrough.

In some embodiments, the guides 7321*y* can be configured to provide additional rigidization to the device 7300. For example, the channels 7348*x* can be sealable and enable application of pressure or vacuum thereto (either separate from or in conjunction with the pressure or vacuum supplied to the main rigidizing device 7300). As pressure or vacuum is provided to the channel 7348*x*, it can seal around the guide 7321*y*, thereby creating a stiffening/rigidizing rib for the device 7300.

In some embodiments, the channels 7348*x* can include elastic-like cuffs or sections configured to keep the channels 7348*x* collapsed against the rigidizing device 7300 when not in use (i.e., when a guide 7321*y* is not extended therethrough).

Although the outer tube 7361*y* is described herein as being used with guides 7321*y*, it should be understood that the outer tube 7361 can, in some embodiments, enable passage of working tools through the channels 7348*x* without the use of a guide.

In some embodiments, a scope can be placed through the guide 7321*y*. Further, in some embodiments, the guide 7321*y* can be steered or otherwise pre-set at a position at various angles (for example, between an angle that is coaxial to the rigidizing device 7300 to an angle perpendicular to the scope).

Figure 74A:
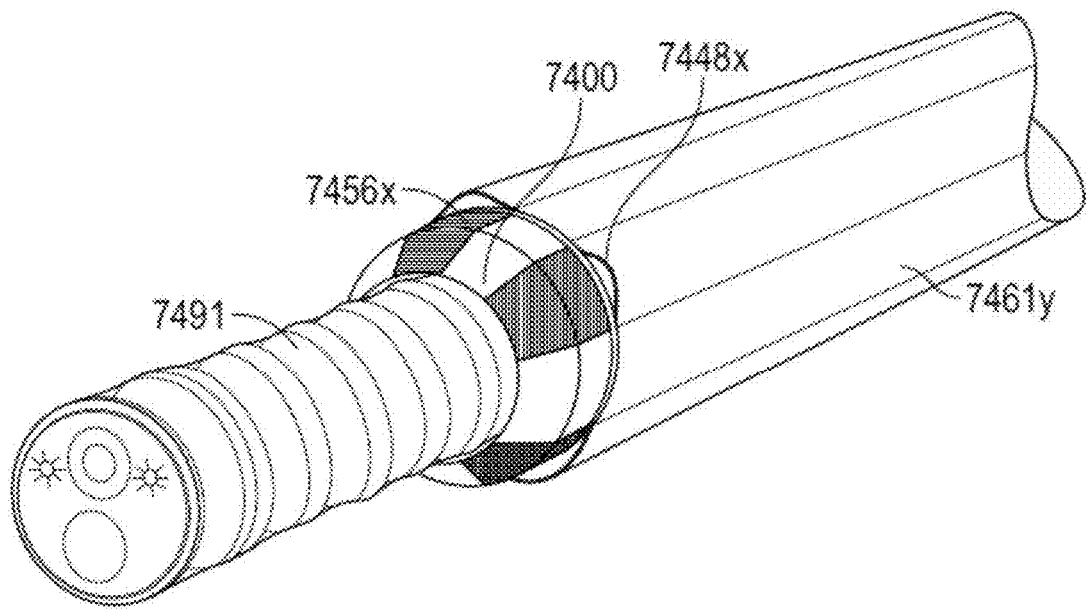
FIGS. 74A-74F show another rigidizing system having an outer tube with removable guides configured to enable insertion of a working tool therethrough.
Figure 74B:
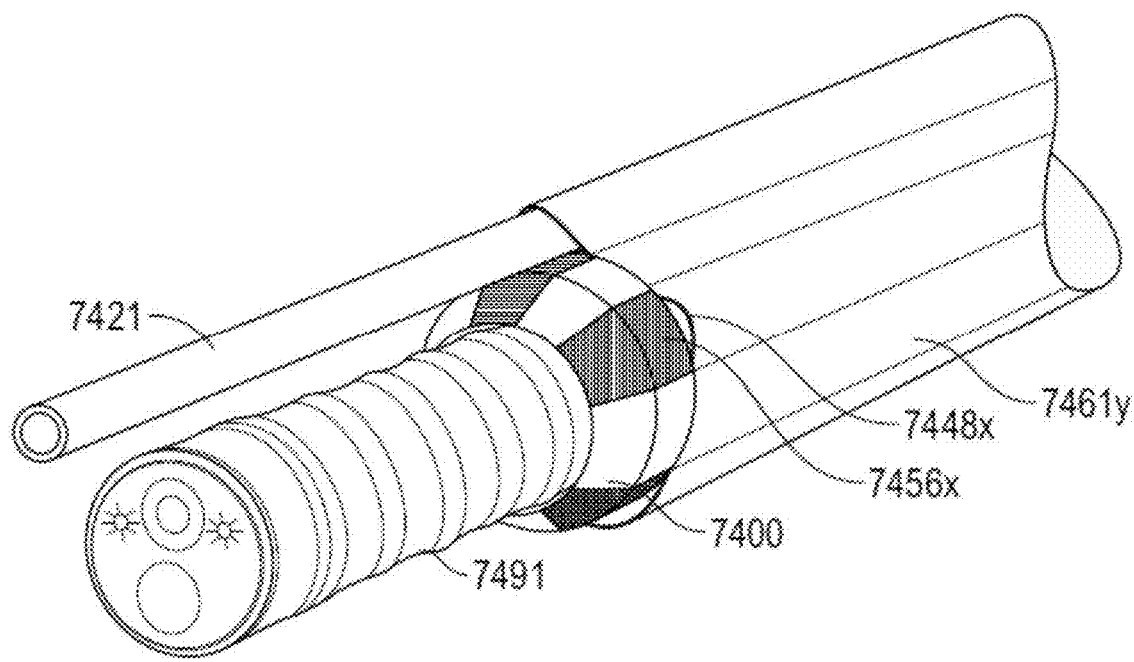
Figure 74C:
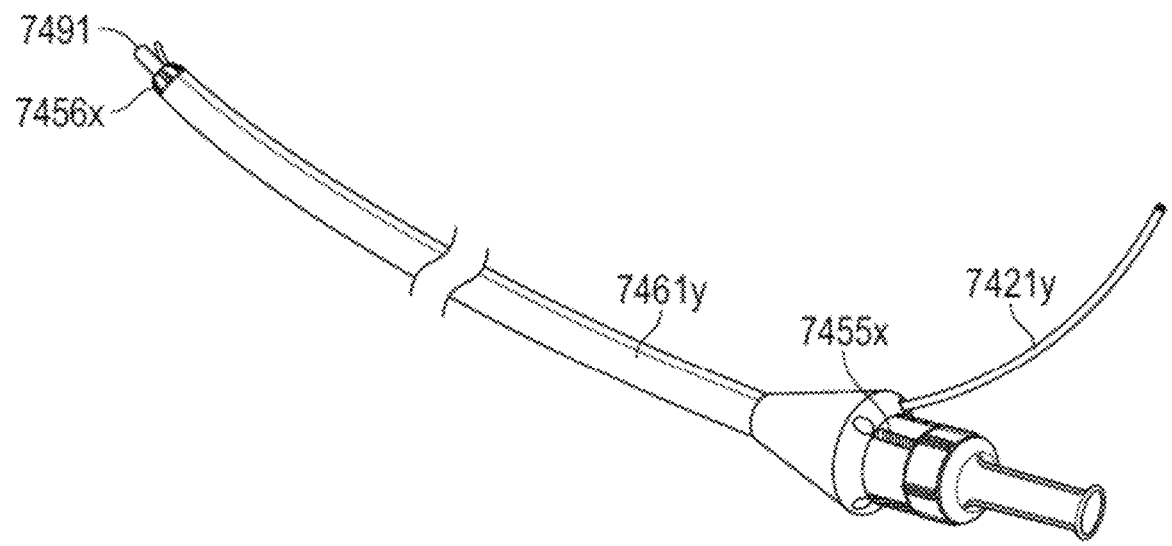
Figure 74D:
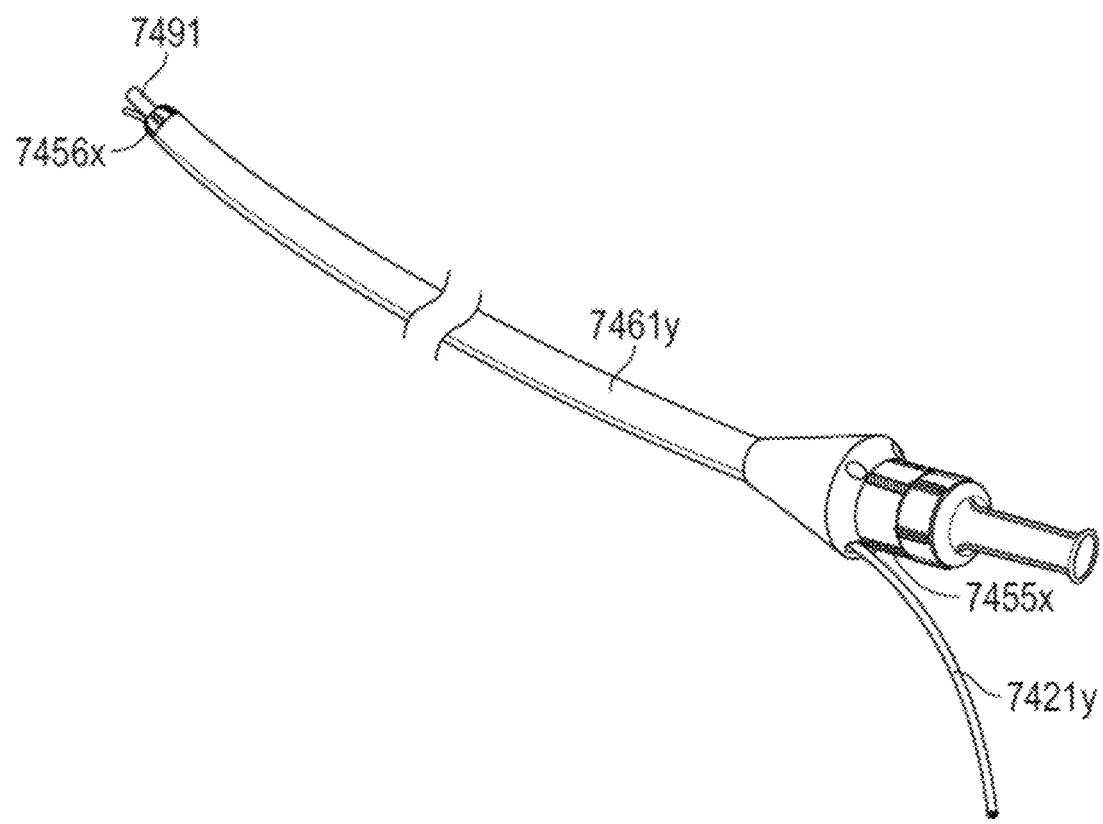
Figure 74E:
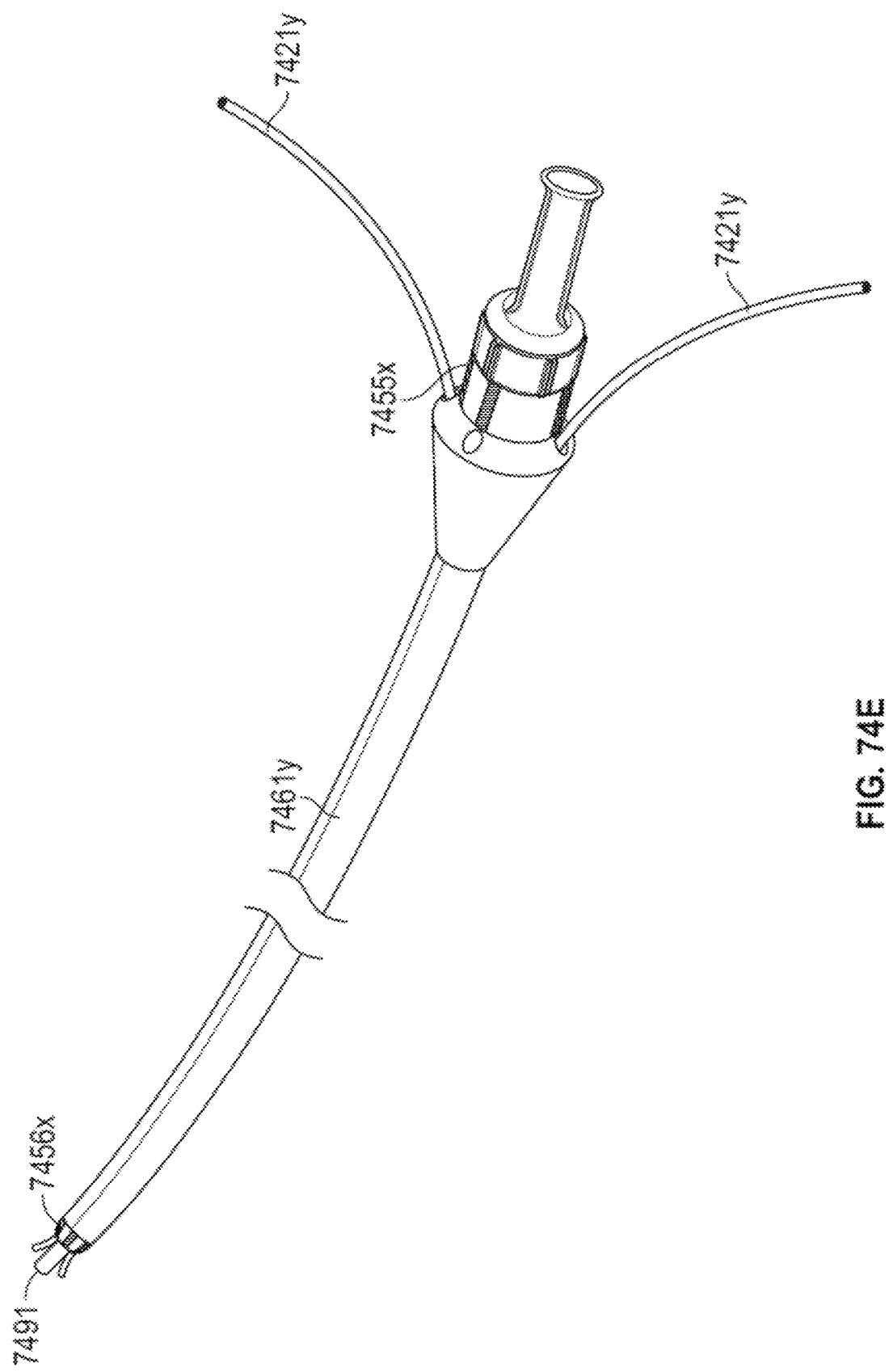
Figure 74F:
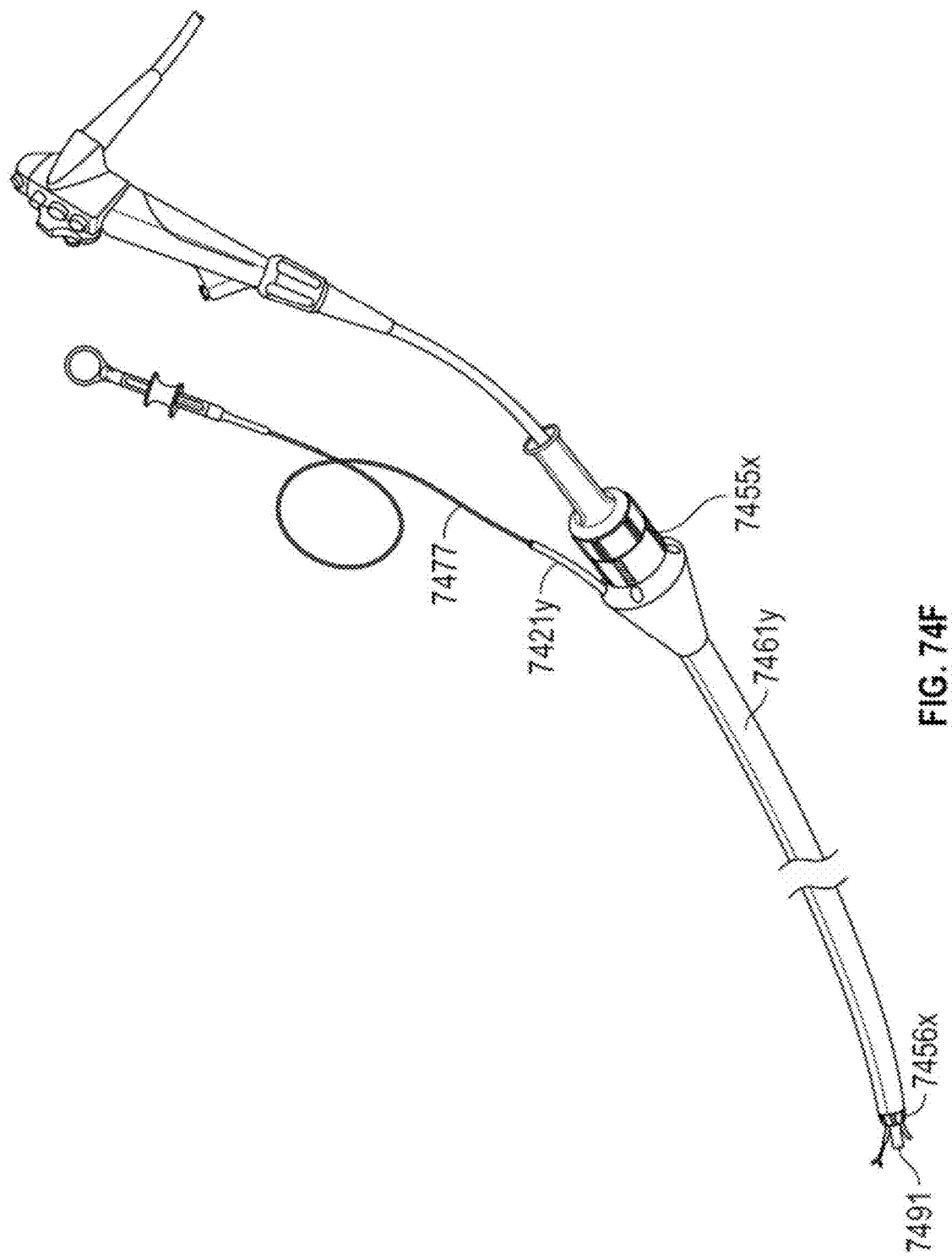

The use of another system similar to that described with respect to FIGS. 73A-73M is shown in FIGS. 74A-74F. At FIG. 74A, a rigidizing device 7400 is positioned around a scope 7491. The rigidizing device 7400 includes an outer tube 7461*y* therearound (that includes a plurality of lay-flat channels 7448*x*). At FIG. 74B, a guide 7421*y* is inserted through a channel 7448*x*. In some embodiments, the user can select the channel 7448*x* based upon one or both of the markers 7455*x* at the proximal end and the corresponding markers 7456*x* at the distal end (e.g., to select the channel 7448*x* closest to the desired treatment location). As shown in FIG. 74E, an additional guide 7421*y* can be used simultaneously with the first guide 7421*y* by placing each guide 7421*y* in a different channel 7448*x*. At FIG. 74F, after the guide(s) 7421*y* have been placed, one or more tools 7477 can be placed therethrough.

Figure 75A:
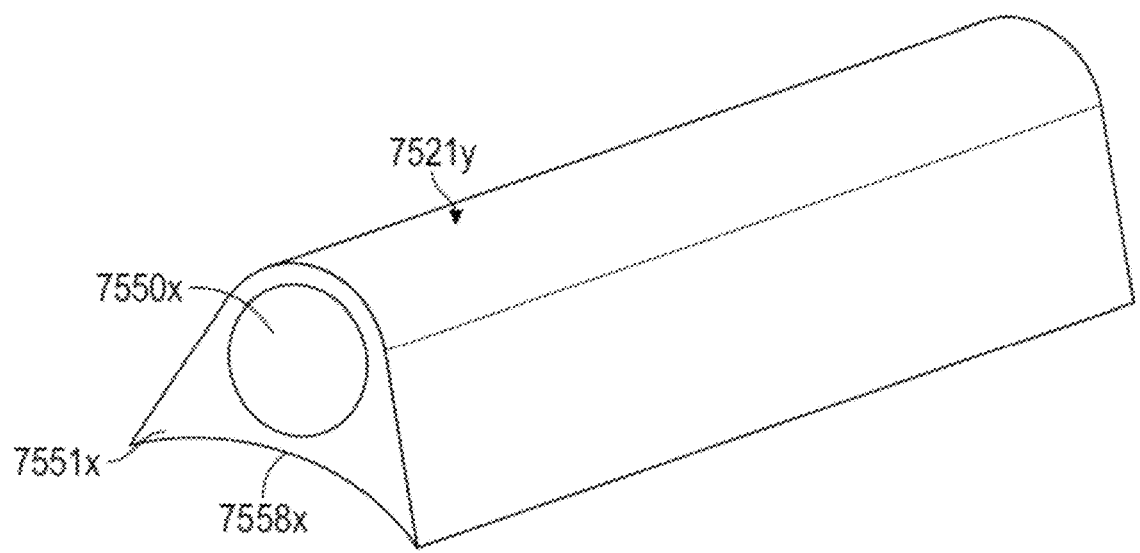
FIGS. 75A-75B show another outer tube with removable guides for use with a rigidizing system.
Figure 75B:
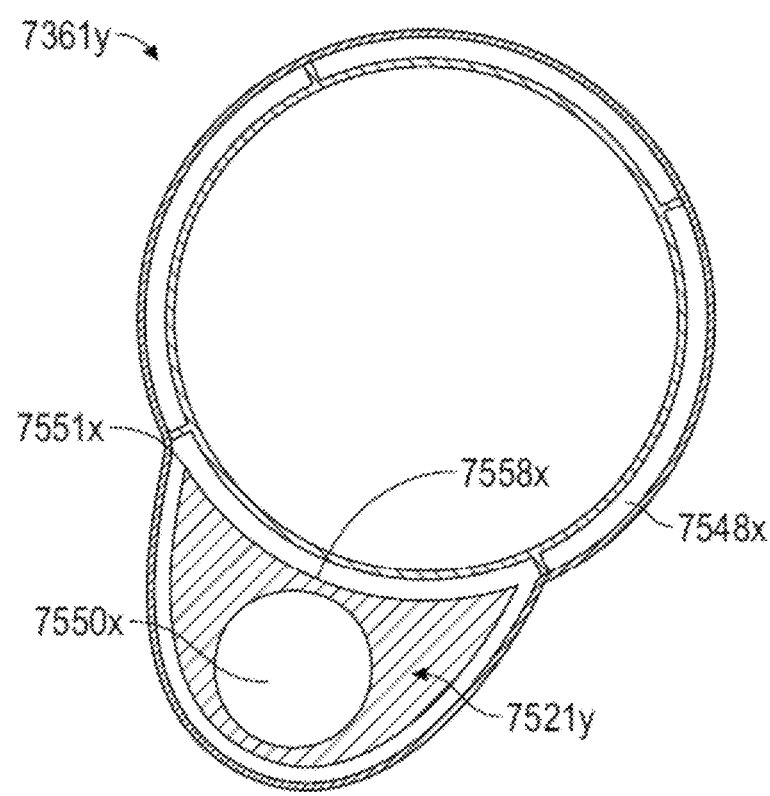

Another exemplary guide 7521*y* (which can be interchangeable with guide 7321*y*) is shown in FIGS. 75A-75B. The guide 7521*y* can include an asymmetric cross-section that is crescent-shaped (e.g., the angled surface 7357*x* of guide 7321*y* can be replaced with a curved surface 7558*x*). The curved surface 7558*x* can have substantially the same curvature as the outer circumference of the rigidizing device (and/or of the inner circumference of the outer tube 7561*y*). Advantageously, the matching curvature can help ensure a secure coupling of the guide 7521*y* to the rigidizing device. Further, the guide 7521*y* may advantageously fit snugly into channel 7548*x* such that there is a beneficial force holding guide 7521*y* securely to the rigidizing device (i.e., the outer walls of the channel 7548*x* can provide a force that pushes the guide 7521*y* towards the center of the rigidizing device). These advantages may additionally provide a beneficial stabilization of the flexible guide 7521*y* with respect to the rigidizing device when the rigidizing device is in a rigid state. This stabilization may include a decreased tendency of the guide 7521*y* to bend, twist or rotate around the center of the rigidizing device. This stabilization may provide a more stable lumen 7550*x* for a tool to travel through, thus increasing the stability of the tool and its ability to make precise motions.

It should be understood that while the walls of the channels 7348*x*, 7548*x* are shown as being spaced away from the guide 7321*y*, 7521*y* for clarity, some or all of the walls can be positioned flush with the guides 7321*y*, 7521*y* (i.e., due to the stretching of the walls when the guide 7321*y*, 7521*y* is passed through the channel 7348*x*, 7548*x*).

Figure 53:
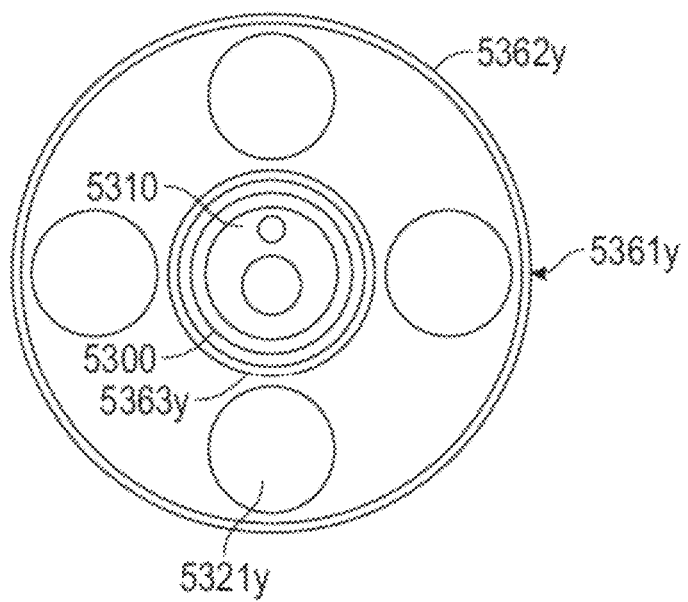
FIG. 53 shows a rigidizing device including another outer tube with working channels.

In another embodiment, shown in FIG. 53, a plurality of guides 5321*y* can be built into an outer tube 5361*y* that rigidizes. One or both of the outer wall 5362*y* and the inner wall 5363*y* of the outer tube 5361 can rigidize as described elsewhere herein. Advantageously, the outer tube 5361*y*, due to its larger diameter, can be very stiff when rigidized, thereby ensuring that the guides 5321*y* therein provide a very stable platform for passing of tools therethrough. In some embodiments, the rigidizing system (here, shown as including an inner rigidizing device 5310 and outer rigidizing device 5300) can be withdrawn from the outer tube 5361*y* after placement to enable a different tool or scope (e.g., a very large tool or a high resolution) to be placed through the outer tube 5361*uy*.

In some embodiments, rather than integrating tool guides with the rigidizing device, a rigidizing nested system without guides can be inserted into the body. After the nested system has reached the desired location (e.g., lesion), the outer rigidizing device without guides can be removed from the body while leaving the inner rigidizing device still in place. An outer rigidizing device including tool guides (e.g., any of the tool guides described herein) can then be placed over the inner rigidizing device.

Figure 50A:
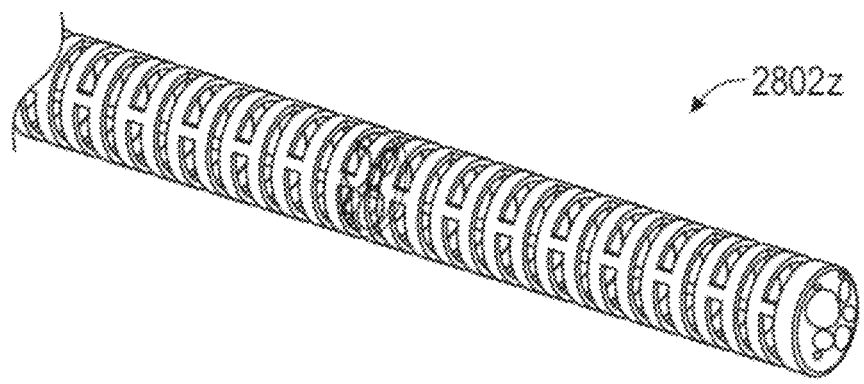
FIGS. 50A-50C show a distal end section of a rigidizing device having lumens for the passage of working tools.
Figure 50B:
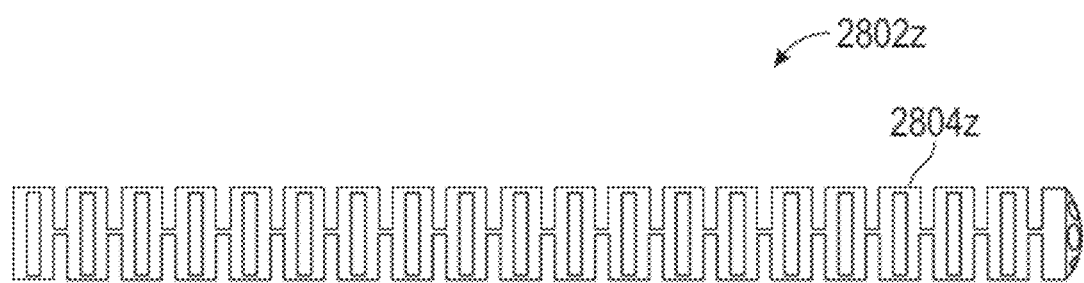
Figure 50C:
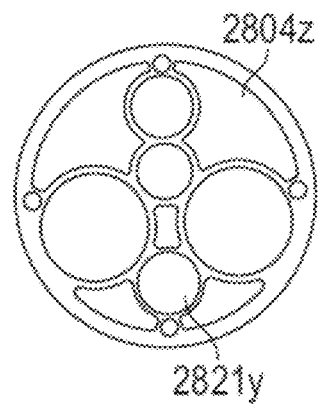

In some embodiments, the guides can be built into the interior of the rigidizing device, such as into the interior of an inner rigidizing device or a single rigidizing device. For example, referring to FIGS. 50A-50C, a distal end section 2802z of a rigidizing device can include linkages 2804z configured to enable the distal end section 2802z to bend. Further, each linkage 2804z can include a plurality of lumens therethrough. In one embodiment, the lumens can be formed in the linkages 2804z via selective laser sintering (SLS). The lumens in each linkage 2804z can be aligned down the length of the distal end section 2802z such that the aligned lumens can together form a segmented guide 2821y. As shown, the lumens can be of varying size to accommodate different sized working channels (e.g., for a camera, forceps, etc.).

Referring back to FIG. 36, in some embodiments, a robotically controlled nested system can include a fitting 9823y at the distal end thereof. The guide(s) 9821y can terminate in fitting 9823y at port(s) 9824y (or if rings are used for the fitting, the rings may align concentrically with port 9824y when the outer rigidizing device 9800 is in the straight configuration). When a tool is passed through a guide 9821y, it can also pass through the corresponding port 9824y and, in some embodiments, lock to the port 9824y. In some embodiments, two, three or more tools maybe locked into fitting 9823y. Further, in some embodiments, the fitting 9823y can include additional ports that may connect to additional tubular structures to provide suction, water, imaging and/or an additional tool channel. These additional tubular structures may extend proximally to or past the cassette (e.g., cassette 9357). In some embodiments, these additional tubular structures may be omitted from the inside of inner rigidizing device 9310 due to their incorporation into the fitting 9823y. In some embodiments, the fitting 9823y can be permanently attached the outer rigidizing device 9800 but temporarily attached to the inner rigidizing device (e.g., rigidizing device 9310) for use during a particular procedure. The fitting 9823y can include a disposable sheath attached thereto. The disposable sheath may be, for instance, a thin plastic rigidizing device, such as an inexpensive layflat rigidizing device. The disposable sheath may cover the inner rigidizing device (e.g., device 9310) and the outer rigidizing device 9800 and connect to the cassette (e.g., cassette 9357). The disposable sheath may include tubular structures that provide features such as suction, water and an additional tool channel as described herein. In some embodiments, the fitting 9823y may be configured to rotate about the outer rigidizing device 9800. For instance, a Bowden cable may be fitted external to outer rigidizing device 9800 and terminated at the distal end in the fitting 9823y and at the proximal end of the rigidizing device, such as in the handle. Rotating the Bowden cable may impart a torque in fitting 9823y, causing the fitting 9823y to rotate. The fitting 9823y may have a limited range of motion; for instance, +/−90 degrees or +/−60 degrees.

Figure 49A:
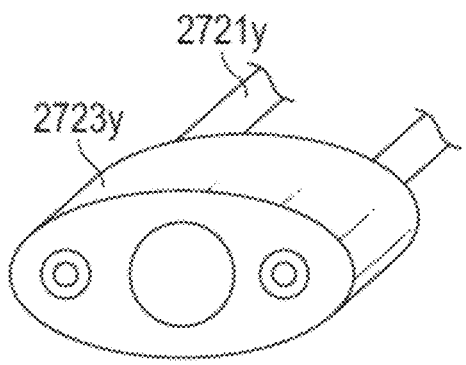
FIGS. 49A-49B shows a fitting including flexible guides.
Figure 49B:
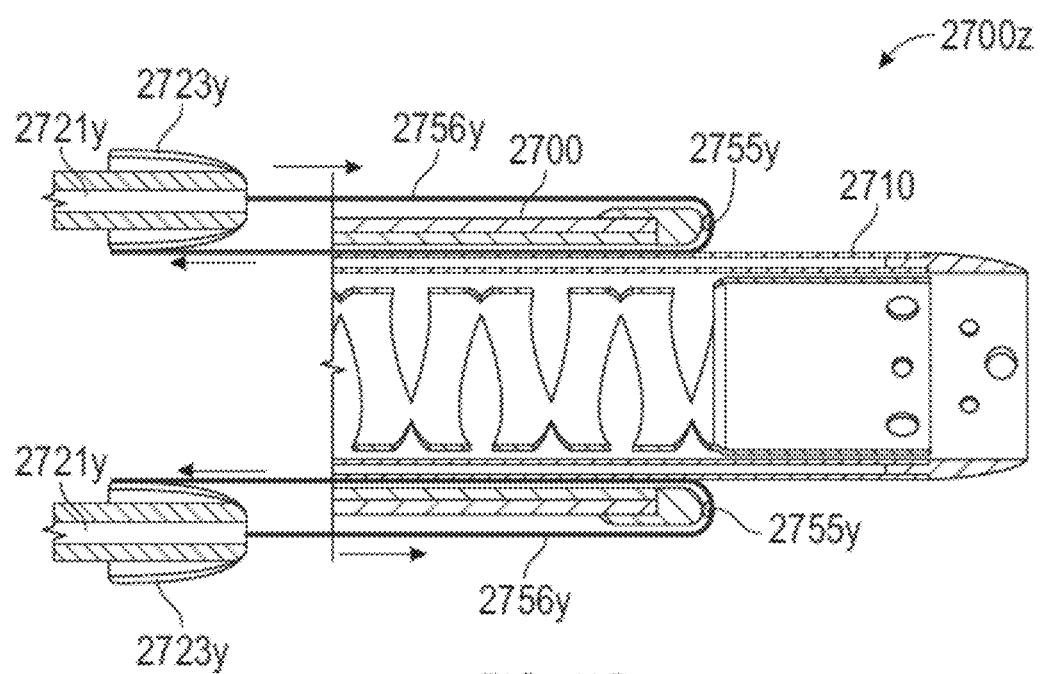

Referring to FIGS. 49A-49B, in some embodiments, the fitting 2723y can be moved into place after insertion of the nested system into the body. For example, the outer rigidizing device 2700 of system 2700z can include a pulley 2755y attached thereto with a cable 2756y running therearound. The cable 2'756y can extend, for example, between the outer rigidizing device 2700 and the inner rigidizing device 2710 and can be attached to the fitting 2723y. Thus, when the cable 2'756y is pulled proximally, the fitting 2723y (and flexible guides 2721y that are attached thereto) can be pulled distally into place. In some embodiments, the guides 2721y can include stiffening portions therealong to help ensure that the guides 2721y are stiff enough, once in place, for tools to be passed therethrough. In some embodiments, the entire system 2700z can include an outer sheath to enable pulling vacuum over the guides 2721y to provide added stiffness.

Figure 42:
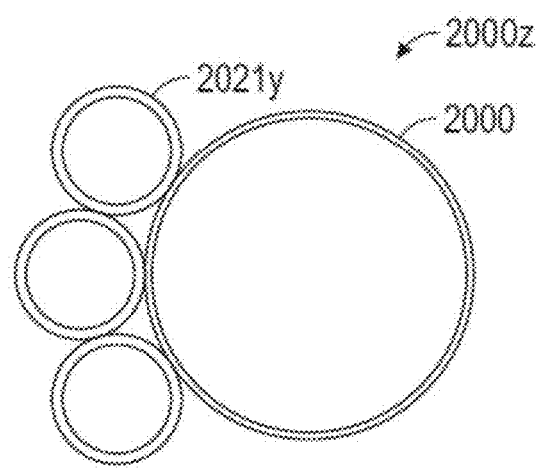
FIG. 42 shows a rigidizing device with working channels positioned adjacent to one another along an outer circumferential section of the rigidizing device.

In some embodiments, referring to FIG. 42, a rigidizing system 2000z (e.g., a robotically controlled nested system) can include a plurality of tool guides 2021y as described herein that are positioned along the outer rigidizing device 2000 adjacent to one another (e.g., at 9 o'clock and 10 o'clock) rather than spaced away from one another (e.g., rather than on opposite sides of the device 2000). In some embodiments, for example, all of the tool guides 2021y can be along an arc that is less than 180 degrees, such as less than 120 degrees, such as 90 degrees or less, of the circumference of the outer rigidizing device 2000. Having the tool guides 2021y adjacent to one another can advantageously make the total circumference of the system smaller, thereby making it easier to maneuver through the body.

Figure 43:
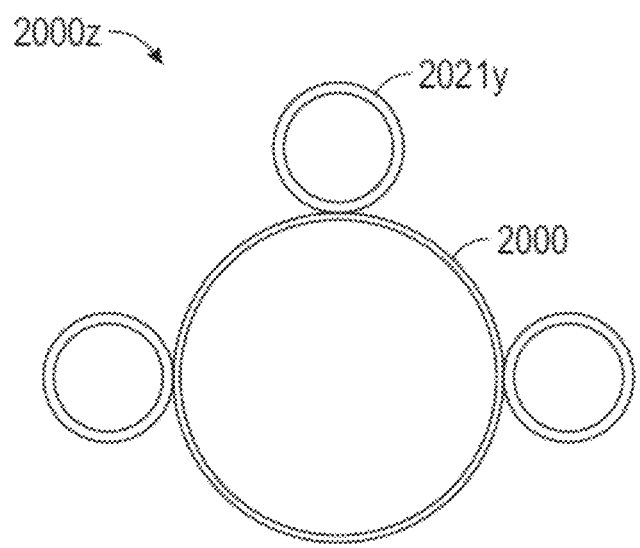
FIG. 43 shows the rigidizing device of FIG. 42 with the working channels moved to positions more spread out around the circumference.

As shown in FIG. 43, in some embodiments, the adjacent guides 2021y can be separated from one another after the rigidizing device 2000 is placed into the body, e.g., for better angular placement relative to the location of interest. One of the guides 2021y (e.g., the middle guide 2021y) can be used, for example, to extend an articulating camera therethrough. The articulating camera can advantageously allow the built-in camera of the nested system 2000z (e.g., of the inner rigidizing element) to be smaller.

In some embodiments, a guide (e.g., any guide described herein) can be attached or otherwise embedded loosely within an outer layer (e.g., a sheath and/or outer layer of the wall) of a rigidizing device. In this embodiment, as a tool is inserted though the guide, the stiffness of the tool and the tool's tendency to want to straighten can rotate the guide around the circumference (i.e., the central axis) of the rigidizing device. This rotation can advantageously put the guide in a position with lower resistance to insertion of a tool and/or can reduce strain on the guide. In some embodiments, the tool can be inserted while the rigidizing device is in the flexible configuration, and when the rigidizing device is rigidized, the braid layer can push into the outer layer, fixing the guide in place.

In other embodiments (e.g., embodiments where the guide is fixed relative to the circumference of the rigidizing device), the rigidizing device can be rotated about its axis to position the guide in the desired low resistance position.

It should be understood that any of the tool guides (and corresponding tools) described herein can be used with a nested rigidizing system or with a single rigidizing system (e.g., a single overtube). Similarly, it should be understood and any of the tool guides (and corresponding tools) described herein can be used with a rigidizing system or a non-rigidizing system.

Figure 37:
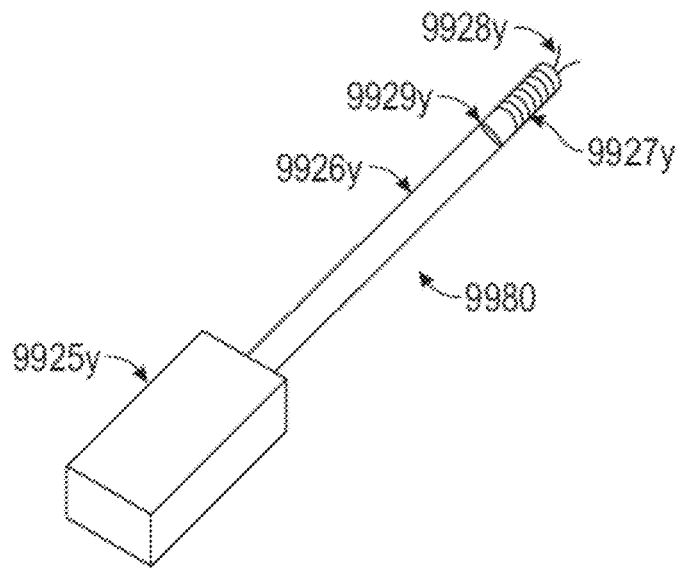
FIG. 37 shows a tool for use with a robotically controlled rigidizing system.

An exemplary tool 9980 for use with a robotic nested system (e.g., system 9300z) is shown in FIG. 37. The tool 9980 can include a cassette 9925y, a flexible shaft 9926y, a bending section 9927y and an end effector 9928y (e.g., forceps, a grasper, or scissors). The cassette 9925y, like the nested system cassette (e.g., cassette 9357) may have disks that can be rotated to control aspects of the tool 9980. For instance, rotating a disk may cause the bending section 9927y to deflect. Another disk may be used to control the end effector 9928y. Additionally, the tool 9980 can include a locking feature 9929y configured to engage with a fitting port (e.g., port 9824y) to lock the tool 9980 in place relative to the outer rigidizing device (e.g., rigidizing device 9800).

The locking feature 9929y can include, for example, a spring pin configured to engage a corresponding slot or hole on the end fitting 3060. Other locking mechanisms are also possible (e.g., magnetic lock, electronic lock, twist lock, breach lock, bayonet lock, and the like).

In one exemplary use, when tool 9980 is inserted into guide 9821y, it can be moved distally until it passes through the port 9824y and the locking feature 9929y is aligned with the inside diameter of port 9824y. In some embodiments, a control on the tool 9980 can be reversibly engaged to longitudinally lock tool 9980 with end fitting 9823y. Alternately, the tool 9980 may automatically lock into place in fitting 9923y. Except for the lock at fitting 9823y, the tool 9980 may be otherwise loosely held or float longitudinally in guide 9821y.

Figure 38:
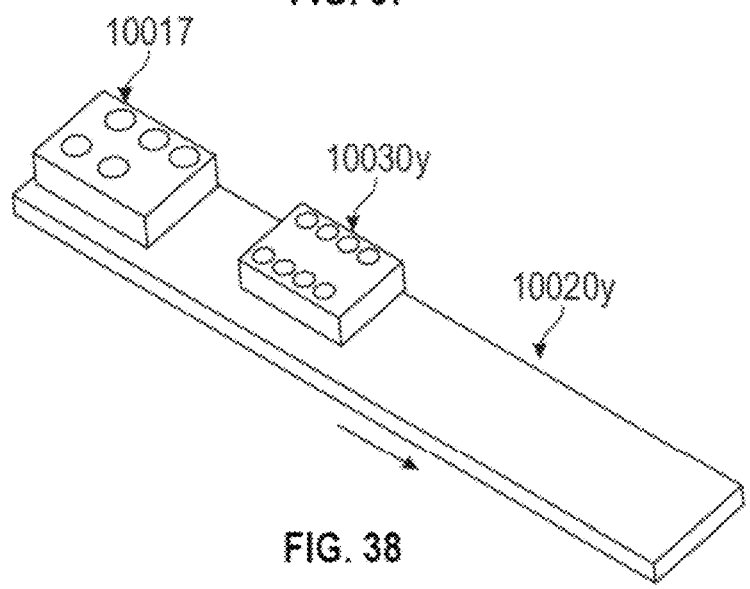
FIG. 38 shows a slide for use with a robotically controlled rigidizing system.

Referring to FIG. 38 and back to FIGS. 31A-31D, in some embodiments, the robotic system (e.g., system 9300z including the inner and outer rigidizing devices 9310, 9300 and cassette 9357) may be positioned on a linear slide 10020y. The linear slide 10020y can further include a drive unit 10017y (similar to drive unit 9517y) configured to control the inner and outer rigidizing devices 9310, 9300. The slide 10020y can allow the inner and outer rigidizing devices 9310, 9300 to be translated together (i.e., simultaneously). In some embodiments, in order to effect relative movement between of the inner rigidizing device 9310 with respect to the outer rigidizing device 9300, the system 9300z can be translated in a first direction (forwards or backwards along the slide 10020y) while simultaneously using the disk 9389 and rack 9382 on the outer rigidizing device 9300 to move the outer rigidizing device 9300 in a second direction, opposite to the first direction. That is, to advance the inner rigidizing device 9310 relative to the outer rigidizing device 9300, the system 9300z including both rigidizing devices 9300, 9310 is advanced along the slide 10020y while simultaneously retracting the outer rigidizing device 9300 using the disk 9389 and rack 9382. Conversely, to retract the inner rigidizing device 9310 relative to the outer rigidizing device 9300, the system 9300z including both rigidizing devices 9300, 9310 can be retracted along the slide 10020y while simultaneously advancing the outer rigidizing device 9300.

Referring to FIG. 38, the linear slide 10020y can further include a second drive unit 10030y configured to control a tool or tools (e.g., tool 9980) used with the inner and outer rigidizing devices. In some embodiments, the first drive unit 10017y and the second drive unit 10030y can independently translate along linear slide 10020y. One, two or more tools 9980 may attach to drive unit 10030Y. The linear slide 10020y can advantageously ensure that the tool(s) used with the nested rigidizing system stay in place at the distal end of the outer rigidizing device despite any translation by the outer rigidizing device. For example, the tool drive unit 10030y can be configured to translate the tool forward when the outer rigidizing device advances relative to the slide 10020y. Similarly, the tool drive unit 10030y can be configured to retract the tool when the outer rigidizing device retracts relative to the slide 10020y. This may ensure, for example, that the tool stays locked into the fitting (e.g., fitting 9823y).

Figure 39A:
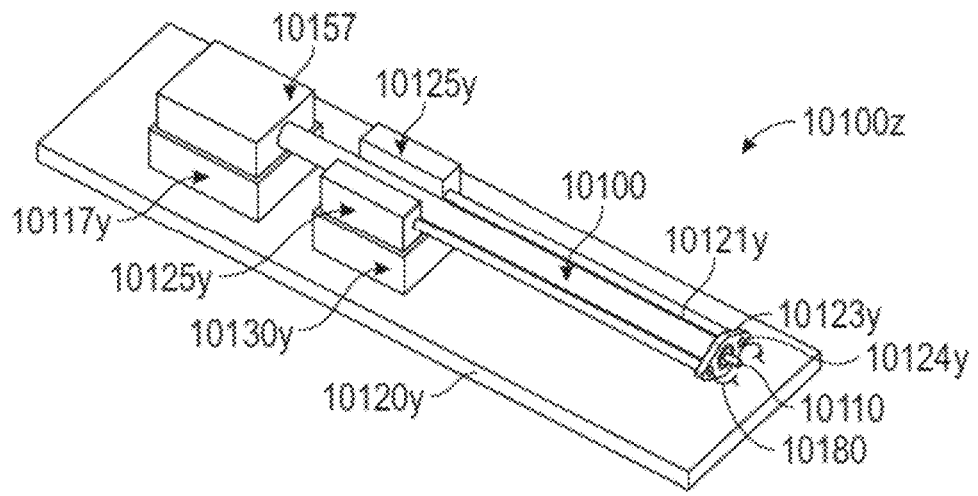
FIGS. 39A-39B show a robotically controlled rigidizing system.
Figure 39B:
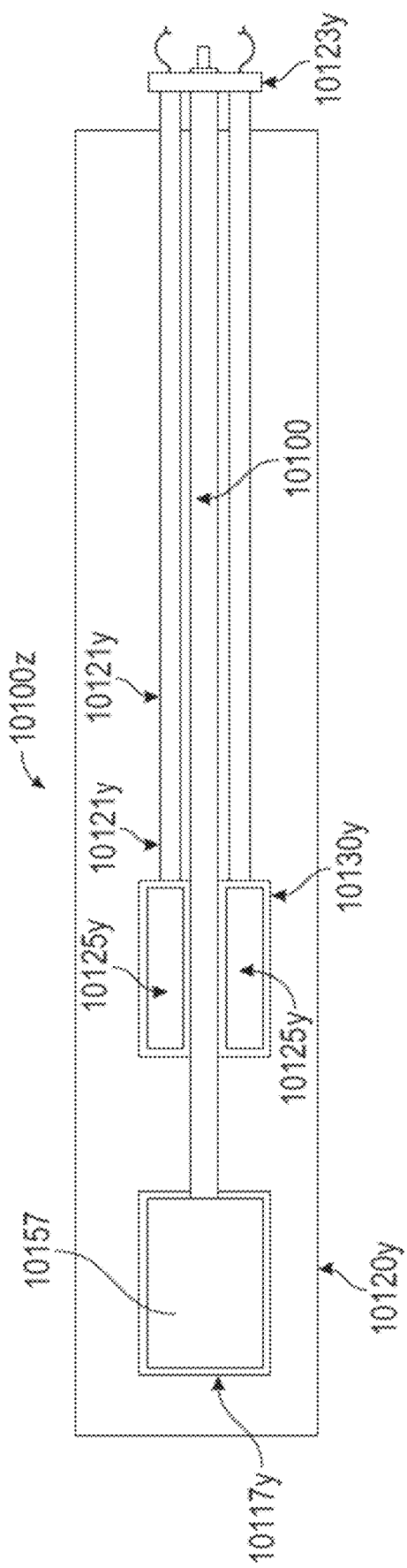

FIGS. 39A and 39B show top perspective and top views, respectively, of an exemplary robotic system 10100z positioned on a slide 10120y with cassette 10157 attached to a drive unit 10117y for control of the nested rigidizing devices 10100, 10110. Two cassettes 10125y for the control of two different tools 10180, are mounted to drive unit 10130y. The tools 10180 are inserted through guide 10121y and locked in fitting 10123y at ports 10124y.

Figure 40:
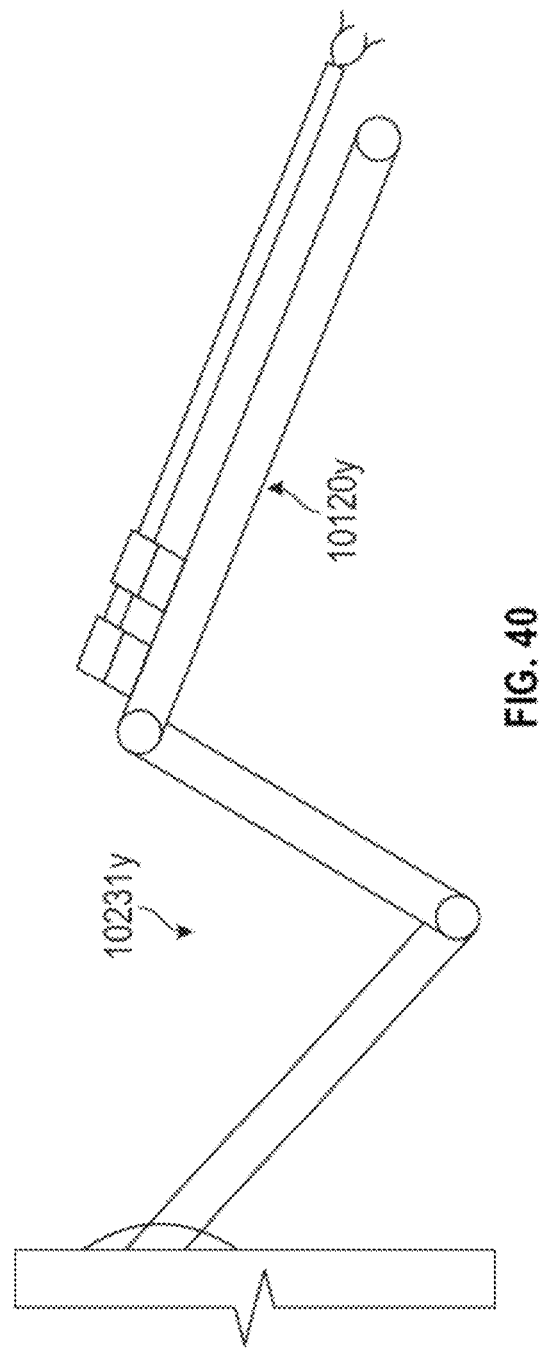
FIG. 40 shows a pivoting arm for a robotically controlled rigidizing system.

FIG. 40 shows an exemplary pivoting arm 10231y that can be connected to the linear slide 10120y so as to orient the slide 10120y and thus the rest of the robotic system (including nested rigidizing devices 10100, 10110 and/or tools 10180) relative to the patient. As such, the linear slide 10120y may be positioned vertically, horizontally or at an angle in between.

The system 10100z may be used in the following exemplary manner. Cassette 10157 is attached to the inner and outer rigidizing devices 10110, 10100, and the inner and outer rigidizing devices 10110, 10100 are advanced into the patient's body (e.g., as detailed in FIGS. 65A-H). In some embodiments, the inner and outer rigidizing devices 10110, 10100 are advanced into the patient's colon or upper GI tract. Reciprocating motion of the inner rigidizing device 10110 and outer rigidizing device 10100 is provided by the motion of disk a disk within the cassette 10157 and the translation of the rigidizing devices 10110, 10100 along the slider 10120y. Rigidization is provided by compressing bellows in cassette 10157. Steering is provided by disks in cassette 10157. When a medical practitioner has reached the place in the body where the procedure is to be performed, a tool can be inserted through guide 10121y and locked to ports 10124y. The cassettes 10125y are then attached to drive unit 10130y for control of the tool.

The drive units described herein may be connected to a computer (e.g., computer, tablet, laptop, etc.) for control. The computer in communication with the drive units may comprise software providing a user interface for a clinician to interact with to control the system and any tools being used. Automation, such as via computer controls of the cassettes and/or drive units described herein, can be used to make repetitive tasks easier to perform. For instance, a program can be developed that automatically moves the distal end of the rigidizing device in an arc while emitting water. A second arc can then be made to suction water and material from the GI tract. This may be useful in cleaning the GI tract. A program can be developed to perform the rigidization steps outlined herein in sequence such that the operator needs only to provide input, with, for example, a joystick, to direct the distal end of the device.

In some embodiments, the inner rigidizing device and the outer rigidizing device may be advanced by the robotic system described herein using small steps (e.g., less than 1 inch steps). Small steps may advantageously allow for more precise control of the placement and orientation of the rigidizing devices. For example, the user may steer the inner tube in the desired direction and, as the inner tube advances ahead of the outer tube by a small amount (for instance, ½, ¾ or just under 1 inch), the sequence of rigidization and advancement or retraction of the outer tube can be triggered automatically. In some embodiments, the present sequence of small steps can be overridden when desired. In some embodiments, the inner rigidizing device and outer rigidizing device may be advanced by the robotic system using medium steps (e.g., 1-3 inch steps) or large steps (e.g., greater than 3 inch steps).

The cassettes and/or tools described herein may be disposable or reusable or used and cleaned for a limited number of cycles.

The linear slides described herein can, in some embodiments, be U-shaped with a corresponding U-shaped tract. Alternatively, the linear slides can, in some embodiments, be circular with a corresponding circular shaped tract.

In some embodiments, the tip of the outer rigidizing device can include one or more cameras to view the end effector of the tool used with a robotic system. This can allow a controller of the robotic system to calculate the relation between the control inputs and effector outputs and adjust accordingly to give the same effector motion regardless of the tooth path (e.g., regardless of drag placed on the tool control cables during bending).

It should be understood that any feature described herein with respect to one embodiment can be combined with or substituted for any feature described herein with respect to another embodiment. For example, the various layers and/or features of the rigidizing devices described herein can be combined, substituted, and/or rearranged relative to other layers.

External Working Channels

As discussed above, described herein are apparatuses (e.g., systems, devices, etc.) including one or more external working channels. In some examples these channels may be referred to as layflat tubes or layflat channels (e.g., as described in FIGS. 35A-35B). These external working channels may be part of the elongate medical device, or they may be part of a working channel sleeve apparatuses that may be worn, applied or attached to the elongate medical device. Any of the external working channels may be expandable working channels. The elongate medical device may be part of the apparatus (e.g., part of the working channel sleeve apparatus) or may be separate from it.

In particular the working channel sleeve apparatuses described herein may include a tube having one or more external working channels that are configured to aid in transporting a medical instrument (e.g., a tool or tool liner) through a body, including along a curved or looped pathway. Any appropriate elongate medical device may be used and/or may form part of the apparatus, including (but not limited to) rigidizing elongate medical devices, such as those described in PCT/US2021/034292, filed on May 26, 2021, entitled "RIGIDIZING DEVICES", the entirety of which is incorporated by reference herein. The tubes including the expandable external working channels described herein may include fabric tubes, such as a knitted, woven, braided, etc. In some examples the tube are non-woven tubes, such as laminate tubes or tubes formed of an elastic sheet, etc., such as a thin elastomer sheet that has numerous cut-outs such forming pores or openings therethrough.

Figure 76:
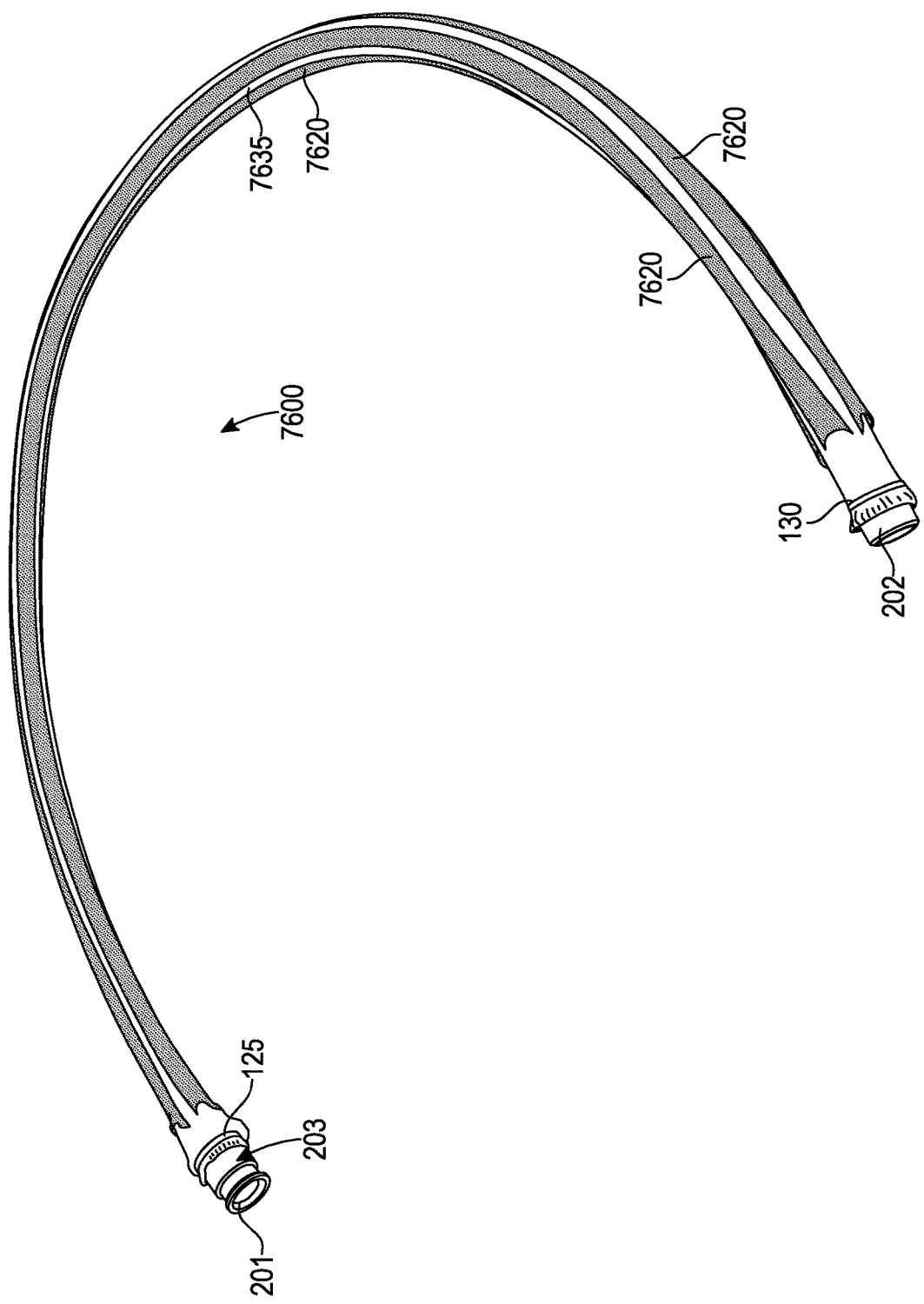
FIG. 76 shows an example of a system including an external working channel and an elongate medical device.

FIG. 76 shows an example of a working channel sleeve apparatus 7600 including a plurality of external working channels and an inner tube. The external working channels for use with the elongate medical device can be formed as part of (e.g., integrated into) an inner tube 7635 (e.g., fabric tube) extending between a proximal end region 160 and a distal end region 130 of the elongate medical device. The proximal end region 125 may be exteriorly accessible when the external expandable working channels 7620 are in use and the distal end region 202 is partially or substantially disposed within a vessel. The tubular material forming the inner tube may be expandable and/or flexible to selectively accommodate travel through angled or curved passages. A plurality of working channels 7620 may be formed on the tube, and in particular, may be formed of one or more filaments that are knitted, woven and/or braided integrally with the tube. The inner tube may comprise a mesh material. In some examples the working channel sleeve apparatus includes both the inner tube and a plurality of external working channels, as shown in FIG. 76.

The tube 7635 of the working channel sleeve apparatus shown in FIG. 76 may include a lumen that may extend from the proximal end region to the distal end region. The tube 7635 may be generally flexible in a relaxed configuration and may be collapsible when nothing is positioned therein, e.g., when not applied or attached over an elongate medical device 200. As mentioned, one or more channels (e.g., expandable working channels 7620) may be formed and/or positioned around the exterior surface of the main tube 7635.

The expandable working channels 7620 may extend longitudinally from the proximal end of the tube 125 to the distal end of the tube 130 (or from the proximal end region to the distal end region). A working channel 7620 may have a lumen extending the entire length of the working channel 7620 allowing for passage of objects that may be slide through the working channel 7620 into the proximal end 125 of the working channels 7620 and out through the distal end 130 of the working channel 7620.

Thus, in any of the working channel sleeve apparatuses described herein, the working channels may be advantageously formed of one or more fibers (e.g., knitted, woven, braided, etc. fibers) and may be expandable (e.g., stretchable). These external working channels may be configured to lay flat (e.g., as "layflat") against the outer surface of the elongate medical device until expanded by inserting a tool or tool inserted. As used herein "flat" refers to substantially flat (e.g., not expanded); a layflat channel or layflat tube does not need to be flush against the outer surface, unless the context indicates otherwise. In particular, these apparatuses may include working channels that may be co-formed as a knit, weave and/or braid, with the tubular body 7635. The tubular body may be a fabric tube, which includes knit, woven, or braided tubular bodies. In some examples the working channel sleeve apparatus is formed of a mesh material (e.g., knitted or woven) so that both the inner tube member and the external working channels are stretchable and flexible. The working channel sleeve apparatus may be arranged relative to the elongate medial device so the entire working channel sleeve apparatus/assembly (including the tube 7635 and the one or more working channels 7620) may be formed as a knitted tube or sleeve that is sized to fit over the elongate medical device so that the working channels may be expanded and used to pass one or more medical tools and/or a liner insert tube that may be inserted to form a more open and lubricious channel for a tool.

The length of a working channel 7620 of a working channel sleeve apparatus may be approximately the same length of the inner tube (e.g., tube 7635) from the proximal end or tip to the distal end or tip of the working channel sleeve apparatus. Alternatively, each of the expandable working channels 7620 may have a length less than that of the tube 7635. For example, a working channel 7620 may extend longitudinally along the outer surface of the tube 7635 whereby a proximal end of the working channel 7620 is positioned on the exterior surface of the tube 7635 between the proximal end and the distal end of the tube 7635. Likewise, the distal end of the working channel may be positioned on the exterior surface of the tube 774035 between the distal end of the tube 7635 and the proximal end of that working channel.

The working channel(s) 7620 on the exterior of the tube 7635 may begin at or substantially near one another and may being at or near the proximal end of the tube 125. The distal end 130 of the working channel(s) 7620 may be positioned at any point along the tube 7635 between the proximal end 125 and the distal end of the tube 7635, including where the distal end of any other working channel(s) and the distal end of the tube 7635 terminate, or substantially nearby.

As mentioned, the external and expandable working channel(s) 7620 may be formed as part of the tube 7635 or in some examples may be affixed to the tube 7635 of the working channel sleeve apparatus. A portion of the exterior surface of the working channel(s) 7620 may contact the exterior surface of the tube 7635 or may be integrally formed as part of the exterior surface of the tube 7635. Expandable working channels 7620 may have a collapsible cross-sectional geometry. The working channel(s) may have an interior surface defining the lumen of the working channel, and an exterior surface of the working channel material may be exposed and visible as the outer most layer of the system 7600. The interior of the working channels may be lubricious (e.g., low friction).

In some of the examples described herein, the system 7600 including the elongate medical device and working channel sleeve apparatus (e.g., inner tube and external working channels) may be equivalently referred to herein as an external working channel system 7600 or external working channel device. In some examples, for convenience these apparatuses may be referred to herein as working channel sleeve apparatuses and may include the elongate medical device.

As mentioned, the expandable working channels 7620 and tube 7635 may be formed of a hybrid elastic and lubricious material 210 (described in greater details in FIG. 82, below) and may be formed by one or more filaments having desired properties. In particular, the one or more filament(s) may be fibers, a network of woven fibers, a yard, a thread, or a combination thereof. In some examples the filaments may have an elastic inner region (e.g., core) with a lubricious outer region (e.g., coating, wrapping, etc.). The elastic core may be sufficiently elastic to allow stretching of the knitted, woven or braided material forming the working channels. For example, the elasticity of the fibers may allow for stretching and dynamic changes in length of the fibers as the external working channel system 7600 is manipulated. The elastic core may be any appropriate biocompatible elastic material, such as a silicone, spandex, biocompatible polyurethane elastomers and/or biocompatible copolymer elastomers. The lubricous outer region may be formed of any appropriate biocompatible lubricous material, such as polypropylene, a polyethylene, or polyester, or a polytetrafluoroethylene (e.g., TEFLON). The materials may be used in totality or partially, and/or combined with other materials.

Figure 82:
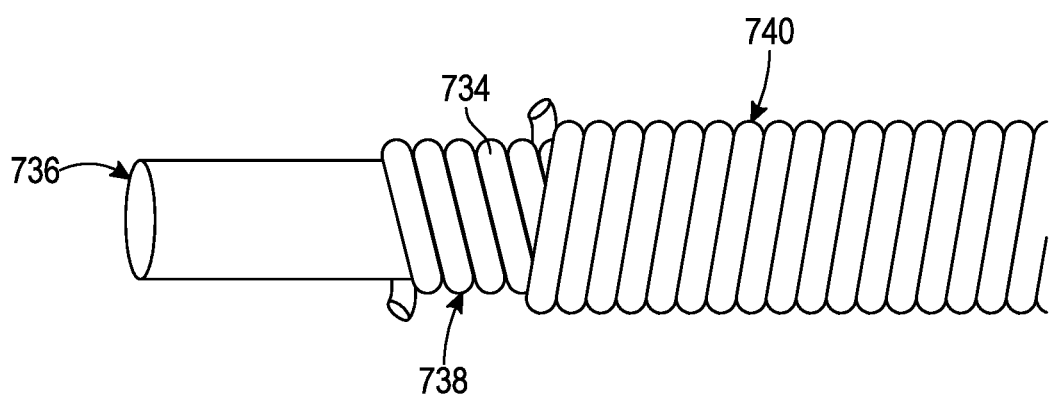
FIG. 82 schematically illustrates an example of a hybrid or composite fiber comprising an elastic core wrapped in a lubricious material.

FIG. 82 schematically illustrates an example of a hybrid material that is both elastic and lubricious and may be used to form the tube and/or expandable external working channels. In this example, a double covered filament (e.g., "yarn") consisting of an elastic core 736 wrapped with two counter-wound layers 738, 740 of more lubricious fibers 734 is shown. In FIG. 82 the hybrid material includes an elastic (e.g., elastomeric) core 736 that is wrapped by a double wrapping of a less elastic, but more lubricious fiber 738. The elastic core may be a single fiber or multiple elastic fibers, which may be arranged in parallel or may be twisted, braided, etc. In some examples a single covering 738 of the lubricous fiber may be wrapped around the elastic core; in some examples a double 738, 740 or more (e.g., triple, etc.) overlapping wrapping of the less elastic but more lubricous material may be used. Although a single covering is possible, a double covering may have more reliable coverage.

In another example, the elastic element and the lubricious element are knitted, woven, or braided together in such a manner that the elastomeric material (e.g., "core") may not be wrapped by a lubricious material completely, but nevertheless does not add to the drag of a sliding member because the elastomeric member is positioned relative to the working channel away from the sliding surface. As such, the elastomeric material (e.g., "core") may provide the requisite elasticity, but does not significantly increase drag.

The tube 7635 may be formed of the same elastic and lubricious material as the expandable working channels or may be formed of a separate material that may be more or less elastic and/or more or less lubricious. For example, the lumen 140 of the tube 7635 that is configured to fit over the elongate medical device may have an adjustable circumference, radius or diameter to accommodate the elongate medical device (e.g., a rigidizing tube) to which it is applied over by being sufficiently elastic. Similarly, each of the expandable working channels may have an expandable lumen 126 with an adjustable circumference, diameter or radius to accept a liner insert tool and/or to directly accommodate tools of different dimensions. In some example, the filaments can have a low-friction coating and/or a low-friction wrapping around the elastic core. The coating material may increase the lubricity of the fiber and may reduce friction when a fiber contacts another surface (e.g., a sliding device or the interior of a body vessel). The use of a low friction filament material similarly ensures reduced friction relative to adjacent sliding materials or surfaces. The lubricious wrapping and/or coating can be a material such as polypropylene or Teflon or a combination thereof. In some examples, the one or more filaments forming the expandable working channels may be wrapped with multiple layers of the lubricious material. In some examples the filament(s) may include an elastic core that is wrapped (e.g., coil wrapped) by a radially attached wrap material (e.g., a polytetrafluoroethylene material) to the elastic core (e.g., a silicone core, a spandex core, a urethane core, etc.). The wrap can include the lubricious material and each filament may have more than one layer of wrap.

In some examples, the forming the working channel(s) 210 and/or the tube can compress against an elongate medical device as the filaments are stretched to accommodate the changes in shape (bending, expand/contract, etc.) of the elongate medical device, allowing the tube and/or working channels to compress or retract. The compression/expansion of the flexible tube and working channels on the elongate medical device may be sufficient to prevent warping, rippling, kinking, wrinkling, buckling, or bunching of the tube and/or working channels as the rigidizing device assembly is advanced through a vessel. The weave and network of filaments can be one example of a knit or woven material forming an expandable working channel 7620 and the tube 7635. The tube 7635 can form a continuous lumen 140 into which the elongate medical device fits. Additionally, the lumen 126 of the working channels may also be formed of the same (or a different) filament or type of filaments.

In any of the tubes having elastic working channels described herein may be knitted, braided and/or woven as described above. The resulting may form pores between the filament(s) forming the fabric. As used in this example "pores" includes windows, openings, gaps, spaces, etc. between filament(s) forming the (e.g., weave, knit, etc.). In general, the tubes described herein may have a pore size that may vary as the working channel is expanded or collapsed. The pores may change shape (i.e., compress, be reduced, expand, or extend) as the working channel shape changes. Smaller pore sizes may prevent snagging or catching of a tool within the expandable working channel(s). The optimal sizing of the pores may depend on the material, including filament size, pore percentage, size of the spacing of pores, pore diameters, etc. For example, in some examples it is beneficial to have a porosity of greater than <80% (less than 75%, less than 70%, less than 65%, less than 60%, less than 55%, less than 50%, etc.,) when the expandable working channel not expanded ("opened"). The pore size of the flexible tubular member may range from 0.05 mm to 4 mm. In general, the flexible tubular member may have a variety of pore sizes and shapes along its length.

The knit may be formed using between 1-4 filament ends, having fibers of Denier (thickness) of between about 10-200. The knitting machine gauge may be between about 10/14 and 16/18.

The lumen of the external working channels may be defined by an exterior surface of the tube 7635 and an interior surface of channel material such that the channel material is connected to the exterior surface of the tube 7635. When a liner insert tube and/or a tool is passed through an external working channel (which may be an expandable working channel), the material forming the external working channel may expand even while the exterior surface of the tube 7635 within the channel lumen does not. Alternatively, in some examples an expandable working channel may have an interior surface of a knitted, woven or braided filament(s) that are separate from the filaments forming the tube and may be affixed to the exterior surface of the tube 7635.

Figure 77:
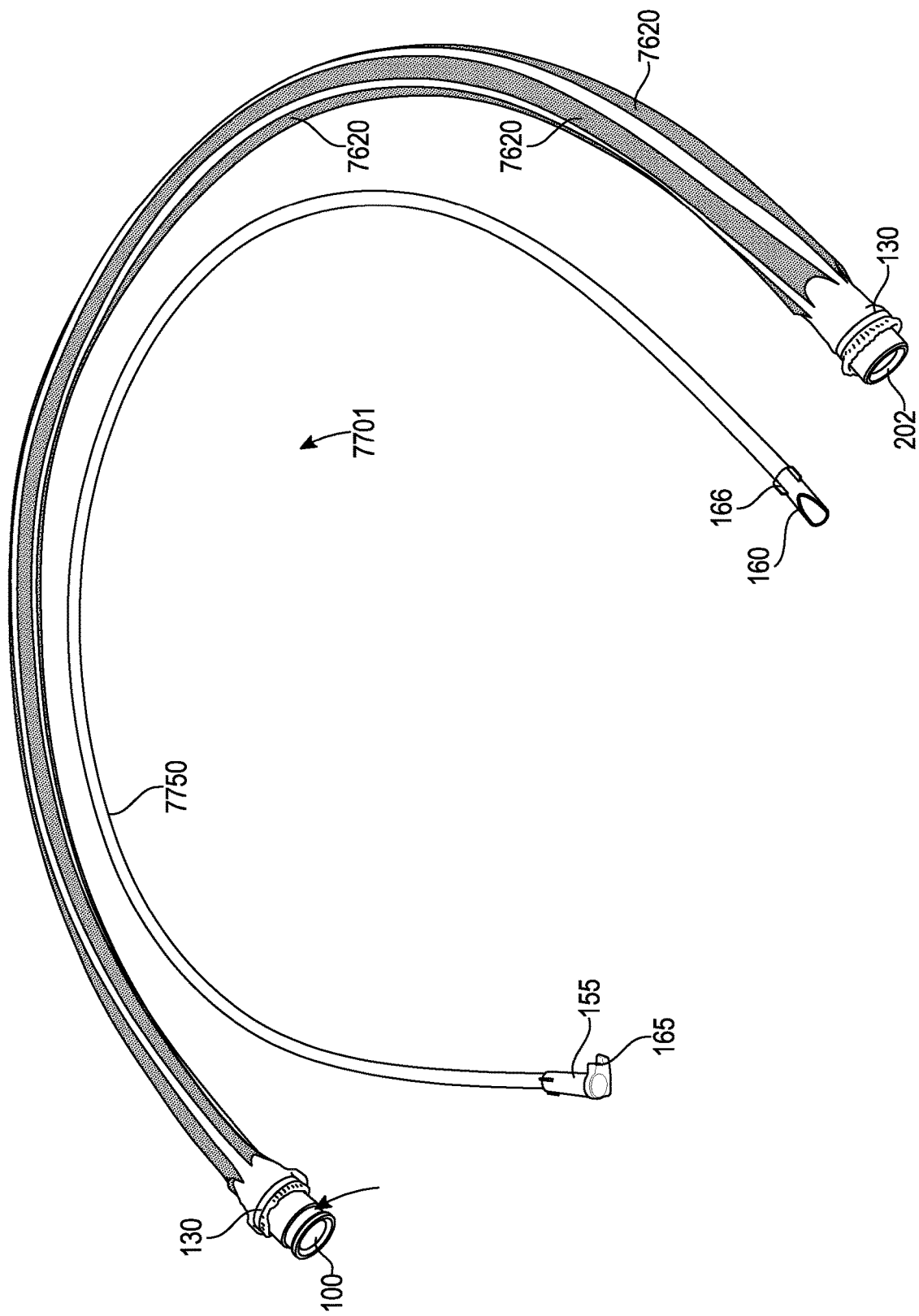
FIG. 77 shows an example of a system including an external working channel system in combination with an elongate medical device (e.g., a rigidizing device) and a liner insert tube.

FIG. 77 shows an example of a working channel sleeve apparatus 7701 similar to that shown in FIG. 76 including an elongate medical device 200 (in this example a rigidizing tube) installed through the tube 7635 having a plurality of expandable working channels 7620. The expandable working channels 7620 are visible around the exterior surface of the tube 7635. This system also includes a liner insert tube 7750 that has a length that is approximately the same as the distance between the proximal end region and the distal end region of the tube and/or the elongate medical device. In some examples, because the distance along the outside of the tube when it is curved may be different than the distance along the inside of the tube when it is curved, the liner (e.g., the liner insert tube 7750) may be longer than the midline path length of the apparatus, such that the liner insert tube can buckle to accommodate when on the inside curve yet may still be long enough when extending along the outside curve of the elongate medical tool. The liner insert tube 7750 may be configured to fit into the lumen of an expandable working channel and may extend from the proximal end to the distal end. In some examples the distal end of the liner insert tube 7750 may engage with the distal end of the tube and/or the distal end of the elongate medical device. The liner insert tube 7750 may be configured to receive one or more tools or instruments passed therethrough, while the liner insert tube 7750 holds the working channel open.

In some examples the liner insert tube 7750 can have a substantially thin wall around a lumen. The liner insert tube 7750 may have an interior surface surrounding the lumen and an exterior surface that may be in contact with an interior surface of a working channel 7620. The liner insert tube 7750 may resist compression by the expandable working channel to facilitate advancement through the external working channel device 7600. Additionally, the liner insert tube 7750 may be bendable and can proceed along a path defined by an interior of a channel 7620 that is curved or bent based on the path of the elongate medical device within the body. The external working channel is disposed on the same path as the elongate medical device 200, and the liner insert tube 7750 may be inserted after the distal end of the elongate medical device is positioned near the target tissue region to be treated or examined. Advantageously, the elongate medical device may be positioned within the body with a small profile that is later expanded to a larger profile to fit one or more tools by inserting and engaging the liner insert tube 7750 in the expandable working channel. Each liner insert tube 7750 may have a tapered distal end with one or more engagers (e.g., engagement elements) that may engage with a distal end region of the external working channel, the tube, and/or the elongate medical device. The engagement element 165 of the tool liner can be configured to communication with a complimentary engagement region or element on either the elongate medical device or the tube, or both. In some examples, a proximal engager (engagement element 165) at the proximal end of the liner insert tube 7750 is configured to engage the extremal geometry of the tube, and/or external working channel and/or elongate medical device. As mentioned, the distal end of the liner insert tube 160 may also or alternatively have a distal engager (e.g., distal engagement element 166) configured to engage or otherwise communicate with a distal end region of the tube and/or elongate medical device. These engagers may be of different shapes, including wing-like.

Figure 78A:
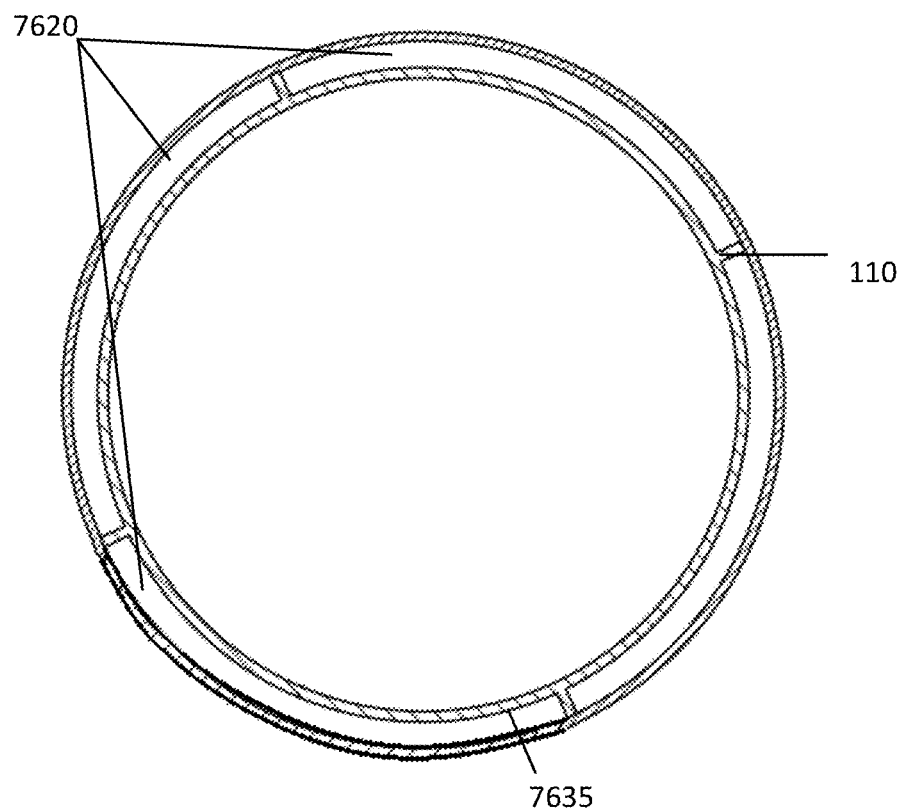
FIGS. 78A and 78B illustrate schematic cross-sectional views of a tube including four expandable external working channels around the perimeter of the tube.
Figure 78B:
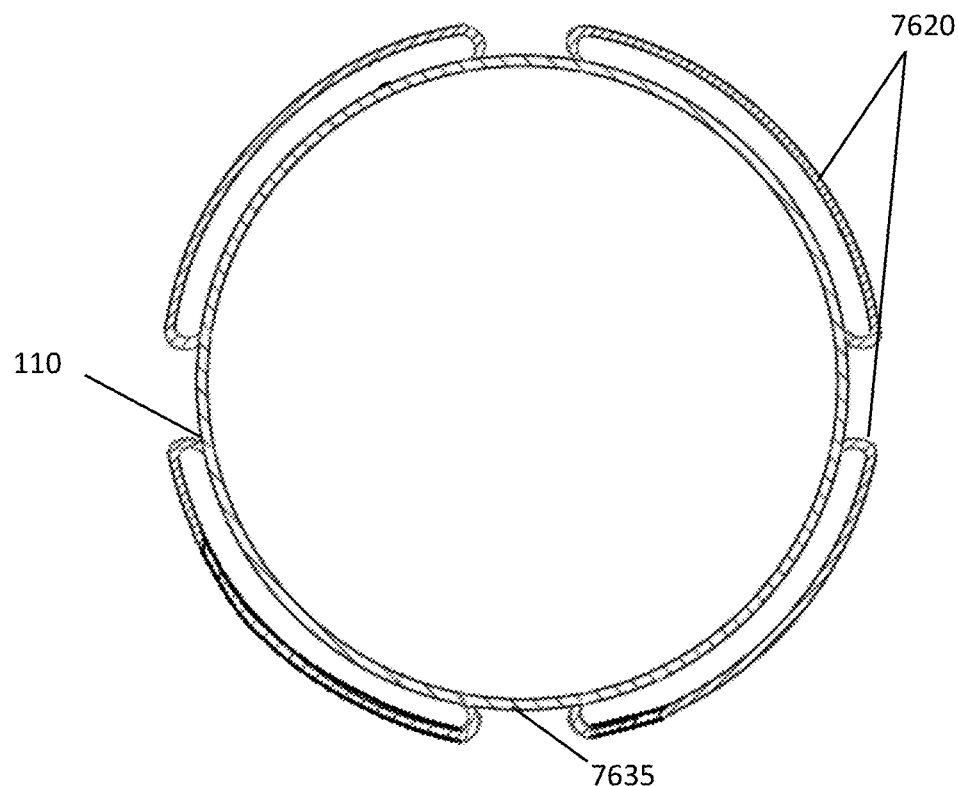

According to some examples, the material forming the external working channels 7620 may form a continuous circumference whereby a region of the outer circumference is affixed to the exterior surface of the tube 7635. Accordingly, the portion of the tube 7635 in forming or in communication with the outside of a working channel may be at a single point up to half of the circumference of the working channel. The amount of the working channel continuous with the tube 7635 may be described in a percentage of the circumference of the working channel. For example, 1%, 5%, 10%, 15%, 20%, 25%, 30%, 35%, 40%, 45%, 50%, or more of the working channel circumference may be formed by the tube 7635. In a relaxed configuration, the cross-sectional area of a working channel may be collapsed relative to the working channel when a liner insert tube or medical tool is inserted therein. The working channels may be formed of discrete region along an outer surface of the tube (as shown in FIG. 78B) or they may extend over the entire outer surface of the tube (as shown in FIG. 78A). In some examples the working channels may be integral with the tube. In FIG. 78A the external working channels 7620 are formed of the same material (e.g., from the same filaments or sharing filaments) as the tube 7635. In some examples (not shown) the working channels may be formed of separate filaments and may be attached to the tube 7635 (e.g., by co-weaving, braiding, local stitches or bonds, or the like). In some examples, the working channels may be affixed to adjacent working channels as they share a common attachment points 110. Alternatively, the external working channels 7620 may be formed integrally with (e.g., woven, braided or knitted into) the tube 7635. In some examples, the external working channels may be radially spaced from each other and do not contact one another (see, e.g., FIG. 78B) and a portion of the exterior surface of the tube 7635 is visible.

In general, as shown in FIGS. 78A and 78B, the external working channels may be in a collapsed configuration (e.g., lying flat on the outer surface of the elongate medical device) until something is inserted into the lumen or channel formed by the external working channel.

Figure 79:
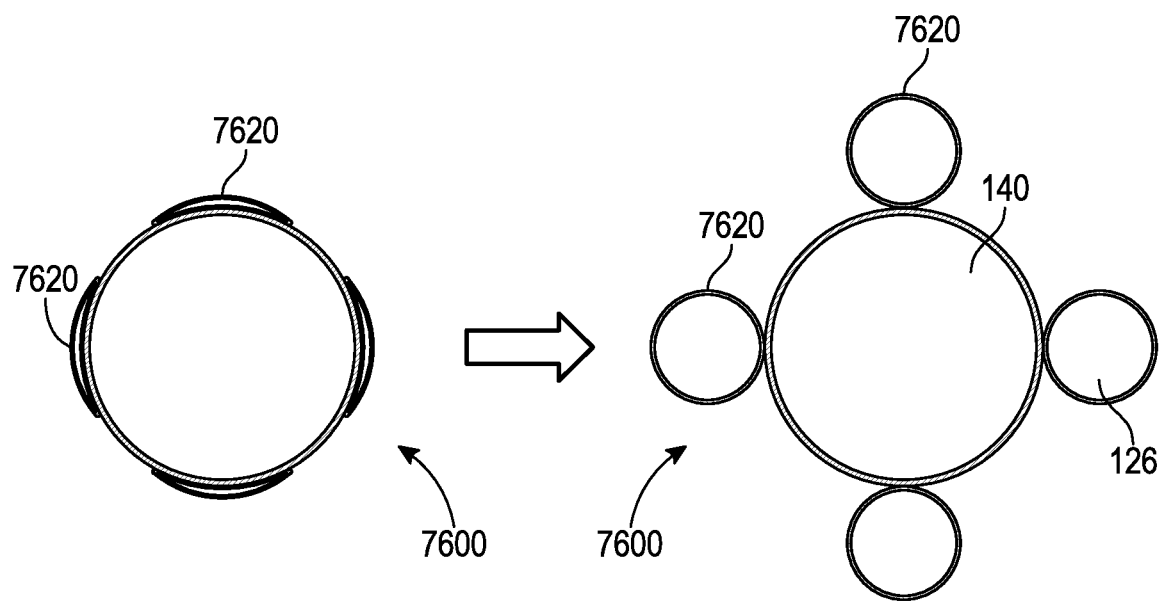
FIG. 79 schematically illustrates the expansion of four external working channels around the exterior of a tube.

In general, the external working channels may increase their cross-sectional area to accept a tool and/or liner insert tube that may be slid or advanced into the working channel as illustrated by FIG. 79. In FIG. 79, the working channels 7620 are shown in a collapsed configuration on the left, having a clear and empty lumen therethrough. The right side illustrates the working channels expanded, e.g., when a tool or liner insert tube is inserted therein. In some examples, in contrast to FIGS. 78A and 78B, the channels could be attached only locally, for example, at points or lines of tangency. The channels can be attached at their full contact circumference, or partial contact locations, all the way down to a single point of tangency. The flexible nature of the working channel may conform to the dimensions and geometry of the liner insert tube. A liner insert tube 7750 may be inserted into the proximal end of the working channel. For example, a distal end 160 of the liner insert tube may be inserted into the proximal opening of the working channel 7620 at the proximal end 125. A length of the liner insert tube may be slid into and through the working channel 7620 towards the working channel distal end 130. The liner insert tube 7750 may be advanced to any position within the length of the working channel 7620. In particular, the liner insert tube may be fully inserted into the external working channel and may be locked into position. For example, the liner insert tube 7750 may be advanced through the working channel lumen 126 such that the distal end 160 of the liner insert tube 7750 extends beyond the distal end 130 of the working channel 7620. The liner insert tube 7750 in some examples may be inserted through the working channel 7620 until the distal end of the liner insert tube 7750 is substantially near or beyond the distal end of the tube 7635. The distal end and/or proximal end of the liner insert tube may engage with the elongate medical device and/or tube.

According to any example described herein, the liner insert tube 7750 can have a geometry (e.g., can be size and spaced) that is configured to allow one or more tools to be passed through the liner insert tube. It may be circular. In some examples a cross-sectional geometry of the liner insert tube lumen may provide for specific orientation of the tool as it is inserted and advanced through the tool liner. For example, the liner insert tube lumen may have a cross-sectional geometry that is semicircular or some form of a polygon corresponding to cross-sectional geometry of a tool passed therethrough. The liner insert tube may remain open even as the force compressing it by the collapsible working channel increases (e.g., when bent or highly curved).

In any of these examples, the liner insert tube may be visualized by a camera (e.g., a camera associated with the elongate medical device. For example, an imaging element may image the liner insert tube during a procedure as it emerges from the distal end region of the working channel. The imaging element can provide spatial awareness of the orientation of the liner insert tube inside a vessel where it may be difficult to image. It could be advantageous, therefore, to have the main endoscope image, and then a secondary endoscopic image, as provided by the endoscope that goes through the external working channel or liner. The second endoscope could also be useful for additional manipulation and grasping, including with a tool through its internal working channel.

Figure 80A:
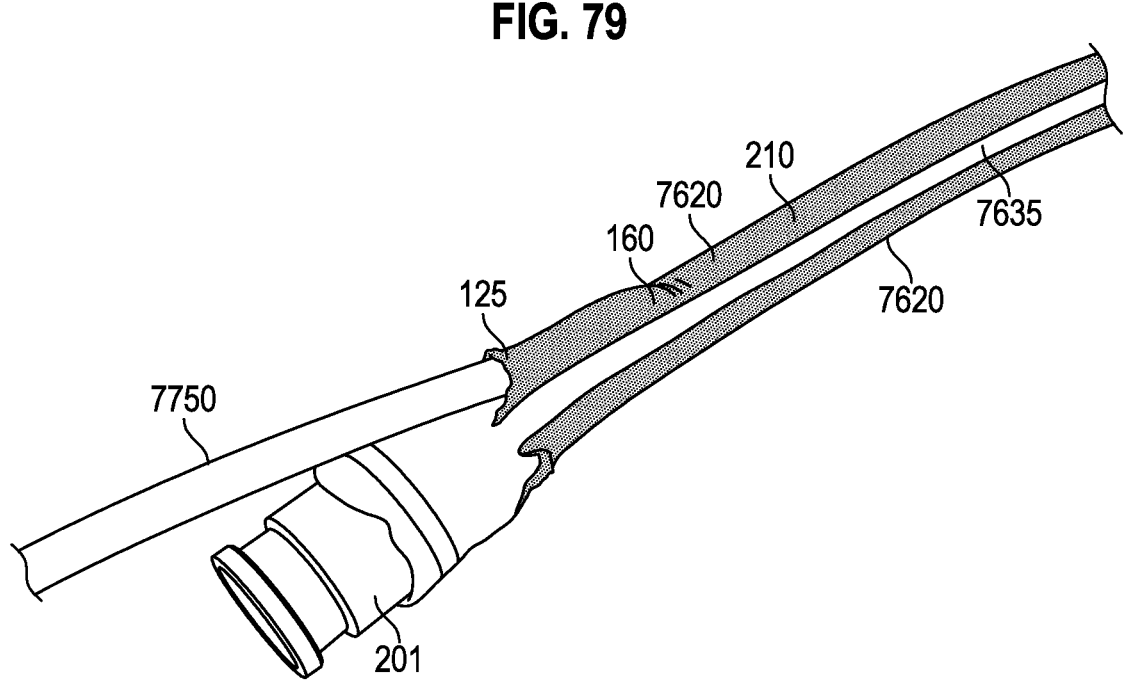
FIGS. 80A and 80B show examples of a proximal end of a tube having an external channel over an elongate medical device, showing the insertion of a liner insert tube from the proximal end of the external working channel.
Figure 80B:
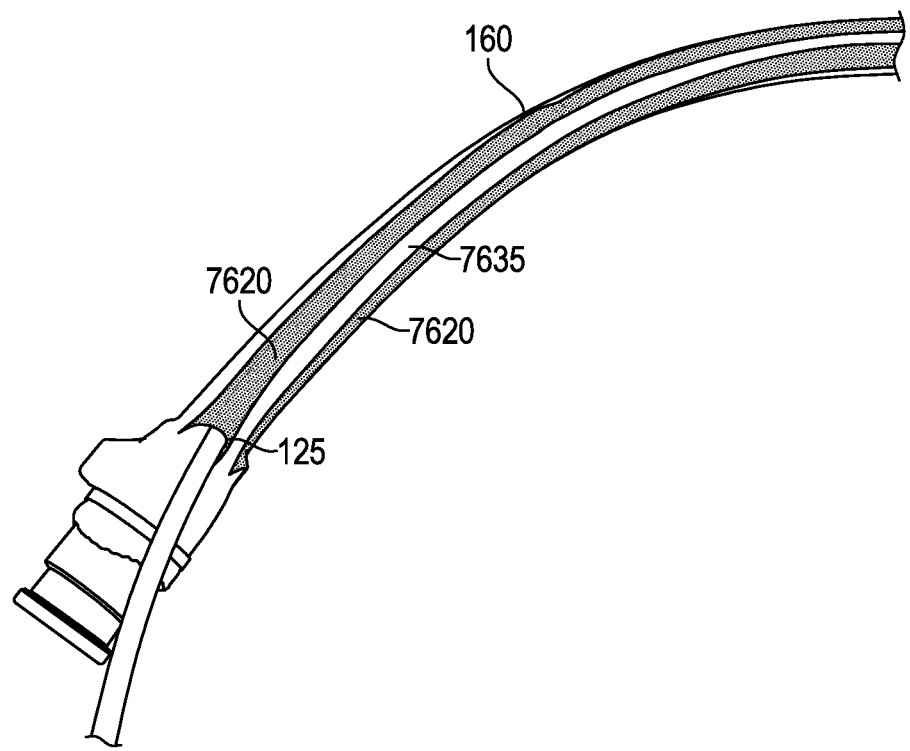

FIGS. 80A and 80B show views of the proximal end of the apparatus assembly (e.g., the elongate medical device and attached flexible tube including multiple external working channels). In FIG. 80A a liner insert tube 7750 is shown inserted into a proximal end 125 of a working channel 7620. The insertion of the liner insert tube 7750 is near the proximal end 201 of the rigidizing device 200, as this may be the end of the system or assembly that would be most accessible during use. The distal end 160 of the liner insert tube 7750 can be seen as within the working channel 7620 as it is advanced through the apparatus through the knitted material forming the working channels in this example (as shown in FIGS. 80A and 80B). In this example the forming the working channel and tube is configured as a knitted filament that comprise the working channels and the tube 7635. As shown, the working channel 7620 expands as the liner insert tube 7750 is first inserted into the proximal opening in FIG. 80A and continues to expand as the liner insert tube 7750 is advanced from a proximal end 125 towards a distal end of the working channel 7620.

The tubes including the working channels described herein may be configured to be worn over an elongate member device. For example the tube may receive an elongate medical device within the lumen 140 of the tube 7635. The elongate medical devices can generally be long, thin, and hollow catheters, scopes, overtubes, or the like. In some examples the elongate medical device can transition from a flexible configuration (i.e., one that is relaxed, limp, or floppy) to a rigid configuration (i.e., one that is stiff and/or holds the shape it is in when it is rigidized). The apparatuses described herein may be particularly well suited for use with rigidizing devices but may be used with non-rigidizing devices. In some examples, a rigidizing device (also referred to as a selectively rigidizing device) may include a plurality of layers (e.g., coiled or reinforced layers, slip layers, braided layers, bladder layers and/or sealing sheaths) that can together form the wall of a rigidizing devices. The rigidizing devices can transition from the flexible configuration to the rigid configuration, for example, by applying a positive or negative pressure to the wall of the rigidizing device or within the wall of the rigidizing device. With the positive or negative pressure removed, the layers can easily shear or move relative to each other. With the positive or negative pressure applied, the layers can transition to a condition in which they exhibit substantially enhanced ability to resist shear, movement, bending, torque and buckling, thereby providing system rigidization. Any appropriate rigidizing member may be used, including rigidizing members that are not formed of layers and/or actuated by pressure (positive and/or negative pressure). For example, the rigidizable members described herein may refer to any appropriate rigidizing device, including members that may be rigidized by jamming particles, by phase change and/or shape memory alloys, by interlocking components (e.g., cables with discs or cones, etc.), EAP (electro-active polymers) or any other rigidizing mechanism.

The elongate medical devices that may be used as part of the apparatuses described herein (both rigidizing and non-rigidizing) may include catheters, sheaths, scopes (e.g., endoscopes), wires, overtubes (e.g., external working channels), trocars or laparoscopic instruments. Rigidizing devices can function as a separate add-on device or can be integrated into the body of catheters, sheaths, scopes, wires, or laparoscopic instruments.

According to some examples, the body with external working channels can be installed with or on a rigidizing device. The lumen 140 of the tube may receive a portion or segment of the rigidizing device 200. For example, a body of the rigidizing elongate device may be contained entirely within the tube 7635 lumen. A distal end and proximal end of the rigidizing device 200 may be exposed as they extend beyond the length of the tube 7635 of the external working channels. Alternatively, a length of the rigidizing device 200 from the distal tip to near the proximal end of the rigidizing device 200 may be within the external working channel.

Figure 81:
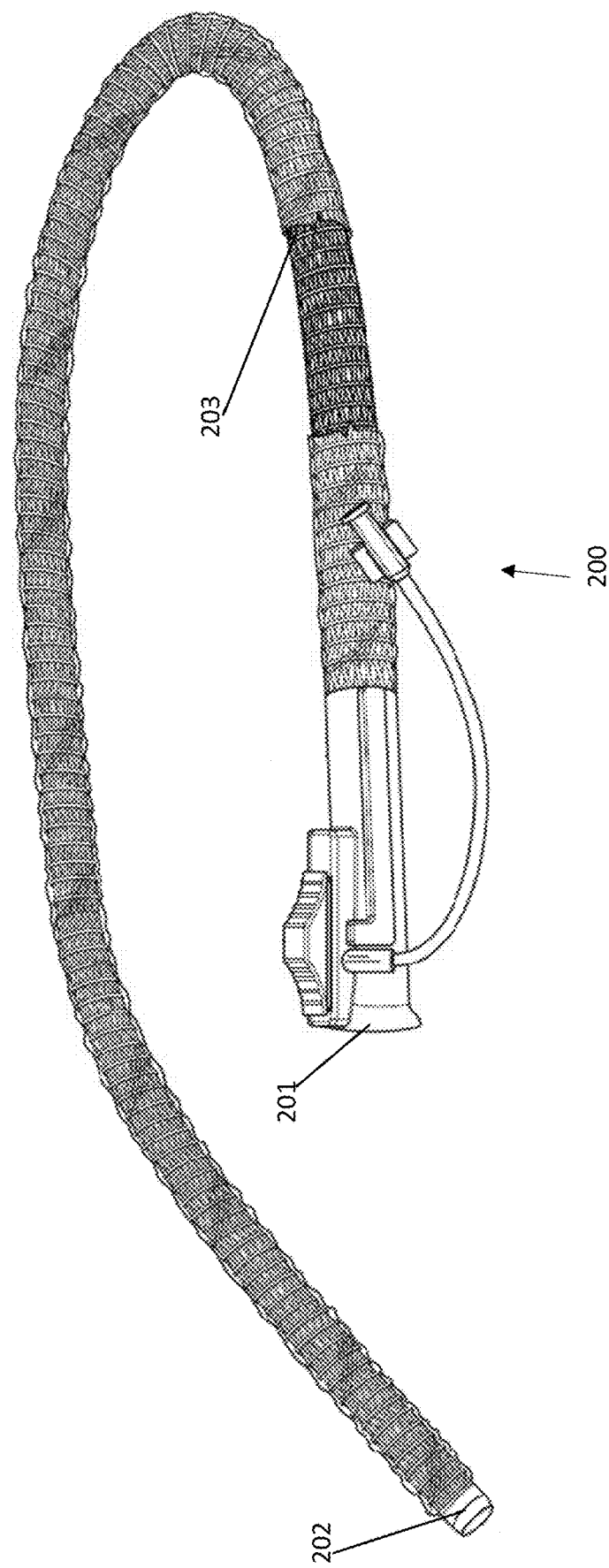
FIG. 81 shows an example of an elongate medical device, in this example a rigidizing device.

An elongate medical device configured as a rigidizing device 200 is shown in FIG. 81. FIG. 81 is similar to FIG. 1, described above. The rigidizing device 200 in this example has a wall with a plurality of layers 203 including a braid layer, an outer layer (part of which is cut away to show the braid 203 thereunder), and an inner layer. The system further includes a handle 201 having a vacuum or pressure inlet to supply vacuum or pressure to the rigidizing device 200. An actuation element can be used to turn the vacuum or pressure on and off to thereby transition the rigidizing device 200 between flexible and rigid configurations. The distal tip 202 of the rigidizing device 200 can be smooth, flexible, and atraumatic to facilitate distal movement of the rigidizing device 200 through the body. Further, the tip can taper from the distal end to the proximal end to further facilitate distal movement of the rigidizing device 200 through the body.

The elongate medical device of FIG. 81 may be used as part of a system including one or more external working channels. For example, the external working channel tube 7635 may cover an entire length of an outer surface of the rigidizing device 200. The tube and working channels may be applied over the rigidizing device, so that the tube may be fitted over the elongate body of the rigidizing device. In any of these examples, the tube and external working channels may be coupled to the elongate medical device either because of the elastic material forming the tube, which may contract down onto the outer surface, and/or because the tube may be attached at one or more points or regions (or along the entire length) of the outer surface of the elongate medical device. In some examples the tube forming the external working channels may be secured just at the distal end region or at both the distal end region and proximal end region. In some examples, the tube forming the external working channels may attach at various points or regions along the length of the elongate medical device (e.g., between about every cm and every 50 cm, between about every 15 cm and every 50 cm, between about every 20 cm and every 50 cm, between about every 25 cm and every 50 cm, between about every 30 cm and every 50 cm, etc.). In general, discrete attachments (and in some cases fewer attachments) may be preferred, to allow the tube and therefore the external working channels to adjust position slightly as the elongate medical device bends or curves, to prevent wrinkling, buckling or kinking of the tube and external working channels. The tube and external working channels may be attached to the outer surface of the elongate medical device by a mechanical attachment (e.g., a tie, a hook, an anchor, etc.), a chemical attachment (e.g., an adhesive, etc.) or any other appropriate attachment.

In some examples, the tube having external working channels may be coupled to the elongate medical device in a manner that prevents prevent relative rotation of the external working channels relative to the elongate medical device. For example, the external working channels may be sufficiently elastic to minimize or prevent significant movement between the two, rotational or otherwise. Thus, in some examples the tube having the elastic (and external) working channels may move with the elongate medical device in a 1:1 ratio.

Figure 83A:
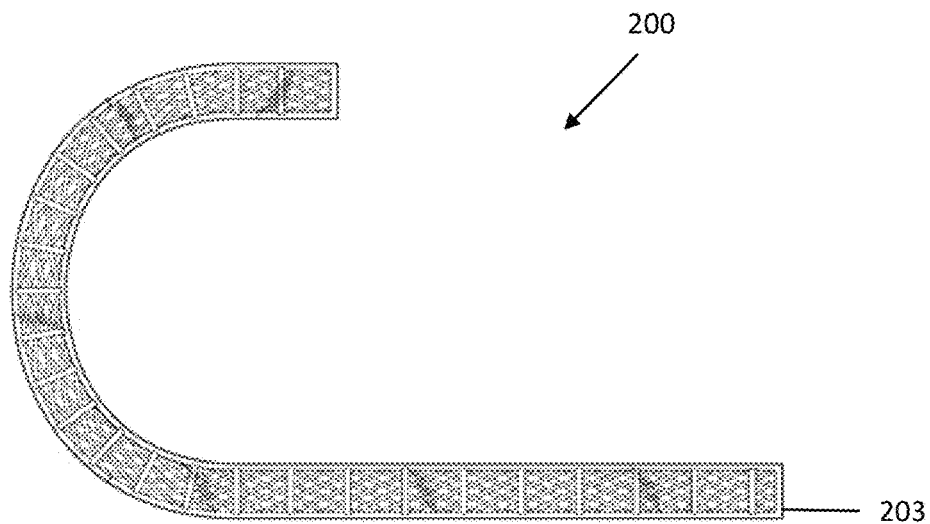
FIGS. 83A and 83B schematically illustrate segments of a rigidizing tube showing examples of contouring between the external working channels and the exterior of the rigidizing tube.
Figure 83B:
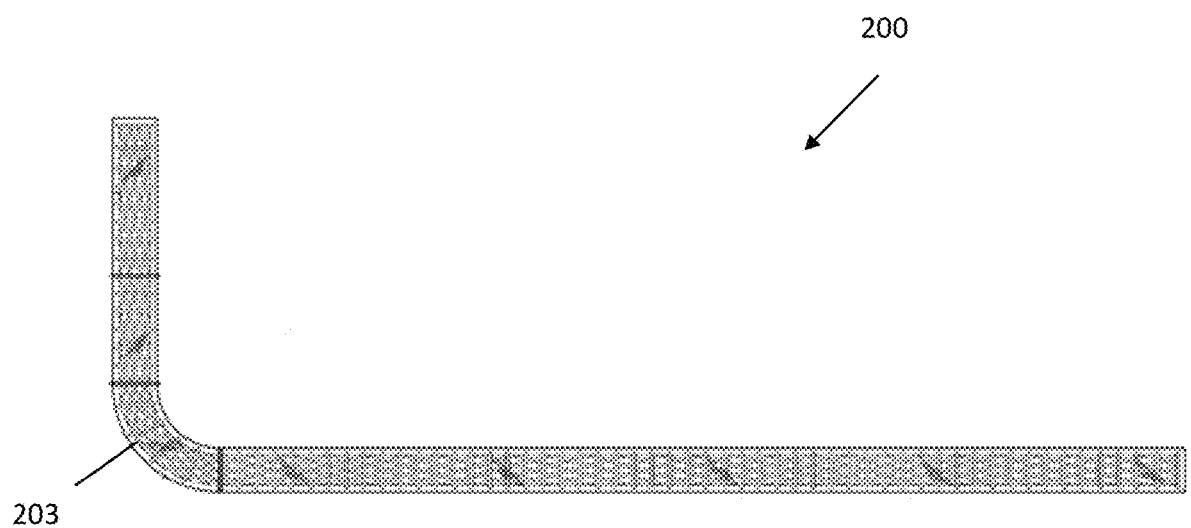

The engagement of the tube including working channels with the elongate medical device may be sufficient to minimize gaps between an interior surface of the tube 7635 of the external channel device and the exterior surface of the elongate medical device (e.g., rigidizing device 200). The system 7600 can include a flexible material, such as a with a weave pattern and/or filament(s) having an elastic core and a lubricious exterior. The elastic filaments forming the external working channels and/or tube may facilitate a snug and substantially close communication with the elongate medical device. As show in FIGS. 83A and 83B, an elongate medical device including a tube with one or more external working channels may operate when bent or curved through even highly tortious cures. FIGS. 83A-83B are similar to FIGS. 26B and 26A, respectively, described above, but may illustrate other (or alternative) features. FIG. 83A illustrates a curve of arc in a segment of the elongate medical device 200. Similarly, FIG. 83B illustrates a sharper bend in a segment of the elongate medical device 200. A tube with external working channels as described herein may be used with either configuration and even more tortuous bends without kinking or blocking passage through the external working channels. As shown in FIGS. 83A and 83B the tube and/or the external working channels may conform to these bends and curves (e.g., between 0 and 180 degrees or more, with a radius of curvature of approximately 1.5× the diameter of the elongate medical device without kinking, wrinkling, or the like. FIG. 83A shows a relatively large radius of curvature, while FIG. 83B shows a very narrow radius of curvature. The tube with external working channels described herein may track both of these curves. In general, where a segment or length of an elongate medical device 200 is curved or bent, the elasticity of the tube external working channels may be sufficient to maintain smooth and consistent contact with the rigidizing device 200 along an entire length which they are in communication with one another. The channels of the external working channels may possess similar capabilities as the tube 7635 of the external channel device, such that the channels also continue a smooth exterior surface of the external channel device and rigidizing device assembly.

In general, a rigidizing devices can toggle between rigid and flexible configurations, with any number of transition cycles. As interventional medical devices are made longer and inserted deeper into the human body, and as they are expected to do more exacting therapeutic procedures, there is an increased need for precision and control. Selectively rigidizing devices as described herein can advantageously provide both the benefits of flexibility (when needed) and the benefits of stiffness (when needed). Further, the rigidizing devices described herein can be used, for example, with classic endoscopes, colonoscopes, overtubes, catheters, robotic systems, and/or navigation systems, such as those described in International Patent Application No. PCT/US2016/050290, filed Sep. 2, 2016, titled "DEVICE FOR ENDOSCOPIC ADVANCEMENT THROUGH THE SMALL INTESTINE," the entirety of which is incorporated by referenced herein. The selectable rigid and flexible configurations of the rigidizing device may be accommodated by the tube with external working channels as described herein.

The elongate medical devices described herein can additionally or alternatively include any of the features described with respect to International Patent Application No. PCT/US2016/050290, filed on Sep. 2, 2016, titled "DEVICE FOR ENDOSCOPIC ADVANCEMENT THROUGH THE SMALL INTESTINE," published as WO 2017/041052, International Patent Application No. PCT/US2018/042946, filed on Jul. 19, 2018, titled "DYNAMICALLY RIGIDIZING OVERTUBE," published as WO 2019/018682, International Patent Application No. PCT/US2019/042650, filed on Jul. 19, 2019, titled "DYNAMICALLY RIGIDIZING COMPOSITE MEDICAL STRUCTURES," published as WO 2020/018934, International Patent Application No. PCT/US2020/013937 filed on Jan. 16, 2020, titled "DYNAMICALLY RIGIDIZING COMPOSITE MEDICAL STRUCTURES," and PCT/US2021/034292, filed on May 26, 2021, entitled "RIGIDIZING DEVICES" the entireties of which are incorporated by reference herein.

In some examples, the external working channels may be configured to allow the advancement of instruments or tools (i.e., working tools), such as surgical or laparoscopic tools, graspers, articulating graspers, fecal wash devices, and/or fecal-suctioning devices therethrough. In some examples, the tool can be a scope (e.g., so as to enable a secondary scope within or alongside a primary scope). The external working channel(s) can allow a tool to be guided along the elongate medical device until it reaches the distal end of the elongate medical device to perform the desired procedure. In some examples, the external working channels can accept a tool therethrough. For example, the elongate medical device may be coupled to a system 7600 including one or more external and external working channels.

Figure 84A:
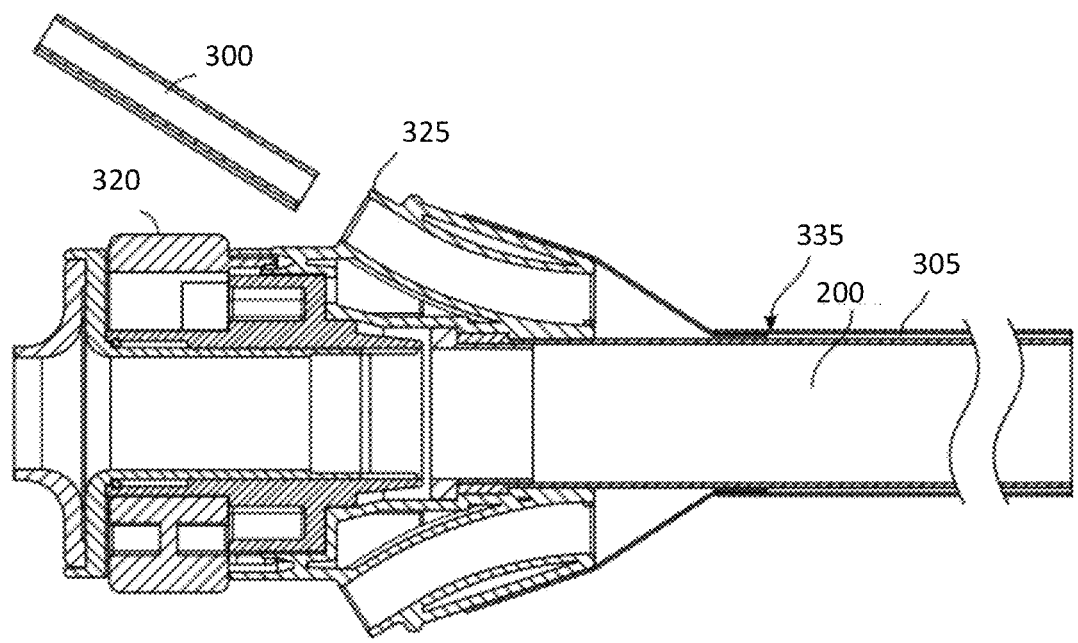
FIGS. 84A-84E show schematic illustrations of one example of an elongate medical device to which a tube comprising a plurality of external, expandable working channels are coupled.
Figure 84B:
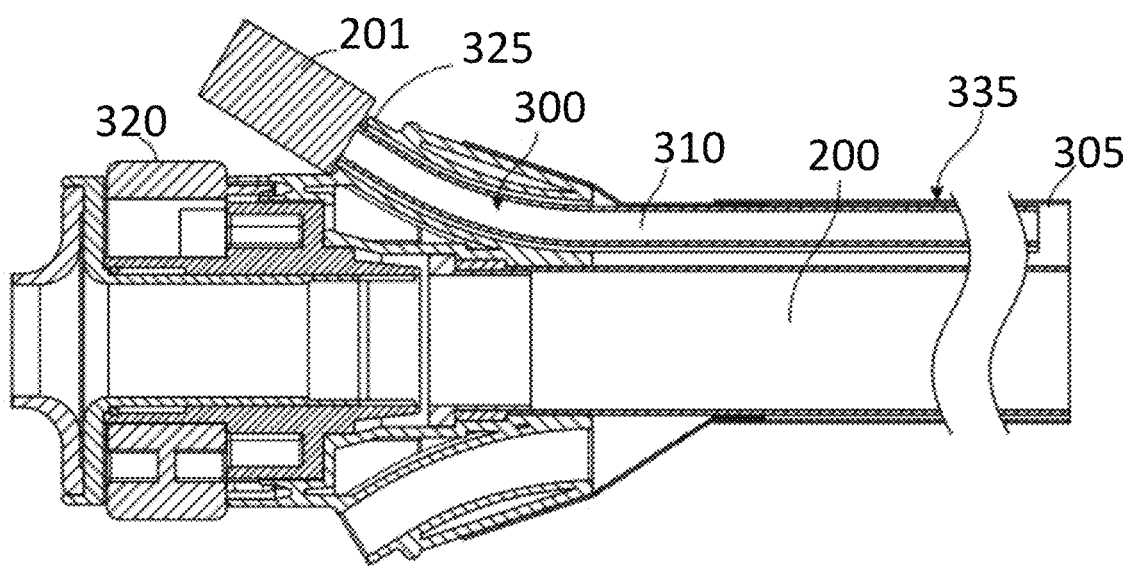
Figure 84C:
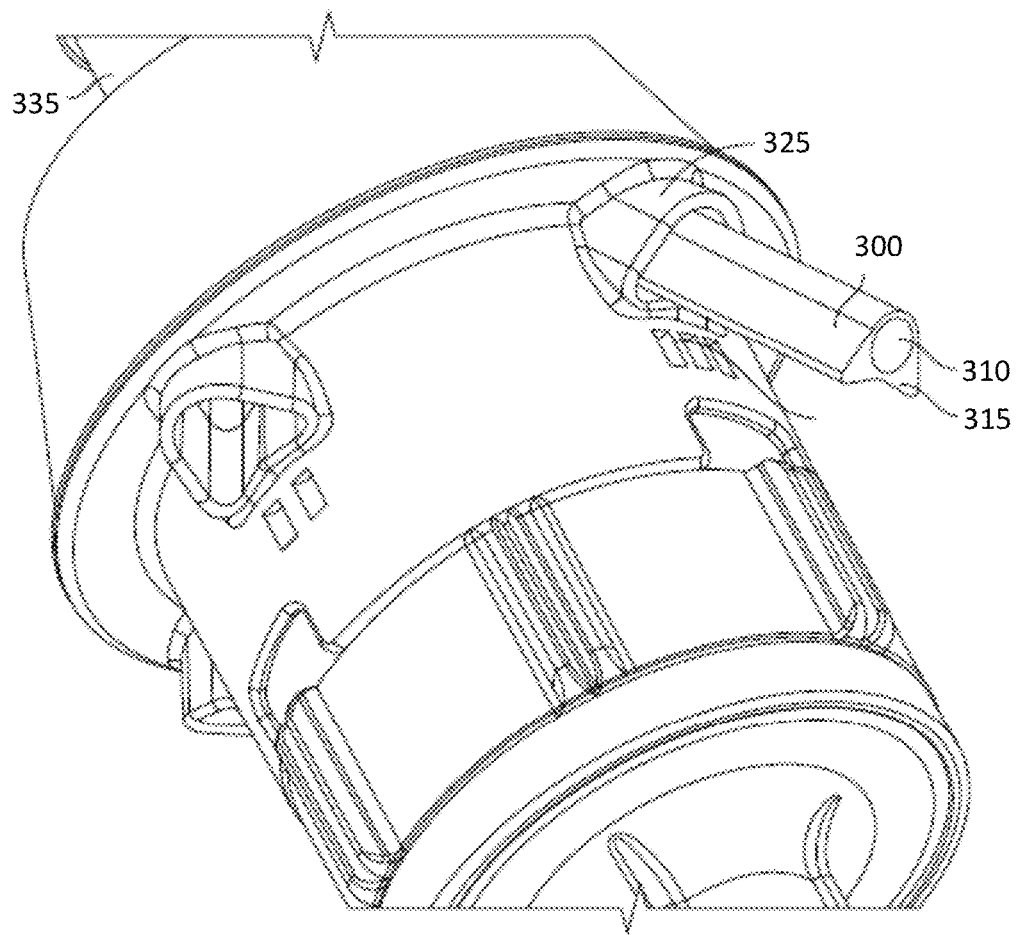

In some examples the proximal end of the tube with external working channels may be configured to engage with the channels formed by the external working channels. FIGS. 84A-84C show expanded views of a proximal end of an elongate medical device onto which a tube with external working channels 305 has been coupled. FIGS. 84A-84C are similar to FIGS. 73A-73B and 73M respectively, described above, but may illustrate other (or alternative) features. The elongate medical device in this example is a rigidizing device. The rigidizing device outer tube can be a thin-walled sleeve, such as an elastomeric sleeve, a plastic sleeve, or a cloth sleeve. In some examples, the rigidizing device outer tube can be a sleeve that is fiber reinforced or wire reinforced. In one specific example, the rigidizing device outer tube can be a cloth material that inherently has some stretch and/or a cloth material that is sewn at a 45° angle (e.g., such that being off-bias provides compliance and/or stretch). In some examples, the tube with external working channels can be permanently attached to (e.g., bonded, heat welded, sewn, or ultrasonically welded) the outer surface of the elongate medical device (e.g., rigidizing device 200). In any of these apparatuses the elastic working channels may be arranged linearly down the length of the elongate medical device at rest; e.g., the working channels may be straight (i.e., axially aligned with the rigidizing device outer tube 335). in some examples, the elastic working channels 305 may be spiraled. For example, the elastic working channels may be co-joined (to each other or to the elastic body) by sewing, bonding, or heat-sealing.

In some examples the elastic working channels may be lined with a hydrophilic, hydrophobic, or low friction (e.g., PTFE) coating. A liner insert tube 300 can include inserts (e.g., molded or extruded inserts) that are configured to be positioned within the external working channels 305 for use. For example, the liner insert tube 300 can be configured to be inserted into one or more external working channels 305 after a rigidizing elongate medical device 200 has been placed and/or rigidized in the body lumen. Each liner insert tube 300 can include a lumen 310 therein (configured for passage of a tool). Each liner insert tube 300 can have a stiffness sufficient to open or expand the external working channel 305 as it extends therethrough. In some examples the liner insert tube can have an inner diameter of between about 1 mm-7 mm, such as 3 mm-5 mm and a wall thickness of, e.g., between about 0.1 mm to 1 mm. The liner insert tube 300 can be made of a polymer, such as Teflon, FEP and/or a polyethylene (such as HDPE or LDPE). The lumen 310 can be lubricious to help enable passage of the tool therethrough. For example, the lumen 310 can be made of a material (e.g., the same material as the liner insert tube 300 itself) having a low coefficient of friction. As another example, the liner insert tube can be a composite structure that is coated with a separate lubricious coating, such as a hydrophilic coating.

Figure 84D:
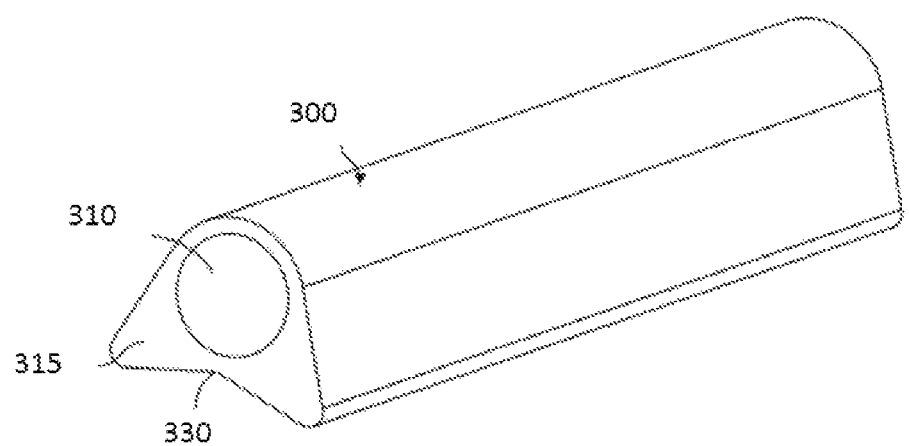
Figure 84E:
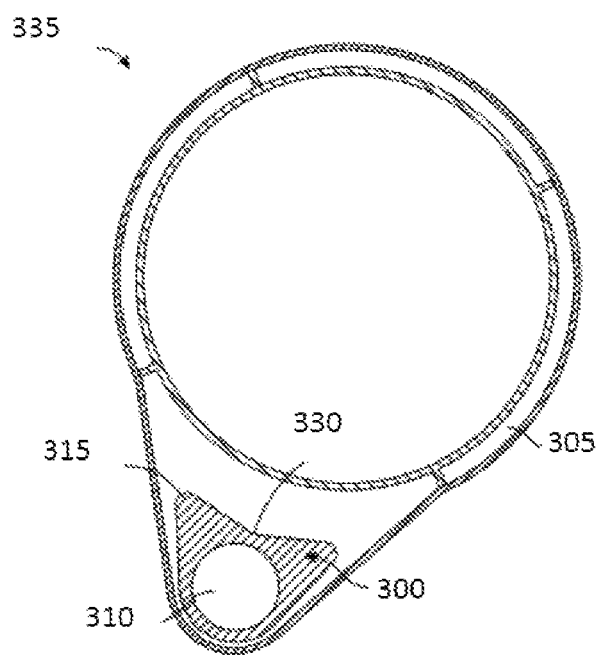

As shown in FIGS. 84D and 84E, in some examples, the liner insert tube 300, which may equivalently be referred to herein as a guide, can include one or more projections (e.g., wings) and/or may have a symmetric or an asymmetric cross-section. FIGS. 84D and 84E are similar to FIGS. 73C and 73D, described above, but may illustrate other (or alternative) features. For example, in some examples the apparatus may include one or more wings 315 that may have an asymmetric cross-section. In some examples the liner insert tube may include a non-circular shape with wings 315 (e.g., rounded triangular-shaped wings) extending from the region around the central lumen. In some examples, the wings 315 can form an angled surface 330 (e.g., having an angle, e.g., of 110° to 130°, such as approximately 120°) configured to conform closely to the outer circumference of the rigidizing device 200. The asymmetric cross section can advantageously ensure proper radial alignment of the liner insert tube 300 (e.g., so that the distal end of the lumen 310 points radially inwards with respect to the rigidizing device 200). Additionally, the asymmetric cross section can advantageously prevent rotational movement of the liner insert tube 300 within the external working channels 305. This can be particularly advantageous when the elongate medical device is a rigidizing device that is in a rigid configuration, as the asymmetric cross-section can help provide rigid and stable access to the desired working area. In other examples, the liner insert tube 300 can be symmetric and/or otherwise configured to be rotatable within the expandable working channel 305. In some examples, the proximal end of the liner insert tube 300 may include an indicator mark configured to indicate the rotational position of the distal end of the liner insert tube 300 relative to the working channel 305 and/or relative to the elongate medical device 200.

In FIGS. 84A-84B, the elongate medical device outer tube 335 can include a proximal manifold 320 attached thereto that may be configured to enable insertion of the liner insert tube 300 therein. For example, the manifold 320 can include ports 325 enabling access to each external working channel 305. In some examples, each port 325 can include a corresponding marker configured to enable identification of the working channel 305 (and thus identification of the distal circumferential position of a tool inserted therethrough). The markers can be shapes, numbers, colors, or any one of a wide variety of input/output matching identifiers. In some examples, the ports 325 can include a valve thereon and/or can be vacuum-sealed.

In some examples, the liner insert tube 300 can include a handle or stop 201 (see FIG. 84B) at the proximal end thereof to limit axial movement of the liner insert tube 300 too far within the working channel 305 and/or the manifold 320 that is coupled to the outside of the elongate medical device 335 (e.g., a rigidizing device outer tube).

FIG. 84C shows an example of a liner insert tube 300 (which may also be referred to herein as a guide) including a lumen 310 and a pair of wings 315; the liner insert tube is inserted into a port 325 that couples with the external and expandable working channels (not visible if FIG. 84C). Any of these apparatuses may include a port at the proximal end of the apparatus to assist in providing entry into the flat (e.g., unexpanded) working channel.

FIGS. 85A-85C illustrate another example of a liner insert tube 1000 as described herein. The liner insert tube may have a length that is approximately the same as (or just slightly longer than) that of the elongate medical device and external channels with which it may be used. The liner insert tube may exhibit high radial and axial stiffness while exhibiting low bending stiffness so that it may track through the external channel. FIG. 85B shows an enlarged view of the proximal end region 1033 and distal end region 1035. The proximal end region 1033 and distal end regions 1035 of the liner insert tube are shown. The proximal end 1033 may include an engagement 1037 that may engage or couple with a connection on the proximal end of either the elongate medical device and/or the tube forming the external channels.

The distal end region 1035 in this example includes a deflector 1041 that may be oriented so as to deflect a medical tool inserted through the elongate channel of the liner insert tube 1000 towards a midline of the elongate medical device or an endoscope inserted through the elongate medical device. For example, the distal tip also may be shaped to deflect a tool which passes out through the distal tip towards the center line of the elongate medical device (e.g., endoscope). This is illustrated in FIG. 85C, showing a deflector 1041 on the liner insert tool, which is designed to deflect a tool 1045 which passes through the liner inert tube 1000 towards the axial centerline of the elongate medical device (e.g., endoscope, not shown).

Both the proximal and distal ends of the liner insert tube 1000 in FIGS. 85A-85C include a pair of wings 1039, 1039' as described above; the wings may guide and/or secure liner insert tube 1000 within the expandable channel. These wings (or "fins") may help keep the liner insert tube 1000 aligned rotationally in the working channel. The fins may help to engage distal geometry so that, once fully advanced, it is 'docked', so as to prevent axial, lateral, and torsional motion.

Figure 86A:
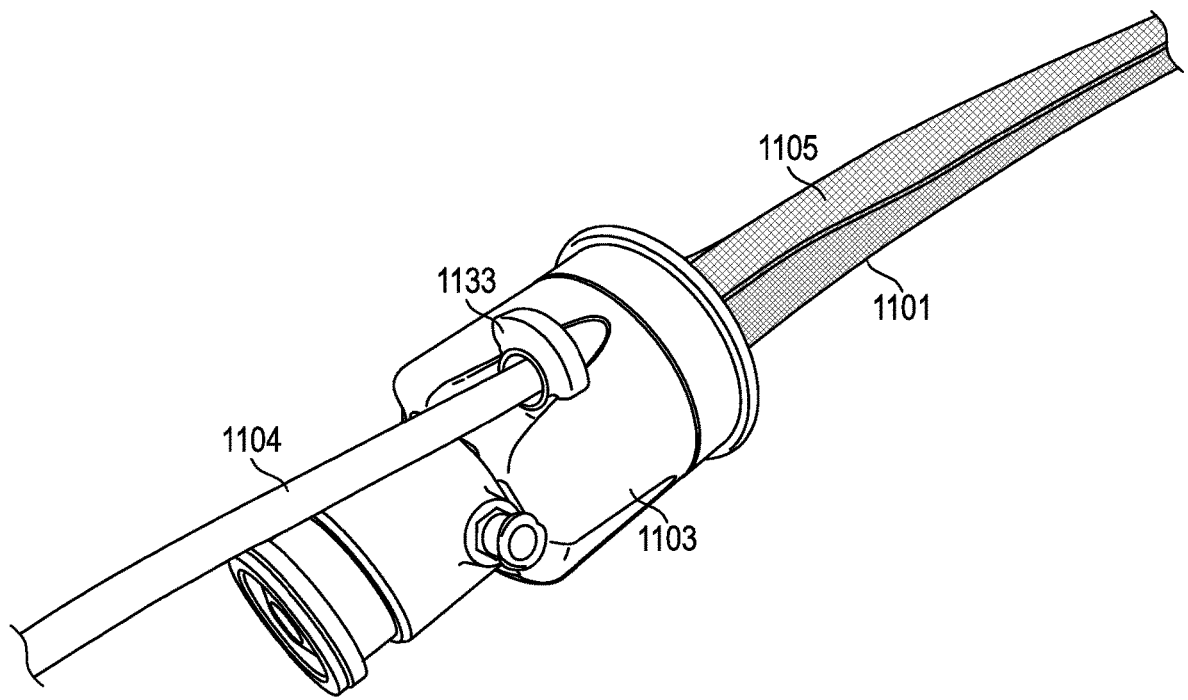
FIGS. 86A-86C illustrate one example of a system including a tube having an expandable external channel coupled to an elongate medical device (in this example, a rigidizing overtube).
Figure 86B:
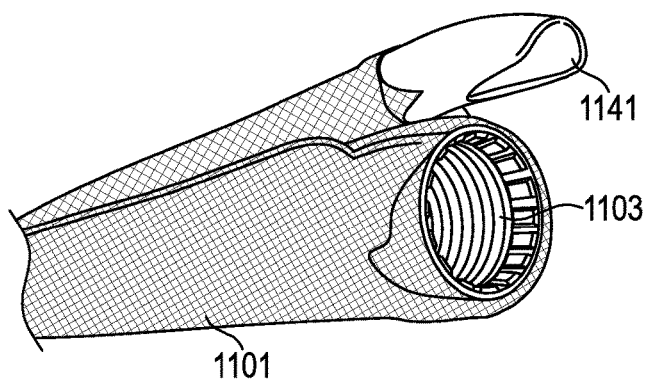
Figure 86C:
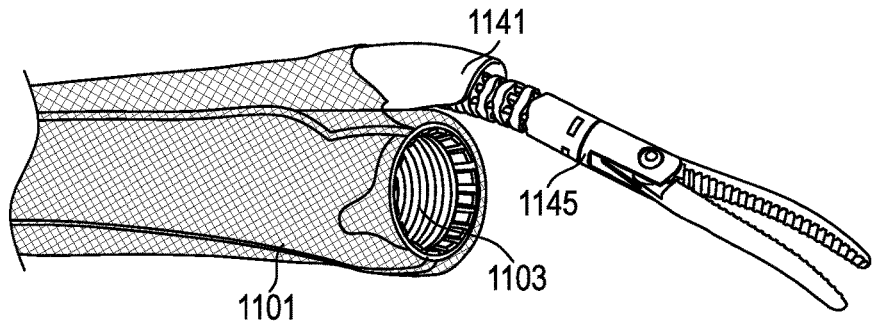

FIGS. 86A-86C illustrate an example of a system as described herein, including a tube 1101 formed of a knitted material that is attached over elongate medical device 1103 (in this example, a rigidizing overtube). The tube 1101 includes at least one expandable external channel 1105 into which a liner insert tube 1104 is inserted and coupled at the proximal end 1133 to the handle of the elongate medical device 1103. The liner insert tube may therefore hold the expandable external channel open and prevent snagging by a medical instrument or tool 1145 as it is passed through the liner insert tube 1100 to exit out of the distal end as shown in FIG. 86C. FIG. 86B shows the distal end of the liner insert tube 1104 including a deflector 1141 that directs the medical tool 1145 towards a midline of the elongate medical device 1103 or in any desired direction.

Figure 86D:
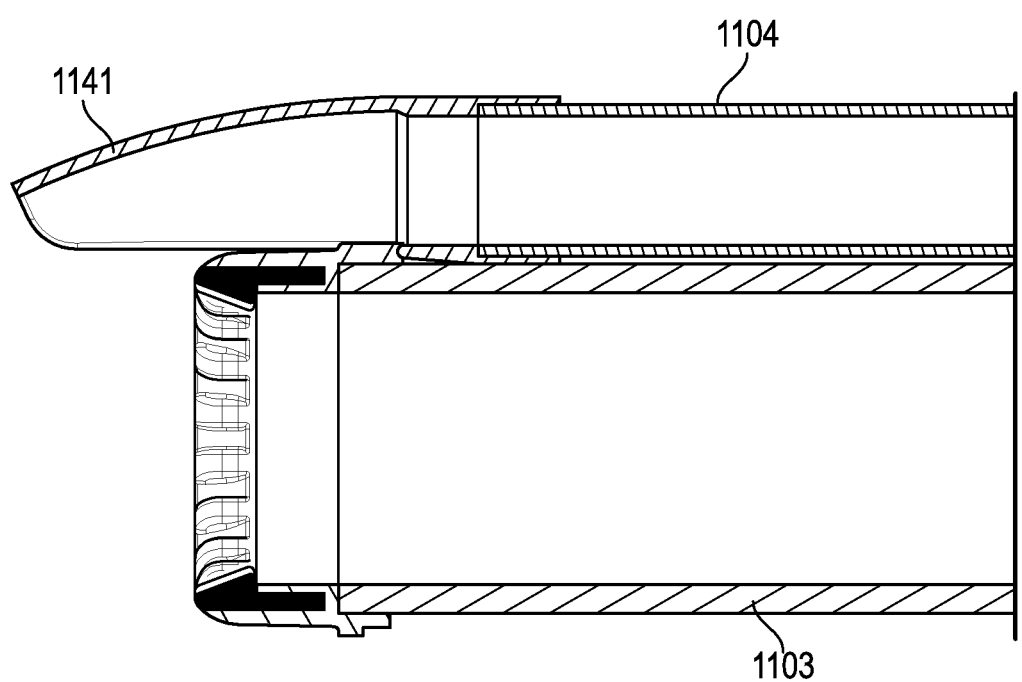
FIG. 86D is a schematic cross-section of a tool liner tube including an engaged deflector extending distally out of the elongate medical device.
Figure 86E:
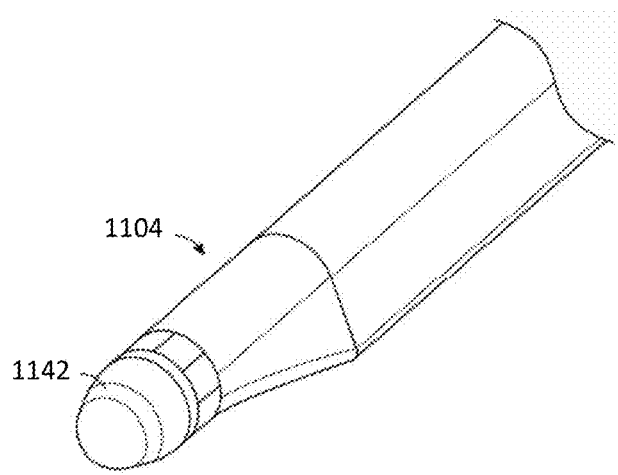
FIGS. 86E-86G show one example of a tool liner tube.
Figure 86F:
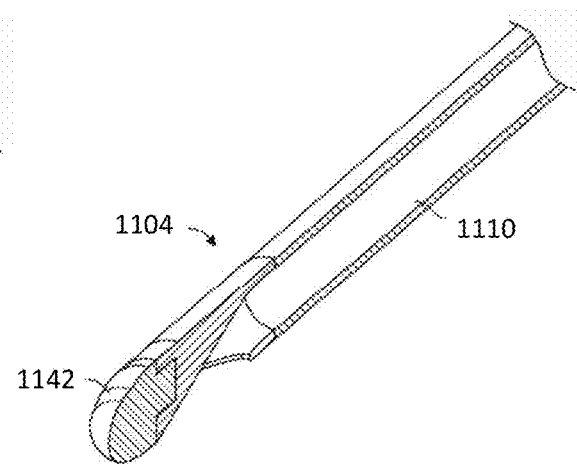
Figure 86G:
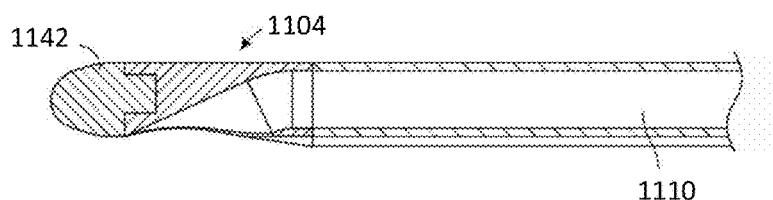
Figure 86H:
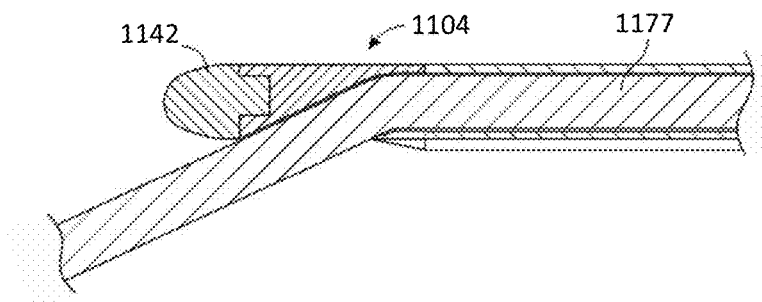
FIGS. 86H-86L illustrate a tool inserted through the tool liner tube shown in FIGS. 86D-86G.
Figure 86I:
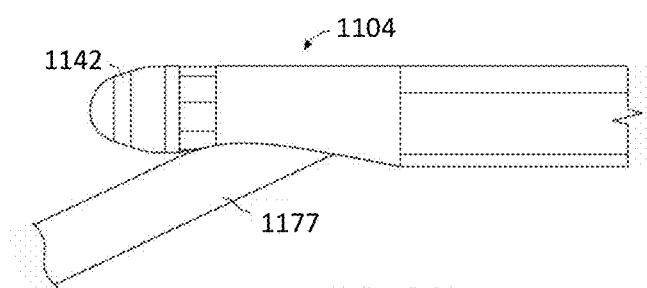

FIG. 86D shows an example of a distal end of a liner insert tube 1104 that is adjacent to an elongate medical device 1103, in this example, configured as an overtube 1103. The liner insert tube also include a deflector 1141 that is formed or attached to a distal end region of the liner insert tube 1104 and has a slight bend or angle at a distal region that directs a tool either distally (straight) or slightly radially inward but may prevent the tool from exiting radially outwards. In some examples the director may be rotated intentionally to direct a tool radially outwards rather than inwards.

In use, a working channel sleeve apparatus as described herein may include or may be part of an elongate medical device, including but not limited to a rigidizing device, for example, the working channel sleeve apparatus may be positioned or attached over an outer surface of the elongate medical device. The working channel sleeve apparatus, including the elongate medical device, may then be positioned at a desired anatomical location. If a user would like to deploy a tool at the anatomical position, a user can select an external working channel (e.g., based upon a marker, such as a color, symbol and/or text marker) at a proximal end of the elongate medical device, and the user can then insert either the tool or a liner insert tube 1104 through a port and into the external working channel. Inserting the liner insert tube (also referred to herein as a "guide") can expand the external working channel. A tool can then be inserted through the liner insert tube. After the procedure is complete, the tool and liner insert tube can be removed, and the external working channel can collapse back down.

The liner insert tube can come in different sizes (e.g., with different sized lumens, such as lumens 1110 that range from 1 mm-7 mm, such as 2 mm-6 mm in diameter) and can be interchangeably used in external working channel(s). In some examples, the liner insert tubes can have a lumen without a bend at the distal end. In other examples, the liner insert tube may include a bend and/or asymmetric jog or turn configured so as to direct a tool inserted into the lumen of the liner insert tube in a desired direction, such as towards the center of the elongate medical device or away from the midline of the elongate medical device (e.g., so as to direct the tool radially outwards, such as for performing a procedure on a wall of the lumen). As described above, in some examples the liner inset tube includes a deflector 1141.

Figure 86J:
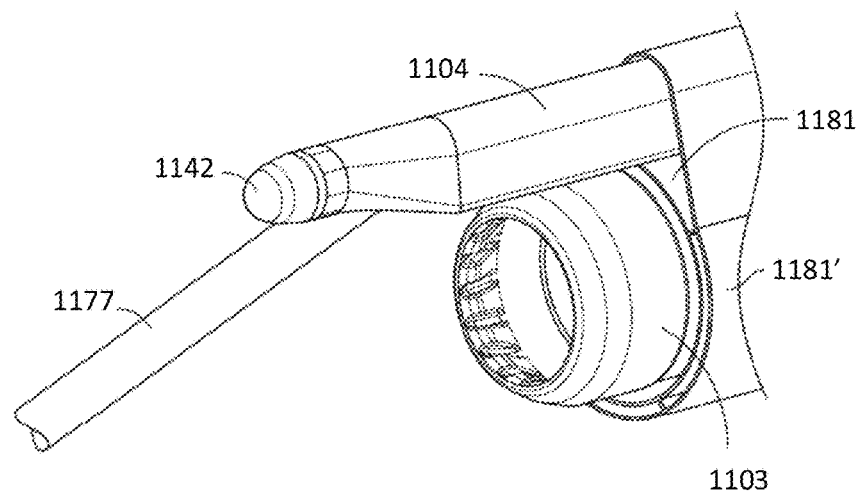
Figure 86K:
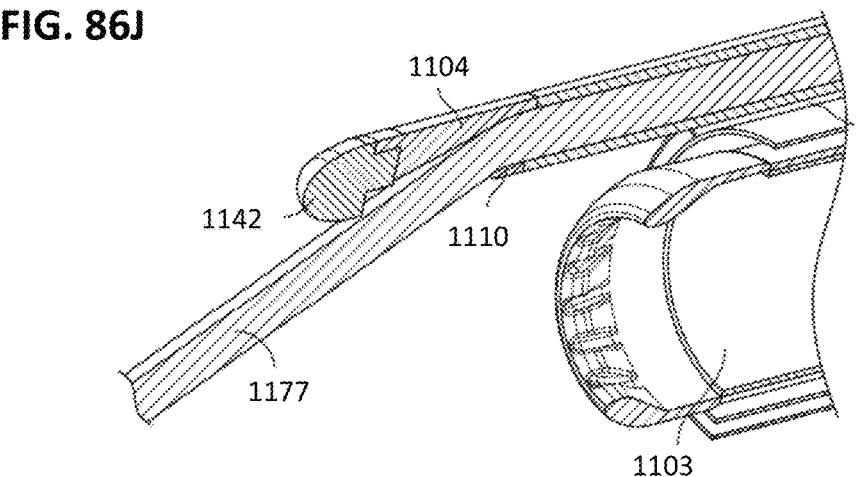
Figure 86L:
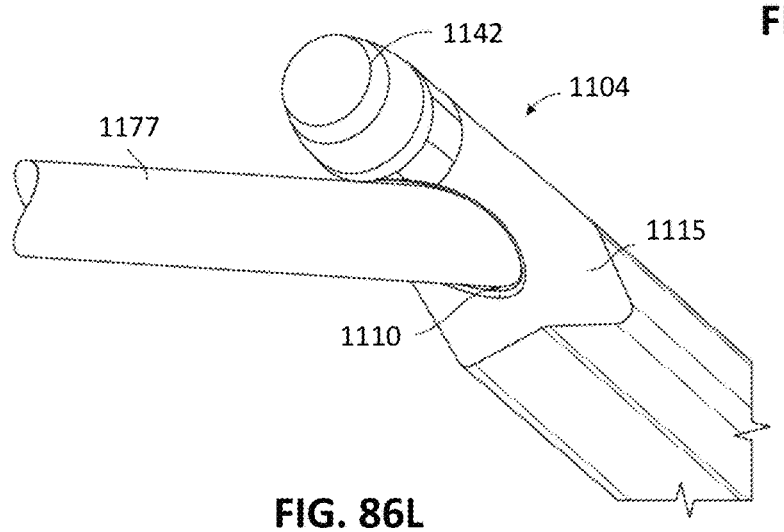

FIGS. 86E-86L illustrate an example of a liner insert tube 1104 that includes an inner lumen 1110 with a distal bend that steers a tool within the liner insert tube in a predefined direction (e.g., the liner insert tube may be configured to steer the tool towards a midline of the elongate medical device and/or may be oriented in the opposite direction, away from the midline of the elongate medical device. FIGS. 86E-86I and 86L are similar to FIGS. 73E-73G and 73J, and FIGS. 86J-86K and 86L are similar to FIGS. 73K-73L and 73I described above, but may illustrate other (or alternative) features. In any of the liner insert tubes described herein, the distal end of the liner insert tube may have an atraumatic and/or soft distal end 1142 configured to extend distally beyond the working channel (as shown in FIGS. 86J-86L). Further, as shown in FIGS. 86F-86I, the lumen 1110 can extend substantially axially within the liner insert tube 1104, but can be curved or slanted, e.g., radially inwards (e.g., at a 30°-60°, such as a 45° angle), just proximal to the soft distal end 1142 so as to direct the tool 1177 in a desired direction, such as towards the center of the elongate medical device. In some examples the liner insert tube 1104 can be steerable (e.g., via pull wires or other steering mechanisms) so as to enable further manipulation or directing of working tools passed therethrough.

The external working channels of the working channel sleeve apparatus may include one or more cuffs (e.g., elastic-like cuffs) or sections that may be configured to keep the external working channels collapsed against the elongate medical device when a tool or liner insert tube is not inserted therein.

FIGS. 86H-86L illustrate a liner insert tube 1104 having a lumen 1110 into which a tool 1177 may be inserted proximally so that it may extend distally from the elongate medical device 1103 at a distal end region, after passing through the external working channel 1181 (a "flat" or unexpanded external working channel 1181' is radially offset from the first external working channel in which a liner insert tube has been inserted. FIGS. 86H-86L also illustrate a liner insert tube 1104 including wings 1115 that may maintain the orientation of the apparatus within the external and expandable working channel 1181. A tool 1177 is shown extended through the example liner insert tube shown in FIGS. 86D-86E.

Figure 87A:
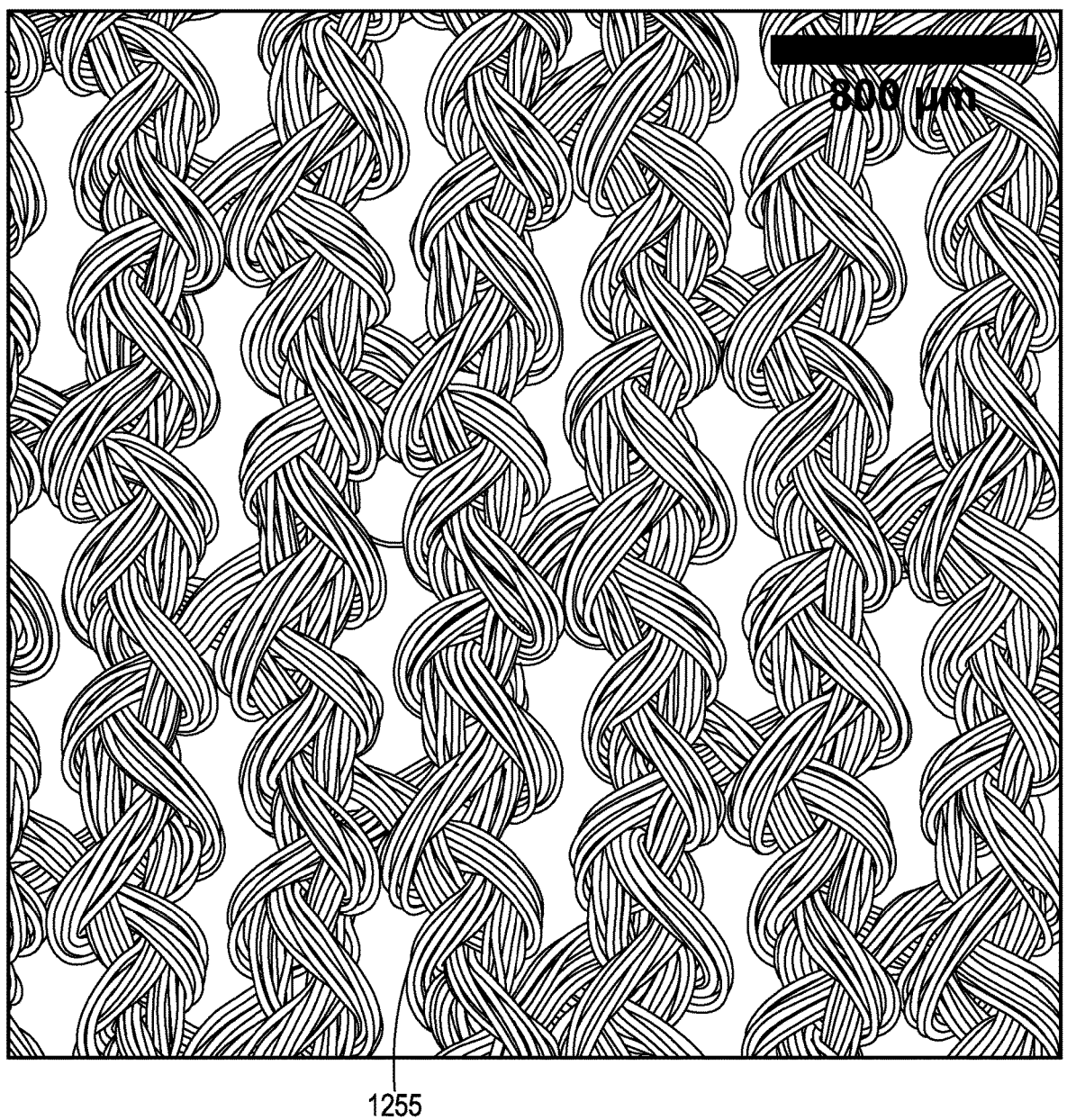
FIG. 87A is a scanning electron micrograph showing knit fibers of one example of a tube having expandable external channels.

As mentioned above, in some examples any of the tubes and/or the external channels formed on or as part of the tube may be formed of a knitted, woven or braided material. In some examples a knit fiber may be used to form the tube and channel(s). For example, FIG. 87A shows one example of knit material forming the tube and working channels described herein. FIG. 87A shows a magnified view of knit fibers 1255 forming a knit sleeve (tube) that includes four external channels. This knit pattern includes cross-connected rows of knit filament bundles. The precise knit pattern may be selected to optimize the expansion and other properties.

Figure 87B:
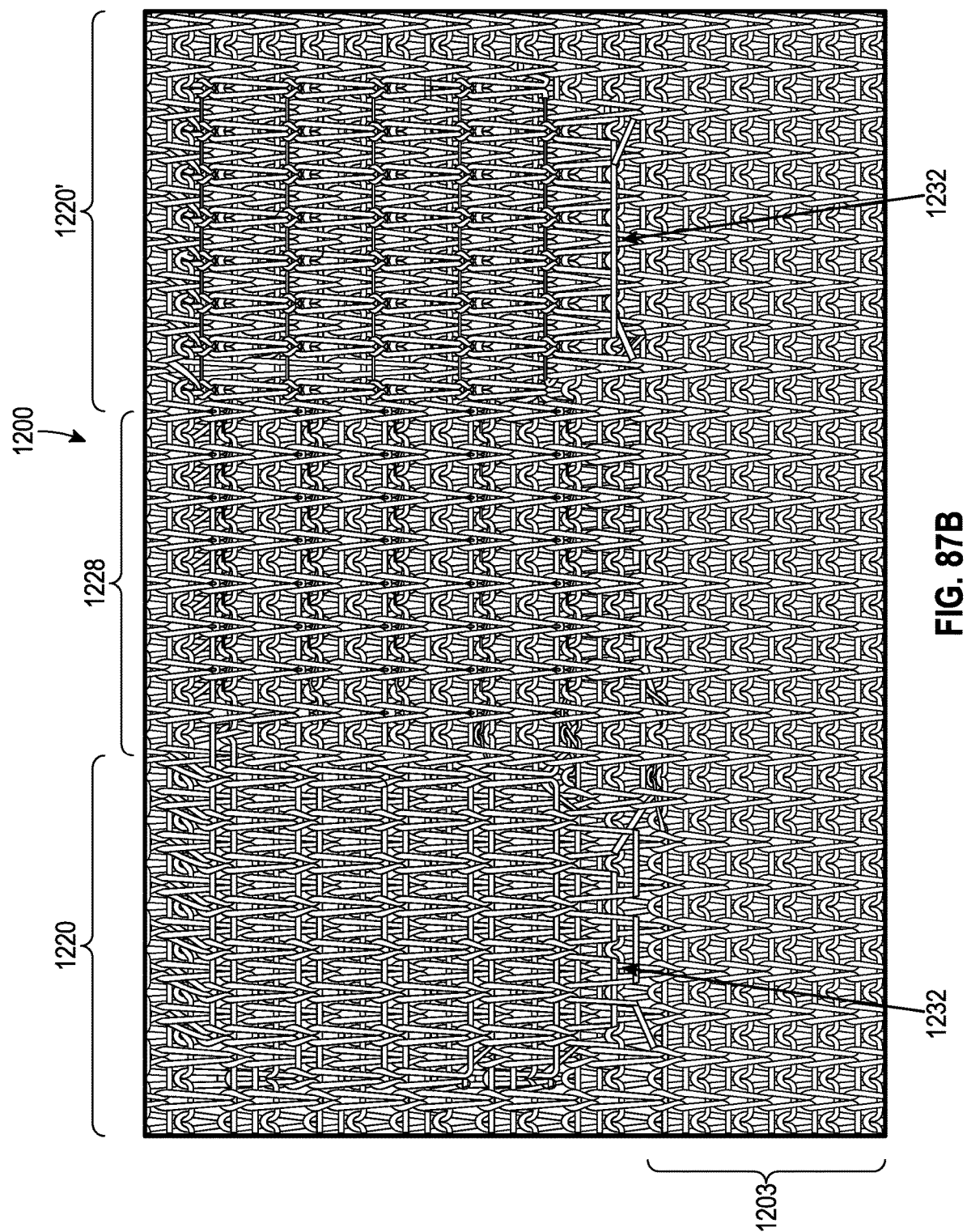
FIG. 87B is example of a knit pattern of a section of an apparatus as described herein (shown with the tubular structure flattened).

For example, FIG. 87B shows a portion of a template pattern for a knitted working channel sleeve 1200 including an inner knitted tube that is concurrently knit with external channels. In FIG. 87B, a front side of a knitted working channel sleeve is show flattened (it may be expanded open to form the tube); the back of the flattened tube portion is not visible. In this example, the bottom region 1203 shows an end of the knitted working channel sleeve before the external working channels 1220, 1220' are begin; this region forms the inner tube of the working channel sleeve. Two external working channels 1220, 1220' are shown on this side of the (flattened) working channel sleeve; these external working channels are knitted together and integrated with the inner tubular body. Each knit external working channel 1220, 1220' include a proximal opening 1232, 1232' on the end of the knit working channel.

The template pattern, including the stitch pattern shown in FIG. 87B may be generated and/or used by a knitting machine, such a flat (e.g., "flatbed") knitting machine. In the example shown in FIG. 87B the knit forming the external working channels 1220, 1220' may have a different pattern as compared to that of the inner tube portion 1203, 1228. For example, the knitted pattern for the working channels may be more elastic than the knitted pattern for the working channels. In some examples the knitted pattern for the working channels may have larger pores or higher porosity than that of the kitted pattern forming for the inner tube. In some examples the fiber(s) forming the knitted pattern for the external working channels may be different from the fiber(s) forming the knitted patter for the inner tube portion. For example, the fiber(s) forming the inner tube 1203 may be formed of a hybrid elastic and lower-friction material, such a hybrid a polytetrafluoroethylene (e.g., ePTFE)/spandex material, whereas the fiber(s) forming the external channels may be a low-friction material alone (e.g., Polytetrafluoroethylene, such as ePTFE), or an elastic material alone (e.g., Spandex).

As mentioned above, any of these working channel sleeve apparatuses may be formed by weft knitting, or warp knitting, including but not limited to tricot, Milanese knit, Raschel knit, and stitch-bonding. Any appropriate size filament(s) may be used. For example in some examples the filament(s) (e.g., fiber or fibers) forming the outer working channel(s) may be about 100 denier to 6000 denier for the outer wrap. Fiber(s) for the inner elastic core could be 400 to 6000 denier for the inner wrap.

In some examples the external channels using this kind of a knitting machine (e.g., a flatbed knitting machine) may have the advantage of being made complete in one piece without any post knitting assembly or sewing required. A knit structure also lends itself to creating stretchy fabrics, more so than with woven constructions.

In some examples a higher gauge knitting machine would be advantageous so that the density of the knit could be made tighter and smoother, reducing sliding friction and making the fabric more puncture resistant. In FIG. 87A, the knit was formed using between 1-4 filament ends, having fibers of Denier (thickness) of between about 10-200. The knitting machine gauge may be between about 10/14 and 16/18. In the example shown in FIG. 87A, the fiber used for knitting may be, e.g., Polypropylene, PTFE, UHMWPE (Ultra High Molecular Weight Polyethylene, otherwise known as Spectra or Dyneema), silicone, polyurethane, etc. As described above, the fiber may be a hybrid elastic/lubricious (e.g., elastic core wrapped with a lubricious material).

Alternatively or additionally a woven material may be used to form the external working channels.

In use, an external working channel device (e.g., a tube having one or more external working channels) may be installed over an elongate medical device (e.g., a rigidizing device). The main tube lumen of the external working channel device 7600 may sufficiently expand against the elastic force of the to receive the elongate medical device 200. The assembly including the elongate medical device and external working channel(s) may then be inserted into a body (e.g., a body lumen, a body vessel, etc.) through a natural or artificial orifice and advanced according to the need of the procedure being performed. When the distal end of the assembly is positioned in the desired location within the body, a working channel of the external working channel device 7600 may be selected to receive a liner insert tube or tool directly therein. The tool or liner insert tube may be advanced through the working channel, expanding it. In examples in which the elongate medical device is rigidizable, the liner insert tube or tool may be inserted after the elongate medical device has been rigidized to retain a shape and define a path of the external working channel through which the liner insert tube or tool may be passed through. The distal end of the liner insert tube or tool may be advanced to a desired location and the procedure may continue through operation of the tool distal end.

Figure 88:
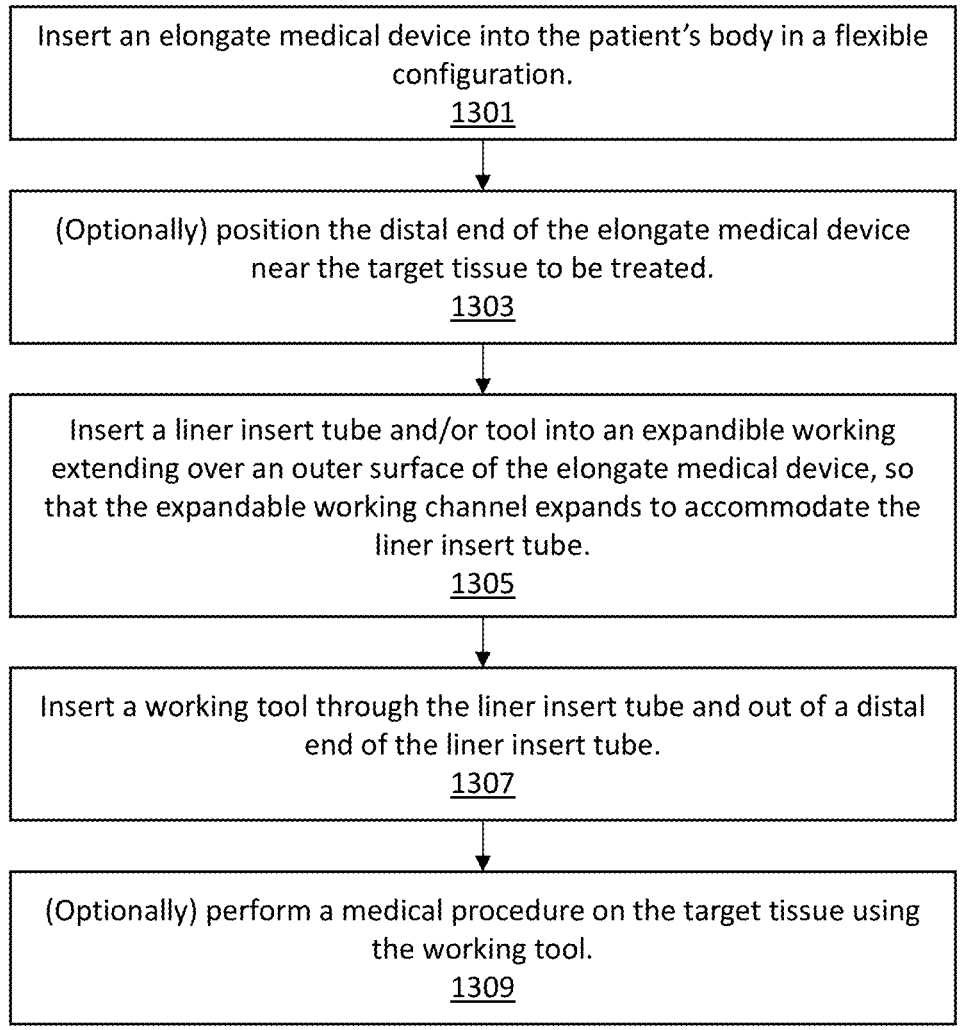
FIG. 88 schematically illustrates one example of a method of operating an apparatus as described herein.

For example, FIG. 88 illustrates a method of positioning a tool within a body. In this example the method may include inserting an elongate medical device into the body, where the elongate medical body includes a tube forming one or more external working channels 1301. In some examples the tube is attached so that it may slide or move slightly relative to the outer surface of the elongate medical device. In examples in which the elongate medical device is configured as a rigidizing member, the rigidizing member may initially be in a flexible configuration. The elongate distal end of the elongate medical device may be positioned at or near a target region of the body to be treated 1303. A liner insert tube and/or a tool may be inserted into an expandable working channel, so that the external working channel expands to accommodate the liner insert tube 1305. In some examples the liner insert tube may be engaged with a distal and/or proximal end of the tube and/or the elongate medical device. A working tool may be inserted through the liner insert tube and out of a distal end of the liner insert tube 1307. Thereafter, a procedure may be performed on the target region using the working tool 1309. Additionally, ridigization could occur, for example, between steps 1303 and 1305 (i.e., 1304)

EXAMPLES

Figure 89A:
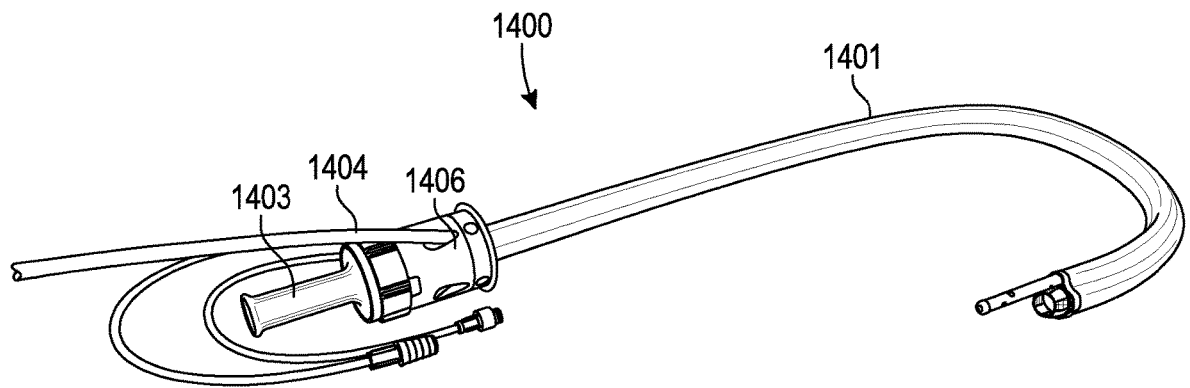
FIGS. 89A-89C illustrate one example of an elongate medical device onto which a tube having a plurality of external and expandable channels is coupled.
Figure 89B:
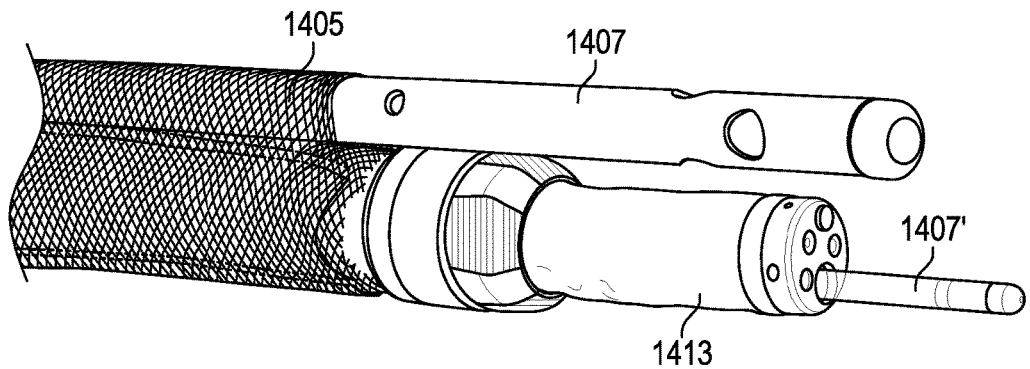
Figure 89C:
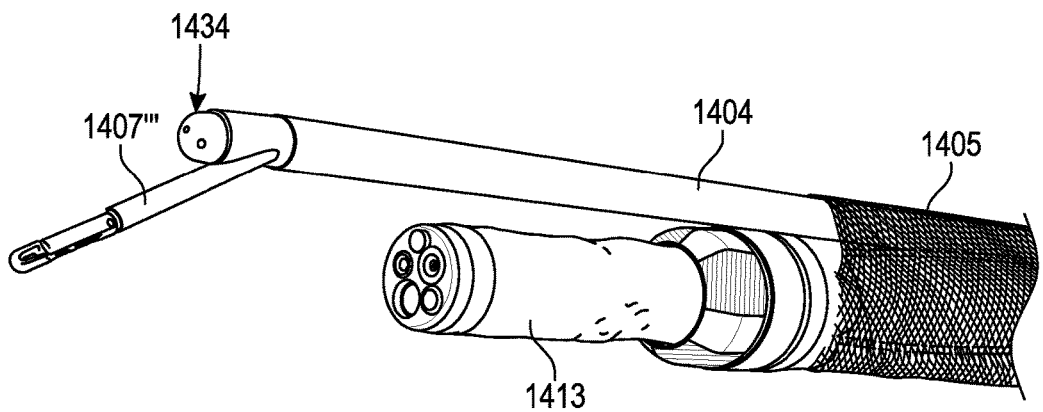

FIG. 89A-89C illustrate one example of a system 1400 including an elongate medical device 1403 (e.g., an overtube into which an endoscope has been inserted in FIGS. 89B and 89C) including a tube 1401 forming a plurality of external and expandable working channels. In FIG. 89A the elongate medical device is shown with the tube attached over the outer surface of the elongate medical device, and a liner insert tube 1404 extends through one of the expandable channels and out of the distal end. As mentioned, the elongate medical tool is configured as a rigidizing overtube over which a tube or sleeve 1401 including a plurality of external working channels have been integrated. The proximal handle 1406 of the rigidizing endoscope also includes access inlet into each of the external working channels. These working channels may be marked (e.g., by a symbol, code, alphanumeric, etc.) so that the user may know where around the radius of the distal end the medical tool will exit the working channel.

FIG. 89B shows an example of both an external working channel 1405 on the rigidizing tube shown in FIG. 89A, with a tool 1407 inserted at proximal end of the endoscope and emerging from distal end, as shown in FIG. 89B. In this example an endoscope 1413 is also included inserted through the overtube, and may itself include a working channel, configured as a traditional internal working channel. In FIG. 89A a second medical tool 1407' is inserted through this internal (endoscope) working channel, as shown.

FIG. 89C illustrate an example of a medical tool 1407''' inserted through a liner insert tube 1404 that is itself inserted through the expandable external working channel 1405. A blunt ended deflector 1434 on the liner insert tube 1404 is shown deflecting the tool radially inward relative to the overtube and endoscope.

Figure 90A:
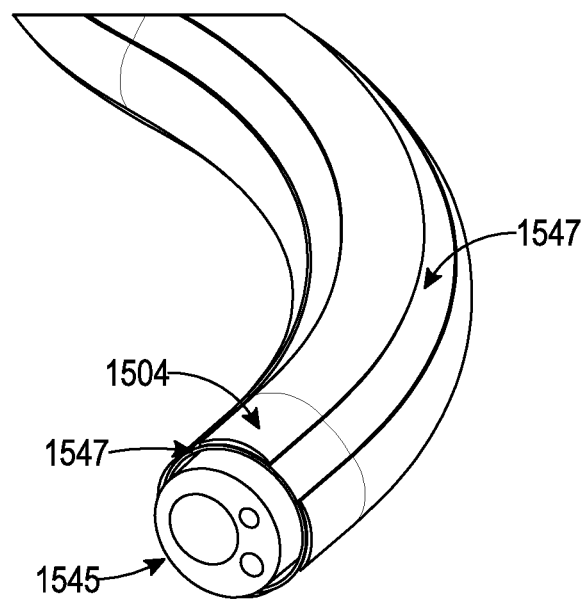
FIGS. 90A-90B illustrate an example of a system including a plurality of external channels.
Figure 90B:
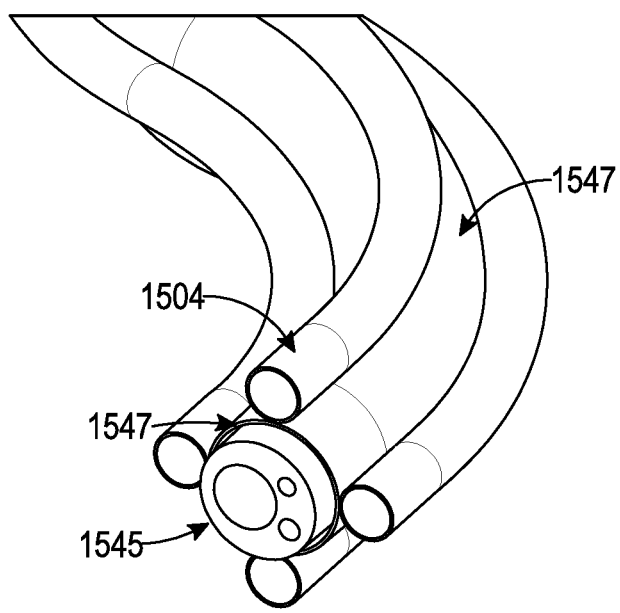

Any of the apparatuses described herein may be used with a robotic system, including a robotic endoscope system. FIGS. 90A and 90B illustrate operation of a system that may include a pair of telescoping devices, including an internal endoscope 1545 ("child") and an external overtube ("mother") over which may be worn an inner tube 1547 including four external working channels 1504. The tubes, such as the knitted, woven and/or braided tubes described above, forming the external working channels may be kept in a collapsed configuration when navigating the apparatus through the body lumen. Once at or near a target region, the external working channels may expand or allowed to expand as shown in FIG. 90B. In this example FIG. 90A shows the apparatus with the external working channels 1504 in a collapsed configuration.

Figure 90C:
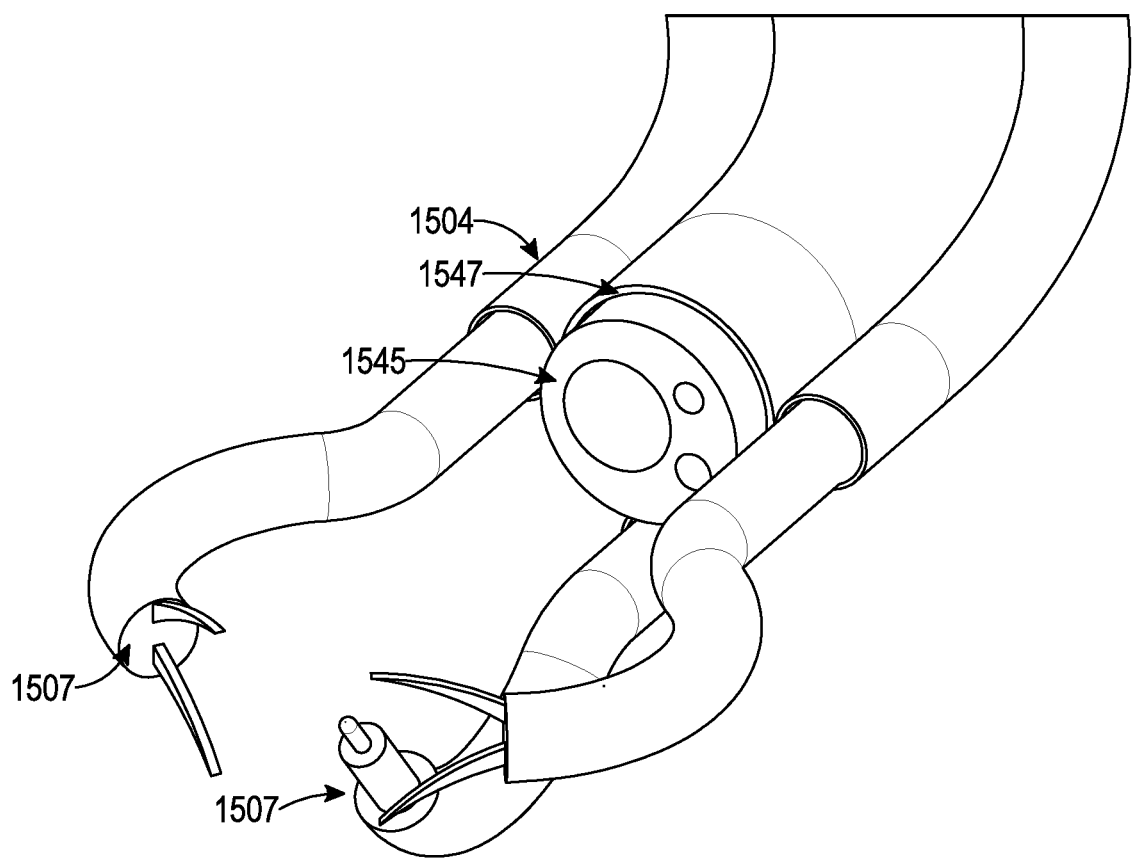
FIG. 90C shows the system of FIG. 90A with a variety of different tools extending from the external working channels.

FIG. 90C shows an example of a distal end region of the endoscope and overtube with external working channels 1504 attached as part of a sleeve or tube on an outside of the overtube. In this example three tools 1507 are shown extending and may manipulate tissue as described herein.

Figure 91A:
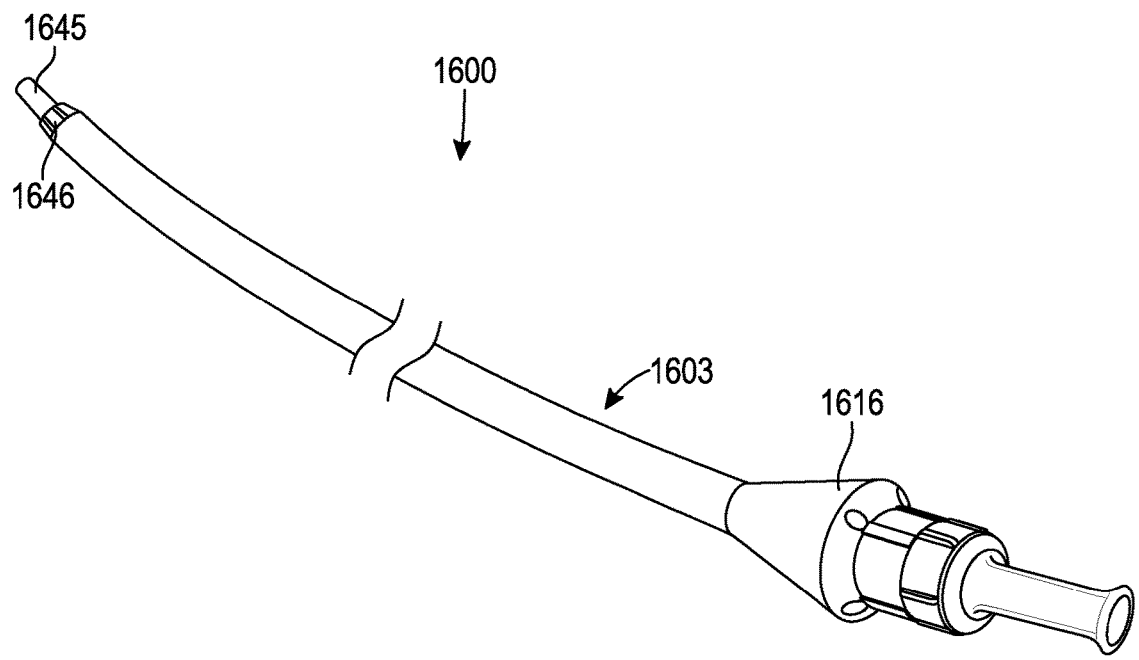
FIGS. 91A-91E illustrate another example of a system as described herein, including a tool liner tube.
Figure 91B:
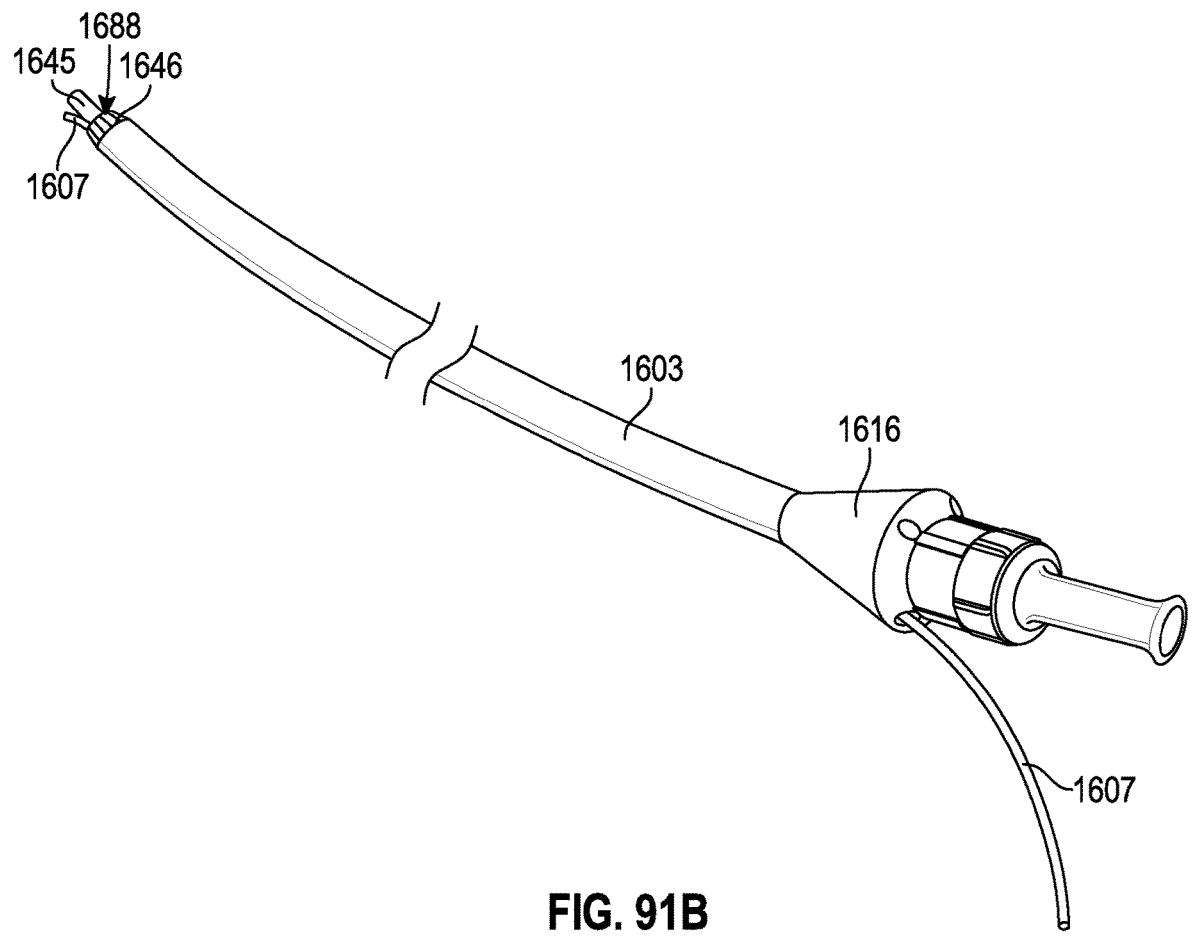
Figure 91C:
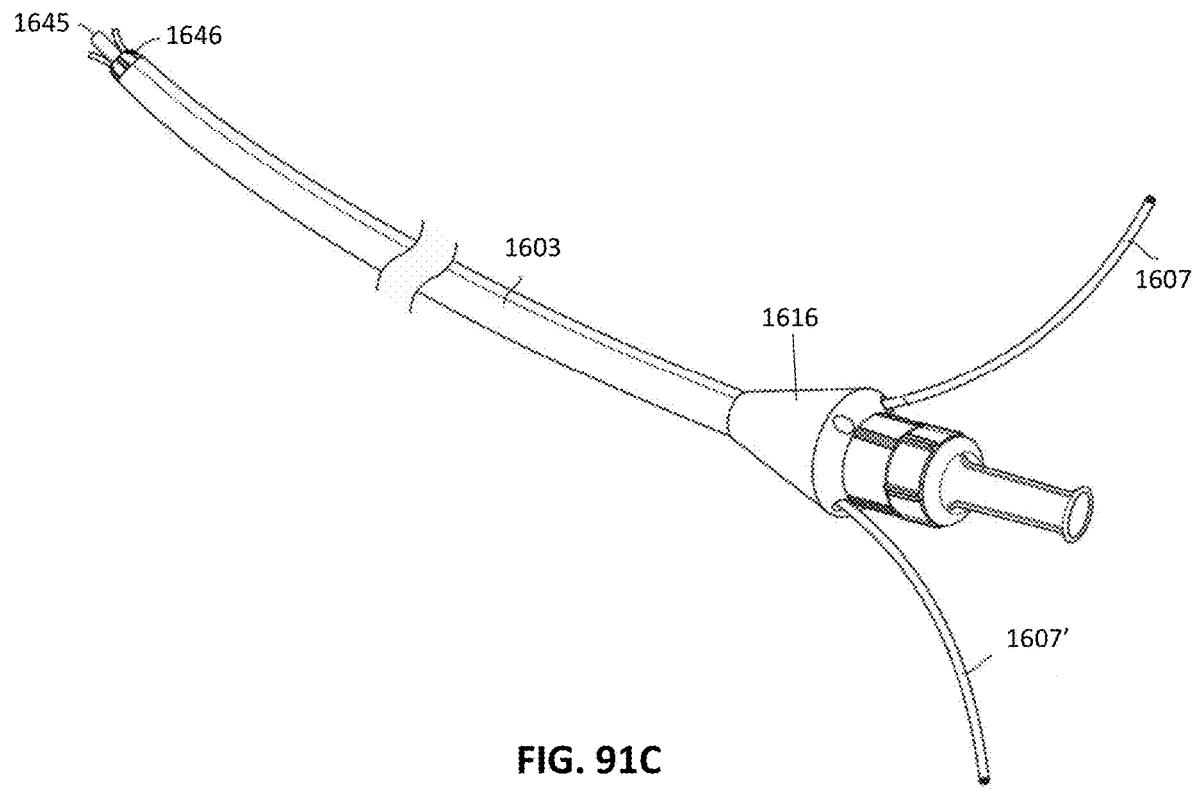
Figure 91D:
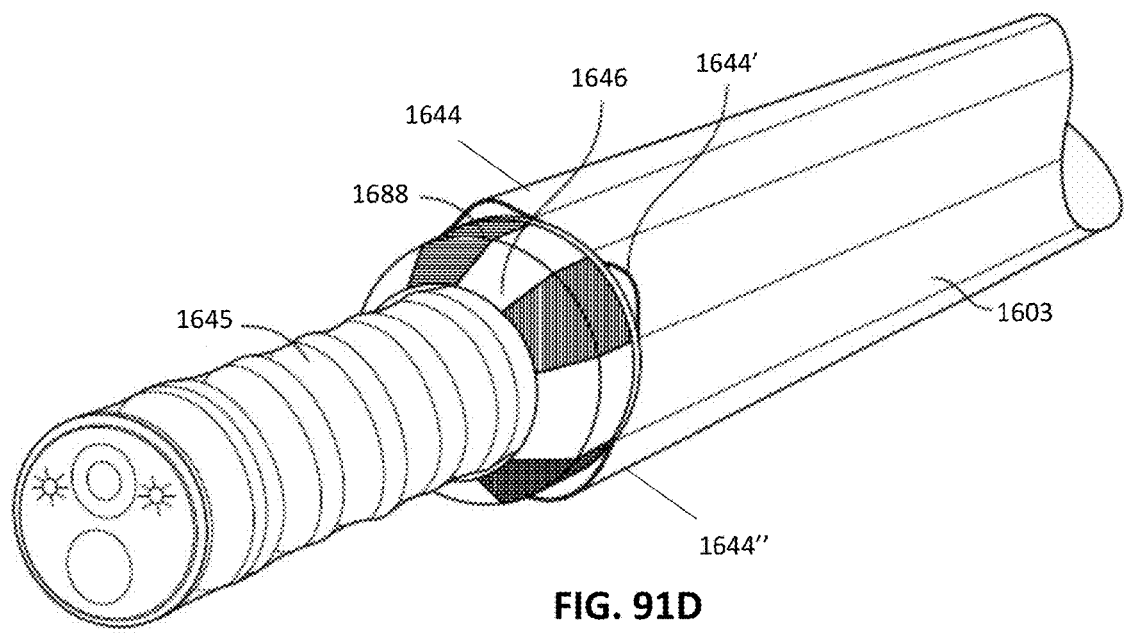
Figure 91E:
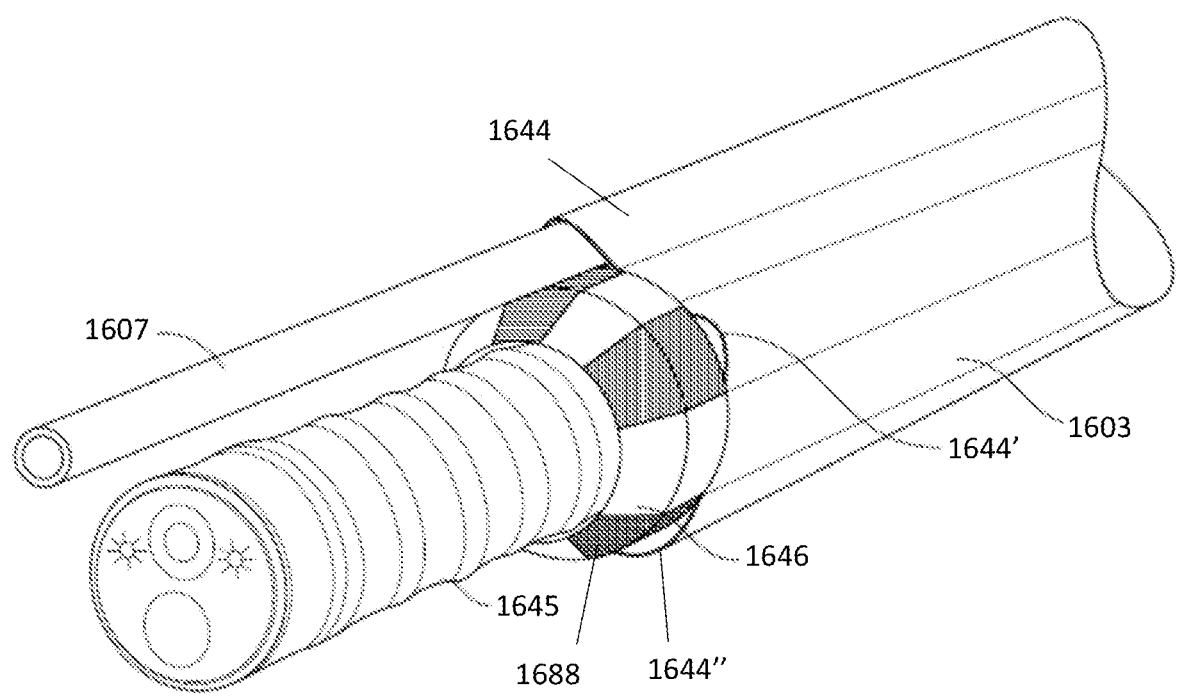

FIGS. 91A-91D illustrate another example of a system 1600 including an outer elongate medical device 1646 onto which a plurality of external working channels 1644, 1644', 1644" have been formed as part of a tube or sleeve 1603 (e.g., working channel sleeve). An inner medical device 1645 (e.g., endoscope) is shown inserted through the outer medical device. The tube or sleeve 1603 is coupled distally to the distal end region of the medical device 1646 and the proximal end is coupled to a proximal end region of the medical device including an introducer region 1616 that provides access into each of the collapsed or partially collapsed external working channels (shown as color coded in this example). In examples including an endoscope 1645 that may visualize the distal end region of the apparatus, the endoscope 1645 may detect when the tool or a liner insert tube 1604 exits by correlating which color and/or marking 1688 indicates where the tool 1607 was inserted or introduced into the working channel. FIG. 91C shows another example of the same system as in FIGS. 91A-91B but with a second tool 1607' inserted into a second channel of the elongate tube. FIGS. 91B-91C are similar to FIGS. 74D-74E and FIGS. 91D-91E are similar to FIGS. 74A-74B described above but may illustrate other (or alternative) features. FIG. 91D shows an enlarged view of the distal end region of the robotic system including an outer elongate medical device 1646 (configured as a mother or overtube), an inner elongate medical device 1645 (configured as a child, shown as an endoscope) and a tool 1607, configured as a suction tube. In some examples a liner insert tool may be used (not shown).

Figure 92:
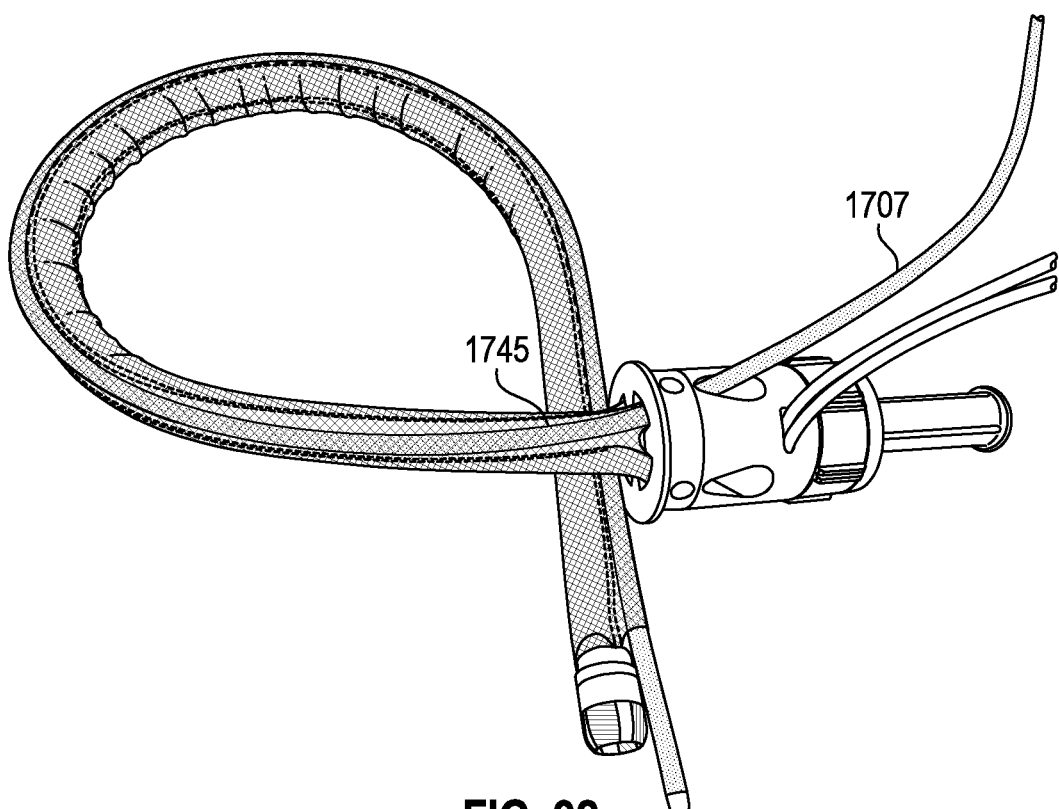
FIG. 92 shows an example of an elongate medical device (e.g., rigidizing device) having an outer tube with a plurality of expandable channels extending over an outer surface of the elongate medical device.
Figure 93:
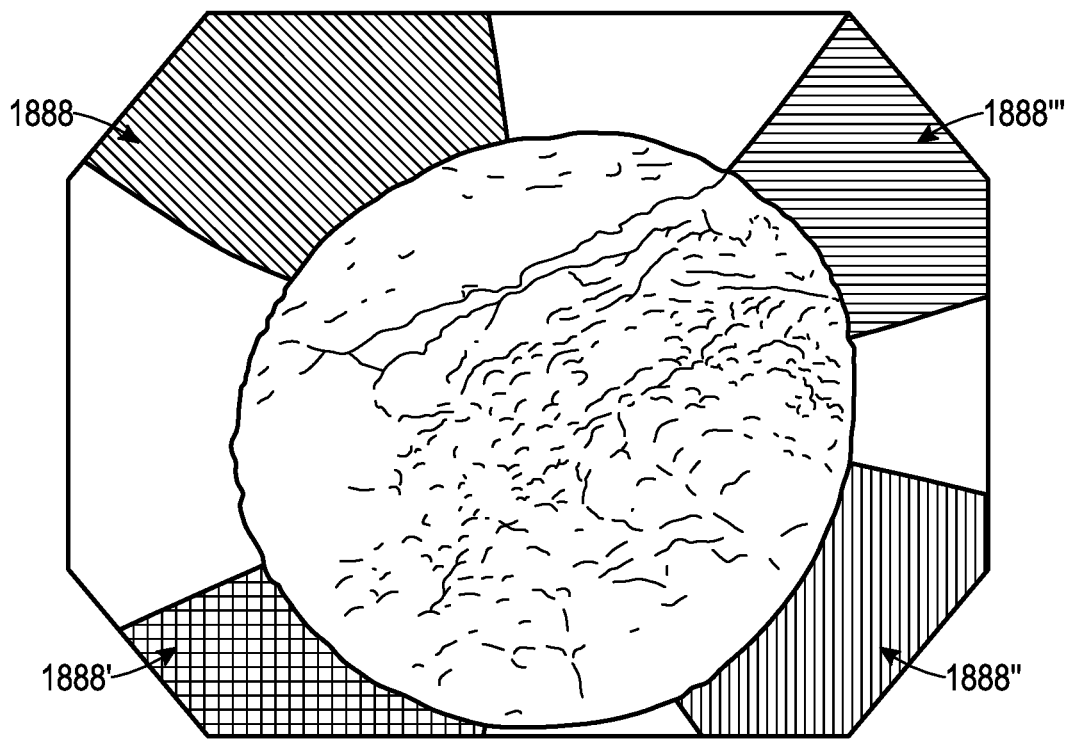
FIG. 93 is an example of the view seen from the endoscope, with the overtube distal end quadrant indicators (e.g., colors) corresponding to the different external channels shown.

FIG. 92 illustrates the use of an expandable external channel 1745 as described above on a rigidizing overtube. In this example a tool 1707 inserted into an external channel 1745 colored orange at the proximal end emerging from the external channel at the distal end, which is also colored (e.g., orange) for identification. For example, FIG. 93 is an example showing the view of the color-coded distal tip from the perspective of an endoscope's camera, showing four color-coded regions 1888, 1888', 1888", 1888'''' indicating where the external channels are located (and where a tool will exit) relative to the patient.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A rigidizing system comprising:
   an elongate rigidizing device configured to be rigidized from a flexible configuration to a rigid configuration; and
   a working channel sleeve comprising one or more expandable external working channels formed of one or more non-elastic filaments, the working channel sleeve positioned along the elongate rigidizing device and configured so that the one or more external working channels expands when a tool is passed therethrough, wherein the one or more non-elastic filaments are knitted, braided or woven to form pores having a pore size that may vary as the external working channel is expanded or collapsed.

2. The rigidizing system of claim 1, wherein the one or more expandable external working channels is coupled to a proximal end region and to a distal end region of the elongate rigidizing device.

3. The rigidizing system of claim 1, further comprising at least one guide configured to be removably inserted into the one or more expandable external working channels, the at least one guide including a lumen configured to expand the expandable external working channel to enable passage of the tool therethrough.

4. The rigidizing system of claim 3, wherein the one or more expandable external working channels is configured to reduce in profile as the at least one guide is removed.

5. The rigidizing system of claim 3, wherein the at least one guide includes an atraumatic distal end.

6. The rigidizing system of claim 3, wherein the at least one guide comprises a protrusion configured to enable rotational alignment of the at least one guide relative to the one or more expandable external working channels.

7. The rigidizing system of claim 1, wherein the one or more expandable external working channels comprises a fluoropolymer material.

8. The rigidizing system of claim 1, wherein the one or more expandable external working channels comprises a hydrophilic coating.

9. The rigidizing system of claim 1, wherein the one or more expandable external working channels comprises a proximal entry marker thereon configured to indicate a distal exit position.

10. The rigidizing system of claim 1, wherein the elongate rigidizing device is configured to rigidized by supplying positive or negative pressure to the elongate rigidizing device.

11. The rigidizing system of claim 1, wherein the one or more non-elastic filaments comprises polytetrafluoroethylene (PTFE).

12. A rigidizing system comprising:
an elongate rigidizing device configured to be rigidized from a flexible configuration to a rigid configuration; and
a working channel sleeve comprising an outer member extending over an outer surface of the elongate rigidizing device, and
one or more expandable external working channels formed of one or more non-elastic filaments and extending along a length of the outer member and configured expand outwards when a tool is inserted therethrough wherein the one or more non-elastic filaments are knitted, braided or woven to form pores having a pore size that may vary as the external working channel is expanded or collapsed.

13. The rigidizing system of claim 12, wherein the outer member is a fabric tube.

14. The rigidizing system of claim 12, wherein the outer member comprises a woven, knit or braided tube.

15. The rigidizing system of claim 12, wherein the outer member is coupled to a proximal end region and to a distal end region of the elongate rigidizing device.

16. The rigidizing system of claim 12, further comprising at least one guide configured to be removably inserted into an expandable external working channel of the one or more expandable external working channels, the at least one guide including a lumen configured to enable passage of the tool therethrough.

17. The rigidizing system of claim 16, wherein the at least one guide comprises a protrusion configured to enable rotational alignment of the at least one guide relative to the elongate rigidizing device.

18. The rigidizing system of claim 12, wherein the outer member comprises an elastomeric, plastic, or composite structure.

19. The rigidizing system of claim 12, wherein the outer member comprises a polyurethane or silicone material.

20. The rigidizing system of claim 12, wherein the outer member comprises a fluoropolymer material.

21. The rigidizing system of claim 12, wherein the outer member comprises a hydrophilic coating.

22. The rigidizing system of claim 12, wherein each of the one or more expandable external working channels comprises a proximal marker thereon configured to indicate a distal exit position.

23. The rigidizing system of claim 12, wherein the elongate rigidizing device is configured to rigidized by supplying positive or negative pressure to the elongate rigidizing device.

24. A rigidizing system comprising:
an elongate rigidizing device configured to be rigidized by vacuum or pressure from a flexible configuration to a rigid configuration; and
a working channel sleeve comprising an outer member extending over an outer surface of the elongate rigidizing device and coupled to a proximal end region and to a distal end region of the elongate rigidizing device, and
one or more expandable external working channels formed of one or more non-elastic filaments and extending along a length of the outer member and configured to lay flat against the elongate rigidizing device in a first configuration and to expand outwards to a second configuration when a tool is inserted therethrough wherein the one or more non-elastic filaments are knitted, braided or woven to form pores having a pore size that may vary as the external working channel is expanded or collapsed.

25. A endoscopic system comprising:
an elongate endoscopic device configured to diagnose and treat disease within the body,
an expandable working channel sleeve extending over an outer surface of the endoscopic device, the expandable working channel formed of one or more non-elastic filaments and configured expand when a tool is inserted therethrough, wherein the one or more non-elastic filaments are knitted, braided or woven to form pores having a pore size that may vary as the external working channel is expanded or collapsed.

* * * * *